(12) United States Patent
Meyer et al.

(10) Patent No.: US 7,238,512 B2
(45) Date of Patent: Jul. 3, 2007

(54) METHOD TO PRODUCE PARA-HYDROXYBENZOIC ACID IN THE STEM TISSUE OF GREEN PLANTS BY USING A TISSUE-SPECIFIC PROMOTER

(75) Inventors: Knut Meyer, Wilmington, DE (US); Kanwarpal S. Dhugga, Johnston, IA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 409 days.

(21) Appl. No.: 10/688,745

(22) Filed: Oct. 17, 2003

(65) Prior Publication Data

US 2005/0086712 A1    Apr. 21, 2005

(51) Int. Cl.
*C12N 9/88* (2006.01)
*C12N 15/00* (2006.01)
*C12N 5/00* (2006.01)
*A01H 1/00* (2006.01)
*A01H 9/00* (2006.01)

(52) U.S. Cl. ........................ 435/232; 435/183; 435/193; 435/320.1; 435/410; 536/23.2; 800/278; 800/295

(58) Field of Classification Search ................ 435/183, 435/193, 232, 320.1, 410; 536/23.2; 800/278, 800/295
See application file for complete search history.

(56) References Cited

U.S. PATENT DOCUMENTS

2003/0215927 A1    11/2003   Viitanen et al.

FOREIGN PATENT DOCUMENTS

| WO | WO 98/00549    | 1/1998  |
| WO | WO 98/18949    | 5/1998  |
| WO | WO 00/04166    | 1/2000  |
| WO | WO 00 70058    | 11/2000 |
| WO | WO 03/066836 A2 | 8/2003 |

OTHER PUBLICATIONS

Viitanen et al. Plant Physiol. Dec. 2004;136(4):4048-60. Epub Nov. 24, 2004.*
Melinda J. Mayer et al., Rerouting the Plant Phenylpropanoid Pathway by Expression of a Novel Bacterial Enoyl-CoA Hydratase/Lyase Enzyme Function, The Plant Cell, vol. 13:1669-1682, Jul. 2001.
Adinpunya Mitra et al., 4-Hydroxycinnamoyl-CoA hydratase/lyase, an enzyme of phenylpropanoid cleavage from *Pseudomonas*, causes formation of C6-C1 acid and alochol glucose conjugates when expressed in hairy roots of *Datura stramonium* L., Planta, vol. 215:79-89, 2002.
National Center for Biotechnology Information General Identifier No. 1773286, Accession No. U71080, May 31, 1997, D. A. Bell-Delong et al., Cinnamate-4-hydroxylase expression in *Arabidopsis*. Regulation in response to development and the environment.
National Center for Biotechnology Information General Identifier No. 609339, Accession No. U18675, Mar. 3, 2000, D. Lee et al., The *Arabidopsis thaliana* 4-coumarate:CoA ligase (4CL) gene: stress and developmentally regulated expression and nucleotide sequence of its cDNA.
Neil G. Taylor et al., Interactions among three distinct CesA proteins essential for cellulose synthesis, PNAS, vol. 100(3):1450-1455, Feb. 4, 2003.
Neil G. Taylor et al., The irregular xylem3 Locus of *Arabidopsis* Encodes a Cellulose Synthase Required for Secondary Cell Wall Synthesis, The Plant Cell, vol. 11:769-779, May 1999.
Todd A. Richmond et al., The Cellulose Synthase Superfamily, Plant Physiology, vol. 124:495-498, Oct. 2000.
Deborah P. Delmer, Cellulose Biosynthesis: Exciting Times for A Difficult Field of Study, Annu. Rev. Plant Physiol. Plant Mol. Biol., vol. 50:245-276, 1999.
Louise Jones et al., Cloning and characterization of irregular xylem4 (Irx4): a severely lignin-deficient mutant of *Arabidopsis*, The Plant Journal, vol. 26(2):205-216, 2001.
Simon R. Turner et al., Collapsed Xylem Phenotype of *Arabidopsis* Identifies Mutants Deficient in Cellulose Deposition in the Secondary Cell Wall, The Plant Cell, vol. 9:689-701, May 1997.
Neil G. Taylor et al., Multiple Cellulose Synthase Catalytic Subunits Are Required for Cellulose Synthesis in *Arabidopsis*, The Plant Cell, vol. 12:2529-2539, Dec. 2000.
Dolly A. Bell-Lelong et al., Cinnamate-4-Hydroxylase Expression in *Arabidopsis*, Plant Physiol., vol. 113:729-738, 1997.
D. Lee et al., The *Arabidopsis thaliana* 4-coumarate:CoA ligase (4CL) gene: stress and developmentally regulated expression and nucleotide sequence of its cDNA, Plant Mol. Biol., vol. 28(5):871-884, 1995.
T. Richmond, Higher plant cellulose synthases, Genome Biol., vol. 1(4):reviews 3001.1-3001.6, 2000.

* cited by examiner

*Primary Examiner*—Tekchand Saidha
*Assistant Examiner*—Christian L. Fronda

(57) ABSTRACT

This invention relates to methods and materials to produce para-hydroxybenzoic acid in the stem tissue of transgenic green plants using a cellulose synthase promoter to operably express a gene encoding HCHL.

10 Claims, 8 Drawing Sheets

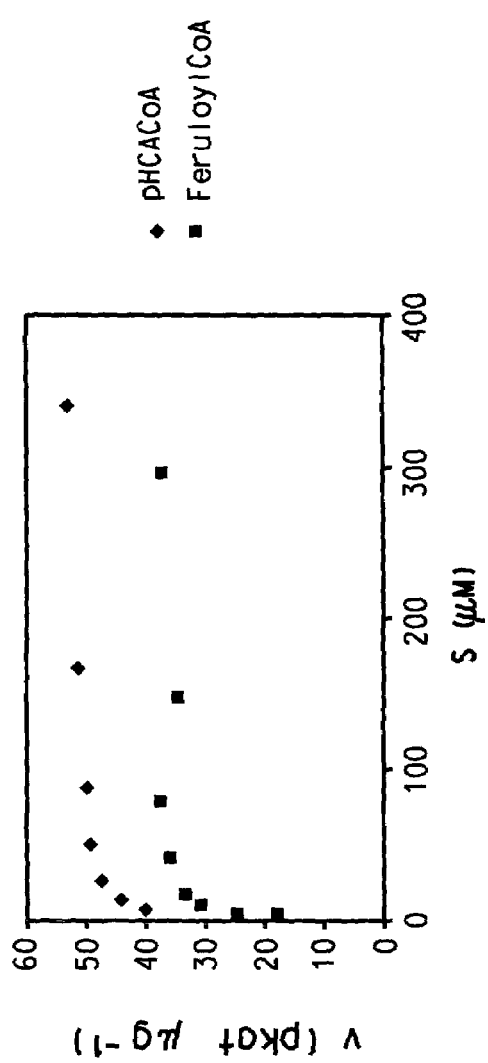
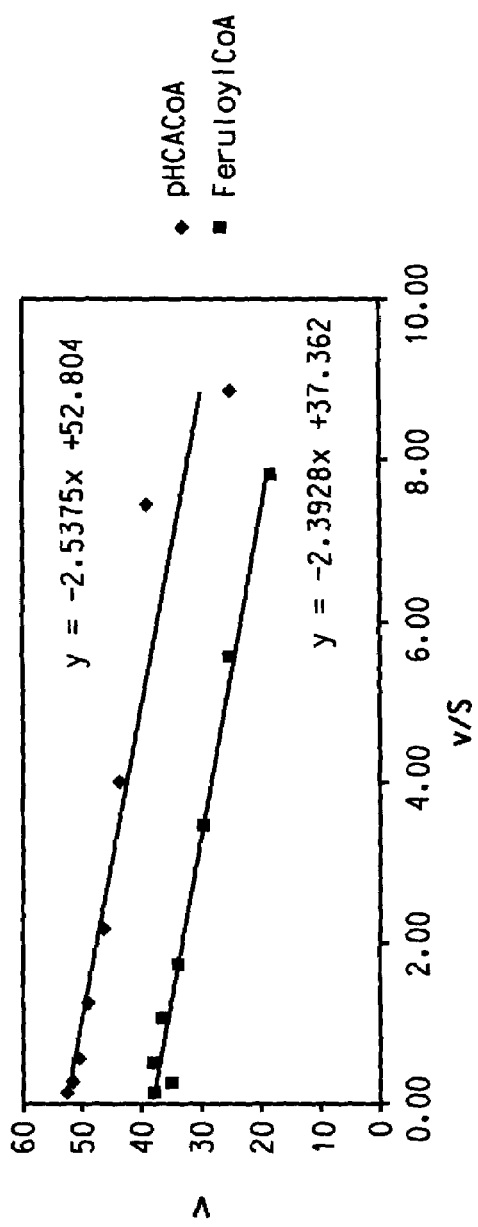
FIG. 2A
FIG. 2B

SEQUENCE LISTING

```
<160> NUMBER OF SEQ ID NOS: 83

<210> SEQ ID NO 1
<211> LENGTH: 29
<212> TYPE: DNA
<213> ORGANISM: Artificial sequence
<220> FEATURE:
<223> OTHER INFORMATION: Primer

<400> SEQUENCE: 1
actatttcat atggcgccac aagaacaag                              29

<210> SEQ ID NO 2
<211> LENGTH: 30
<212> TYPE: DNA
<213> ORGANISM: Artificial sequence
<220> FEATURE:
<223> OTHER INFORMATION: Primer

<400> SEQUENCE: 2
ggttgaaatc aagcttcaca atcccatttg                             30
```

<210> SEQ ID NO 3
<211> LENGTH: 26
<212> TYPE: DNA
<213> ORGANISM: Artificial sequence
<220> FEATURE:
<223> OTHER INFORMATION: Primer

<400> SEQUENCE: 3
ccatgagcac atacgaaggt cgctgg                                              26

<210> SEQ ID NO 4
<211> LENGTH: 24
<212> TYPE: DNA
<213> ORGANISM: Artificial sequence
<220> FEATURE:
<223> OTHER INFORMATION: Primer

<400> SEQUENCE: 4
tcagcgcttg atggcttgca ggcc                                                24

<210> SEQ ID NO 5
<211> LENGTH: 833
<212> TYPE: DNA
<213> ORGANISM: Pseudomonas putida

<400> SEQUENCE: 5
ccatgagcac atacgaaggt cgctgggcta ccgtgaaggt cgaactggag tcgggcattg          60
cctgggtcac cctcaaccgg ccggaaaagc gcaatgcaat gagccccacg ctgaaccggg         120
aaatggtcga cgtgctggaa accctggaac aggacggcga agccggggtg ctcgtgctga         180
ccggcgcggg tgaatcgtgg acggcaggca tggacctgaa ggaatacttc cgtgaggtgg         240
acgccggccc ggaaatcctc caggaaaaaa tccgccgcga tgcctcgcaa tggcaatgga         300
ggctgctgcg catgtacgcc aagccgacta tcgccatggt caacggctgg tgctttggcg         360
gcggcttcag cccgctggtg gcctgcgacc tggccatctg tgccgacgag ccacctttg          420
gcctgtcgga aatcaactgg ggcatcccac cgggcaacct ggtcagcaaa gccatggccg         480
ataccgttgg ccaccgccag tcgctgtact acatcatgac cggcaagact ttcggcgggc         540
ctaaagctgc cgagatgggg ctggttaacg agagcgtgcc gctggcgcaa ttgcgcgacg         600
tcacccgcga actggcgctc aacctgctgg aaaagaaccc ggtggtgctg cgtgcggcca         660
agaacggttt caagcgctgc cgcgaactga cctgggagca gaacgaagac tacctgtacg         720
ccaagctcga ccagtcccgt ctgctggaca ccgaaggtgg cgcgagcag ggcatgaagc          780
agttcctcga cgacaagagc atcaagccag gcctgcaagc catcaagcgc tga               833

<210> SEQ ID NO 6
<211> LENGTH: 276
<212> TYPE: PRT
<213> ORGANISM: Pseudomonas putida

<400> SEQUENCE: 6

Met Ser Thr Tyr Glu Gly Arg Trp Ala Thr Val Lys Val Glu Leu Glu
1               5                   10                  15

Ser Gly Ile Ala Trp Val Thr Leu Asn Arg Pro Glu Lys Arg Asn Ala
            20                  25                  30

Met Ser Pro Thr Leu Asn Arg Glu Met Val Asp Val Leu Glu Thr Leu
        35                  40                  45

Glu Gln Asp Gly Glu Ala Gly Val Leu Val Leu Thr Gly Ala Gly Glu
    50                  55                  60

```
Ser Trp Thr Ala Gly Met Asp Leu Lys Glu Tyr Phe Arg Glu Val Asp
 65                  70                  75                  80

Ala Gly Pro Glu Ile Leu Gln Glu Lys Ile Arg Arg Asp Ala Ser Gln
                 85                  90                  95

Trp Gln Trp Arg Leu Leu Arg Met Tyr Ala Lys Pro Thr Ile Ala Met
            100                 105                 110

Val Asn Gly Trp Cys Phe Gly Gly Phe Ser Pro Leu Val Ala Cys
        115                 120                 125

Asp Leu Ala Ile Cys Ala Asp Glu Ala Thr Phe Gly Leu Ser Glu Ile
        130                 135                 140

Asn Trp Gly Ile Pro Pro Gly Asn Leu Val Ser Lys Ala Met Ala Asp
145                 150                 155                 160

Thr Val Gly His Arg Gln Ser Leu Tyr Tyr Ile Met Thr Gly Lys Thr
                165                 170                 175

Phe Gly Gly Pro Lys Ala Ala Glu Met Gly Leu Val Asn Glu Ser Val
            180                 185                 190

Pro Leu Ala Gln Leu Arg Asp Val Thr Arg Glu Leu Ala Leu Asn Leu
        195                 200                 205

Leu Glu Lys Asn Pro Val Val Leu Arg Ala Ala Lys Asn Gly Phe Lys
210                 215                 220

Arg Cys Arg Glu Leu Thr Trp Glu Gln Asn Glu Asp Tyr Leu Tyr Ala
225                 230                 235                 240

Lys Leu Asp Gln Ser Arg Leu Leu Asp Thr Glu Gly Arg Glu Gln
                245                 250                 255

Gly Met Lys Gln Phe Leu Asp Asp Lys Ser Ile Lys Pro Gly Leu Gln
            260                 265                 270

Ala Ile Lys Arg
        275

<210> SEQ ID NO 7
<211> LENGTH: 24
<212> TYPE: DNA
<213> ORGANISM: Artificial sequence
<220> FEATURE:
<223> OTHER INFORMATION: Primer

<400> SEQUENCE: 7
catatgagca catacgaagg tcgc                                          24

<210> SEQ ID NO 8
<211> LENGTH: 27
<212> TYPE: DNA
<213> ORGANISM: Artificial sequence
<220> FEATURE:
<223> OTHER INFORMATION: Primer

<400> SEQUENCE: 8
aagcttcagc gcttgatggc ttgcagg                                       27

<210> SEQ ID NO 9
<211> LENGTH: 24
<212> TYPE: DNA
<213> ORGANISM: Artificial sequence
<220> FEATURE:
<223> OTHER INFORMATION: Primer

<400> SEQUENCE: 9
aagcttgcgc ttgatggctt gcag                                          24
```

<210> SEQ ID NO 10
<211> LENGTH: 289
<212> TYPE: PRT
<213> ORGANISM: Artificial sequence
<220> FEATURE:
<223> OTHER INFORMATION: His-tagged HCHL variant

<400> SEQUENCE: 10

```
Met Ser Thr Tyr Glu Gly Arg Trp Ala Thr Val Lys Val Glu Leu Glu
1               5                   10                  15

Ser Gly Ile Ala Trp Val Thr Leu Asn Arg Pro Glu Lys Arg Asn Ala
            20                  25                  30

Met Ser Pro Thr Leu Asn Arg Glu Met Val Asp Val Leu Glu Thr Leu
        35                  40                  45

Glu Gln Asp Gly Glu Ala Gly Val Leu Val Leu Thr Gly Ala Gly Glu
    50                  55                  60

Ser Trp Thr Ala Gly Met Asp Leu Lys Glu Tyr Phe Arg Glu Val Asp
65                  70                  75                  80

Ala Gly Pro Glu Ile Leu Gln Glu Lys Ile Arg Arg Asp Ala Ser Gln
                85                  90                  95

Trp Gln Trp Arg Leu Leu Arg Met Tyr Ala Lys Pro Thr Ile Ala Met
            100                 105                 110

Val Asn Gly Trp Cys Phe Gly Gly Gly Phe Ser Pro Leu Val Ala Cys
        115                 120                 125

Asp Leu Ala Ile Cys Ala Asp Glu Ala Thr Phe Gly Leu Ser Glu Ile
    130                 135                 140

Asn Trp Gly Ile Pro Pro Gly Asn Leu Val Ser Lys Ala Met Ala Asp
145                 150                 155                 160

Thr Val Gly His Arg Gln Ser Leu Tyr Tyr Ile Met Thr Gly Lys Thr
                165                 170                 175

Phe Gly Gly Pro Lys Ala Ala Glu Met Gly Leu Val Asn Glu Ser Val
            180                 185                 190

Pro Leu Ala Gln Leu Arg Asp Val Thr Arg Glu Leu Ala Leu Asn Leu
        195                 200                 205

Leu Glu Lys Asn Pro Val Val Leu Arg Ala Ala Lys Asn Gly Phe Lys
    210                 215                 220

Arg Cys Arg Glu Leu Thr Trp Glu Gln Asn Glu Asp Tyr Leu Tyr Ala
225                 230                 235                 240

Lys Leu Asp Gln Ser Arg Leu Leu Asp Thr Glu Gly Gly Arg Glu Gln
                245                 250                 255

Gly Met Lys Gln Phe Leu Asp Asp Lys Ser Ile Lys Pro Gly Leu Gln
            260                 265                 270

Ala Ile Lys Arg Lys Leu Ala Ala Leu Glu His His His His
        275                 280                 285

His
```

<210> SEQ ID NO 11
<211> LENGTH: 29
<212> TYPE: DNA
<213> ORGANISM: Artificial sequence
<220> FEATURE:
<223> OTHER INFORMATION: Primer

<400> SEQUENCE: 11 caactattttt tatgtatgca agagtcagc                29

```
<210> SEQ ID NO 12
<211> LENGTH: 26
<212> TYPE: DNA
<213> ORGANISM: Artificial sequence
<220> FEATURE:
<223> OTHER INFORMATION: Primer

<400> SEQUENCE: 12
ccatggttta tgagctgcaa acacac                                            26

<210> SEQ ID NO 13
<211> LENGTH: 1220
<212> TYPE: DNA
<213> ORGANISM: Arabidopsis thaliana

<400> SEQUENCE: 13
caactatttt tatgtatgca agagtcagca tatgtataat tgattcagaa tcgttttgac       60
gagttcggat gtagtagtag ccattattta atgtacatac taatcgtgaa tagtgatatg      120
atgaaacatt gtatcttatt gtataaatat ccataaacac atcatgaaag acactttctt      180
tcacggtctg aattaattat gatacaattc taatagaaaa cgaattaaat tacgttgaat      240
tgtatgaaat ctaattgaac aagccaacca cgacgacgac taacgttgcc tggattgact      300
cggtttaagt taaccactaa aaaaacggag ctgtcatgta acacgcggat cgagcaggtc      360
acagtcatga agccatcaaa gcaaaagaac taatccaagg gctgagatga ttaattagtt      420
taaaaattag ttaacacgag ggaaaaggct gtctgacagc caggtcacgt tatctttacc      480
tgtggtcgaa atgattcgtg tctgtcgatt ttaattattt ttttgaaagg ccgaaaataa      540
agttgtaaga gataaacccg cctatataaa ttcatatatt ttcctctccg ctttgaattg      600
tctcgttgtc ctcctcactt tcatcagccg ttttgaatct ccggcgactt gacagagaag      660
aacaaggaag aagactaaga gagaaagtaa gagataatcc aggagattca ttctccgttt      720
tgaatcttcc tcaatctcat cttcttccgc tctttctttc caaggtaata ggaactttct      780
ggatctactt tatttgctgg atctcgatct tgttttctca atttccttga gatctggaat      840
tcgtttaatt tggatctgtg aacctccact aaatcttttg gttttactag aatcgatcta      900
agttgaccga tcagttagct cgattatagc taccagaatt tggcttgacc ttgatggaga      960
gatccatgtt catgttacct gggaaatgat ttgtatatgt gaattgaaat ctgaactgtt     1020
gaagttagat tgaatctgaa cactgtcaat gttagattga atctgaacac tgtttaagtt     1080
agatgaagtt tgtgtataga ttcttcgaaa ctttaggatt tgtagtgtcg tacgttgaac     1140
agaaagctat ttctgattca atcagggttt atttgactgt attgaactct ttttgtgtgt     1200
ttgcagctca taaaccatgg                                                 1220

<210> SEQ ID NO 14
<211> LENGTH: 23
<212> TYPE: DNA
<213> ORGANISM: Artificial sequence
<220> FEATURE:
<223> OTHER INFORMATION: Primer

<400> SEQUENCE: 14
tcatgagcac atacgaaggt cgc                                              23

<210> SEQ ID NO 15
<211> LENGTH: 33
<212> TYPE: DNA
<213> ORGANISM: Artificial sequence
<220> FEATURE:
```

<223> OTHER INFORMATION: Primer

<400> SEQUENCE: 15
gagagcatcc atatgagcac atacgaaggt cgc                                33

<210> SEQ ID NO 16
<211> LENGTH: 33
<212> TYPE: DNA
<213> ORGANISM: Artificial sequence
<220> FEATURE:
<223> OTHER INFORMATION: Primer

<400> SEQUENCE: 16
cgcagcgtca agcttcagcg tttatacgct tgc                                33

<210> SEQ ID NO 17
<211> LENGTH: 2771
<212> TYPE: DNA
<213> ORGANISM: Arabidopsis thaliana

<400> SEQUENCE: 17

| | | | | | |
|---|---|---|---|---|---|
| gagcagaaaa | gagaagctat | aagacagctt | tgtatgtctc | ttgaccatta | cagagatggg | 60 |
| tacgacagac | tttggagagt | tgttgcagga | cataagagta | agagagtagt | ggtcttatca | 120 |
| acttgaagtg | taagaacaat | gagtcaatga | ctacgtgcag | acattggac | ataccgtgtg | 180 |
| ttctttttgga | ttgaaatgtt | gtttcgaagg | gctgttagtt | gatgttgaaa | ataggttgaa | 240 |
| gttgaataat | gcatgttgat | atagtaaata | tcaatggtaa | tattttctca | tttcccaaaa | 300 |
| ctcaaatgat | atcatttaac | tataaactaa | cgtaaactgt | tgacaataca | cttatggtta | 360 |
| aaaatttgga | gtcttgtttt | agtatacgta | tcaccaccgc | acggtttcaa | aaccacataa | 420 |
| ttgtaaatgt | tattggaaaa | tagaactcgc | aatacgtatt | gtattttggt | aaacatagct | 480 |
| ctaagcctct | aatatataag | ctctcaacaa | ttctggctaa | tggtcccaag | taagaaaagc | 540 |
| ccatgtattg | taaggtcatg | atctcaaaaa | cgagggtgag | gtggaatact | aacatgagga | 600 |
| gaaagtaagg | tgacaaattt | ttggggcaat | agtggtggat | atggtgggga | ggtaggtagc | 660 |
| atcatttctc | caagtcgctg | tctttcgtgg | taatggtagg | tgtgtctctc | tttatattat | 720 |
| ttattactac | tcattgtaaa | tttcttttttt | ctacaatttg | tttctgactc | caaaatacgt | 780 |
| cacaaatata | atactaggca | aataattatt | ttattataag | tcaatagagt | ggttgttgta | 840 |
| aaattgattt | tttgatattg | aaagagttca | tggacggatg | tgtatgcgcc | aaatggtaag | 900 |
| cccttgtact | gtgccgcgcg | tatattttaa | ccaccactag | ttgtttctct | ttttcaaaaa | 960 |
| acacaaaaaa | aaataatttt | gttttcttaa | cggcgtcaaa | tctgacggcg | tctcaatacg | 1020 |
| ttcaattttt | ttctttctttt | cacatggttt | ctcatagctt | tgcattgacc | ataggtaaag | 1080 |
| ggataaggat | aatggttttt | tctcttgttt | gttttatcct | tattattcaa | aaaggataaa | 1140 |
| aaaacagtga | tatttagatt | tctttgatta | aaaaagtcat | tgaaattcat | atttgatttt | 1200 |
| ttgctaaatg | tcaacacaga | gacacaaacg | taatgcactg | tcgccaatat | tcatggatca | 1260 |
| tgacaataaa | tatcactaga | ataattaaaa | atcagtagaa | tgcaaacaaa | gcattttcta | 1320 |
| agtaaaacag | tcttttatat | tcacgtaatt | ggaatttcct | ttttttttttt | ttgtcgtaat | 1380 |
| tggaattttcc | tttatcaaac | ccaaagtcca | aacaatcgg | caatgttttg | caaaatgttc | 1440 |
| aaaactattg | gcgggttggt | ctatccgaat | tgaagatctt | ttctccatat | gatagaccaa | 1500 |
| cgaaattcgg | catacgtgtt | ttttttttttg | ttttgaaaac | cctttaaaca | accttaattc | 1560 |
| aaaatactaa | tgtaactttta | ttgaacgtgc | atctaaaaat | tttgaacttt | gcttttgaga | 1620 |

```
aataatcaat gtaccaataa agaagatgta gtacatacat tataattaaa tacaaaaaag    1680
gaatcaccat atagtacatg gtagacaatg aaaaacttta aaacatatac aatcaataat    1740
actctttgtg cataactttt tttgtcgtct cgagtttata tttgagtact tatacaaact    1800
attagattac aaactgtgct cagatacatt aagttaatct tatatacaag agcactcgag    1860
tgttgtcctt aagttaatct taagatatct tgaggtaaat agaaatagtt gactcgtttt    1920
tatcttcttc ttttttttacc atgagcaaaa aagatgaaat aagttcaaaa cgtgacgaat    1980
ctatatgtta ctactagta tgtgtcaatc attaaatcgg gaaaacttca tcatttcagg    2040
agtattacaa aactcctaag agtgagaacg actacatagt acatattttg ataaaagact    2100
tgaaaacttg ctaaaacgaa tttgcgaaaa taatcata caagtgccag tgattttgat    2160
cgaattattc atagctttgt aggatgaact taattaaata atatctcaca aaagtattga    2220
cagtaaccta gtactatact atctatgtta gaatatgatt atgatataat ttatcccctc    2280
acttattcat atgattttg aagcaactac tttcgttttt ttaacatttt cttttgttgg    2340
ttattgttaa tgagcatatt tagtcgtttc ttaattccac tgaaatagaa atacaaaga    2400 gaactttagt taatagatat gaacataatc tcacatcctc ctcctacctt caccaaacac    2460
ttttacatac actttgtggt ctttctttac ctaccaccat caacaacaac accaagcccc    2520
actcacacac acgcaatcac gttaaattta acgccgttta ttatctcatc attcaccaac    2580
tcccacgtac ctaacgccgt ttacctttg ccgttggtcc tcatttctca aaccaaccaa    2640 acctctcccct cttataaaat cctctctccc ttctttattt cttcctcagc agcttcttct    2700
gctttcaatt actctcgccg acgatttct caccggaaaa aacaatatc attgcggata    2760 cacaaactat a                                                         2771
```

<210> SEQ ID NO 18
<211> LENGTH: 30
<212> TYPE: DNA
<213> ORGANISM: Artificial sequence
<220> FEATURE:
<223> OTHER INFORMATION: Primer

<400> SEQUENCE: 18
cctagaagtg ttgcagctga aggtactaac                                     30

<210> SEQ ID NO 19
<211> LENGTH: 30
<212> TYPE: DNA
<213> ORGANISM: Artificial sequence
<220> FEATURE:
<223> OTHER INFORMATION: Primer

<400> SEQUENCE: 19
gttcttgtgg cgccatggta aatagtaaat                                     30

<210> SEQ ID NO 20
<211> LENGTH: 2739
<212> TYPE: DNA
<213> ORGANISM: Arabidopsis thaliana

<400> SEQUENCE: 20
cctagaagtg ttgcagctga aggtactaac aagcaaacaa tcagcaaaat aaactttatt    60
tcttcaatat tttgattcat ttttctggtt aagaagacga agtaaggtgg ttacacagat   120
aatgacacta acaatagca cataagattt ggattatgag aggagttgag aagttatatg   180

```
atggaaactg aaaagtaaat cttttttgcag agctgtagaa tcaatcaaca tttgatgact    240
tggacttctt caccatgtgt gttggtgtgg accattgaat tgacggtttt gccattcacc    300
aacaacagca tgagtttttg agtcttcatg tttggtaaag gttaggctta ttaggagaca    360
cgggtaagag actagagaga gacattctcc aaacctttct tttgcatgtt ttgtaagaaa    420
catttccgaa aatgaaagaa atcttacaca acattcatat aatttgtttg aaatataaca    480
aaatgataat ttatactctc aagtaaaatg cctaaacttt tatcaattgg aaaagacatc    540
acacacaagc gtgaagcgta tcttattacc aaacccaact aagcatgggt ctcgatactt    600
gccataatta ctttaatcca ttctcttttt gagaaatgta taaaacatga ctttgcataa    660
atagtctttt actaattact atgtaaataa ttcctaagac tggtttcatg gtacatatta    720
tcgttttatc cttgttttaa gaatattcag atgtttggtc tatggaatat agtctattct    780
tcatgtttaa aactattatt tgataagaaa atatgtacta atatgttttt gcatacaaat    840
gttgatcagt tcgtagcatt tgaattaata cattctcaat cactttcaag cattattatg    900
taataaatga ttcatgtcga aaagtaatag tatcactgtc cattacattt ggcatatata    960
tttttttgtc aaagccttac atttggcata ttgacgaagc agttttgtat tcacttatat   1020
tttgacatcg ctttcacaaa aataaatagc tatatatgat tattatccat taattgtctc   1080
tttttctttg ctgacacaat tggttgtaaa tgcaatgcca atatccatag catttgtgtg   1140
gtgaatcttt ttctaagcct aatagtaaat aaatctcaat acaagaaccc atttacgaac   1200
aaatcaaacc aagttgtgat gggttagtac ttagtagccc gtttgaaatg tagaattttt   1260
gatgagattt tacgttttat atagattttt ctcagaaaac aaaaaattct tgcatcttgc   1320
attttggtca tttgtaaata ttttttttagt cttaaaaaag acccaaattc ttattaattt   1380
caaaattttc ggtctctaat acctccggtt ttaaaaaaaa acatatcagt tgaaggatga   1440
gtttggtgaa ggctatattg tccattgatt ttggagatat atgtattatg gtcatgatta   1500
ttacgatttt tatataaaag aatattaaaa atggtggggt tggtgaagaa atgaagattt   1560
atcgtcaaat atttcaattt ttacttggac tattgcttcg gttatatcgt caacatgggc   1620
ccactcttcc accaaagccc aatcaatata tctctcgcta tcttcaccaa cccactcttc   1680
ttctcttacc aaacccattt cctttatttc caacccctacc cctttatttc tcaagcttta   1740 cactttttagc ccataacttt cttttatttcc aaatggattt gactggtctc caaagttgaa   1800
ttaaatggtt gtagaaataa aataaaatta tacgggttca attgttcaat tgttcatata   1860
ccgttgacgt tcaattgttc atatacgggt tccgtggtcg ttggtaatat atatgtcttt   1920
tatggaacca aaatagacca aatcaacaac aaatgaagaa attgttagag tatgatacac   1980
tcatatatac ccaaatatag catatatta taatataact tttggctatg tcattttaca   2040
tgattttttt ggcttatcta ttaaaagtat catacaaact gttttactt cttttttttc   2100 ttagaatata tatgcccaaa atggaaaaga acatatgcca aggttgattt tatcgcttat   2160
atggtaaaaa ttggaaaaac atacaaatca ttactttatt taattaaatc atgtgaagaa   2220
acatattcaa ttacggtaat acgttatcaa aacattttttt tttacattaa ttgttacatt   2280 ttttttttttt gcaaatattc ttaaataacc attctttttt tatttactat aattaacata   2340
aaataaaata aaatataaca tttcaacaaa gaatttgct tatgaaaaat acaaatcca   2400 gttaattttt cagaaaaata caaatttgct tataaatata ttaccactag tttatgtgat   2460
tttaaaagaa agaaatgcag cttaccaaac gcaacgtgaa aatttgagaa acccatactc   2520
aaaaaagatt aaatgacaaa atcaccctca gcaaaatcat gaaacaacaa cactaacatt   2580
```

| | |
|---|---|
| ttcaccaacc ccaccgtcta ctccggtgaa ttgtctatat gaactcctcc gatacaactc | 2640 |
| ctgtttcctt caggccaaag cctaaaattc acacaaccaa aaaaaccaac ctttttttc | 2700 |
| cacctaaatc tttgaatatc acaatattta ctatttacc | 2739 |

<210> SEQ ID NO 21
<211> LENGTH: 32
<212> TYPE: DNA
<213> ORGANISM: Artificial sequence
<220> FEATURE:
<223> OTHER INFORMATION: Primer

<400> SEQUENCE: 21

| | |
|---|---|
| cgattttgat cgttgactag ctatacaatc cc | 32 |

<210> SEQ ID NO 22
<211> LENGTH: 33
<212> TYPE: DNA
<213> ORGANISM: Artificial sequence
<220> FEATURE:
<223> OTHER INFORMATION: Primer

<400> SEQUENCE: 22

| | |
|---|---|
| gctattagaa accacgccat ggagttttgc ttc | 33 |

<210> SEQ ID NO 23
<211> LENGTH: 2705
<212> TYPE: DNA
<213> ORGANISM: Arabidopsis thaliana

<400> SEQUENCE: 23

| | |
|---|---|
| cgattttgat cgttgactag ctatacaatc ccgtgtaatc actacatttg gtattggtac | 60 |
| gcatctgtta cataccattt ttacggcggt tttagtgaac tatattataa aaaaaaatcg | 120 |
| taagttttt tgtgtgtgtg ttaacaatgt actcactact cactgttcca tatttttgat | 180 |
| gtacgtatat cgaaaacatt ctgccaacaa atgcaaacat aacaaaagtc aaaaacaata | 240 |
| acataaccgg gaattaaacc aaaatgtaat tgcttttat tagtgtcagg ccttctgctt | 300 |
| aaaaatattc tcggcccaga gcccattaac acctatctca attcatattg aagaaaatga | 360 |
| ctatattact tgacaaaaac tttagtcaga aaaatatgga atctctttcg gtactgctaa | 420 |
| gtgctaacct taaatagtat agaattctta gttcattctc aaaaacatag ctatatgtag | 480 |
| attataaaag ttcgatatta tttcctgcaa agatgttat aatgttacaa cttacaagaa | 540 |
| aatgatgtat atgtagattt tataaactgg taccgtaatt cataaaagat ggtggtgggt | 600 |
| atgtatcagt aacggaactt acatatgcgt gtgtattact atgtctatat ggtgtattcc | 660 |
| tttgtgtgga acaatgcacg tcagagttgt ttattttctt atagaattta aggaatcaat | 720 |
| tattggattt ctcaaggtga aagtggactt ctttgcacgc aaggtctagt tgccgacttg | 780 |
| ccgttgcatg taacatgatt gttgaaataa agtgaattga gagaagtttg ccagacatt | 840 |
| ttaaatttaa cccaaaaaaa gtagggccta acacaaaata taacctctct ttgttcaaag | 900 |
| gaaataacac ctacgtctta taattgaacc aaacattgaa tcattgaact cacctataat | 960 |
| aattataata acacgaattc acaagacacc taaagaaaa agttcacaaa acaaataaa | 1020 |
| aatttacctc tcaccaaaca cactcaccta cccgtctggt cccactgacc ccaacataca | 1080 |
| acaccgactc tctcccacac caattttttt ttttggcgtt ttaaaacaaa taaactatct | 1140 |
| atttttttt cttaccaact gattaattcg tgaataatct attatcttct tctttttttt | 1200 |

```
gtgacggatg attagtgcgt ggggaaatca aaatttacaa aatttgggat gattccgatt    1260
tttgccattc gattaatttt ggttaaaaga tatactattg attcaccaag ttttcagatg    1320
agtctaaaag ataatatcat ttcactagtc acttaaaaaa agggttaaaa gaacatcaat    1380
aatatcactg gtttccttag gtgacccaaa aaaagaagaa aaagtcacta gtttcttttt    1440
ggaaatttta ctgggcatat agacgaagtt gtaatgagtg agtttaaatt tatctatggc    1500
acgcagctac gtctggtcgg actataccaa gttaccaact ctctctactt catgtgattg    1560
ccaataaaag gtgacgtctc tctctctctc accaacccca aaccactttc cccactcgct    1620
ctcaaaacgc ttgccaccca atctatggc ttacggggac atgtattaac atatatcact    1680
gagtgaaaag aagggtttat taccgttgga ccagtgatca acgtgtttt ataaaaattt    1740 ggaattgaaa acatgatttg acattttaa tgatggcagc agacgaaacc aacaacacta    1800
agtttaacgt tcgtggagta tacttttcta ttttcgaaga agacatataa ctaagctgat    1860
tgttattctt catagatttc ttttcactgc gaataaaagt ttgtgaacat gtcaccgttt    1920
gaacactcaa caatcataag cgttttacct ttgtggggtg gagaagatga caatgagaaa    1980
gtcgtcgtac atataattta agaaaatact attctgactc tggaacgtgt aaataattat    2040
ctaaacagat tgcgaatgtt ctctactttt tttttgttta cattaaaaat gcaaatttta    2100
taacatttta catcgcgtaa atattcctgt tttatctata attaatgaaa gctactgaaa    2160 aaaacatcc aggtcaggta catgtatttc acctcaactt agtaaataac cagtaaaatc    2220
caaagtaatt acctttctc tggaaatttt cctcagtagt ttataccagt caaattaaaa    2280
cctcaaatct gaatgttgaa aatttgatat ccaagaaatt ttctcattgg aataaaagtt    2340
caatctgaaa atagatattt ctctacctct gttttttttt ttctccacca actttcccct    2400
acttatcact atcaataatc gacattatcc atcttttta ttgtcttgaa ctttgcaatt    2460
taattgcata ctagtttctt gttttacata aaagaagttt ggtggtagca aatatatatg    2520
tctgaaattg attatttaaa aacaaaaaaa gataaatcgg ttcaccaacc ccctccctaa    2580
tataaatcaa agtctccacc acatatatct agaagaattc tacaagtgaa ttcgatttac    2640 acttttttt gtccttttt attaataaat cactgacccg aaaataaaaa tagaagcaaa    2700
actcc                                                                2705
```

<210> SEQ ID NO 24
<211> LENGTH: 32
<212> TYPE: DNA
<213> ORGANISM: Artificial sequence
<220> FEATURE:
<223> OTHER INFORMATION: Primer

<400> SEQUENCE: 24
cagtttatct gggtaagttc ttgattttaa gc                                  32

<210> SEQ ID NO 25
<211> LENGTH: 33
<212> TYPE: DNA
<213> ORGANISM: Artificial sequence
<220> FEATURE:
<223> OTHER INFORMATION: Primer

<400> SEQUENCE: 25
gaccggcgct agctttcatg aggacggccg gag                                 33

<210> SEQ ID NO 26
<211> LENGTH: 2134

<210> SEQ ID NO 26
<211> LENGTH: 2134
<212> TYPE: DNA
<213> ORGANISM: Arabidopsis thaliana

<400> SEQUENCE: 26

| | | | | | |
|---|---|---|---|---|---|
| tctagatatg | gaacgaatac | agtgtttcat | tattttttt | gatgtataca | taataattgt | 60 |
| catacaatac | tattaatcta | atctaattaa | tatttccttt | aaaatggttc | caaaaggcat | 120 |
| caccaacatg | gaaggtggca | agctaggatc | ggaagagtcg | ccgtaacaa | agacctctac | 180 |
| ttgggaactt | tcggtacatt | ttccaataaa | atctatatac | tataagatat | taaatataca | 240 |
| caaatatatc | taagtgaatc | atacaaatta | tgtaggcaca | caggaagagg | ctgctgaggc | 300 |
| ttatgacatt | gcagccatta | aattcagagg | attaagcgca | gtgactaact | tcgacatgaa | 360 |
| cagatacaat | gttaaagcaa | tcctcgagag | cccgagtcta | cctattggta | gttctgcgaa | 420 |
| acgtctcaag | gacgttaata | atccggttcc | agctatgatg | attagtaata | acgtttcaga | 480 |
| gagtgcaaat | aatgttagcg | gttggcaaaa | cactgcgttt | cagcatcatc | agggaatgga | 540 |
| tttgagctta | ttgcagcaac | agcaggagag | gtacgttggt | tattacaatg | gaggaaactt | 600 |
| gtctaccgag | agtactaggg | tttgtttcaa | acaagaggag | gaacaacaac | acttcttgag | 660 |
| aaactcgccg | agtcacatga | ctaatgttga | tcatcatagc | tcgacctctg | atgattctgt | 720 |
| taccgtttgt | ggaaatgttg | ttagttatgg | tggttatcaa | ggattcgcaa | tccctgttgg | 780 |
| aacatcggtt | aattacgatc | cctttactgc | tgctgagatt | gcttacaacg | caagaaatca | 840 |
| ttattactat | gctcagcatc | agcaacaaca | gcagattcag | cagtcgccgg | gaggagattt | 900 |
| tccggtggcg | atttcgaata | accatagctc | taacatgtac | tttcacgggg | aaggtggtgg | 960 |
| agaaggggct | ccaacgtttt | cagtttggaa | cgacacttag | aaaaataagt | aaaagatctt | 1020 |
| ttagttgttt | gctttgtatg | ttgcgaacag | tttgattctg | tttttctttt | tcctttttt | 1080 |
| gggtaatttt | cttataactt | ttttcatagt | ttcgattatt | tggataaaat | tttcagattg | 1140 |
| aggatcattt | tatttattta | ttagtgtagt | ctaatttagt | tgtataacta | taaaattgtt | 1200 |
| gtttgtttcc | gaatcataag | tttttttttt | ttttggtttt | gtattgatag | gtgcaagaga | 1260 |
| ctcaaaattc | tggtttcgat | gttaacagaa | ttcaagtagc | tgcccacttg | attcgatttg | 1320 |
| ttttgtattt | ggaaacaacc | atggctggtc | aaggcccagc | ccgttgtgct | tctgaacctg | 1380 |
| cctagtccca | tggactagat | ctttatccgc | agactccaaa | agaaaaagga | ttggcgcaga | 1440 |
| ggaattgtca | tggaaacaga | atgaacaaga | aagggtgaag | aagatcaaag | gcatatatga | 1500 |
| tctttacatt | ctctttagct | tatgtatgca | gaaaattcac | ctaattaagg | acagggaacg | 1560 |
| taacttggct | tgcactcctc | tcaccaaacc | ttaccccta | actaattta | attcaaaatt | 1620 |
| actagtattt | tggccgatca | ctttatataa | taagatacca | gatttattat | atttacgaat | 1680 |
| tatcagcatg | catatactgt | atatagtttt | tttttgtta | aagggtaaaa | taataggatc | 1740 |
| cttttgaata | aaatgaacat | atataattag | tataatgaaa | acagaaggaa | atgagattag | 1800 |
| gacagtaagt | aaaatgagag | agacctgcaa | aggataaaaa | agagaagctt | aaggaaaccg | 1860 |
| cgacgatgaa | agaaagacat | gtcatcagct | gatggatgtg | agtgatgagt | ttgttgcagt | 1920 |
| tgtgtagaaa | ttttactaa | aacagttgtt | tttacaaaaa | agaaataata | taaaacgaaa | 1980 |
| gcttagcttg | aaggcaatgg | agactctaca | acaaactatg | taccatacag | agagagaaac | 2040 |
| taaaagcttt | tcacacataa | aaaccaaact | tattcgtctc | tcattgatca | ccgtttgtt | 2100 |
| ctctcaagat | cgctgctaat | ctccggccgt | ccct | | | 2134 |

<210> SEQ ID NO 27

<211> LENGTH: 3552
<212> TYPE: DNA
<213> ORGANISM: artificial sequence
<220> FEATURE:
<223> OTHER INFORMATION: Chimeric gene. C4H promoter operably linked to HCHL coding sequence.

<400> SEQUENCE: 27

| | | | | | |
|---|---|---|---|---|---|
| cagagatggg | tacgacagac | tttggagagt | tgttgcagga | cataagagta | agagagtagt | 60 |
| ggtcttatca | acttgaagtg | taagaacaat | gagtcaatga | ctacgtgcag | gacattggac | 120 |
| ataccgtgtg | ttcttttgga | ttgaaatgtt | gtttcgaagg | gctgttagtt | gatgttgaaa | 180 |
| ataggttgaa | gttgaataat | gcatgttgat | atagtaaata | tcaatggtaa | tattttctca | 240 |
| tttcccaaaa | ctcaaatgat | atcatttaac | tataaactaa | cgtaaactgt | tgacaataca | 300 |
| cttatggtta | aaaatttgga | gtcttgtttt | agtatacgta | tcaccaccgc | acggtttcaa | 360 |
| aaccacataa | ttgtaaatgt | tattggaaaa | tagaactcgc | aatacgtatt | gtattttggt | 420 |
| aaacatagct | ctaagcctct | aatatataag | ctctcaacaa | ttctggctaa | tggtcccaag | 480 |
| taagaaaagc | ccatgtattg | taaggtcatg | atctcaaaaa | cgagggtgag | gtggaatact | 540 |
| aacatgagga | gaaagtaagg | tgacaaattt | ttggggcaat | agtggtggat | atggtgggga | 600 |
| ggtaggtagc | atcatttctc | caagtcgctg | tctttcgtgg | taatggtagg | tgtgtctctc | 660 |
| tttatattat | ttattactac | tcattgtaaa | tttcttttt | ctacaatttg | tttctgactc | 720 |
| caaaatacgt | cacaaatata | atactaggca | aataattatt | ttattataag | tcaatagagt | 780 |
| ggttgttgta | aaattgattt | tttgatattg | aaagagttca | tggacggatg | tgtatgcgcc | 840 |
| aaatggtaag | cccttgtact | gtgccgcgcg | tatattttaa | ccaccactag | ttgtttctct | 900 |
| ttttcaaaaa | acacaaaaaa | aaaataattt | gttttcttaa | cggcgtcaaa | tctgacggcg | 960 |
| tctcaatacg | ttcaattttt | ttctttcttt | cacatggttt | ctcatagctt | gcattgacc | 1020 |
| ataggtaaag | ggataaggat | aatggttttt | tctcttgttt | gttttatcct | tattattcaa | 1080 |
| aaaggataaa | aaaacagtga | tatttagatt | tctttgatta | aaaaagtcat | tgaaattcat | 1140 |
| atttgatttt | ttgctaaatg | tcaacacaga | gacacaaacg | taatgcactg | tcgccaaatt | 1200 |
| tcatggatca | tgacaataaa | tatcactaga | ataattaaaa | atcagtagaa | tgcaaacaaa | 1260 |
| gcattttcta | agtaaaacag | tcttttatat | tcacgtaatt | ggaatttcct | ttttttttt | 1320 |
| ttgtcgtaat | tggaatttcc | tttatcaaac | ccaaagtcca | aaacaatcgg | caatgttttg | 1380 |
| caaaatgttc | aaaactattg | gcgggttggt | ctatccgaat | tgaagatctt | ttctccatat | 1440 |
| gatagaccaa | cgaaattcgg | catacgtgtt | ttttttttg | ttttgaaaac | cctttaaaca | 1500 |
| accttaattc | aaaatactaa | tgtaactttta | ttgaacgtgc | atctaaaaat | tttgaacttt | 1560 |
| gcttttgaga | ataatcaat | gtaccaataa | agaagatgta | gtacatacat | tataattaaa | 1620 |
| tacaaaaaag | gaatcaccat | atagtacatg | gtagacaatg | aaaaacttta | aaacatatac | 1680 |
| aatcaataat | actctttgtg | cataactttt | tttgtcgtct | cgagtttata | tttgagtact | 1740 |
| tatacaaact | attagattac | aaactgtgct | cagatacatt | aagttaatct | tatatacaag | 1800 |
| agcactcgag | tgttgtcctt | aagttaatct | taagatatct | tgaggtaaat | agaaatagtt | 1860 |
| gactcgtttt | tatcttcttc | ttttttttacc | atgagcaaaa | aagatgaaat | aagttcaaaa | 1920 |
| cgtgacgaat | ctatatgtta | ctacttagta | tgtgtcaatc | attaaatcgg | gaaaacttca | 1980 |
| tcatttcagg | agtattacaa | aactcctaag | agtgagaacg | actacatagt | acatattttg | 2040 |
| ataaaagact | tgaaaacttg | ctaaaacgaa | tttgcgaaaa | tataatcata | caagtgccag | 2100 |

```
tgattttgat cgaattattc atagctttgt aggatgaact taattaaata atatctcaca    2160
aaagtattga cagtaaccta gtactatact atctatgtta gaatatgatt atgatataat    2220 ttatccctc acttattcat atgattttg aagcaactac tttcgttttt ttaacatttt     2280
cttttgttgg ttattgttaa tgagcatatt tagtcgtttc ttaattccac tgaaatagaa    2340
aatacaaaga gaactttagt taatagatat gaacataatc tcacatcctc ctcctacctt    2400
caccaaacac ttttacatac actttgtggt ctttctttac ctaccaccat caacaacaac    2460
accaagcccc actcacacac acgcaatcac gttaaattta acgccgttta ttatctcatc    2520
attcaccaac tcccacgtac ctaacgccgt ttacctttg ccgttggtcc tcatttctca    2580
aaccaaccaa acctctcccct cttataaaat cctctctccc ttctttattt cttcctcagc    2640
agcttcttct gctttcaatt actctcgccg acgattttct caccggaaaa aaacaatatc    2700
attgcggata cacaaactac catgagcaca tacgaaggtc gctgggctac cgtgaaggtc    2760
gaactggagt cggcattgc ctgggtcacc ctcaaccggc cggaaaagcg caatgcaatg    2820
agccccacgc tgaaccggga atggtcgac gtgctggaaa ccctggaaca ggacggcgaa    2880
gccggggtgc tcgtgctgac cggcgcgggt gaatcgtgga cggcaggcat ggacctgaag    2940
gaatacttcc gtgaggtgga cgccggcccg gaaatcctcc aggaaaaaat ccgccgcgat    3000
gcctcgcaat ggcaatggag gctgctgcgc atgtacgcca agccgactat cgccatggtc    3060
aacggctggt gctttggcgg cggcttcagc ccgctggtgg cctgcgacct ggccatctgt    3120
gccgacgagg ccaccttggg cctgtcggaa atcaactggg gcatcccacc gggcaacctg    3180
gtcagcaaag ccatggccga taccgttggc caccgccagt cgctgtacta catcatgacc    3240
ggcaagactt tcggcgggcc taaagctgcc gagatggggc tggttaacga gagcgtgccg    3300
ctggcgcaat tgcgcgacgt caccccgcgaa ctggcgctca acctgctgga aaagaacccg    3360
gtggtgctgc gtgcggccaa gaacggtttc aagcgctgcc gcgaactgac ctgggagcag    3420
aacgaagact acctgtacgc caagctcgac cagtcccgtc tgctggacac cgaaggtggg    3480
cgcgagcagg gcatgaagca gttcctcgac gacaagagca tcaagccagg cctgcaagcc    3540
atcaagcgct ga                                                       3552

<210> SEQ ID NO 28
<211> LENGTH: 3570
<212> TYPE: DNA
<213> ORGANISM: artificial sequence
<220> FEATURE:
<223> OTHER INFORMATION: Chimeric gene.  4CL1 promoter operably linked
      to HCHL coding sequence.

<400> SEQUENCE: 28
cctagaagtg ttgcagctga aggtactaac aagcaaacaa tcagcaaaat aaactttatt      60
tcttcaatat tttgattcat ttttctggtt aagaagacga agtaaggtgg ttacacagat     120
aatgacacta acaatagca cataagattt ggattatgag aggagttgag aagttatatg     180
atggaaactg aaaagtaaat cttttttgcag agctgtagaa tcaatcaaca tttgatgact    240
tggacttctt caccatgtgt gttggtgtgg accattgaat tgacggtttt gccattcacc     300
aacaacagca tgagttttg agtcttcatg tttggtaaag gttaggctta ttaggagaca     360
cgggtaagag actagagaga gacattctcc aaacctttct tttgcatgtt ttgtaagaaa     420
catttccgaa aatgaaagaa atcttacaca acattcatat aatttgtttg aaatataaca     480
aaatgataat ttatactctc aagtaaaatg cctaaacttt tatcaattgg aaaagacatc     540
```

```
acacacaagc gtgaagcgta tcttattacc aaacccaact aagcatgggt ctcgatactt      600
gccataatta ctttaatcca ttctcttttt gagaaatgta taaaacatga ctttgcataa      660
atagtctttt actaattact atgtaaataa ttcctaagac tggtttcatg gtacatatta      720
tcgttttatc cttgttttaa gaatattcag atgtttggtc tatggaatat agtctattct      780
tcatgtttaa aactattatt tgataagaaa atatgtacta atatgttttt gcatacaaat      840
gttgatcagt tcgtagcatt tgaattaata cattctcaat cactttcaag cattattatg      900
taataaatga ttcatgtcga aaagtaatag tatcactgtc cattacattt ggcatatata      960 ttttttttgtc aaagccttac atttggcata ttgacgaagc agttttgtat tcacttatat     1020
tttgacatcg ctttcacaaa aataaatagc tatatatgat tattatccat taattgtctc     1080
ttttcttttg ctgacacaat tggttgtaaa tgcaatgcca atatccatag catttgtgtg     1140
gtgaatcttt ttctaagcct aatagtaaat aaatctcaat acaagaaccc atttacgaac     1200
aaatcaaacc aagttgtgat gggttagtac ttagtagccc gtttgaaatg tagaattttt     1260
gatgagattt tacgttttat atagattttt ctcagaaaac aaaaaattct tgcatcttgc     1320
attttggtca tttgtaaata ttttttttagt cttaaaaaag acccaaattc ttattaatttt    1380 caaaattttc ggtctctaat acctccggtt ttaaaaaaaa acatatcagt tgaaggatga     1440
gtttggtgaa ggctatattg tccattgatt ttggagatat atgtattatg gtcatgatta     1500
ttacgatttt tatataaaag aatattaaaa atggtggggt tggtgaagaa atgaagattt     1560
atcgtcaaat atttcaattt ttacttggac tattgcttcg gttatatcgt caacatgggc     1620
ccactcttcc accaaagccc aatcaatata tctctcgcta tcttcaccaa cccactcttc     1680
ttctcttacc aaacccatttt cctttatttc caacccctacc cctttatttc tcaagcttta    1740
cacttttagc ccataacttt cttttttatcc aaatggattt gactggtctc caaagttgaa    1800
ttaaatggtt gtagaaataa aataaaatta tacgggttca attgttcaat tgttcatata     1860
ccgttgacgt tcaattgttc atatacgggt tccgtggtcg ttggtaatat atatgtcttt     1920
tatggaacca aaatagacca aatcaacaac aaatgaagaa attgttagag tatgatacac     1980
tcatatatac ccaaatatag catatattta taatataact tttggctatg tcattttaca     2040 tgatttttttt ggcttatcta ttaaaagtat catacaaact gtttttactt cttttttttttc   2100 ttagaatata tatgcccaaa atggaaagaa acatatgcca aggttgattt tatcgcttat     2160
atggtaaaaa ttgaaaaaac atacaaatca ttactttatt taattaaatc atgtgaagaa     2220
acatattcaa ttacggtaat acgttatcaa aacattttttt tttacattaa ttgttacatt    2280
tttttttttt gcaaatattc ttaaataacc attcttttttt tatttactat aattaacata    2340
aaaataaata aaatataaca tttcaacaaa gaaatttgct tatgaaaaat acaaaatcca     2400
gttaattttt cagaaaaata caaatttgct tataaatata ttaccactag tttatgtgat     2460
tttaaaagaa agaaatgcag cttaccaaac gcaacgtgaa aatttgagaa acccatactc     2520
aaaaaagatt aaatgacaaa atcaccctca gcaaaatcat gaaacaacaa cactaacatt     2580
ttcaccaacc ccaccgtcta ctccggtgaa ttgtctatat gaactcctcc gatacaactc     2640
ctgtttcctt caggccaaag cctaaaattc acacaaccaa aaaaaccaac ctttttttttc    2700 cacctaaatc tttgaatatc acaatatttta ctatttacca tgagcacata cgaaggtcgc    2760
tgggctaccg tgaaggtcga actggagtcg ggcattgcct gggtcaccct caaccggccg     2820
gaaaagcgca atgcaatgag ccccacgctg aaccggaaaa tggtcgacgt gctgaaaacc     2880
ctggaacagg acggcgaagc cggggtgctc gtgctgaccg gcgcgggtga atcgtggacg     2940
```

```
gcaggcatgg acctgaagga atacttccgt gaggtggacg ccggcccgga atcctccag   3000 gaaaaaatcc gccgcgatgc ctcgcaatgg caatggaggc tgctgcgcat gtacgccaag   3060
ccgactatcg ccatggtcaa cggctggtgc tttggcggcg gcttcagccc gctggtggcc   3120
tgcgacctgg ccatctgtgc cgacgaggcc acctttggcc tgtcggaaat caactggggc   3180
atcccaccgg gcaacctggt cagcaaagcc atggccgata ccgttggcca ccgccagtcg   3240
ctgtactaca tcatgaccgg caagactttc ggcgggccta agctgccga gatggggctg   3300 gttaacgaga gcgtgccgct ggcgcaattg cgcgacgtca cccgcgaact ggcgctcaac   3360
ctgctggaaa agaacccggt ggtgctgcgt gcggccaaga acggtttcaa gcgctgccgc   3420
gaactgaccc tgggagcagaa cgaagactac ctgtacgcca agctcgacca gtcccgtctg   3480
ctggacaccg aaggtgggcg cgagcagggc atgaagcagt cctcgacga caagagcatc   3540 aagccaggcc tgcaagccat caagcgctga                                    3570

<210> SEQ ID NO 29
<211> LENGTH: 3536
<212> TYPE: DNA
<213> ORGANISM: artificial sequence
<220> FEATURE:
<223> OTHER INFORMATION: Chimeric gene.  C3H promoter operably linked to
      HCHL coding sequence.

<400> SEQUENCE: 29
cgattttgat cgttgactag ctatacaatc ccgtgtaatc actacatttg gtattggtac    60
gcatctgtta cataccattt ttacggcggt tttagtgaac tatattataa aaaaaaatcg   120 taagttttt tgtgtgtgtg ttaacaatgt actcactact cactgttcca tattttgat    180 gtacgtatat cgaaaacatt ctgccaacaa atgcaaacat aacaaaagtc aaaaacaata   240
acataaccgg gaattaaacc aaaatgtaat tgcttttat tagtgtcagg ccttctgctt   300
aaaaatattc tcggcccaga gcccattaac acctatctca attcatattg aagaaaatga   360
ctatattact tgacaaaaac tttagtcaga aaaatatgga atctctttcg gtactgctaa   420
gtgctaacct taaatagtat agaattctta gttcattctc aaaaacatag ctatatgtag   480
attataaaag ttcgatatta tttcctgcaa aagatgttat aatgttacaa cttacaagaa   540
aatgatgtat atgtagattt tataaactgg taccgtaatt cataaaagat ggtggtgggt   600
atgtatcagt aacggaactt acatatgcgt gtgtattact atgtctatat ggtgtattcc   660
tttgtgtgga acaatgcacg tcagagttgt ttattttctt atagaattta aggaatcaat   720
tattggattt ctcaaggtga agtggactt cttttgcacgc aaggtctagt tgccgacttg   780
ccgttgcatg taacatgatt gttgaaataa agtgaattga gagaagtttg ccagacatt   840 ttaaattta cccaaaaaaa gtagggccta acacaaaata taacctctct ttgttcaaag   900
gaaataacac ctacgtctta taattgaacc aaacattgaa tcattgaact cacctataat   960
aattataata acacgaattc acaagacacc taaagaaaaa agttcacaaa acaaataaa   1020 aatttacctc tcaccaaaca cactcaccta cccgtctggt cccactgacc caacataca   1080 acaccgactc tctcccacac caattttttt ttttggcgtt ttaaaacaaa taaactatct   1140
attttttttt cttaccaact gattaattcg tgaataatct attatcttct tctttttttt   1200
gtgacggatg attagtgcgt ggggaaatca aaatttacaa aatttgggat gattccgatt   1260
tttgccattc gattaatttt ggttaaaaga tatactattc attcaccaag ttttcagatg   1320
agtctaaaag ataatatcat ttcactagtc acttaaaaaa agggttaaaa gaacatcaat   1380
```

```
aatatcactg gtttccttag gtgacccaaa aaaagaagaa aaagtcacta gtttcttttt      1440
ggaaatttta ctgggcatat agacgaagtt gtaatgagtg agtttaaatt tatctatggc      1500
acgcagctac gtctggtcgg actataccaa gttaccaact ctctctactt catgtgattg      1560
ccaataaaag gtgacgtctc tctctctctc accaacccca aaccactttc cccactcgct      1620
ctcaaaacgc ttgccaccca aatctatggc ttacggggac atgtattaac atatatcact      1680
gagtgaaaag aagggtttat taccgttgga ccagtgatca aacgtgtttt ataaaaattt      1740
ggaattgaaa acatgatttg acatttttaa tgatggcagc agacgaaacc aacaacacta      1800
agtttaacgt tcgtggagta tacttttcta ttttcgaaga agacatataa ctaagctgat      1860
tgttattctt catagatttc ttttcactgc gaataaaagt ttgtgaacat gtcaccgttt      1920
gaacactcaa caatcataag cgttttacct ttgtggggtg gagaagatga caatgagaaa      1980
gtcgtcgtac atataattta agaaaatact attctgactc tggaacgtgt aaataaattat     2040 ctaaacagat tgcgaatgtt ctctactttt tttttgttta cattaaaaat gcaaatttta      2100
taacatttta catcgcgtaa atattcctgt tttatctata attaatgaaa gctactgaaa      2160
aaaaacatcc aggtcaggta catgtatttc acctcaactt agtaaataac cagtaaaatc      2220
caaagtaatt accttttctc tggaaatttt cctcagtagt ttataccagt caaattaaaa      2280
cctcaaatct gaatgttgaa aatttgatat ccaagaaatt ttctcattgg aataaaagtt      2340
caatctgaaa atagatattt ctctacctct gttttttttt ttctccacca actttcccct      2400
acttatcact atcaataatc gacattatcc atcttttttta ttgtcttgaa ctttgcaatt     2460
taattgcata ctagtttctt gttttacata aaagaagttt ggtggtagca aatatatatg      2520
tctgaaattg attatttaaa aacaaaaaaa gataaatcgg ttcaccaacc ccctccctaa      2580
tataaatcaa agtctccacc acatatatct agaagaattc tacaagtgaa ttcgatttac      2640 acttttttt gtccttttt attaataaat cactgacccg aaaataaaaa tagaagcaaa        2700
actccatgag cacatacgaa ggtcgctggg ctaccgtgaa ggtcgaactg gagtcgggca      2760
ttgcctgggt caccctcaac cggccggaaa agcgcaatgc aatgagcccc acgctgaacc      2820
gggaaatggt cgacgtgctg gaaaccctgg aacaggacgg cgaagccggg gtgctcgtgc      2880
tgaccggcgc gggtgaatcg tggacggcag gcatggacct gaaggaatac ttccgtgagg      2940
tggacgccgg cccggaaatc ctccaggaaa aaatccgccg cgatgcctcg caatggcaat      3000
ggaggctgct gcgcatgtac gccaagccga ctatcgccat ggtcaacggc tggtgctttg      3060
gcggcggctt cagcccgctg gtggcctgcg acctggccat ctgtgccgac gaggccacct      3120
ttggcctgtc ggaaatcaac tggggcatcc caccgggcaa cctggtcagc aaagccatgg      3180
ccgataccgt tggccaccgc cagtcgctgt actacatcat gaccggcaag actttcggcg      3240
ggcctaaagc tgccgagatg gggctggtta acgagagcgt gccgctggcg caattgcgcg      3300
acgtcacccg cgaactggcg ctcaacctgc tggaaaagaa cccggtggtg ctgcgtgcgg      3360
ccaagaacgg tttcaagcgc tgccgcgaac tgacctggga gcagaacgaa gactacctgt      3420
acgccaagct cgaccagtcc cgtctgctgg acaccgaagg tgggcgcgag cagggcatga      3480
agcagttcct cgacgacaag agcatcaagc caggcctgca agccatcaag cgctga         3536
```

<210> SEQ ID NO 30
<211> LENGTH: 2965
<212> TYPE: DNA
<213> ORGANISM: artificial sequence
<220> FEATURE:

<223> OTHER INFORMATION: Chimeric gene. AtCesA7(IRX3) promoter operably linked to HCHL coding sequence.

<400> SEQUENCE: 30

| | | | | | |
|---|---|---|---|---|---|
| tctagatatg | gaacgaatac | agtgtttcat | tattttttt | gatgtataca | taataattgt | 60 |
| catacaatac | tattaatcta | atctaattaa | tatttccttt | aaaatggttc | caaaaggcat | 120 |
| caccaacatg | gaaggtggca | agctaggatc | ggaagagtcg | ccgtaacaa | agacctctac | 180 |
| ttgggaactt | tcggtacatt | ttccaataaa | atctatatac | tataagatat | taaatataca | 240 |
| caaatatatc | taagtgaatc | atacaaatta | tgtaggcaca | caggaagagg | ctgctgaggc | 300 |
| ttatgacatt | gcagccatta | aattcagagg | attaagcgca | gtgactaact | tcgacatgaa | 360 |
| cagatacaat | gttaaagcaa | tcctcgagag | cccgagtcta | cctattggta | gttctgcgaa | 420 |
| acgtctcaag | gacgttaata | atccggttcc | agctatgatg | attagtaata | acgtttcaga | 480 |
| gagtgcaaat | aatgttagcg | gttggcaaaa | cactgcgttt | cagcatcatc | agggaatgga | 540 |
| tttgagctta | ttgcagcaac | agcaggagag | gtacgttggt | tattacaatg | gaggaaactt | 600 |
| gtctaccgag | agtactaggg | tttgtttcaa | caagaggag | gaacaacaac | acttcttgag | 660 |
| aaactcgccg | agtcacatga | ctaatgttga | tcatcatagc | tcgacctctg | atgattctgt | 720 |
| taccgtttgt | ggaaatgttg | ttagttatgt | ggttatcaa | ggattcgcaa | tccctgttgg | 780 |
| aacatcggtt | aattacgatc | cctttactgc | tgctgagatt | gcttacaacg | caagaaatca | 840 |
| ttattactat | gctcagcatc | agcaacaaca | gcagattcag | cagtcgccgg | gaggagattt | 900 |
| tccggtggcg | atttcgaata | accatagctc | taacatgtac | tttcacgggg | aagtggtgg | 960 |
| agaagggct | ccaacgtttt | cagtttggaa | cgacacttag | aaaaataagt | aaagatctt | 1020 |
| ttagttgttt | gctttgtatg | ttgcgaacag | tttgattctg | tttttctttt | tccttttttt | 1080 |
| gggtaatttt | cttataactt | ttttcatagt | ttcgattatt | tggataaat | tttcagattg | 1140 |
| aggatcattt | tatttattta | ttagtgtagt | ctaatttagt | tgtataacta | taaaattgtt | 1200 |
| gtttgttttcc | gaatcataag | tttttttttt | ttttggtttt | gtattgatag | gtgcaagaga | 1260 |
| ctcaaaattc | tggtttcgat | gttaacagaa | ttcaagtagc | tgcccacttg | attcgatttg | 1320 |
| ttttgtattt | ggaaacaacc | atggctggtc | aaggcccagc | ccgttgtgct | tctgaacctg | 1380 |
| cctagtccca | tggactagat | ctttatccgc | agactccaaa | agaaaaagga | ttggcgcaga | 1440 |
| ggaattgtca | tggaaacaga | atgaacaaga | aagggtgaag | aagatcaaag | gcatatatga | 1500 |
| tctttacatt | ctcttagct | tatgtatgca | gaaaattcac | ctaattaagg | acagggaacg | 1560 |
| taacttggct | tgcactcctc | tcaccaaacc | ttacccccta | actaattta | attcaaaatt | 1620 |
| actagtattt | tggccgatca | ctttatataa | taagatacca | gatttattat | atttacgaat | 1680 |
| tatcagcatg | catatactgt | atatagtttt | tttttgtta | aagggtaaaa | taataggatc | 1740 |
| cttttgaata | aaatgaacat | atataattag | tataatgaaa | acagaaggaa | atgagattag | 1800 |
| gacagtaagt | aaaatgagag | agacctgcaa | aggataaaaa | agagaagctt | aaggaaaccg | 1860 |
| cgacgatgaa | agaaagacat | gtcatcagct | gatggatgtg | agtgatgagt | ttgttgcagt | 1920 |
| tgtgtagaaa | ttttactaa | aacagttgtt | tttacaaaaa | agaaataata | taaaacgaaa | 1980 |
| gcttagcttg | aaggcaatgg | agactctaca | acaaactatg | taccatacag | agagagaaac | 2040 |
| taaaagcttt | tcacacataa | aaaccaaact | tattcgtctc | tcattgatca | ccgttttgtt | 2100 |
| ctctcaagat | cgctgctaat | ctccggccgt | cctcatgagc | acatacgaag | gtcgctgggc | 2160 |
| taccgtgaag | gtcgaactgg | agtcgggcat | tgcctgggtc | accctcaacc | ggccggaaaa | 2220 |

-continued

```
gcgcaatgca atgagcccca cgctgaaccg ggaaatggtc gacgtgctgg aaaccctgga    2280
acaggacggc gaagccgggg tgctcgtgct gaccggcgcg ggtgaatcgt ggacggcagg    2340
catggacctg aaggaatact tccgtgaggt ggacgccggc ccggaaatcc tccaggaaaa    2400
aatccgccgc gatgcctcgc aatggcaatg gaggctgctg cgcatgtacg ccaagccgac    2460
tatcgccatg gtcaacgcgt ggtgctttgg cggcggcttc agcccgctgg tggcctgcga    2520
cctggccatc tgtgccgacg aggccacctt tggcctgtcg gaaatcaact ggggcatccc    2580
accgggcaac ctggtcagca agccatggcc cgataccgtt ggccaccgcc agtcgctgta    2640
ctacatcatg accggcaaga ctttcggcgg gcctaaagct gccgagatgg ggctggttaa    2700
cgagagcgtg ccgctggcgc aattgcgcga cgtcacccgc gaactggcgc tcaacctgct    2760
ggaaaagaac ccggtggtgc tgcgtgcggc caagaacggt tcaagcgct gccgcgaact     2820
gacctgggag cagaacgaag actacctgta cgccaagctc gaccagtccc gtctgctgga    2880
caccgaaggt gggcgcgagc agggcatgaa gcagttcctc gacgacaaga gcatcaagcc    2940
aggcctgcaa gccatcaagc gctga                                         2965
```

<210> SEQ ID NO 31
<211> LENGTH: 3470
<212> TYPE: DNA
<213> ORGANISM: Zea mays

<400> SEQUENCE: 31

```
gcccccggtc gatcgctcgg caatcggcat ggacgccggc tcggtcaccg gtggcctcgc      60
cgcgggctcg cacatgcggg acgagctgca tgtcatgcgc gcccgcgagg agccgaacgc    120
caaggtccgg agcgccgacg tgaagacgtg ccgcgtgtgc gccgacgagg tcgggacgcg    180
ggaggacggg cagcccttcg tggcgtgcgc cgagtgcggc ttccccgtct gccggccctg    240
ctacgagtac gagcgcagcg agggcacgca gtgctgcccg cagtgcaaca cccgctacaa    300
gcgccagaaa gggtgcccga gggtggaagg ggacgaggag gagggcccgg agatggacga    360
cttcgaggac gagttccccg ccaagagccc caagaagcct cacgagcctg tcgcgttcga    420
cgtctactcg gagaacggcg agcacccggc gcagaaatgg cggacgggtg ccagacgct    480
gtcgtccttc accggaagcg tcgccggaa ggacctggag gcggagaggg agatggaggg    540
gagcatggag tggaaggacc ggatcgacaa gtggaagacc aagcaggaga gagggggcaa    600
gctcaaccac gacgacagcg acgacgacga cgacaagaac gaagacgagt acatgctgct    660
tgccgaggcc cgacagccgc tgtggcgcaa ggttccgatc ccgtcgagca tgatcaaccc    720
gtaccgcatc gtcatcgtgc tccgcctggt ggtgctctgc ttcttcctca agttccggat    780
cacgacgccc gccacggacg ccgtgcctct gtggctggcg tccgtcatct gcgagctctg    840
gttcgccttc tcctggatcc tggaccagct gccaaagtgg gcgccggtga cgcgggagac    900
gtacctggac cgcctggcgc tgcggtacga ccgtgagggc gaggcgtgcc ggctgtcccc    960
catcgacttc ttcgtcagca cggtggaccc gctcaaggag ccgcccatca tcaccgccaa   1020
caccgtgctg tccatcctcg ccgtcgacta ccccgtggac cgcgtcagct gctacgtctc   1080
cgacgacggc gcgtccatgc tgctcttcga cgcgctgtcc gagaccgccg agttcgcgcg   1140
ccgctggctg ccccttctgca agaagttcgc cgtggagccg cgcgcccgg agttctactt   1200
ctcgcagaag atcgactacc tcaaggacaa ggtgcagccg acgttcgtca aggagcgccg   1260
cgccatgaag agggagtacg aggagttcaa ggtgcgcatc aacgcgctgg tggccaaggc   1320
gcagaagaag cccgaggagg ggtgggtcat gcaggacggc acgccgtggc ccgggaacaa   1380
```

-continued

```
cacgcgcgac cacccgggta tgatccaggt ctacctcggc aaccagggcg cgctggacgt    1440
ggagggccac gagctgccgc gcctcgtcta cgtgtcccgt gagaagcgcc ccgggtacaa    1500
ccaccacaag aaggcgggcg ccatgaacgc gctggtgcgc gtctccgccg tgctcaccaa    1560
cgcgcccttc atcctcaacc tcgactgcga ccactacgtc aacaacagca aggccgtgcg    1620
cgaggccatg tgcttcctca tggacccgca gctggggaag aagctctgct acgtccagtt    1680
cccgcagcgc ttcgatggca tcgatcgcca cgaccgatac gccaaccgca acgtcgtctt    1740
cttcgacatc aacatgaagg ggctggacgg catccagggc ccggtgtacg tcggcacggg    1800
gtgcgtgttc aaccgccagg cgctgtacgg ctacgacccg ccgcggcccg agaagcggcc    1860
caagatgacg tgcgactgct ggccgtcgtg gtgctgctgc tgctgctgct cggcggcgg    1920 caagcgcggc aaggcgcgca aggacaagaa gggcgacggg ggcgaggagc cgcgccgggg    1980
cctgctcggc ttctacagga agcggagcaa gaaggacaag ctcggcggcg ggtcggtggc    2040
cggcagcaag aagggcggcg ggctgtacaa gaagcaccag cgcgcgttcg agctggagga    2100
gatcgaggag gggctggagg ggtacgacga gctggagcgc tcctcgctca tgtcgcagaa    2160
gagcttcgag aagcggttcg gccagtcgcc cgtgttcatc gcctccacgc tcgtcgagga    2220
cggcggcctg ccgcagggcg ccgccgccga ccccgccgcg ctcatcaagg aggccatcca    2280
cgtcatcagc tgcggatacg aggagaagac cgagtggggc aaggagattg ggtggatcta    2340
tgggtcggtg acagaggata tcctgacggg gttcaagatg cactgccggg ggtggaagtc    2400
cgtgtactgc acgccgacac ggccggcgtt caaggggtcg cgcgcccatca acttgtctga    2460 tcgtctccac caggtgctgc gctgggcgct ggggtccgtg gagatcttca tgagccgcca    2520
ctgcccgctc cggtacgcct acggcggccg gctcaagtgg ctggagcgct cgcctacac    2580 caacaccatc gtgtacccct tcacctccat cccgctcctc gcctactgca ccatccccgc    2640
cgtctgcctc ctcaccggca agttcatcat tcccacgctg aacaacctcg ccagcatctg    2700
gttcatcgcg ctcttcctgt ccatcatcgc gacgagcgtc ctggagctgc ggtggagcgg    2760
ggtgagcatc gaggactggt ggcgcaacga gcagttctgg gtcatcggcg gcgtgtccgc    2820
gcatctcttc gccgtgttcc agggcttcct caaggttctg ggcggcgtgg acaccagctt    2880
caccgtcacc tccaaggcgg ccggcgacga ggccgacgcc ttcggggacc tctacctctt    2940
caagtggacc accctgctgg tgcccccac cacgctcatc atcatcaaca tggtgggcat    3000
cgtggccggc gtgtccgacg ccgtcaacaa cggctacggc tcctggggcc cgctcttcgg    3060
caagctcttc ttctccttct gggtcatcgt ccacctctac ccgttcctca aggggctcat    3120
ggggaggcag aaccggacgc ccaccatcgt cgtgctctgg tccatcctcc tcgcctccat    3180
cttctcgctc gtctgggtca ggatcgaccc gtttatcccg aaggccaagg gccccatcct    3240
caagccatgc ggagtcgagt gctgagctca cctagctacc ttcttgttgc atgtacggac    3300
gccgccgtgc gtttggacat acaggcactt ttgggccagg ctactcatgt tcgactttt    3360 ttttaattt gtacaagatt tgtgatcgag tgactgagtg agacagagtg ttgggtgtaa    3420
gaactgtgat ggaattcact caaattaatg gacatttttt ttcttcaaaa              3470
```

<210> SEQ ID NO 32
<211> LENGTH: 1078
<212> TYPE: PRT
<213> ORGANISM: Zea mays

<400> SEQUENCE: 32

-continued

```
Met Asp Ala Gly Ser Val Thr Gly Gly Leu Ala Ala Gly Ser His Met
1               5                   10                  15

Arg Asp Glu Leu His Val Met Arg Ala Arg Glu Pro Asn Ala Lys
            20                  25                  30

Val Arg Ser Ala Asp Val Lys Thr Cys Arg Val Cys Ala Asp Glu Val
        35                  40                  45

Gly Thr Arg Glu Asp Gly Gln Pro Phe Val Ala Cys Ala Glu Cys Gly
    50                  55                  60

Phe Pro Val Cys Arg Pro Cys Tyr Glu Tyr Glu Arg Ser Glu Gly Thr
65                  70                  75                  80

Gln Cys Cys Pro Gln Cys Asn Thr Arg Tyr Lys Arg Gln Lys Gly Cys
                85                  90                  95

Pro Arg Val Glu Gly Asp Glu Glu Gly Pro Glu Met Asp Asp Phe
            100                 105                 110

Glu Asp Glu Phe Pro Ala Lys Ser Pro Lys Lys Pro His Glu Pro Val
            115                 120                 125

Ala Phe Asp Val Tyr Ser Glu Asn Gly Glu His Pro Ala Gln Lys Trp
        130                 135                 140

Arg Thr Gly Gly Gln Thr Leu Ser Ser Phe Thr Gly Ser Val Ala Gly
145                 150                 155                 160

Lys Asp Leu Glu Ala Glu Arg Glu Met Glu Gly Ser Met Glu Trp Lys
            165                 170                 175

Asp Arg Ile Asp Lys Trp Lys Thr Lys Gln Glu Lys Arg Gly Lys Leu
        180                 185                 190

Asn His Asp Asp Ser Asp Asp Asp Asp Lys Asn Glu Asp Glu Tyr
    195                 200                 205

Met Leu Leu Ala Glu Ala Arg Gln Pro Leu Trp Arg Lys Val Pro Ile
    210                 215                 220

Pro Ser Ser Met Ile Asn Pro Tyr Arg Ile Val Ile Leu Arg Leu
225                 230                 235                 240

Val Val Leu Cys Phe Phe Leu Lys Phe Arg Ile Thr Thr Pro Ala Thr
                245                 250                 255

Asp Ala Val Pro Leu Trp Leu Ala Ser Val Ile Cys Glu Leu Trp Phe
            260                 265                 270

Ala Phe Ser Trp Ile Leu Asp Gln Leu Pro Lys Trp Ala Pro Val Thr
        275                 280                 285

Arg Glu Thr Tyr Leu Asp Arg Leu Ala Leu Arg Tyr Asp Arg Glu Gly
    290                 295                 300

Glu Ala Cys Arg Leu Ser Pro Ile Asp Phe Phe Val Ser Thr Val Asp
305                 310                 315                 320

Pro Leu Lys Glu Pro Pro Ile Ile Thr Ala Asn Thr Val Leu Ser Ile
                325                 330                 335

Leu Ala Val Asp Tyr Pro Val Asp Arg Val Ser Cys Tyr Val Ser Asp
            340                 345                 350

Asp Gly Ala Ser Met Leu Leu Phe Asp Ala Leu Ser Glu Thr Ala Glu
        355                 360                 365

Phe Ala Arg Arg Trp Val Pro Phe Cys Lys Lys Phe Ala Val Glu Pro
    370                 375                 380

Arg Ala Pro Glu Phe Tyr Phe Ser Gln Lys Ile Asp Tyr Leu Lys Asp
385                 390                 395                 400

Lys Val Gln Pro Thr Phe Val Lys Glu Arg Arg Ala Met Lys Arg Glu
                405                 410                 415

Tyr Glu Glu Phe Lys Val Arg Ile Asn Ala Leu Val Ala Lys Ala Gln
```

-continued

```
                420             425             430
Lys Lys Pro Glu Glu Gly Trp Val Met Gln Asp Gly Thr Pro Trp Pro
            435             440             445
Gly Asn Asn Thr Arg Asp His Pro Gly Met Ile Gln Val Tyr Leu Gly
        450             455             460
Asn Gln Gly Ala Leu Asp Val Glu Gly His Glu Leu Pro Arg Leu Val
465             470             475             480
Tyr Val Ser Arg Glu Lys Arg Pro Gly Tyr Asn His His Lys Lys Ala
                485             490             495
Gly Ala Met Asn Ala Leu Val Arg Val Ser Ala Val Leu Thr Asn Ala
            500             505             510
Pro Phe Ile Leu Asn Leu Asp Cys Asp His Tyr Val Asn Asn Ser Lys
        515             520             525
Ala Val Arg Glu Ala Met Cys Phe Leu Met Asp Pro Gln Leu Gly Lys
530             535             540
Lys Leu Cys Tyr Val Gln Phe Pro Gln Arg Phe Asp Gly Ile Asp Arg
545             550             555             560
His Asp Arg Tyr Ala Asn Arg Asn Val Val Phe Phe Asp Ile Asn Met
                565             570             575
Lys Gly Leu Asp Gly Ile Gln Gly Pro Val Tyr Val Gly Thr Gly Cys
            580             585             590
Val Phe Asn Arg Gln Ala Leu Tyr Gly Tyr Asp Pro Pro Arg Pro Glu
        595             600             605
Lys Arg Pro Lys Met Thr Cys Asp Cys Trp Pro Ser Trp Cys Cys Cys
610             615             620
Cys Cys Cys Phe Gly Gly Gly Lys Arg Gly Lys Ala Arg Lys Asp Lys
625             630             635             640
Lys Gly Asp Gly Gly Glu Pro Arg Arg Gly Leu Leu Gly Phe Tyr
                645             650             655
Arg Lys Arg Ser Lys Lys Asp Lys Leu Gly Gly Ser Val Ala Gly
            660             665             670
Ser Lys Lys Gly Gly Gly Leu Tyr Lys Lys His Gln Arg Ala Phe Glu
        675             680             685
Leu Glu Glu Ile Glu Glu Gly Leu Glu Gly Tyr Asp Glu Leu Glu Arg
        690             695             700
Ser Ser Leu Met Ser Gln Lys Ser Phe Glu Lys Arg Phe Gly Gln Ser
705             710             715             720
Pro Val Phe Ile Ala Ser Thr Leu Val Glu Asp Gly Gly Leu Pro Gln
                725             730             735
Gly Ala Ala Ala Asp Pro Ala Ala Leu Ile Lys Glu Ala Ile His Val
            740             745             750
Ile Ser Cys Gly Tyr Glu Glu Lys Thr Glu Trp Gly Lys Glu Ile Gly
        755             760             765
Trp Ile Tyr Gly Ser Val Thr Glu Asp Ile Leu Thr Gly Phe Lys Met
    770             775             780
His Cys Arg Gly Trp Lys Ser Val Tyr Cys Thr Pro Thr Arg Pro Ala
785             790             795             800
Phe Lys Gly Ser Ala Pro Ile Asn Leu Ser Asp Arg Leu His Gln Val
                805             810             815
Leu Arg Trp Ala Leu Gly Ser Val Glu Ile Phe Met Ser Arg His Cys
            820             825             830
Pro Leu Arg Tyr Ala Tyr Gly Gly Arg Leu Lys Trp Leu Glu Arg Phe
        835             840             845
```

```
Ala Tyr Thr Asn Thr Ile Val Tyr Pro Phe Thr Ser Ile Pro Leu Leu
            850                 855                 860
Ala Tyr Cys Thr Ile Pro Ala Val Cys Leu Leu Thr Gly Lys Phe Ile
865                 870                 875                 880
Ile Pro Thr Leu Asn Asn Leu Ala Ser Ile Trp Phe Ile Ala Leu Phe
                885                 890                 895
Leu Ser Ile Ile Ala Thr Ser Val Leu Glu Leu Arg Trp Ser Gly Val
            900                 905                 910
Ser Ile Glu Asp Trp Trp Arg Asn Glu Gln Phe Trp Val Ile Gly Gly
        915                 920                 925
Val Ser Ala His Leu Phe Ala Val Phe Gln Gly Phe Leu Lys Val Leu
930                 935                 940
Gly Gly Val Asp Thr Ser Phe Thr Val Thr Ser Lys Ala Ala Gly Asp
945                 950                 955                 960
Glu Ala Asp Ala Phe Gly Asp Leu Tyr Leu Phe Lys Trp Thr Thr Leu
                965                 970                 975
Leu Val Pro Pro Thr Thr Leu Ile Ile Ile Asn Met Val Gly Ile Val
            980                 985                 990
Ala Gly Val Ser Asp Ala Val Asn  Asn Gly Tyr Gly Ser  Trp Gly Pro
        995                 1000                1005
Leu Phe Gly Lys Leu Phe Phe  Ser Phe Trp Val Ile  Val His Leu
    1010                1015                 1020
Tyr Pro  Phe Leu Lys Gly Leu  Met Gly Arg Gln Asn  Arg Thr Pro
    1025                1030                 1035
Thr Ile Val Val Leu Trp Ser  Ile Leu Leu Ala Ser  Ile Phe Ser
    1040                 1045                 1050
Leu Val  Trp Val Arg Ile Asp  Pro Phe Ile Pro Lys  Ala Lys Gly
    1055                 1060                1065
Pro Ile  Leu Lys Pro Cys Gly  Val Glu Cys
    1070                1075

<210> SEQ ID NO 33
<211> LENGTH: 3231
<212> TYPE: DNA
<213> ORGANISM: Zea mays

<400> SEQUENCE: 33
ccacgcgtcc gggagggggcc atgatggagt cggcggcggc ccagtcctgc gcggcgtgcg      60
gggacgacgc gcgcgctgcc tgccgcgcgt gcagctacgc gctctgcagg gcgtgcctcg     120
acgaggacgc cgccgagggc cgcaccacat gcgcgcgctg cggagggac tacgccgcta      180 tcaacccagc gcgcgccagc gagggaaccg aggcggagga ggaggtggtg gagaaccacc     240
acaccgccgg tggcctgcgt gagagggtca ccatgggcag ccacctcaat gatcgccagg     300
atgaagtaag ccacgccagg accatgagca gcttgtcggg aattggtagt gaattgaatg     360
atgaatctgg taagcccatc tggaagaaca gggtggagag ttggaaggaa aagaagaatg     420
agaagaaagc ctcggccaaa aagactgcag ctaaagcaca gcctccgcct gtcgaagaac     480
agatcatgga tgaaaaagac ttgacagatg catatgagcc actctcccgg gtcatcccaa     540
tatcaaagaa caagctcaca ccttacagag cagtgatcat tatgcggtta attgttcttg     600
ggctcttctt tcactaccgt atcaccaatc ctgttaacag tgcctttggt ctctggatga     660
catcagttat atgtgagatc tggtttggtt tctcctggat attggatcaa ttcccgaagt     720
ggtatcctat caatcgtgag acttatgttg ataggctgat tgcacgatat ggagatggtg     780
```

```
aagaatctgg gttagcacct gtagatttct ttgtcagtac agtggatcca ttgaaagagc    840
ctccactaat cactgcaaac actgtgctgt ctattcttgc tgtggactat cccgttgaga    900
agatctcatg ctatgtatct gatgatggtt ctgctatgct cacatttgaa tcgctcgcag    960
agactgcaga atatgctaga aagtgggtgc cgttttgcaa gaagtacgcc attgagccac   1020
gagctcctga gttctacttc tcacagaaaa ttgactactt gaaggacaag atacacccat   1080
cttttgtcaa ggagcgtagg gctatgaaga gagactatga agagtacaag gtgaggataa   1140
atgctttggt tgccaaggct caaaagacac ctgatgaagg ctggatcatg caagacggta   1200
caccatggcc tgggaacaat cctcgtgacc accctggcat gatccaggtt ttcctgggtg   1260
agactggtgc acgggacttt gatggaaatg aacttcctcg gttagtgtat gtgtcaagag   1320
agaaaagacc aggctaccaa caccacaaga aggcaggggc tatgaatgct ctggtccgag   1380
tgtctgctgt tctgacaaat gccccttaca ttcttaatct tgattgtgat cactatgtta   1440
acaacagcaa agctgttcgt gaagcaatgt gcttcatgat ggaccctact gttggcagag   1500
atgtctgcta tgtacaattc ccccagaggt tcgatggcat tgatcgcagt gatcgatatg   1560
ccaataggaa cgttgtgttc tttgatgtta atatgaaagg acttgatggc ctccaaggcc   1620
cagtttatgt gggaactggt tgttgtttca ataggcaagc actttatggt tatgggcctc   1680
catctctgcc cgcacttcca aagtcttcga tttgttcctg gtgttgctgc tgctgtccca   1740 agaaaaggt tgaaagaagt gagagggaaa tcaacagaga ctctcggcga aagacctcg   1800 agtctgccat ttttaacctt cgcgaaattg acaactacga tgagtacgag aggtccatgc   1860
tcatctctca gatgagcttc gagaagtctt ttgggctgtc ctcggtcttt attgaatcga   1920
cccttatgga gaatgggggc gtccctgaat ctgcaaaccc atctacccta attaaagaag   1980
ccattcatgt cattagctgt ggatatgaag agaaaactga atggggaaaa gagattggct   2040
ggatctatgg ttcagttaca gaggatattc tgactgggtt taagatgcac tgccgtggct   2100
ggagatccat ctactgcatg ccggtgagac ctgcattcaa gggatcagcc ccaatcaatc   2160
tttccgatcg tcttcaccaa gttctccggt gggctcttgt ttctgtcgag atcttcttca   2220
gtcggcactg cccgctgtgg tacggttacg gtggcggccg tctgaaatgg ctccagaggc   2280
tctcctacat caacaccatc gtgtacccgt tcacttctct tcctctcgtt gcctactgtt   2340
gcctgcctgc catttgcctg ctcacaggaa agttcattat acctacgctg tccaacgctg   2400
caacgatatg gtttcttggc ctcttcatgt ccatcatcgt gacgagcgtg ttggagctgc   2460
ggtggagtgg catcgggatc gaggactggt ggcgcaacga gcagttctgg gtcatcggag   2520
gcgtgtccgc gcacctgttc gccgtgttcc agggtatcct caagatgatt gccgggctgg   2580
acaccaactt cacggtcacg gcaaaggcca cggacgacac tgagttcggg gagctgtacc   2640
tgttcaagtg gacgacggtg ctgatcccgc ccacaagcat cctggtgctg aacctggtgg   2700
gcgtggtggc tgggttctcg gccgcgctca acagcggcta cgagtcctgg ggcccgctct   2760
tcggtaaggt gttcttcgcc atgtgggtga tcatgcacct gtaccgttc tcaagggtc   2820 tcatgggccg ccagaaccgc acgccgacca tcgtggtgct ctggtccgtc ctcctcgcct   2880
ccgtcttctc cctcctgtgg gtcaagatcg acccattcgt tggaggaacc gagaccgtca   2940
acaccaacaa ctgcaacaca catctgctga ttcaccatcg gtcagctgct gtcgtgccgc   3000
ggcggacgtg tttctggtgt tgcaaacgtg ggttgcctgc ctgatgcggg tctcctctgt   3060
ctatctcgca tctgggcttt tgccccagga tctgaagcgg gtggtgtagg ttagctttat   3120
```

```
tttgcgtcca agtgttgatt gatgttgtct gtgttatgaa aagttttggt ggtgaaacct    3180
gaaatgttaa aattcggctc aattgtgaga aaaaaaaaaa aaaaaaaaaa a             3231
```

<210> SEQ ID NO 34
<211> LENGTH: 1007
<212> TYPE: PRT
<213> ORGANISM: Zea mays

<400> SEQUENCE: 34

```
Met Met Glu Ser Ala Ala Ala Gln Ser Cys Ala Ala Cys Gly Asp Asp
1               5                   10                  15

Ala Arg Ala Ala Cys Arg Ala Cys Ser Tyr Ala Leu Cys Arg Ala Cys
                20                  25                  30

Leu Asp Glu Asp Ala Ala Glu Gly Arg Thr Thr Cys Ala Arg Cys Gly
            35                  40                  45

Gly Asp Tyr Ala Ala Ile Asn Pro Ala Arg Ala Ser Glu Gly Thr Glu
        50                  55                  60

Ala Glu Glu Glu Val Val Glu Asn His His Thr Ala Gly Gly Leu Arg
65                  70                  75                  80

Glu Arg Val Thr Met Gly Ser His Leu Asn Asp Arg Gln Asp Glu Val
                85                  90                  95

Ser His Ala Arg Thr Met Ser Ser Leu Ser Gly Ile Gly Ser Glu Leu
            100                 105                 110

Asn Asp Glu Ser Gly Lys Pro Ile Trp Lys Asn Arg Val Glu Ser Trp
        115                 120                 125

Lys Glu Lys Lys Asn Glu Lys Lys Ala Ser Ala Lys Lys Thr Ala Ala
130                 135                 140

Lys Ala Gln Pro Pro Val Glu Glu Gln Ile Met Asp Glu Lys Asp
145                 150                 155                 160

Leu Thr Asp Ala Tyr Glu Pro Leu Ser Arg Val Ile Pro Ile Ser Lys
                165                 170                 175

Asn Lys Leu Thr Pro Tyr Arg Ala Val Ile Ile Met Arg Leu Ile Val
            180                 185                 190

Leu Gly Leu Phe Phe His Tyr Arg Ile Thr Asn Pro Val Asn Ser Ala
        195                 200                 205

Phe Gly Leu Trp Met Thr Ser Val Ile Cys Glu Ile Trp Phe Gly Phe
    210                 215                 220

Ser Trp Ile Leu Asp Gln Phe Pro Lys Trp Tyr Pro Ile Asn Arg Glu
225                 230                 235                 240

Thr Tyr Val Asp Arg Leu Ile Ala Arg Tyr Gly Asp Gly Glu Glu Ser
                245                 250                 255

Gly Leu Ala Pro Val Asp Phe Phe Val Ser Thr Val Asp Pro Leu Lys
            260                 265                 270

Glu Pro Pro Leu Ile Thr Ala Asn Thr Val Leu Ser Ile Leu Ala Val
        275                 280                 285

Asp Tyr Pro Val Glu Lys Ile Ser Cys Tyr Val Ser Asp Asp Gly Ser
    290                 295                 300

Ala Met Leu Thr Phe Glu Ser Leu Ala Glu Thr Ala Glu Tyr Ala Arg
305                 310                 315                 320

Lys Trp Val Pro Phe Cys Lys Lys Tyr Ala Ile Glu Pro Arg Ala Pro
                325                 330                 335

Glu Phe Tyr Phe Ser Gln Lys Ile Asp Tyr Leu Lys Asp Lys Ile His
            340                 345                 350

Pro Ser Phe Val Lys Glu Arg Arg Ala Met Lys Arg Asp Tyr Glu Glu
```

-continued

```
                355                 360                 365
Tyr Lys Val Arg Ile Asn Ala Leu Val Ala Lys Ala Gln Lys Thr Pro
    370                 375                 380
Asp Glu Gly Trp Ile Met Gln Asp Gly Thr Pro Trp Pro Gly Asn Asn
385                 390                 395                 400
Pro Arg Asp His Pro Gly Met Ile Gln Val Phe Leu Gly Glu Thr Gly
                405                 410                 415
Ala Arg Asp Phe Asp Gly Asn Glu Leu Pro Arg Leu Val Tyr Val Ser
                420                 425                 430
Arg Glu Lys Arg Pro Gly Tyr Gln His His Lys Lys Ala Gly Ala Met
            435                 440                 445
Asn Ala Leu Val Arg Val Ser Ala Val Leu Thr Asn Ala Pro Tyr Ile
        450                 455                 460
Leu Asn Leu Asp Cys Asp His Tyr Val Asn Asn Ser Lys Ala Val Arg
465                 470                 475                 480
Glu Ala Met Cys Phe Met Met Asp Pro Thr Val Gly Arg Asp Val Cys
                485                 490                 495
Tyr Val Gln Phe Pro Gln Arg Phe Asp Gly Ile Asp Arg Ser Asp Arg
                500                 505                 510
Tyr Ala Asn Arg Asn Val Val Phe Phe Asp Val Asn Met Lys Gly Leu
            515                 520                 525
Asp Gly Leu Gln Gly Pro Val Tyr Val Gly Thr Gly Cys Cys Phe Asn
        530                 535                 540
Arg Gln Ala Leu Tyr Gly Tyr Gly Pro Pro Ser Leu Pro Ala Leu Pro
545                 550                 555                 560
Lys Ser Ser Ile Cys Ser Trp Cys Cys Cys Cys Pro Lys Lys Lys
                565                 570                 575
Val Glu Arg Ser Glu Arg Glu Ile Asn Arg Asp Ser Arg Arg Glu Asp
                580                 585                 590
Leu Glu Ser Ala Ile Phe Asn Leu Arg Glu Ile Asp Asn Tyr Asp Glu
            595                 600                 605
Tyr Glu Arg Ser Met Leu Ile Ser Gln Met Ser Phe Glu Lys Ser Phe
        610                 615                 620
Gly Leu Ser Ser Val Phe Ile Glu Ser Thr Leu Met Glu Asn Gly Gly
625                 630                 635                 640
Val Pro Glu Ser Ala Asn Pro Ser Thr Leu Ile Lys Glu Ala Ile His
                645                 650                 655
Val Ile Ser Cys Gly Tyr Glu Glu Lys Thr Glu Trp Gly Lys Glu Ile
                660                 665                 670
Gly Trp Ile Tyr Gly Ser Val Thr Glu Asp Ile Leu Thr Gly Phe Lys
            675                 680                 685
Met His Cys Arg Gly Trp Arg Ser Ile Tyr Cys Met Pro Val Arg Pro
        690                 695                 700
Ala Phe Lys Gly Ser Ala Pro Ile Asn Leu Ser Asp Arg Leu His Gln
705                 710                 715                 720
Val Leu Arg Trp Ala Leu Val Ser Val Glu Ile Phe Phe Ser Arg His
                725                 730                 735
Cys Pro Leu Trp Tyr Gly Tyr Gly Gly Arg Leu Lys Trp Leu Gln
                740                 745                 750
Arg Leu Ser Tyr Ile Asn Thr Ile Val Tyr Pro Phe Thr Ser Leu Pro
            755                 760                 765
Leu Val Ala Tyr Cys Cys Leu Pro Ala Ile Cys Leu Leu Thr Gly Lys
        770                 775                 780
```

```
Phe Ile Ile Pro Thr Leu Ser Asn Ala Ala Thr Ile Trp Phe Leu Gly
785                 790                 795                 800

Leu Phe Met Ser Ile Ile Val Thr Ser Val Leu Glu Leu Arg Trp Ser
            805                 810                 815

Gly Ile Gly Ile Glu Asp Trp Trp Arg Asn Glu Gln Phe Trp Val Ile
            820                 825                 830

Gly Gly Val Ser Ala His Leu Phe Ala Val Phe Gln Gly Ile Leu Lys
            835                 840                 845

Met Ile Ala Gly Leu Asp Thr Asn Phe Thr Val Thr Ala Lys Ala Thr
850                 855                 860

Asp Asp Thr Glu Phe Gly Glu Leu Tyr Leu Phe Lys Trp Thr Thr Val
865                 870                 875                 880

Leu Ile Pro Pro Thr Ser Ile Leu Val Leu Asn Leu Val Gly Val Val
            885                 890                 895

Ala Gly Phe Ser Ala Ala Leu Asn Ser Gly Tyr Glu Ser Trp Gly Pro
            900                 905                 910

Leu Phe Gly Lys Val Phe Phe Ala Met Trp Val Ile Met His Leu Tyr
            915                 920                 925

Pro Phe Leu Lys Gly Leu Met Gly Arg Gln Asn Arg Thr Pro Thr Ile
            930                 935                 940

Val Val Leu Trp Ser Val Leu Leu Ala Ser Val Phe Ser Leu Leu Trp
945                 950                 955                 960

Val Lys Ile Asp Pro Phe Val Gly Gly Thr Glu Thr Val Asn Thr Asn
            965                 970                 975

Asn Cys Asn Thr His Leu Leu Ile His His Arg Ser Ala Ala Val Val
            980                 985                 990

Pro Arg Arg Thr Cys Phe Trp Cys  Cys Lys Arg Gly Leu  Pro Ala
            995                 1000                1005

<210> SEQ ID NO 35
<211> LENGTH: 3443
<212> TYPE: DNA
<213> ORGANISM: Zea mays

<400> SEQUENCE: 35
ctgcgtcgcc ctgcctcgca atcgcgaatc tgtcgagcac ctgagggtc ggaggccgag    60 agctagccta gcacgccggc ctccgcgcgc gatggaggcc agcgccgggc tggtggccgg   120
ctcgcacaac cggaacgagc tggtgctgat ccggggccac gaggacccca gccgctgcg   180 ggcgctgagc gggcaggtgt gcgagatatg cggcgacgag gtcgggctca cggtggacgg   240
cgacctcttc gtcgcctgca acgagtgcgg cttccccgtg tgccggccct gctacgagta   300
cgagcgccgg gagggcacgc agaactgccc ccagtgcaag acgcgctaca gcgcctcaa   360 ggggagcccg agggttgccg gggacgatga cgaggaggac atcgacgacc tggagcacga   420
gttcaacatc gacgacgaga atcagcagag gcagctggag ggcaacatgc agaacagcca   480
gatcaccgag gcgatgctgc acggcaggat gagctacggg aggggccccg acgacggcga   540
cggcaacaac accccgcaga tcccgcccat catcaccggc tcccgctccg tgccggtgag   600
cggtgagttt ccgattacca acgggtatgg ccacggcgag gtctcgtctt ccctgcacaa   660
gcgcatccat ccgtaccctg tgtctgagcc agggagtgcc aagtgggacg agaagaaaga   720
agtgagctgg aaggagagga tggacgactg gaagtccaag cagggcatcc tcggcggcgg   780
cgccgatccc gaagacatgg acgccgacgt ggcactgaac gacgaggcga ggcagccgct   840
```

```
gtcgaggaag gtgtcgatcg cgtcgagcaa ggtgaacccg taccggatgg tgatcgtggt    900
gcgtctcgtt gtgctcgcct tcttcctccg gtaccgtatc ctgcaccccg tcccggacgc    960
catcgggctg tggctcgtct ccatcatctg cgagatctgg ttcgccatct cctggatcct   1020
cgaccagttc cccaagtggt tccccatcga ccgcgagacg tacctcgacc gcctctccct   1080
caggtacgag agggaagggg agccgtcgct gctgtcggcg gtggaccgtg tcgtgagcac   1140
ggtggacccg ctcaaggagc cgccgctggt gaccgccaac accgtgctct ccatcctcgc   1200
cgtagactac cccgtggaca aggtctcctg ctacgtctcc gacgacggcg cgtcgatgct   1260
gacgttcgag tcgctgtcgg agacggccga gttcgcgcgc aagtgggtgc ccttctgcaa   1320
gaagttcggc atcgagcccc gcgccccgga gttctacttc tcgctcaagg tcgactacct   1380
caaggacaag gtgcagccca ccttcgtgca ggagcgccgc gccatgaaga gagagtatga   1440
ggagttcaag gtccggatca acgcgctggt ggccaaggcc atgaaggtgc cggcagaggg   1500
gtggatcatg aaggacggca cgccgtggcc cgggaacaac acccgcgacc acccggcat    1560 gatccaggtg ttcctgggcc acagcggcgg ccacgacacc gagggcaacg agctgccccg   1620
cctcgtgtac gtctcccgtg agaagcgccc gggattccag caccacaaga aggccggcgc   1680
catgaacgct ctgattcgcg tctccgccgt gctgaccaac gcgccattca tgctcaactt   1740
ggactgtgat cactacatca acaacagcaa ggccatccgg gaggcatgt gcttcctcat    1800 ggaccctcag gtcggccgga aggtctgcta cgttcagttc ccgcagaggt tcgacggcat   1860
cgacgtgcac gaccgatacg ctaacaggaa caccgtcttc ttcgacatca acatgaaggg   1920
gctggacggc atccaaggcc cggtgtacgt cgggacaggg tgcgtgttcc ggcgccaggc   1980
gctctacggc tacaaccctc ccaagggacc caagaggccc aagatggtga cctgcgactg   2040
ctgcccgtgc ttcggccgca agaagcggaa acacgccaag gacgggctgc cggagggcac   2100
cgctgatatg ggagtagata cgacaagga gatgctcatg tcccacatga acttcgagaa    2160
gcggttcggg cagtccgcgg cgttcgtcac gtcgacgctg atggaggaag cggcgtccc    2220 tccttcgtcg agccccgccg cgctcctcaa ggaggccatc catgtcatca gctgcggcta   2280
cgaggacaag accgactggg ggctggagct ggggtggatc tacgggtcga tcacggagga   2340
catcctgacg gggttcaaga tgcactgccg cgggtggcgc tccgtgtact gcatgccgaa   2400
gcgggcggcg ttcaaggggt cggcgccgat caatctatcg gaccgtctca accaggtgct   2460
ccggtgggcg ctgggtccg tcgagatctt cttcagccgg cacagccccc tgctgtacgg    2520
ctacaagaac ggcaacctca gtggctgga gcgcttcgcc tacatcaaca ccaccatcta    2580 cccettcacc tcgctcccgc tgctcgccta ctgcaccctc cccgccgtct gcctcctcac   2640
cggcaagttc atcatgccgt cgattagcac gttcgccagc ctcttcttca tcgccctctt   2700
catgtccatc ttcgcgacgg gcatcctgga gatgcggtgg agcggggtga gcatcgagga   2760
gtggtggagg aacgagcagt tctgggtcat cggcggcgtg tccgcgcatc tcttcgccgt   2820
cgtgcagggc ctgctcaagg tcctcgccgg gatcgacacc aacttcaccg tcacctccaa   2880
ggccaccggc gacgaggacg acgagttcgc cgagctctac gccttcaagt ggaccacgct   2940
cctcatcccg cccaccacgc tgctcatcat taacgtcatc ggcgtcgtgg ccggcatctc   3000
cgacgccatc aacaacgggt accagtcctg ggggcccctc ttcggcaagc tcttcttcgc   3060 cttctctggtc atcgtccacc tctacccgtt cctcaagggg ctcatggggc gccagaacag   3120
gacgcccacc gttgttgtca tctggtccat tctgctggcc tccatcttct ccctgctctg   3180
ggtcaggatc gaccctttca tcgtcaggac caagggcccg gacgtcaggc agtgtggcat   3240
```

```
caattgctga gctgtttatt aaggttcaaa attctggagc ttgtgcatag ggagaaaaaa      3300
acaatttaga aattttgtaa ggttgttgtg tctgtaatgt tatggtaccc agaattgtcg      3360
gacgaggaat tgaacaaagg acaaggtttg attgttaaat ggcaaaaaaa aaaaaaaaaa      3420
aaaaaaaaaa aaaaaaaaa aaa                                              3443
```

<210> SEQ ID NO 36
<211> LENGTH: 1052
<212> TYPE: PRT
<213> ORGANISM: Zea mays

<400> SEQUENCE: 36

```
Met Glu Ala Ser Ala Gly Leu Val Ala Gly Ser His Asn Arg Asn Glu
1               5                   10                  15

Leu Val Leu Ile Arg Gly His Glu Asp Pro Lys Pro Leu Arg Ala Leu
            20                  25                  30

Ser Gly Gln Val Cys Glu Ile Cys Gly Asp Glu Val Gly Leu Thr Val
        35                  40                  45

Asp Gly Asp Leu Phe Val Ala Cys Asn Glu Cys Gly Phe Pro Val Cys
    50                  55                  60

Arg Pro Cys Tyr Glu Tyr Glu Arg Arg Glu Gly Thr Gln Asn Cys Pro
65                  70                  75                  80

Gln Cys Lys Thr Arg Tyr Lys Arg Leu Lys Gly Ser Pro Arg Val Ala
                85                  90                  95

Gly Asp Asp Asp Glu Glu Asp Ile Asp Asp Leu Glu His Glu Phe Asn
            100                 105                 110

Ile Asp Asp Glu Asn Gln Gln Arg Gln Leu Glu Gly Asn Met Gln Asn
        115                 120                 125

Ser Gln Ile Thr Glu Ala Met Leu His Gly Arg Met Ser Tyr Gly Arg
    130                 135                 140

Gly Pro Asp Asp Gly Asp Gly Asn Asn Thr Pro Gln Ile Pro Pro Ile
145                 150                 155                 160

Ile Thr Gly Ser Arg Ser Val Pro Val Ser Gly Glu Phe Pro Ile Thr
                165                 170                 175

Asn Gly Tyr Gly His Gly Glu Val Ser Ser Ser Leu His Lys Arg Ile
            180                 185                 190

His Pro Tyr Pro Val Ser Glu Pro Gly Ser Ala Lys Trp Asp Glu Lys
        195                 200                 205

Lys Glu Val Ser Trp Lys Glu Arg Met Asp Asp Trp Lys Ser Lys Gln
    210                 215                 220

Gly Ile Leu Gly Gly Ala Asp Pro Glu Asp Met Asp Ala Asp Val
225                 230                 235                 240

Ala Leu Asn Asp Glu Ala Arg Gln Pro Leu Ser Arg Lys Val Ser Ile
                245                 250                 255

Ala Ser Ser Lys Val Asn Pro Tyr Arg Met Val Ile Val Arg Leu
            260                 265                 270

Val Val Leu Ala Phe Phe Leu Arg Tyr Arg Ile Leu His Pro Val Pro
        275                 280                 285

Asp Ala Ile Gly Leu Trp Leu Val Ser Ile Cys Glu Ile Trp Phe
    290                 295                 300

Ala Ile Ser Trp Ile Leu Asp Gln Phe Pro Lys Trp Phe Pro Ile Asp
305                 310                 315                 320

Arg Glu Thr Tyr Leu Asp Arg Leu Ser Leu Arg Tyr Glu Arg Glu Gly
                325                 330                 335
```

```
Glu Pro Ser Leu Leu Ser Ala Val Asp Leu Phe Val Ser Thr Val Asp
                340                 345                 350

Pro Leu Lys Glu Pro Pro Leu Val Thr Ala Asn Thr Val Leu Ser Ile
            355                 360                 365

Leu Ala Val Asp Tyr Pro Val Asp Lys Val Ser Cys Tyr Val Ser Asp
        370                 375                 380

Asp Gly Ala Ser Met Leu Thr Phe Glu Ser Leu Ser Glu Thr Ala Glu
385                 390                 395                 400

Phe Ala Arg Lys Trp Val Pro Phe Cys Lys Lys Phe Gly Ile Glu Pro
                405                 410                 415

Arg Ala Pro Glu Phe Tyr Phe Ser Leu Lys Val Asp Tyr Leu Lys Asp
            420                 425                 430

Lys Val Gln Pro Thr Phe Val Gln Glu Arg Arg Ala Met Lys Arg Glu
        435                 440                 445

Tyr Glu Glu Phe Lys Val Arg Ile Asn Ala Leu Val Ala Lys Ala Met
    450                 455                 460

Lys Val Pro Ala Glu Gly Trp Ile Met Lys Asp Gly Thr Pro Trp Pro
465                 470                 475                 480

Gly Asn Asn Thr Arg Asp His Pro Gly Met Ile Gln Val Phe Leu Gly
                485                 490                 495

His Ser Gly Gly His Asp Thr Glu Gly Asn Glu Leu Pro Arg Leu Val
            500                 505                 510

Tyr Val Ser Arg Glu Lys Arg Pro Gly Phe Gln His His Lys Lys Ala
        515                 520                 525

Gly Ala Met Asn Ala Leu Ile Arg Val Ser Ala Val Leu Thr Asn Ala
    530                 535                 540

Pro Phe Met Leu Asn Leu Asp Cys Asp His Tyr Ile Asn Asn Ser Lys
545                 550                 555                 560

Ala Ile Arg Glu Ala Met Cys Phe Leu Met Asp Pro Gln Val Gly Arg
                565                 570                 575

Lys Val Cys Tyr Val Gln Phe Pro Gln Arg Phe Asp Gly Ile Asp Val
            580                 585                 590

His Asp Arg Tyr Ala Asn Arg Asn Thr Val Phe Phe Asp Ile Asn Met
        595                 600                 605

Lys Gly Leu Asp Gly Ile Gln Gly Pro Val Tyr Val Gly Thr Gly Cys
    610                 615                 620

Val Phe Arg Arg Gln Ala Leu Tyr Gly Tyr Asn Pro Pro Lys Gly Pro
625                 630                 635                 640

Lys Arg Pro Lys Met Val Thr Cys Asp Cys Cys Pro Cys Phe Gly Arg
                645                 650                 655

Lys Lys Arg Lys His Ala Lys Asp Gly Leu Pro Glu Gly Thr Ala Asp
            660                 665                 670

Met Gly Val Asp Ser Asp Lys Glu Met Leu Met Ser His Met Asn Phe
        675                 680                 685

Glu Lys Arg Phe Gly Gln Ser Ala Ala Phe Val Thr Ser Thr Leu Met
    690                 695                 700

Glu Glu Gly Gly Val Pro Pro Ser Ser Pro Ala Ala Leu Leu Lys
705                 710                 715                 720

Glu Ala Ile His Val Ile Ser Cys Gly Tyr Glu Asp Lys Thr Asp Trp
                725                 730                 735

Gly Leu Glu Leu Gly Trp Ile Tyr Gly Ser Ile Thr Glu Asp Ile Leu
            740                 745                 750
```

```
Thr Gly Phe Lys Met His Cys Arg Gly Trp Arg Ser Val Tyr Cys Met
        755                 760                 765

Pro Lys Arg Ala Ala Phe Lys Gly Ser Ala Pro Ile Asn Leu Ser Asp
        770                 775                 780

Arg Leu Asn Gln Val Leu Arg Trp Ala Leu Gly Ser Val Glu Ile Phe
785                 790                 795                 800

Phe Ser Arg His Ser Pro Leu Leu Tyr Gly Tyr Lys Asn Gly Asn Leu
                805                 810                 815

Lys Trp Leu Glu Arg Phe Ala Tyr Ile Asn Thr Thr Ile Tyr Pro Phe
        820                 825                 830

Thr Ser Leu Pro Leu Leu Ala Tyr Cys Thr Leu Pro Ala Val Cys Leu
        835                 840                 845

Leu Thr Gly Lys Phe Ile Met Pro Ser Ile Ser Thr Phe Ala Ser Leu
        850                 855                 860

Phe Phe Ile Ala Leu Phe Met Ser Ile Phe Ala Thr Gly Ile Leu Glu
865                 870                 875                 880

Met Arg Trp Ser Gly Val Ser Ile Glu Glu Trp Arg Asn Glu Gln
                885                 890                 895

Phe Trp Val Ile Gly Gly Val Ser Ala His Leu Phe Ala Val Val Gln
                900                 905                 910

Gly Leu Leu Lys Val Leu Ala Gly Ile Asp Thr Asn Phe Thr Val Thr
                915                 920                 925

Ser Lys Ala Thr Gly Asp Glu Asp Asp Glu Phe Ala Glu Leu Tyr Ala
        930                 935                 940

Phe Lys Trp Thr Thr Leu Leu Ile Pro Pro Thr Thr Leu Leu Ile Ile
945                 950                 955                 960

Asn Val Ile Gly Val Val Ala Gly Ile Ser Asp Ala Ile Asn Asn Gly
                965                 970                 975

Tyr Gln Ser Trp Gly Pro Leu Phe Gly Lys Leu Phe Phe Ala Phe Trp
                980                 985                 990

Val Ile Val His Leu Tyr Pro Phe  Leu Lys Gly Leu Met  Gly Arg Gln
                995                 1000                1005

Asn Arg  Thr Pro Thr Val Val  Val Ile Trp Ser Ile  Leu Leu Ala
    1010                1015                1020

Ser Ile  Phe Ser Leu Leu Trp  Val Arg Ile Asp Pro  Phe Ile Val
    1025                1030                1035

Arg Thr  Lys Gly Pro Asp Val  Arg Gln Cys Gly Ile  Asn Cys
    1040                1045                1050

<210> SEQ ID NO 37
<211> LENGTH: 3191
<212> TYPE: DNA
<213> ORGANISM: Oryza savita

<400> SEQUENCE: 37
atggacaccg cctccgtcac cggtggcgag cacaagggga aggagaagac gtgccgggtg      60
tgcggcgagg aggtggcggc gagggaggac gggaagccgt cgtggcgtg cgccgagtgc     120 ggcttcccgg tgtgcaagcc ctgctacgag tacgagcgca gcgagggcac ccagtgctgc     180
ccccagtgca acacccgcta caagcgccac aaagggtgcc cacgggtgga aggcgacgag     240
gacgacggcg gcgacatgga cgacttcgag gaggagttcc agatcaagag ccccaccaag     300
cagaaacccc cccacgagcc cgtcaacttc gacgtctact cggagaacgg cgagcagccg     360
gcacagaagt ggcgccctgg aggcccggcg ctctcttcct tcaccggaag cgtggctggg     420
```

-continued

| | |
|---|---|
| aaggatctgg agcaggagag ggagatggag ggtggcatgg agtggaagga caggatcgac | 480 |
| aagtggaaga cgaagcagga aagcgggggc aagctcaacc gcgacgacag cgacgacgac | 540 |
| gacgacaaga acgacgacga gtacatgctg ctcgcggagg cgaggcagcc gctgtggagg | 600 |
| aaggtgccga tcccgtcgag caagatcaac ccgtaccgga tcgtgatcgt gctccggctg | 660 |
| gtggtgctct gcttcttcct caagttccgg atcacgacgc cggcgatgga cgcggtgccg | 720 |
| ctgtggctgg cctcggtgat ctgcgagctg tggttcgcgc tgtcgtggat cctcgaccag | 780 |
| ctgcccaagt ggtcgccggt gacgagggag acgtacctgg accggctggc cctccggtac | 840 |
| gagcgcgacg cgagccgtg cgcctggccc cgatcgattt cttcgtcagc acggtggacc | 900 |
| cgctcaagga gccgcccatc atcaccgcca acaccgtgct gtccatcctc gccgtcgact | 960 |
| accccgtcga ccgcgtctcc tgctacgtct ccgacgacgg cgcgtccatg ctgctcttcg | 1020 |
| acacgctctc cgagaccgcc gagttcgccc gccggtgggt cccccttctgc aagaagttca | 1080 |
| ccatcgagcc ccgcgccccc gagttctact tctcccagaa gatcgactac ctcaaggaca | 1140 |
| aggtccagcc caccttcgtc aaagaacgcc gcgccatgaa gagagagtat gaggagttca | 1200 |
| aggtgaggat aaacgcgctg gtggcgaagg cgcagaagaa gccggaggaa gggtgggtga | 1260 |
| tgcaggacgg gacgccatgg ccggggaaca acacgaggga ccacccgggg atgatccagg | 1320 |
| tgtacctggg cagccagggc gcgctcgacg tcgagggcag cgagctgccg cggctggtgt | 1380 |
| acgtgtcccg cgagaagcgg cccggctaca accaccacaa gaaggccggc gccatgaact | 1440 |
| ccctcgttcg cgtctccgcc gtgcttacca acgccccctt catcctcaac ctcgactgcg | 1500 |
| accactacgt caacaacagc aaggccgtcc gcgaggccat gtgcttcctc atggacaagc | 1560 |
| agctcggcaa gaagctgtgc tacgtccagt tcccccagcg cttcgacggc atcgaccgcc | 1620 |
| acgatcgcta cgccaaccgc aacaccgtct tcttcgacat caacatgaag gggctggacg | 1680 |
| ggatacaggg gccggtgtac gtggggacgg ggacggtgtt caacaggcag cgcgctgtacg | 1740 |
| gatacgaccc gccgcggccg gagaagaggc cgaagatgac gtgcgactgc tggccgtcgt | 1800 |
| ggtgctgctg ctgctgctgc ttcggcgggg ggaagcgcgg caagtcgcac aagaacaaga | 1860 |
| agggcggcg cggcggcgag ggcggcggcc tcgacgagcc gcgccgcggg ctgctcgggt | 1920 |
| tctacaagaa gaggagcaag aaggacaagc tcggcgtcg cgcggcgtcg ctcgccggag | 1980 |
| ggaagaaagg gtaccggaag caccagcgcg ggttcgagct ggaggagatc gaggagggcc | 2040 |
| tcgaggggta cgacgagctg gagcgctcgt cgctcatgtc gcagaagagc ttcgagaagc | 2100 |
| ggttcggcca gtcgccggtg ttcatcgcct ccaccctcgt cgaggacggc ggcctccccc | 2160 |
| agggcgccgc cgccgacccc gccgccctca tcaaggaggc catccacgtc atcagctgcg | 2220 |
| gctacgagga gaagaccgag tggggcaagg agattgggtg gatctacggg tcggtgacgg | 2280 |
| aggacatctt aacggggttc aagatgcatt gccgtgggtg gaagtcggtg tactgcacgc | 2340 |
| cggcgagggc ggcattcaag gggtcggcgc ccatcaacct gtcggatcgt ctgcaccagg | 2400 |
| tgctccggtg ggcgctcggc tccgtcgaga tcttcatgag ccgccattgc ccgctctggt | 2460 |
| acgcctatgg cggccgcctc aagtggctcg agcgcttcgc ctacaccaac accatcgtct | 2520 |
| acccccttcac ctccattccc ctcctcgcct actgcaccat cccgccgtc tgcctcctca | 2580 |
| ccggcaagtt catcatcccc acgcttaaca atttggcgag catatggttc atagcgcttt | 2640 |
| tcctgtcgat catcgcgacg ggggtgctgg agctgcggtg gagcggggtg agcatcgagg | 2700 |
| actggtggag gaacgagcag ttctgggtga tcggcggcgt gtcggcgcac ctgttcgccg | 2760 |
| tgttccaggg cctcctcaag gtgctcggcg gcgtggacac caacttcacg gtgacgtcca | 2820 |

```
aggccgccgc cgacgagacc gacgcgttcg gcgagctcta cctgttcaag tggacgacgc    2880
tgctggtgcc gccgacgacg ctgatcatca tcaacatggt ggggatcgtc gccggcgtgt    2940
cggacgccgt gaacaacggg tacgggtcgt ggggcccgct gttcgggaag ctcttcttct    3000
ccttctgggt catcctccac ctctaccoct tcctcaaggg gctcatgggg aggcagaacc    3060
ggacgcccac cattgtcgtg ctctggtcca tcctcctcgc ctccatcttc tccctcgtct    3120
gggtcaggat cgaccccttc atccccaagc ccaagggccc cgtcctcaag ccatgcgggg    3180
tctcgtgctg a                                                         3191
```

<210> SEQ ID NO 38
<211> LENGTH: 1063
<212> TYPE: PRT
<213> ORGANISM: Oryza savita

<400> SEQUENCE: 38

```
Met Asp Thr Ala Ser Val Thr Gly Gly Glu His Lys Gly Lys Glu Lys
1               5                   10                  15

Thr Cys Arg Val Cys Gly Glu Val Ala Ala Arg Glu Asp Gly Lys
            20                  25                  30

Pro Phe Val Ala Cys Ala Glu Cys Gly Phe Pro Val Cys Lys Pro Cys
        35                  40                  45

Tyr Glu Tyr Glu Arg Ser Glu Gly Thr Gln Cys Cys Pro Gln Cys Asn
    50                  55                  60

Thr Arg Tyr Lys Arg His Lys Gly Cys Pro Arg Val Glu Gly Asp Glu
65                  70                  75                  80

Asp Asp Gly Gly Asp Met Asp Asp Phe Glu Glu Glu Phe Gln Ile Lys
                85                  90                  95

Ser Pro Thr Lys Gln Lys Pro Pro His Glu Pro Val Asn Phe Asp Val
            100                 105                 110

Tyr Ser Glu Asn Gly Glu Gln Pro Ala Gln Lys Trp Arg Pro Gly Gly
        115                 120                 125

Pro Ala Leu Ser Ser Phe Thr Gly Ser Val Ala Gly Lys Asp Leu Glu
    130                 135                 140

Gln Glu Arg Glu Met Glu Gly Gly Met Glu Trp Lys Asp Arg Ile Asp
145                 150                 155                 160

Lys Trp Lys Thr Lys Gln Glu Lys Arg Gly Lys Leu Asn Arg Asp Asp
                165                 170                 175

Ser Asp Asp Asp Asp Lys Asn Asp Asp Glu Tyr Met Leu Leu Ala
            180                 185                 190

Glu Ala Arg Gln Pro Leu Trp Arg Lys Val Pro Ile Pro Ser Ser Lys
        195                 200                 205

Ile Asn Pro Tyr Arg Ile Val Ile Val Leu Arg Leu Val Val Leu Cys
    210                 215                 220

Phe Phe Leu Lys Phe Arg Ile Thr Thr Pro Ala Met Asp Ala Val Pro
225                 230                 235                 240

Leu Trp Leu Ala Ser Val Ile Cys Glu Leu Trp Phe Ala Leu Ser Trp
                245                 250                 255

Ile Leu Asp Gln Leu Pro Lys Trp Ser Pro Val Thr Arg Glu Thr Tyr
            260                 265                 270

Leu Asp Arg Leu Ala Leu Arg Tyr Glu Arg Asp Gly Glu Pro Cys Arg
        275                 280                 285

Leu Ala Pro Ile Asp Phe Phe Val Ser Thr Val Asp Pro Leu Lys Glu
    290                 295                 300
```

```
Pro Pro Ile Ile Thr Ala Asn Thr Val Leu Ser Ile Leu Ala Val Asp
305                 310                 315                 320

Tyr Pro Val Asp Arg Val Ser Cys Tyr Val Ser Asp Asp Gly Ala Ser
                325                 330                 335

Met Leu Leu Phe Asp Thr Leu Ser Glu Thr Ala Glu Phe Ala Arg Arg
                340                 345                 350

Trp Val Pro Phe Cys Lys Lys Phe Thr Ile Glu Pro Arg Ala Pro Glu
                355                 360                 365

Phe Tyr Phe Ser Gln Lys Ile Asp Tyr Leu Lys Asp Lys Val Gln Pro
    370                 375                 380

Thr Phe Val Lys Glu Arg Arg Ala Met Lys Arg Glu Tyr Glu Glu Phe
385                 390                 395                 400

Lys Val Arg Ile Asn Ala Leu Val Ala Lys Ala Gln Lys Lys Pro Glu
                405                 410                 415

Glu Gly Trp Val Met Gln Asp Gly Thr Pro Trp Pro Gly Asn Asn Thr
                420                 425                 430

Arg Asp His Pro Gly Met Ile Gln Val Tyr Leu Gly Ser Gln Gly Ala
            435                 440                 445

Leu Asp Val Glu Gly Ser Glu Leu Pro Arg Leu Val Tyr Val Ser Arg
    450                 455                 460

Glu Lys Arg Pro Gly Tyr Asn His His Lys Lys Ala Gly Ala Met Asn
465                 470                 475                 480

Ser Leu Val Arg Val Ser Ala Val Leu Thr Asn Ala Pro Phe Ile Leu
                485                 490                 495

Asn Leu Asp Cys Asp His Tyr Val Asn Asn Ser Lys Ala Val Arg Glu
                500                 505                 510

Ala Met Cys Phe Leu Met Asp Lys Gln Leu Gly Lys Lys Leu Cys Tyr
            515                 520                 525

Val Gln Phe Pro Gln Arg Phe Asp Gly Ile Asp Arg His Asp Arg Tyr
    530                 535                 540

Ala Asn Arg Asn Thr Val Phe Phe Asp Ile Asn Met Lys Gly Leu Asp
545                 550                 555                 560

Gly Ile Gln Gly Pro Val Tyr Val Gly Thr Gly Thr Val Phe Asn Arg
                565                 570                 575

Gln Ala Leu Tyr Gly Tyr Asp Pro Pro Arg Pro Glu Lys Arg Pro Lys
            580                 585                 590

Met Thr Cys Asp Cys Trp Pro Ser Trp Cys Cys Cys Cys Cys Cys Phe
            595                 600                 605

Gly Gly Gly Lys Arg Gly Lys Ser His Lys Asn Lys Lys Gly Gly Gly
    610                 615                 620

Gly Gly Glu Gly Gly Gly Leu Asp Glu Pro Arg Arg Gly Leu Leu Gly
625                 630                 635                 640

Phe Tyr Lys Lys Arg Ser Lys Lys Asp Lys Leu Gly Gly Gly Ala Ala
                645                 650                 655

Ser Leu Ala Gly Gly Lys Lys Gly Tyr Arg Lys His Gln Arg Gly Phe
                660                 665                 670

Glu Leu Glu Glu Ile Glu Glu Gly Leu Glu Gly Tyr Asp Glu Leu Glu
            675                 680                 685

Arg Ser Ser Leu Met Ser Gln Lys Ser Phe Glu Lys Arg Phe Gly Gln
            690                 695                 700

Ser Pro Val Phe Ile Ala Ser Thr Leu Val Glu Asp Gly Gly Leu Pro
705                 710                 715                 720
```

Gln Gly Ala Ala Ala Asp Pro Ala Ala Leu Ile Lys Glu Ala Ile His
                725                 730                 735

Val Ile Ser Cys Gly Tyr Glu Glu Lys Thr Glu Trp Gly Lys Glu Ile
            740                 745                 750

Gly Trp Ile Tyr Gly Ser Val Thr Glu Asp Ile Leu Thr Gly Phe Lys
        755                 760                 765

Met His Cys Arg Gly Trp Lys Ser Val Tyr Cys Thr Pro Ala Arg Ala
    770                 775                 780

Ala Phe Lys Gly Ser Ala Pro Ile Asn Leu Ser Asp Arg Leu His Gln
785                 790                 795                 800

Val Leu Arg Trp Ala Leu Gly Ser Val Glu Ile Phe Met Ser Arg His
            805                 810                 815

Cys Pro Leu Trp Tyr Ala Tyr Gly Gly Arg Leu Lys Trp Leu Glu Arg
        820                 825                 830

Phe Ala Tyr Thr Asn Thr Ile Val Tyr Pro Phe Thr Ser Ile Pro Leu
    835                 840                 845

Leu Ala Tyr Cys Thr Ile Pro Ala Val Cys Leu Leu Thr Gly Lys Phe
850                 855                 860

Ile Ile Pro Thr Leu Asn Asn Leu Ala Ser Ile Trp Phe Ile Ala Leu
865                 870                 875                 880

Phe Leu Ser Ile Ile Ala Thr Gly Val Leu Glu Leu Arg Trp Ser Gly
            885                 890                 895

Val Ser Ile Glu Asp Trp Trp Arg Asn Glu Gln Phe Trp Val Ile Gly
        900                 905                 910

Gly Val Ser Ala His Leu Phe Ala Val Phe Gln Gly Leu Leu Lys Val
    915                 920                 925

Leu Gly Gly Val Asp Thr Asn Phe Thr Val Thr Ser Lys Ala Ala Ala
930                 935                 940

Asp Glu Thr Asp Ala Phe Gly Glu Leu Tyr Leu Phe Lys Trp Thr Thr
945                 950                 955                 960

Leu Leu Val Pro Pro Thr Thr Leu Ile Ile Ile Asn Met Val Gly Ile
            965                 970                 975

Val Ala Gly Val Ser Asp Ala Val Asn Asn Gly Tyr Gly Ser Trp Gly
        980                 985                 990

Pro Leu Phe Gly Lys Leu Phe Phe Ser Phe Trp Val Ile Leu His Leu
    995                 1000                1005

Tyr Pro Phe Leu Lys Gly Leu Met Gly Arg Gln Asn Arg Thr Pro
    1010                1015                1020

Thr Ile Val Val Leu Trp Ser Ile Leu Leu Ala Ser Ile Phe Ser
    1025                1030                1035

Leu Val Trp Val Arg Ile Asp Pro Phe Ile Pro Lys Pro Lys Gly
    1040                1045                1050

Pro Val Leu Lys Pro Cys Gly Val Ser Cys
    1055                1060

<210> SEQ ID NO 39
<211> LENGTH: 2820
<212> TYPE: DNA
<213> ORGANISM: Oryza savita

<400> SEQUENCE: 39
atggagtcgg gggtcccgcc ctgcgccgcg tgcggggacg acgcgcacgc cgcctgccgc      60
gcctgcagct acgcgctctg caaggcctgc ctcgacgagg acgccgccga gggacgcacc     120
acctgcgcgc gctgcggcgg ggagtacggc gcgcccgacc cagcgcatgg ccaggggggcg     180

-continued

```
gtcgtggagg aggaagtgga agagagccac gagccggcgg ccggcggtgt tcgcgagagg    240
gtcaccatgg ccagccaact cagcgatcac caggatgaag gagttcatgc caggactatg   300
agcacccatg ccaggacaat tagcagtgtc tctggagttg ggagtgaatt gaatgatgaa   360
tctgggaagc ccatctggaa gaacagggtg gagagctgga aggagaaaaa gaaagagaag   420
aaagcctcag caaagaaagc tgcagcaaaa gctcaagctc cacctgttga agaacagatt   480
atggatgaaa aagacttgac agatgcatat gagccacttt ctcggatcat tcctatatcg   540
aagaacaagc tcacaccttta cagggcagta atcattatgc gtctggtagt tctggggctc   600
ttctttcact accgtatcac caaccctgtt tacagcgcct ttggtctctg gatgacatca   660
gtcatatgtg gatctggtt tggattctcc tggatcctgg atcagttccc caagtggtgt   720
cctatcaatc gcgaaactta tgttgatagg ctgattgcac gatatggaga tggagaagat   780
tctgggttgg cacctgtaga tttctttgtc agtacagtgg atccattgaa agagcctcct   840
ctaatcactg cgaatactgt tctgtccatt cttgccgtgg actatccagt tgagaagatt   900
tcgtgttacg tgtcagacga tggttcggct atgctcacat ttgaatcact tgcggaaaca   960
gcagaatttg ctaggagatg ggttccattt tgcaagaagt actccattga gccacgtgcc   1020
cctgagttct acttctcaca gaagattgac tacttgaagg acaagataca cccatctttc   1080
gtcaaggagc gtcgggctat gagagggat tacgaagaat acaaggtgag gataaatgct   1140
ttggttgcta aggctcagaa gacacctgag gaaggctgga ttatgcaaga tgggacacca   1200
tggcctggga acaaccctcg tgaccaccct ggaatgatcc aggttttcct tggtgagacc   1260
ggtgctcggg actttgacgg aaatgagctt cctcggctag tctatgtttc gagagagaaa   1320
agaccagggt accaacacca caagaaagca ggggccatga acgctttggt tcgagtatcc   1380
gcagttctga caaatgcccc ttacattctt aatcttgact gtgatcacta tgttaacaat   1440
agcaaagctg ttcgtgaagc gatgtgtttc atgatggacc cttctgttgg tagagatgtc   1500
tgctatgtcc aattcccaca aaggttcgat ggcattgatc gcagcgatcg ttatgccaat   1560
aggaatgttg tgttctttga cgttaacatg aaagggcttg atggcctcca aggtccggtt   1620
tatgtgggaa ctggttgttg tttctatagg caagcgctct atggttatgg accaccatca   1680
ctgcctgcgc ttccaaagtc ttctgtctgt tcatggtgct gctgctgctg tcctaagaaa   1740
aaagctgaaa aaagtgagaa agaaatgcat agagactctc gacgtgaaga ccttgagtcc   1800
gccattttca atcttcggga aattgacaac tatgatgagt atgaacgctc gatgcttatc   1860
tcccagatga gctttgagaa gtcgtttgga ctgtcatcag tgttcataga atcaactctt   1920
atggagaatg gaggcgttcc tgagtccgca aacccatcta cactgatcaa agaggccatt   1980
catgtcatta gctgtggata tgaagagaaa actgaatggg gaaaagaggt tctccggtgg   2040
gctctcggtt ccgttgagat cttcctcagc cggcactgcc cactctggta cggctacggt   2100
ggtggtcgtc tgaaatggct ccagagattg tcctacatca acaccatcgt ctaccgttc    2160 acctctcttc ctcttattgc atactgttgc ctgcccgcca tttgcctgct cacaggcaaa   2220
ttcatcattc ccacgctctc caacgctgca accatatggt ttcttggcct cttcatctcc   2280
atcatcgtga cgagcgtcct ggagctgcgc tggagtggca tcggcatcga ggactggtgg   2340
cgcaacgagc agttctgggt catcggtggc gtctccgccc acctcttcgc cgtgttccag   2400
ggtatcctca agatgattgc tgggctggac accaacttca ccgttacggc caaggcgacg   2460
gacgacaccg agttcggcga gctgtacgtg ttcaagtgga cgacggtgct gatcccgccg   2520
```

-continued

```
acctccatcc tggtgctcaa cctcgtcggc gtggtggccg ggttctccga cgcgctcaac    2580
agcggctacg agtcctgggg cccgctcttc ggcaaggtgt tcttcgccat gtgggtgatc    2640
atgcacttgt accccttcct caagggtctc atgggtcgcc agaaccggac gcccaccatc    2700
gtcgtgctct ggtctgtcct gctcgcctcc gtcttctccc tcctctgggt caagatcgac    2760
ccgttcatcg gcagctccga gaccaccacc accaacagct gcgccaactt cgactgctga    2820
```

<210> SEQ ID NO 40
<211> LENGTH: 939
<212> TYPE: PRT
<213> ORGANISM: Oryza savita

<400> SEQUENCE: 40

```
Met Glu Ser Gly Val Pro Pro Cys Ala Ala Cys Gly Asp Asp Ala His
1               5                   10                  15

Ala Ala Cys Arg Ala Cys Ser Tyr Ala Leu Cys Lys Ala Cys Leu Asp
            20                  25                  30

Glu Asp Ala Ala Glu Gly Arg Thr Cys Ala Arg Cys Gly Gly Glu
        35                  40                  45

Tyr Gly Ala Pro Asp Pro Ala His Gly Gln Gly Ala Val Val Glu Glu
    50                  55                  60

Glu Val Glu Glu Ser His Glu Pro Ala Ala Gly Gly Val Arg Glu Arg
65                  70                  75                  80

Val Thr Met Ala Ser Gln Leu Ser Asp His Gln Asp Glu Gly Val His
                85                  90                  95

Ala Arg Thr Met Ser Thr His Ala Arg Thr Ile Ser Ser Val Ser Gly
            100                 105                 110

Val Gly Ser Glu Leu Asn Asp Glu Ser Gly Lys Pro Ile Trp Lys Asn
        115                 120                 125

Arg Val Glu Ser Trp Lys Glu Lys Lys Glu Lys Lys Ala Ser Ala
    130                 135                 140

Lys Lys Ala Ala Ala Lys Ala Gln Ala Pro Pro Val Glu Glu Gln Ile
145                 150                 155                 160

Met Asp Glu Lys Asp Leu Thr Asp Ala Tyr Glu Pro Leu Ser Arg Ile
                165                 170                 175

Ile Pro Ile Ser Lys Asn Lys Leu Thr Pro Tyr Arg Ala Val Ile Ile
            180                 185                 190

Met Arg Leu Val Val Leu Gly Leu Phe Phe His Tyr Arg Ile Thr Asn
        195                 200                 205

Pro Val Tyr Ser Ala Phe Gly Leu Trp Met Thr Ser Val Ile Cys Glu
    210                 215                 220

Ile Trp Phe Gly Phe Ser Trp Ile Leu Asp Gln Phe Pro Lys Trp Cys
225                 230                 235                 240

Pro Ile Asn Arg Glu Thr Tyr Val Asp Arg Leu Ile Ala Arg Tyr Gly
                245                 250                 255

Asp Gly Glu Asp Ser Gly Leu Ala Pro Val Asp Phe Val Ser Thr
            260                 265                 270

Val Asp Pro Leu Lys Glu Pro Pro Leu Ile Thr Ala Asn Thr Val Leu
        275                 280                 285

Ser Ile Leu Ala Val Asp Tyr Pro Val Glu Lys Ile Ser Cys Tyr Val
    290                 295                 300

Ser Asp Asp Gly Ser Ala Met Leu Thr Phe Glu Ser Leu Ala Glu Thr
305                 310                 315                 320

Ala Glu Phe Ala Arg Arg Trp Val Pro Phe Cys Lys Lys Tyr Ser Ile
```

-continued

```
                325                 330                 335
Glu Pro Arg Ala Pro Glu Phe Tyr Phe Ser Gln Lys Ile Asp Tyr Leu
            340                 345                 350
Lys Asp Lys Ile His Pro Ser Phe Val Lys Glu Arg Arg Ala Met Lys
            355                 360                 365
Arg Asp Tyr Glu Glu Tyr Lys Val Arg Ile Asn Ala Leu Val Ala Lys
            370                 375                 380
Ala Gln Lys Thr Pro Glu Glu Gly Trp Ile Met Gln Asp Gly Thr Pro
385                 390                 395                 400
Trp Pro Gly Asn Asn Pro Arg Asp His Pro Gly Met Ile Gln Val Phe
                405                 410                 415
Leu Gly Glu Thr Gly Ala Arg Asp Phe Asp Gly Asn Glu Leu Pro Arg
            420                 425                 430
Leu Val Tyr Val Ser Arg Glu Lys Arg Pro Gly Tyr Gln His His Lys
            435                 440                 445
Lys Ala Gly Ala Met Asn Ala Leu Val Arg Val Ser Ala Val Leu Thr
            450                 455                 460
Asn Ala Pro Tyr Ile Leu Asn Leu Asp Cys Asp His Tyr Val Asn Asn
465                 470                 475                 480
Ser Lys Ala Val Arg Glu Ala Met Cys Phe Met Met Asp Pro Ser Val
                485                 490                 495
Gly Arg Asp Val Cys Tyr Val Gln Phe Pro Gln Arg Phe Asp Gly Ile
                500                 505                 510
Asp Arg Ser Asp Arg Tyr Ala Asn Arg Asn Val Val Phe Phe Asp Val
            515                 520                 525
Asn Met Lys Gly Leu Asp Gly Leu Gln Gly Pro Val Tyr Val Gly Thr
            530                 535                 540
Gly Cys Cys Phe Tyr Arg Gln Ala Leu Tyr Gly Tyr Gly Pro Pro Ser
545                 550                 555                 560
Leu Pro Ala Leu Pro Lys Ser Ser Val Cys Ser Trp Cys Cys Cys Cys
                565                 570                 575
Cys Pro Lys Lys Lys Ala Glu Lys Ser Glu Lys Glu Met His Arg Asp
            580                 585                 590
Ser Arg Arg Glu Asp Leu Glu Ser Ala Ile Phe Asn Leu Arg Glu Ile
            595                 600                 605
Asp Asn Tyr Asp Glu Tyr Glu Arg Ser Met Leu Ile Ser Gln Met Ser
            610                 615                 620
Phe Glu Lys Ser Phe Gly Leu Ser Ser Val Phe Ile Glu Ser Thr Leu
625                 630                 635                 640
Met Glu Asn Gly Gly Val Pro Glu Ser Ala Asn Pro Ser Thr Leu Ile
                645                 650                 655
Lys Glu Ala Ile His Val Ile Ser Cys Gly Tyr Glu Glu Lys Thr Glu
            660                 665                 670
Trp Gly Lys Glu Val Leu Arg Trp Ala Leu Gly Ser Val Glu Ile Phe
            675                 680                 685
Leu Ser Arg His Cys Pro Leu Trp Tyr Gly Tyr Gly Gly Gly Arg Leu
            690                 695                 700
Lys Trp Leu Gln Arg Leu Ser Tyr Ile Asn Thr Ile Val Tyr Pro Phe
705                 710                 715                 720
Thr Ser Leu Pro Leu Ile Ala Tyr Cys Cys Leu Pro Ala Ile Cys Leu
                725                 730                 735
Leu Thr Gly Lys Phe Ile Ile Pro Thr Leu Ser Asn Ala Ala Thr Ile
            740                 745                 750
```

```
Trp Phe Leu Gly Leu Phe Ile Ser Ile Ile Val Thr Ser Val Leu Glu
            755                 760                 765
Leu Arg Trp Ser Gly Ile Gly Ile Glu Asp Trp Trp Arg Asn Glu Gln
        770                 775                 780
Phe Trp Val Ile Gly Val Ser Ala His Leu Phe Ala Val Phe Gln
785                 790                 795                 800
Gly Ile Leu Lys Met Ile Ala Gly Leu Asp Thr Asn Phe Thr Val Thr
                805                 810                 815
Ala Lys Ala Thr Asp Asp Thr Glu Phe Gly Glu Leu Tyr Val Phe Lys
            820                 825                 830
Trp Thr Thr Val Leu Ile Pro Pro Thr Ser Ile Leu Val Leu Asn Leu
        835                 840                 845
Val Gly Val Val Ala Gly Phe Ser Asp Ala Leu Asn Ser Gly Tyr Glu
    850                 855                 860
Ser Trp Gly Pro Leu Phe Gly Lys Val Phe Phe Ala Met Trp Val Ile
865                 870                 875                 880
Met His Leu Tyr Pro Phe Leu Lys Gly Leu Met Gly Arg Gln Asn Arg
                885                 890                 895
Thr Pro Thr Ile Val Val Leu Trp Ser Val Leu Leu Ala Ser Val Phe
            900                 905                 910
Ser Leu Leu Trp Val Lys Ile Asp Pro Phe Ile Gly Ser Ser Glu Thr
        915                 920                 925
Thr Thr Thr Asn Ser Cys Ala Asn Phe Asp Cys
    930                 935

<210> SEQ ID NO 41
<211> LENGTH: 3168
<212> TYPE: DNA
<213> ORGANISM: Oryza savita

<400> SEQUENCE: 41
atggaggcga gcgccgggct ggtggccggg tcgcacaacc ggaacgagct ggtgctgatc      60
cgggggcacg aggagcccaa gccgctgcgg gcgctgagcg gcaggtgtg cgagatatgc     120
ggcgacgagg tcggccgcac cgtcgacggc gacctcttcg tcgcctgcaa cgagtgcggc     180
ttcccggtgt gccgccctg ctacgagtac gagcgccgcg agggcaccca gaactgcccc     240
cagtgcaaga cccgctacaa cgcctcaag gggagcccga gggtgccgg ggacgaggac     300
gaggaggaca ttgacgacct ggagcacgag ttcaacatcg acgacgagaa gcagaagcag     360
ctgcagcagg atcaggatgg catgcagaac agccacatca ccgaggcgat gctgcacggc     420
aagatgagct acggggaggg ccccgacgac ggcgacggca acagccccc gctcccgccg     480
atcatcaccg gcgctcgctc cgtcccggtg agcggggagt tcccgatatc gaacagccat     540
ggccatggcg agttctcctc ttccctgcac aagcgcatcc cccctaccc ggtgtctgag     600
ccagggagtg caaagtggga cgagaagaaa gaggtgagct ggaaggagag gatggacgac     660
tggaaatcca agcagggcat cgtcgccggc ggcgcccccg atcccgacga ctacgacgcc     720
gacgtcccac tgaacgacga ggcgaggcag ccgctgtcga ggaaggtgtc gatcgcgtcg     780
agcaaggtga accgtaccg gatggtgatc atcctccgtc tcgtggtgct cggcttcttc     840
ctccggtacc gcatcctcca cccggtgccc gacgccatcc gctgtggct cacctccatc     900
atctgcgaga tctggttcgc cgtgtcgtgg atcctcgacc agttcccaa gtggtacccg     960
atcgacaggg agacctacct cgaccgcctc tccctccgct acgagcgcga gggggagccg    1020
```

```
tcgctgctgt cggcggtgga cctgttcgtc agcacggtgg atccgctcaa ggagccgccg    1080
ctggtcacgg ccaacaccgt gctgtccatc ctcgccgtcg actacccgt cgacaaggtg     1140 tcctgctacg tctccgacga cggcgcgtcc atgctcacgt tcgagtcgct gtcggagacg    1200
gcggagttcg cccgcaagtg ggtgccattc tgcaagaagt tcagcatcga gccccgcgcc   1260
ccggagttct acttctccca gaaggtcgac tacctcaagg acaaggtcca tcccaacttc    1320
gtccaggagc gccgcgccat gaagagagag tacgaggagt caaggtgag gatcaacgcg    1380 ctggtggcga aggcgcagaa ggtgccggcg gaagggtgga tcatgaagga cgggacgcca    1440
tggccgggga caacacccg cgaccacccg ggcatgatcc aggtgttcct cggccacagc    1500
ggcggccacg acaccgaggg caacgagctc ccccgcctcg tctacgtctc ccgtgagaag    1560
cgccccggct ccagcacca agaaggcc ggcgccatga acgccctcat tcgtgtgtcg    1620
gccgtgctga cgaacgcgcc gttcatgctc aacttggatt gcgatcacta catcaacaac    1680
agcaaggcca tcaggaggc gatgtgcttc ctcatggatc cgcaggtcgg acggaaggtt    1740
tgctacgtgc agttcccgca gaggttcgac ggcatcgacg tccacgaccg atacgccaac    1800
cgcaacaccg tcttcttcga catcaacatg aaggggcttg atgggatcca gggcccggtg    1860
tacgtcggga cagggtgcgt gttcaggcgg caggcgctgt acggatacaa cccacccaag    1920
ggacccaaga ggcccaagat ggtgacctgc gactgctgcc cttgcttcgg gaggaagaag    1980
cggaagcacg gcaaggacgg cctccggag gccgtcgccg ccgacggcgg gatggacagc    2040
gacaaggaga tgctcatgtc gcagatgaac ttcgagaagc ggttcgggca gtcggcggcg    2100
ttcgtgacgt cgacgctgat ggaggaaggc ggcgtcccgc cgtcgtccag ccccgccgcg    2160
ctcctcaagg aggccatcca tgtcatcagc tgcggctacg aggacaagac cgactggggt    2220
ctcgagctgg ggtggatcta cgggtcgatc acggaggaca tcctaacggg gttcaagatg    2280
cactgccgcg ggtggaggtc ggtgtactgc atgccgaaga gggcggcgtt caagggtca    2340 gcgccgatca acctatctga ccgtctcaac caggtgctcc ggtgggcgct cggctccgtc    2400
gagatcttct tcagccggca cagcccgctc tctacggct acaagaacgg caacctcaag    2460
tggctcgagc gcttctccta catcaacacc accatctacc ccttcacttc tctcccctc    2520 ctcgcctact gcacccctacc cgccgtctgc ctcctcaccg gcaagttcat catgcctccg    2580
attagcacgt ttgcgagttt gttcttcatc gcgctcttca tctccatctt cgcgacgggc    2640
atcctggaga tgaggtggag cggggtgagc atcgaggagt ggtggaggaa cgagcagttc    2700
tgggtcatcg gcggcgtgtc ggcgcacctg ttcgcggtgg tgcagggcct gctcaaggtg    2760
ctggccggga tcgacaccaa cttcaccgtc acgtccaagg ccaccggaga cgaggacgac    2820
gagttcgcgg agctctacgc cttcaagtgg accaccctcc tcatcccgcc caccacgctg    2880
ctcatcctca acatcatcgg cgtcgtcgcc ggcgtctccg acgccatcaa caacggctcc    2940
gaggcgtggg gcccgctctt cgggaagctc ttcttcgcct tctgggtcat cgtccacctc    3000 tacccttcc tcaagggct catggggag cagaaccgga cgcccaccat tgttgtcatc     3060
tggtccgtgc tgctcgcctc catcttttcc ttgctctggg tcaggattga tcccttcacc    3120
atcaaggcca ggggccctga cgtcaggcag tgcggcatca actgctga                3168
```

<210> SEQ ID NO 42
<211> LENGTH: 1055
<212> TYPE: PRT
<213> ORGANISM: Oryza savita

<400> SEQUENCE: 42

-continued

```
Met Glu Ala Ser Ala Gly Leu Val Ala Gly Ser His Asn Arg Asn Glu
1               5                   10                  15

Leu Val Leu Ile Arg Gly His Glu Glu Pro Lys Pro Leu Arg Ala Leu
            20                  25                  30

Ser Gly Gln Val Cys Glu Ile Cys Gly Asp Glu Val Gly Arg Thr Val
        35                  40                  45

Asp Gly Asp Leu Phe Val Ala Cys Asn Glu Cys Gly Phe Pro Val Cys
    50                  55                  60

Arg Pro Cys Tyr Glu Tyr Glu Arg Arg Glu Gly Thr Gln Asn Cys Pro
65              70                  75                  80

Gln Cys Lys Thr Arg Tyr Lys Arg Leu Lys Gly Ser Pro Arg Val Pro
                85                  90                  95

Gly Asp Glu Asp Glu Asp Ile Asp Leu Glu His Glu Phe Asn
                100                 105                 110

Ile Asp Asp Glu Lys Gln Lys Gln Leu Gln Gln Asp Gln Asp Gly Met
            115                 120                 125

Gln Asn Ser His Ile Thr Glu Ala Met Leu His Gly Lys Met Ser Tyr
130                 135                 140

Gly Arg Gly Pro Asp Asp Gly Asp Gly Asn Ser Thr Pro Leu Pro Pro
145                 150                 155                 160

Ile Ile Thr Gly Ala Arg Ser Val Pro Val Ser Gly Glu Phe Pro Ile
                165                 170                 175

Ser Asn Ser His Gly His Gly Glu Phe Ser Ser Ser Leu His Lys Arg
            180                 185                 190

Ile His Pro Tyr Pro Val Ser Glu Pro Gly Ser Ala Lys Trp Asp Glu
        195                 200                 205

Lys Lys Glu Val Ser Trp Lys Glu Arg Met Asp Asp Trp Lys Ser Lys
    210                 215                 220

Gln Gly Ile Val Ala Gly Gly Ala Pro Asp Pro Asp Asp Tyr Asp Ala
225                 230                 235                 240

Asp Val Pro Leu Asn Asp Glu Ala Arg Gln Pro Leu Ser Arg Lys Val
                245                 250                 255

Ser Ile Ala Ser Ser Lys Val Asn Pro Tyr Arg Met Val Ile Ile Leu
            260                 265                 270

Arg Leu Val Val Leu Gly Phe Phe Leu Arg Tyr Arg Ile Leu His Pro
        275                 280                 285

Val Pro Asp Ala Ile Pro Leu Trp Leu Thr Ser Ile Ile Cys Glu Ile
    290                 295                 300

Trp Phe Ala Val Ser Trp Ile Leu Asp Gln Phe Pro Lys Trp Tyr Pro
305                 310                 315                 320

Ile Asp Arg Glu Thr Tyr Leu Asp Arg Leu Ser Leu Arg Tyr Glu Arg
                325                 330                 335

Glu Gly Glu Pro Ser Leu Leu Ser Ala Val Asp Leu Phe Val Ser Thr
            340                 345                 350

Val Asp Pro Leu Lys Glu Pro Pro Leu Val Thr Ala Asn Thr Val Leu
        355                 360                 365

Ser Ile Leu Ala Val Asp Tyr Pro Val Asp Lys Val Ser Cys Tyr Val
370                 375                 380

Ser Asp Asp Gly Ala Ser Met Leu Thr Phe Glu Ser Leu Ser Glu Thr
385                 390                 395                 400

Ala Glu Phe Ala Arg Lys Trp Val Pro Phe Cys Lys Lys Phe Ser Ile
                405                 410                 415
```

-continued

```
Glu Pro Arg Ala Pro Glu Phe Tyr Phe Ser Gln Lys Val Asp Tyr Leu
            420                 425                 430
Lys Asp Lys Val His Pro Asn Phe Val Gln Glu Arg Arg Ala Met Lys
        435                 440                 445
Arg Glu Tyr Glu Glu Phe Lys Val Arg Ile Asn Ala Leu Val Ala Lys
    450                 455                 460
Ala Gln Lys Val Pro Ala Glu Gly Trp Ile Met Lys Asp Gly Thr Pro
465                 470                 475                 480
Trp Pro Gly Asn Asn Thr Arg Asp His Pro Gly Met Ile Gln Val Phe
            485                 490                 495
Leu Gly His Ser Gly Gly His Asp Thr Glu Gly Asn Glu Leu Pro Arg
            500                 505                 510
Leu Val Tyr Val Ser Arg Glu Lys Arg Pro Gly Phe Gln His His Lys
        515                 520                 525
Lys Ala Gly Ala Met Asn Ala Leu Ile Arg Val Ser Ala Val Leu Thr
530                 535                 540
Asn Ala Pro Phe Met Leu Asn Leu Asp Cys Asp His Tyr Ile Asn Asn
545                 550                 555                 560
Ser Lys Ala Ile Arg Glu Ala Met Cys Phe Leu Met Asp Pro Gln Val
            565                 570                 575
Gly Arg Lys Val Cys Tyr Val Gln Phe Pro Gln Arg Phe Asp Gly Ile
            580                 585                 590
Asp Val His Asp Arg Tyr Ala Asn Arg Asn Thr Val Phe Phe Asp Ile
            595                 600                 605
Asn Met Lys Gly Leu Asp Gly Ile Gln Gly Pro Val Tyr Val Gly Thr
    610                 615                 620
Gly Cys Val Phe Arg Arg Gln Ala Leu Tyr Gly Tyr Asn Pro Pro Lys
625                 630                 635                 640
Gly Pro Lys Arg Pro Lys Met Val Thr Cys Asp Cys Pro Cys Phe
            645                 650                 655
Gly Arg Lys Lys Arg Lys His Gly Lys Asp Gly Leu Pro Glu Ala Val
            660                 665                 670
Ala Ala Asp Gly Gly Met Asp Ser Asp Lys Glu Met Leu Met Ser Gln
        675                 680                 685
Met Asn Phe Glu Lys Arg Phe Gly Gln Ser Ala Ala Phe Val Thr Ser
    690                 695                 700
Thr Leu Met Glu Glu Gly Gly Val Pro Pro Ser Ser Pro Ala Ala
705                 710                 715                 720
Leu Leu Lys Glu Ala Ile His Val Ile Ser Cys Gly Tyr Glu Asp Lys
            725                 730                 735
Thr Asp Trp Gly Leu Glu Leu Gly Trp Ile Tyr Gly Ser Ile Thr Glu
            740                 745                 750
Asp Ile Leu Thr Gly Phe Lys Met His Cys Arg Gly Trp Arg Ser Val
    755                 760                 765
Tyr Cys Met Pro Lys Arg Ala Ala Phe Lys Gly Ser Ala Pro Ile Asn
770                 775                 780
Leu Ser Asp Arg Leu Asn Gln Val Leu Arg Trp Ala Leu Gly Ser Val
785                 790                 795                 800
Glu Ile Phe Phe Ser Arg His Ser Pro Leu Leu Tyr Gly Tyr Lys Asn
            805                 810                 815
Gly Asn Leu Lys Trp Leu Glu Arg Phe Ser Tyr Ile Asn Thr Thr Ile
            820                 825                 830
Tyr Pro Phe Thr Ser Leu Pro Leu Leu Ala Tyr Cys Thr Leu Pro Ala
```

```
                   835              840              845
Val Cys Leu Leu Thr Gly Lys Phe Ile Met Pro Pro Ile Ser Thr Phe
            850              855              860
Ala Ser Leu Phe Phe Ile Ala Leu Phe Ile Ser Ile Phe Ala Thr Gly
865              870              875              880
Ile Leu Glu Met Arg Trp Ser Gly Val Ser Ile Glu Trp Trp Arg
                    885              890              895
Asn Glu Gln Phe Trp Val Ile Gly Val Ser Ala His Leu Phe Ala
                900              905              910
Val Val Gln Gly Leu Leu Lys Val Leu Ala Gly Ile Asp Thr Asn Phe
            915              920              925
Thr Val Thr Ser Lys Ala Thr Gly Asp Glu Asp Glu Phe Ala Glu
            930              935              940
Leu Tyr Ala Phe Lys Trp Thr Thr Leu Leu Ile Pro Pro Thr Thr Leu
945              950              955              960
Leu Ile Leu Asn Ile Ile Gly Val Val Ala Gly Val Ser Asp Ala Ile
                965              970              975
Asn Asn Gly Ser Glu Ala Trp Gly Pro Leu Phe Gly Lys Leu Phe Phe
            980              985              990
Ala Phe Trp Val Ile Val His Leu Tyr Pro Phe Leu Lys Gly Leu Met
            995              1000              1005
Gly Arg Gln Asn Arg Thr Pro Thr Ile Val Val Ile Trp Ser Val
      1010              1015              1020
Leu Leu Ala Ser Ile Phe Ser Leu Leu Trp Val Arg Ile Asp Pro
      1025              1030              1035
Phe Thr Ile Lys Ala Arg Gly Pro Asp Val Arg Gln Cys Gly Ile
      1040              1045              1050
Asn Cys
    1055

<210> SEQ ID NO 43
<211> LENGTH: 2500
<212> TYPE: DNA
<213> ORGANISM: Oryza savita

<400> SEQUENCE: 43
gtgggaagac ccagagtgtg caaatggggg caaatggact gtgccatgta gcaggaagac      60
cacccttgag aacatgtggc ttgaaacggt acatttcctc taaaatcatt gcttagtttg     120
gtcggaggct ctgaagtgct ttggatataa catctgttgc ttgacctatc ttctaaagtt     180
tctatcattt ctgctgacaa acttttcgaa catgcagctg atggctctga ttggagagca     240
gtttgatgaa agtgaggaaa tttgtggagt tgttgctagt gtccgccaga gaggagacaa     300
gcttgcattg tggactagga ctgccagcaa tgaagccgtt caggttggtt ttttgaaaaa     360
tactgtagta taacaatatg agtgtatttg ctcatatatt tgatgtagca agcaatttaa     420
tctgtagtac attgttttcc caccacctct atagtcaaca ttaaacatgt tgttcaaagc     480
tgccatgttc tctttagtat tctgttcatc aaatttgtcc acttcactaa ttttgctcaa     540
tttatttggg atacagttga caagtatttg atggtaggct agactttaca ttttgtttgc     600
ttttctgagt tccatatctt atttgatacc atttatctgc ttgttttatt ggaacaattt     660
atttctgtct tgagtagaga actattttgt ttgatttgac tttcagtcaa tttaagctat     720
gcttgataaa gcctattgtg tgagctaaat ccctattagg taatttgatg ccgtgtcaaa     780
gagactcaag actcttaaag tcatctggtg cccacatcat gcaatactat tgatggttga     840
```

-continued

```
tgcatccatt atgattgcca tctattttgt ttctgatata gtgatatatt gcattggtat    900
gataacaaaa acataaacac aacatcaatg ctggtttgca ttgatgagca ccataatagt    960
actaaaacgt ttcacatttt gcaatgaagc aatcgctttg taattcccta actcttcaac   1020
catcctgtct cttttttctg cacttcataa attttcatt gttaccacag gtctgtgcat   1080
tcaaaggaca tctctatatg tgttttttt tgagatttga gcattacctt ttgaaacatg   1140
gcttcaacca tagaccaatg ataactagag aaaactaaca tgcctttgct ttgcaggtaa   1200
acattggcaa gaaatggaag gagattgttg actacaatga taagatggtc tacagcttcc   1260
atgtatgtgt ttagactatt tttgttgtct caataacata ttatttttta gtcacctgta   1320
gaatagatca aatacgtcca tagctcattc tatttggatg gtgcttcaac ttcaatgcag   1380
gatgacgcca agagggagaa accaagcaga ggtggacggt acaacgtgta agtcaccgca   1440
aaacgttgca gcttggatag tggccatcga gtggtgtgcc gataccggcg cctgttcttt   1500
acagcctcag ctagtgttgt tgtccgaggc aattttccg acctattgtg ttgctttcct   1560
ctctgatagc ttatggtaaa agatacaaag atgttgagga gtttgtacgc cacttaattt   1620
tgctcgtaac atacattgac aatcaagagg agccatggca ttgcgatctg cttacacggc   1680
atattcttac tggatggtgt acactactta ccctttttaa tgcaagcatc aatccattgc   1740
ttttctcact gcacacctga ttcgtactga aaacgtgaaa cataaaaaa aacaaaaatc   1800
tagctgatgt tggctctcgg ggcctcgagt ctagtttgtc ctagatggct aacctgatat   1860
gtgttggtca cgctcacgtt tgaaccgaga agagtgtgt gtgtgtgtgt gtcggcgtgc   1920
tgctacacca gagcctccct gaatcgcaat gcgtgttaac gccagcatcg caggatttca   1980
tctcacttga caggttcaga tggccttcct cctaccgtct gccatttata cacgcagtga   2040
cttaacgctt acacgagccg gatggcccgg atctccccc tgcaccatct caccagaaaa   2100
acggtgaggc gtcaccgcaa cccacccacc aaacacatcc acgtcccttc accgttggcc   2160
ttcgattttg cttcagctgc actacgaccc ctccaacaca tttccctcgc gtctcgttgc   2220
gatctcacct tacgacgatc tcgttccagc agcagcagca tcggcagcgg cggcttgctt   2280
ccgaagcgag caatgcatgg cgcgcgcggc cgcgtgcgtg cgtgccttgg cttgcgctct   2340
aatcaaaccg ggacgcccca actcacggtt ggtgcgggac gccaccccgc cacccttaccg   2400
cccccgcctc cctgcatctg atcatcaacc agctgctata tcacctagct agccgccgcc   2460
tcctcctcgc ccaccaacgt cgcttccccg gcacctcacc                         2500
```

<210> SEQ ID NO 44
<211> LENGTH: 2500
<212> TYPE: DNA
<213> ORGANISM: Oryza savita

<400> SEQUENCE: 44

```
gatcaatttg gaccgagtaa ctttgttatc ttttgagttt ggatcacccc caaacaattt     60
cttcagtact catcaagaat ctcaatcaaa tcaattttga tacaacgttg aacttccccg    120
tctatatgca ggtaatatat tcagcagcat ggtgggtgga tacaaatagt aaagagagtt    180
aggtggtcca aaccgaaaat atggtaaagt tacccaggtc caaagtgaaa agattagttt    240
atggatggtc caaagtaaaa cttaggcgat aaaagataga ttagactgta cttttttact    300
ttttctctaa tagttactac tgtaagtaag cgccgcagct ttggcaaatg aaaaatgggt    360
cgatcacatc aggcatgatc tgaacttgac attggttcag gaattctttg cggtctacca    420
```

```
gcttgtttgg agcagcgaac tagcattatc agaagggact gaggacacgg tcatttggag    480
atggatgaat actggcaaat acacagcaaa atcggcatac atgcccagt tcgctggcag     540
agaggaatca agggcagcca ccgtgatttg gacatcatgg gcactgtcca agtgcaagaa    600
ttttgcttgg ttattactgc ataacagatt acggacagcg gatcgattgc aaatcagaca    660
gtggccaaat tgttactttt gtcagctttg ctacagaaac ctggaaacgg cgcagcactt    720
gttcaaggat tgcccgttca cacgagaggt ctggaacaga gtagctgcga gactggaatg    780
cagtcaatta tttctagcgc acaatccaga ggagaagctg attgaatggt gggaaaagag    840
gacatcccag caggacaaga gacaaacaaa gggattgcga tcgctacacg tgcttctctg    900
ttgggaagta tggtgtgaaa gaaatagacg aatcttcaag gataaataac tctcaatgct    960
tcaggtggtg gcgaaggtgc tggatgaggt ccagttatgg tctgtttgtg gggctaaaga   1020
cattgtgaga atagcacatt aaaactatac gttgtggcaa gctgtttttt ttatatactt   1080
tgggtgtgtt tagttcacat caaaattaga gtttggttg aaatttgaac gatgtgacgg    1140
aaaagttaaa agtttgtgta tagaaaagtt ttgatgtgat gaaaaagtta aagtttgaa    1200
taaaaagttt ggaactaaac tcggccttcc tcttcctttt cctctctaat caccgtgggt   1260
gattatgtac agttcttcct ctgcttaata taaaatcagc tcaggctgac ttaggtttta   1320
aaaaaaaaag taagcgccga gtcagtgcaa acgagggagt taaattgata tggttttgtc   1380
tgtcaaggtg ccgtttctat ggttggagga ggaaaatgaa attaggggaa tagaacagtc   1440
gcaatccaaa agctattgtt ctctcttcta cggtagttga tagttcgata cgtgtgtttg   1500
atgtgagaga ctgagaggag tgcacggtgc acctgccccg taaggacgcg gaactacatt   1560
atcagaggct aggccggtac tgttatacgc gacgttcacg aatcacgatg cgtaaaaaag   1620
tgaagcatga aacagtacta ggctctccac gggccacatc atgaaaaaac tggtgcgacg   1680
ccacgcttaa caatttgtcg gtcgtaaact cgtaaagtta aaagccccac gacattgtca   1740
accaatatct cagcacatga acttctctaa cgagtacaac gaaaccgcat ccgcaaaagc   1800
gccgtgaacc aaagctcttg ccgtgctgtg ccgtgccggt ggccgtgaac atgtggaaca   1860
cgaagaactc ttgcgcgaga tcggagcacc tgacctccca cctcgcgtcc ggcccgtcgc   1920
cgtcgcagca agcgggctgt caaaaacgac gccacagcgc gagcgctctc gccgatccgg   1980
cggacccacc ctcctcacct cgcgcaccaa ccgcccgttc gctagtccga tcccccaccc   2040
ctcatccccc ctacgccttg caggttacgc gcctcgccgc ggccaacgca aaccaaacca   2100
aatcccccgt caccttcgct tcgaaacccc gcaaaacccc atggaagaaa acaccgaaca   2160
cctgccgcgc gcacgcctcc tcctcccccg cctctcctcc tctctcccgt tccatgtccg    2220
ctcaaccttg cttccattct ttccatccac ccgccgatcg acgcgatgcc gacgcccaa    2280
cccccaccac cgcctgccag cgccacccca cctcgcgcct ctgcggctat ggctatatca   2340
ccatgcctcc aacctccggt acgcttagcc tctctctctc tcccctccc attctgcgca   2400
ttgctctctg cgcgcggtcg cgtgctgctg ctcgcggcgc cccggagcgt ctcctttggg    2460
ggagaggaga ggagaggaga ggagaggggg gtgagccatg                          2500
```

<210> SEQ ID NO 45
<211> LENGTH: 2500
<212> TYPE: DNA
<213> ORGANISM: Oryza savita

<400> SEQUENCE: 45

```
ctattatgat ctaacggtct attttttttc ttcttttctc cgattaatgt gagaattttt     60
```

-continued

```
agcccccaca gcgaacatgg tgtctccttt caaagctgtc tgagtgttgt cggtgacggt      120
gttataatag atagatagat agatgtgtga cggtgtgagt agtttatata tatgctgtat      180
gagtgttgtc atttattttt catacgaggg gtatcccctt gatggtttaa aacggtttct      240
ccatattttc atagagcacc gctacacgta ctaaatttt cttactaaat ttgtactaac      300
aatcatctca accgtttgat tcaagtagat ggaagttata aaaaatctag atgcactcat      360
agcatgacat gtcagtgtta gtaaaaattt agtaagaaaa agttagtacg tatagacttt      420
tccattttca tatttccctg ccatcattcc tcgcaagaaa aaaaaagtgc tacatctctg      480

taggtgcaat ggtacaaatg gacgcttata caatgcgcat taaactgcta atttgtatta      540

tacatatgta taaaaatat atagatacgt ataacatga gagacttata gagggagaaa      600
cccaccgcgc cctcgagaga gtggttgcgt ataaggcgcc cccaacgtac gggcgcaaga      660 aaacagcagc ттаataгcg tagaatgca caatcgtctt agcaacttta cатcтccсттт      720 cttccaaatt gcaaaaccaa tattattag aacatgagca acactgcagc tagccgaggg      780
agagaacaca tcaactcccg gcccaatata tagcacacca caaggaacag agaacagcag      840
gccggcgcaa ggaggggcta gccccagtaa gctacagttt ccataгcgac agtgatactt      900 cgcctttaac acgaggcaga tctcgcaaca acgacaggat gatcaccagc caaaatcaaa      960
acttgcgtcc taagatgctt cagccagctg ctgctgctgc tgccctcac ctgcatttca      1020 catccaggat ggggacgttt cttcctccag gtcgtcactg gacgcaacga catgatatgc      1080
tgcgtacctt cggtgacagc agaagacgca tctgccaggt ttcatcgtga cggттттctтc      1140

тттcстccтттт ttccggcgat gatcagatt catatgttca gatgccaatg gaagctgaag      1200 cттттcgтggc gtttttgtat atgtgtgt gt gcgctacacg atcacaacgt gtggttggtg      1260
gcaaactggc agggtgtgtg atggatgatg ctaccaaact aaggtgcctg gtcaccttct      1320
ctgaatcgct ggggatgcca agaaaaaaaa agaaaagaa aaggtgatcg atcgatgcct      1380 cgттттgcтта tggctcaatg ctgtgactcg atcgatgggc agaaacgtgc gtttggcttg      1440
ggacagacca acttactcta gacttgaaca gcaaтттттcg gttggatttg agttgatagg      1500
aacgactatt tgtgcaccgc aagtagaaag aaatcagttc aggagtacta gggacatctt      1560
gtcaaaaaga ctagttttga tcggtttagc tattgaactc ggaatccatt tcttgtaatc      1620

tgtcactga actgaaaaaa agtggttgtc cttcacttac agcttccagt aatcccgtat      1680
aaacaatggc gtcctatatc aaatgtgcat tatctagact tccgtataaa caatgtgcag      1740 actctagaaa атттggacттc cttggacgca taatctcgtc ggtgtgcgtc agtcattcca      1800
gtgtactaat ctactccagt aatcaactgg agaggacttc cgtactcacc aaactaatct      1860
tgaagcaagc tcaggtagaa ttactcgcgg caaccatgca tcaaatttta aatgccccaa      1920

tattggtact actacaacta tactactacc actcaccaat ataatctagc cctttaat      1980 cttgtttgtt taaataaaag agcaaagggg agaaaatga ggagatggcg ggaaagccaa      2040
gcatcggttg gtgactgatc tcgcgggttg gtccgcgaac gcagcctgac aacaacggca      2100
gcagctgcat ctgcagcagc agcagcagca gccaacgcac gcacgcaggc ctcctctcct      2160
ctcctccctc gcgccaacgc gccaccatgc aaagcaagca agcaacacac aaccccttcg      2220
cttcacttgg cggcaacgga gacgccgcac ccaaccaacc cgccaccgtc tcccacacgc      2280
gccgacgcct cctcgacccc tcctctcccg cgcgcgcgcg aacaaacagc cacccctcac      2340
ctctcgatcc ctcccacccg ccaaaacccc ccctcccata tagcccctgc cacaagcggg      2400
```

```
tggagcaagc gatcgatcgc ccttcctcct cctcctctcc tccttcctgc gtcgcctccc    2460
tgatcagccg cagctcgttg ccggccgttg ttgcgcggcc                          2500
```

<210> SEQ ID NO 46
<211> LENGTH: 2520
<212> TYPE: DNA
<213> ORGANISM: Arabidopsis thaliana

<400> SEQUENCE: 46

```
ttaaggtgat tgttaatta acaatatcaa aaaatcttc ctaaaaaaaa ttaacccata       60
catgtgatgc tatagttagt agtactagaa ctaaacccat ccagtagtaa atctaataaa    120
cttcattttt ttttgtattt tgttgacttg cacttcgaca tactctatat aaacacaacc    180
atattagaga tcagatccca acaccactaa taaactcaac atggctagat ccttgttgct    240
ctcgctaacc ctcacattcc tcttcgccgg aattgtctca gctcgtgact ggaacatcct    300
gagccagctc aaaggaacca caaccaccac gaagactagc caaaccggcg tcacatcttt    360
gaaagctccc aacctaaacg gatactgtga gagctggaga gtcaacgtgg agcttaacaa    420
cataagggac tttaaggtgg ttccacagga atgtgtatgg ttcgtccaaa agtacatgac    480
ctcatctcaa tacgaagatg acgtggagag agccgtcgat gaagccatcc tctacctcgg    540
aaaaacttgt tgcgagaaga agacatgcga tggcatggat gcttggatct ttgacattga    600
tgacactctt ctctcaacca ttccttacca aagagcaac ggttgtttcg ggtaaataaa    660
ctaaacttaa ccatatacat tagccttgat tcggttttttg gtttgattta tggatattaa    720
agatccgaat tatatttgaa caaaaaaaaa tgattatgtc acataaaaaa aaattggctt    780
gaattttggt ttagatgggt ttaaatgtct acctctaatc atttcatttg ttttctggtt    840
agctttaatt cggtttagaa tgaaaccggg attgacatgt acattgatt tgaaacagtg    900 gtgagcaact gaacacgacc aagttcgagg aatggcaaaa ttcgggcaag gcaccagcgg    960
ttccacacat ggtgaagttg taccatgaga tcagagagag aggtttcaag atcttttga    1020 tctcttctcg taaagagtat ctcagatctg ccaccgtcga aaatcttatt gaagccggtt    1080
accacagctg gtctaacctc cttctgaggt tcgaatcata tttaataacc gcattaaacc    1140
gaaatttaaa ttctaattc accaaatcaa aagtaaaac tagaacactt cagataaatt    1200
ttgtcgttct gttgacttca tttattctct aaacacaaag aactatagac cataatcgaa    1260
ataaaaaccc taaaaccaa attatctat taaaacaaa cattagctat ttgagtttct    1320
tttaggtaag ttatttaagg ttttggagac tttagatgt tttcagcatt tatggttgtg    1380
tcattaattt gtttagttta gtaaagaaag aaaagatagt aattaaagag ttggttgtga    1440
aatcatattt aaaacattaa taggtattta tgtctaattt ggggacaaaa tagtggaatt    1500
ctttatcata tctagctagt tcttatcgag tttgaactcg ggttatgatt atgttacatg    1560
cattggtcca tataatctat tgagcaatca atataattcg agcattttgg tataacataa    1620
tgagccaagt ataacaaaag tatcaaacct atgcagggga aagatgatg aaaagaagag    1680 tgtgagccaa tacaaagcag atttgaggac atggcttaca agtcttgggt acagagtttg    1740
gggagtgatg ggtgcacaat ggaacagctt ctctggttgt ccagttccca agagaaccctt   1800 caagctccct aactccatct actatgtcgc ctgattaaat cttatttact aacaaaacaa    1860
taagatcaga gtttcattct gattcttgag tctttttttt ctctctccct cttttcattt    1920
ctggtttata taaccaattc aaatgcttat gatccatgca tgaaccatga tcatctttgt    1980 gtttttttttt ccttctgtat taccattttg ggcctttgtg aaattgatt tgggcttttg     2040
```

```
ttatataatc tcctctttct ctttctctac ctgattggat tcaagaacat agccagattt   2100
ggtaaagttt ataagataca aaatattaag taagactaaa gtagaaatac ataataactt   2160
gaaagctact ctaagttata caaattctaa agaactcaaa agaataacaa acagtagaag   2220
ttggaagctc aagcaattaa attatataaa aacactaact acactgagct gtctccttct   2280
tccaccaaat cttgttgctg tctcttgaag ctttcttatg acacaaacct tagacccaat   2340
ttcactcaca gtttggtaca acctcagttt tcttcacaac aaattcaaac atcttaccct   2400
tatattacct ctттатстст тсаатсатса аасасатад тсататсат ттстстаccc    2460 caccttctgc tctgcttccg agagctcagt gtacctcgcc atggaaccaa acaccatggc   2520
```

<210> SEQ ID NO 47
<211> LENGTH: 30
<212> TYPE: DNA
<213> ORGANISM: Artificial sequence
<220> FEATURE:
<223> OTHER INFORMATION: Primer

<400> SEQUENCE: 47

```
tattttgttc tagagcactt cgacatactc                                       30
```

<210> SEQ ID NO 48
<211> LENGTH: 28
<212> TYPE: DNA
<213> ORGANISM: Artificial sequence
<220> FEATURE:
<223> OTHER INFORMATION: Primer

<400> SEQUENCE: 48

```
ggtgtttggt tccatggcga ggtacact                                         28
```

<210> SEQ ID NO 49
<211> LENGTH: 3000
<212> TYPE: DNA
<213> ORGANISM: Arabidopsis thaliana

<400> SEQUENCE: 49

```
ttactaagat gacgggatcc accgtttccc gccaagaaaa cagccctaag agaccaaacg     60
acagtaacgg cgaattcaaa cgtctattag ttcccgaaac ctctcagcca gaggaggacg    120
agcttcacga atcgccaccg gagaatcaga tcctgaacgt agaagaagac agagacaaaa    180
cctacgattc agttccgcca ttctcatggg caaagctatg gaaattcacc ggacctggat    240
ttctcatgag catcgcgttt ctagatccag gaaatatcga aggagattta caagccggag    300
ctgtggctgg ttactctctc ctatggcttc ttctatgggc gacgctaatg ggacttctga    360
tgcagcttct ctctgctcgt atcggtgtcg ccacgggtcg acatttagcg gagatttgtc    420
gaagtgagta tccttcgtgg gcgcgaatct tgctttggtt catggcggag gttgctttga    480
tcggagctga tattcaagaa gtcatcggaa gcgcgatcgc tcttcagatt ttgactcgag    540
ggtttttacc tatttgggtt ggtgttatca tcacatcatt tgattggtaa gcaaaactag    600
gtctttggct tagaacgcct ttaggatcac ctgagttatt aaaaaacaaa ataggtcttt    660
ttgcggtgtt gtttgtaaca caagttttga tttgtgttgt ttgtgaaaaa acagcttctt    720
gatttcgtat ttggagaaat gtggaatgag gaaattagaa ggtcttttcg cggttttgat    780
tgcgacaatg gcgctttcgt tcgcttggat gtttaatgaa actaagccaa gtgttgaaga    840
actattcata ggtaagtttg taagattaag cattgtctct tatttgatgt catttcttga    900
```

```
tttggtttta tcttgatgat gattttgaaa ggtattatta ttccgaaact cggatcaaag    960
acgattagag aagctgttgg agttgtggga tgtgtaataa cgcctcacaa tgtgttcttg   1020
cattcagctt tagtgcagtc taggaagacg gatccaaagg agataaacag agttcaagaa   1080
gctcttaact actatacaat cgaatcgtca gccgcgcttt ttgtttcgtt catgatcaat   1140
ttgtttgtaa ctgcggtttt cgcgaaaggg ttttatggaa ccaaacaagc tgatagtata   1200
ggactggtta acgcgggata ttacctacaa gagaaatatg gcggtggtgt tttcccgata   1260
ctatacattt gggggattgg tttattagct gctggacaaa gcagtactat aaccgggact   1320
tatgctggac agtttataat ggaagggttc ttagatcttc aaatggaaca atggctatca   1380
gcttttataa cgagaagctt tgctattgta cctactatgt tgttgctat tatgtttaac    1440
acatccgagg gctcgctcga tgttttaaac gaatggctta acattcttca gtcgatgcag   1500
attcctttcg cggttattcc tcttttgact atggtttcta atgaacatat catgggtgtc   1560
ttcaagatcg gaccttcgct tgaggtaaag caattttttg tcatctctct ttattgttat   1620
gtgcttttga ttgtaacgag ttagttggga tctttgcaga agctagcttg gactgtggcg   1680
gtgtttgtga tgatgataaa tgggtatctt cttctagatt tcttcatggc tgaagtggaa   1740
gggtttcttg ttgggtttct ggttttttggt ggagtagttg gatacatcag tttcatcatc   1800
tatcttgttt cttatagaag ctcacaatct tcttcctggt cgagtttaga aatgtcagag   1860
agagttgttt ccacagagac gtagaaaccc ataactttag tattcttcaa cccttacaac   1920
ttatctgagc aaaatcagaa ggtcgaattt gatggatgat tttgctgtat ttggtcaacg   1980
gttttatttg agacagtaga ccagaggaaa ctcagatgtg atgatgcaaa gactgaattg   2040
gttaagagtg tagattgatt tgttctaaca ttgcaaatgt agagtagaat tatgcaaaaa   2100
acgttaatga acagagaagt gattaagcag aaacaaaatt agagaagtga tattatatct   2160
caaaatttat ttttggtaca gctaaagctc aaattgttat agagattaga gatattaaac   2220
caaatgacga gtgttttctt tagtagtaaa cggtgaaaat tctcttctga caaagacaat   2280
taaaatttta ggtttaagac tttaatattt gtcacaaatt gtcatttacc taaataaaaa   2340
aaaaactaaa tattttttt agatacatat gtgtcttata atttaactta aaatttttaa    2400
ttttatgtct taaataattg tttacactat aaatttaaat attttaatgc taaaattaat   2460
ttgattcaaa aaagtgattt taattcttat ttttcttata gaaagttggt gattgaaaag   2520
atttacttaa aaattataac aacttcaatg gtgaataacc cgacccgaat aaaccggata   2580
taacaacttc aatgttagct tgatatagaa agtacggtga cgcttaggag gcaagcaagc   2640
tagtatctgc cgctggttag agacaaagaa catgtgtcac tcctctcaac taaaactttc   2700
cttcactttc ccgcaaaatc atttcaaaaa agctccaaat ttagcttacc catcagcttt   2760
ctcagaaaac cagtgaaaga aacttctcaa cttccgattt ttcacaatcc accaaacttt   2820
ttttaataac tttttttcct cttattacaa aacctccact ctcatggctt ctcaaacttg   2880
ttatccatcc aaatctcaat ccctaattag ggttcatttc tctgtttctc caaacagggg   2940
aattcgaaga tgatggagtc taggtctccc atctgcaaca cttgtggtga agagattggt   3000
```

<210> SEQ ID NO 50
<211> LENGTH: 33
<212> TYPE: DNA
<213> ORGANISM: Artificial sequence
<220> FEATURE:
<223> OTHER INFORMATION: Primer

<400> SEQUENCE: 50

```
gggacttatg ctggacagtt tataatggga ggg                                33
```

<210> SEQ ID NO 51
<211> LENGTH: 34
<212> TYPE: DNA
<213> ORGANISM: Artificial sequence
<220> FEATURE:
<223> OTHER INFORMATION: Primer

<400> SEQUENCE: 51

```
gggagaccta gactccacca tggtcgaaat cccc                               34
```

<210> SEQ ID NO 52
<211> LENGTH: 30
<212> TYPE: DNA
<213> ORGANISM: ARTIFICIAL SEQUENCE
<220> FEATURE:
<223> OTHER INFORMATION: Primer

<400> SEQUENCE: 52

```
gtgggaagtc tagaagtgtg caaatggggg                                    30
```

<210> SEQ ID NO 53
<211> LENGTH: 35
<212> TYPE: DNA
<213> ORGANISM: ARTIFICIAL SEQUENCE
<220> FEATURE:
<223> OTHER INFORMATION: Primer

<400> SEQUENCE: 53

```
tcatgatgag gtgccgggga agcgacgttg gtggg                              35
```

<210> SEQ ID NO 54
<211> LENGTH: 30
<212> TYPE: DNA
<213> ORGANISM: ARTIFICIAL SEQUENCE
<220> FEATURE:
<223> OTHER INFORMATION: Primer

<400> SEQUENCE: 54

```
caatttggac tctagaactt tgttatcttt                                    30
```

<210> SEQ ID NO 55
<211> LENGTH: 30
<212> TYPE: DNA
<213> ORGANISM: ARTIFICIAL SEQUENCE
<220> FEATURE:
<223> OTHER INFORMATION: Primer

<400> SEQUENCE: 55

```
catatgtcac cccctctcc tctcctctcc                                     30
```

<210> SEQ ID NO 56
<211> LENGTH: 30
<212> TYPE: DNA
<213> ORGANISM: ARTIFICIAL SEQUENCE
<220> FEATURE:
<223> OTHER INFORMATION: Primer

<400> SEQUENCE: 56

```
cgattaatgt gagaattttt agcccccaca                                    30
```

<210> SEQ ID NO 57
<211> LENGTH: 39
<212> TYPE: DNA

-continued

<210> SEQ ID NO 57
<211> LENGTH: ...
<213> ORGANISM: ARTIFICIAL SEQUENCE
<220> FEATURE:
<223> OTHER INFORMATION: Primer

<400> SEQUENCE: 57
ccatggccgc gcaacaacgg ccggcaacga gctgcggct           39

<210> SEQ ID NO 58
<211> LENGTH: 831
<212> TYPE: DNA
<213> ORGANISM: Pseudomonas fluorescens AN103

<400> SEQUENCE: 58
atgagcacat acgaaggtcg ctggaaaacg gtcaaggtcg aaatcgaaga cggcatcgcg    60
tttgtcatcc tcaatcgccc ggaaaaacgc aacgcgatga gcccgaccct gaaccgcgag   120
atgatcgatg ttctggaaac cctcgagcag gaccctgccg ccggtgtgct ggtgctgacc   180
ggtgcgggcg aagcctggac cgcaggcatg gacctcaagg aatacttccg cgaagtggac   240
gccggcccgg aaatcctcca ggaaaaaatc cgccgcgaag cctcgcaatg caatggaaa    300
ctgctgcgca tgtacgccaa gccgaccatc gccatggtca atggctggtg cttcggcggc   360
ggtttcagcc cgctggtggc ctgcgacctg gcgatctgcg ccgacgaagc aaccttcggt   420
ctctcggaaa tcaactgggg tatcccgccg ggcaacctgg tgagcaaggc catggccgac   480
accgtgggcc accgccagtc gctctactac atcatgaccg gcaagaccttc ggtgggcag    540
aaagccgccg agatgggcct ggtcaacgaa agcgtgcccc tggcgcaact gcgcgaagtc   600
accatcgagc tggcgcgtaa cctgctcgaa aaaacccgg tggtgctgcg tgccgccaaa    660
cacggttcca aacgctgccg cgaactgacc tgggagcaga acgaggatta cctgtacgcc   720
aagctcgatc agtcgcgttt gctggacacc gaaggcggtc gcgagcaggg catgaagcaa   780
ttcctcgacg acaagagcat caagcctggc ctgcaagcgt ataaacgctg a            831

<210> SEQ ID NO 59
<211> LENGTH: 714
<212> TYPE: DNA
<213> ORGANISM: Pseudomonas putida WCS358

<400> SEQUENCE: 59
atgagcccaa cgctcaaccg tgaaatgcgc gatgtactgg aaaccgtcga gcaggatgcc    60
gacgcacgcg tgctggtgtt gaccggtgag ggcagcgcct ggaccgccgg catggacctc   120
aaggagtact tccgcgaggt ggacgcaggc cccgagatcc ttcaggagcg attccgtcgc   180
gatgcctcgg aatggcagtg gaagctgctg cgcttcatca gcaaacccac catcgccatg   240
gtcaacggct ggtgcttcgg cggtggtttc agcccgctgg tcgcttgcga cctggctatc   300
tgcgccgacg aggccacctt cggcctgtct gaaatcaact ggggtattcc accgggcaac   360
ctggtcagca aggccatggc cgacaccgtg gccaccgtg aatcgcgtat catcatgacc    420
ggcaagacct tcgacgggca gaaagccgcg cagatggggc tggtcaacaa gagcgtgccg   480
gttgcgcagt tgcgcgatga agtggtgctg ctcgcccagg accttctcga caagaacccg   540
gttgtgctgc gcgccgccaa aaacggcttc aagcgctgcc gcgagttgac ctgggagcag   600
aacgaggact acctgtacgc caagctgcgt gacccgagc cccgcgcgca aggcctgaag   660
cagttcctcg acgacaaaag cataaagcca ggcctgcaag ccatcaagcg ctga         714

<210> SEQ ID NO 60
<211> LENGTH: 828

-continued

```
<212> TYPE: DNA
<213> ORGANISM: Caulobacter crescentus

<400> SEQUENCE: 60
atgacagacg ccaacgacac cgcgacctat cgggtcgaga accgcatcgc ctgggtgaag      60
ttcaatcgcc ccgataagcg caactgcatg agccccaccc tgaaccgtcg catgatggag     120
gtgctggatg agctggagtt ccgtgacgac gtcggcgtcc tggtcctgac cggcgaaggc     180
tcggcctggt cggcgggcat ggacctgaag gagtacttcc gcgaaaccga ggccaagggt     240
ctgggcgcta cgcgtcaggc tcagcgcgag tcctacggct ggtggcgtcg cctgcgctgg     300
taccagaagc cgacgatcgc catggtcaac ggctggtgct ttggcggcgg ctatggcccg     360
ctgtactcgt gcgacctggc gatcgccgcc gacgaggctc agttcgccct gtcggagatc     420
aactggggca tcctgccggg cggcggcgca accaaggtcg tggtcgacct tatgccgctg     480
cgcgacgcca tgtaccacgc catgaccggc gagctgatcg atggccggaa ggccgccgcc     540
tggcgcctgg tcaacgagag cgtgccgctg agcgcctgga ggcgcgcgt gcgcgagctg      600 gccgaggtgc tgttgaaaaa gaacccggtg gccctgaagg ccaccaagga cgccgtccga     660
cgtgttaagg aaatgaacta cgacaacgcc gaggactacc tggtccgggc ccaggaggcg     720
gccaactcct tcgacaacga cggtcgcaag gagggcatca agcagttcat cgacgacaag     780
acctacaagc ccggcctggg cgcctacgat ctggccaagc agagctga                 828

<210> SEQ ID NO 61
<211> LENGTH: 275
<212> TYPE: PRT
<213> ORGANISM: Caulobacter crescentus

<400> SEQUENCE: 61

Met Thr Asp Ala Asn Asp Thr Ala Thr Tyr Arg Val Glu Asn Arg Ile
1               5                   10                  15

Ala Trp Val Lys Phe Asn Arg Pro Asp Lys Arg Asn Cys Met Ser Pro
            20                  25                  30

Thr Leu Asn Arg Arg Met Met Glu Val Leu Asp Glu Leu Glu Phe Arg
        35                  40                  45

Asp Asp Val Gly Val Leu Val Leu Thr Gly Glu Gly Ser Ala Trp Ser
    50                  55                  60

Ala Gly Met Asp Leu Lys Glu Tyr Phe Arg Glu Thr Glu Ala Lys Gly
65                  70                  75                  80

Leu Gly Ala Thr Arg Gln Ala Gln Arg Glu Ser Tyr Gly Trp Trp Arg
                85                  90                  95

Arg Leu Arg Trp Tyr Gln Lys Pro Thr Ile Ala Met Val Asn Gly Trp
            100                 105                 110

Cys Phe Gly Gly Gly Tyr Gly Pro Leu Tyr Ser Cys Asp Leu Ala Ile
        115                 120                 125

Ala Ala Asp Glu Ala Gln Phe Ala Leu Ser Glu Ile Asn Trp Gly Ile
    130                 135                 140

Leu Pro Gly Gly Gly Ala Thr Lys Val Val Asp Leu Met Pro Leu
145                 150                 155                 160

Arg Asp Ala Met Tyr His Ala Met Thr Gly Glu Leu Ile Asp Gly Arg
                165                 170                 175

Lys Ala Ala Ala Trp Arg Leu Val Asn Glu Ser Val Pro Leu Glu Arg
            180                 185                 190

Leu Glu Ala Arg Val Arg Glu Leu Ala Glu Val Leu Leu Lys Lys Asn
        195                 200                 205
```

```
Pro Val Ala Leu Lys Ala Thr Lys Asp Ala Val Arg Arg Val Lys Glu
    210                 215                 220
Met Asn Tyr Asp Asn Ala Glu Asp Tyr Leu Val Arg Ala Gln Glu Ala
225                 230                 235                 240
Ala Asn Ser Phe Asp Asn Asp Gly Arg Lys Glu Gly Ile Lys Gln Phe
            245                 250                 255
Ile Asp Asp Lys Thr Tyr Lys Pro Gly Leu Gly Ala Tyr Asp Leu Ala
        260                 265                 270
Lys Gln Ser
        275

<210> SEQ ID NO 62
<211> LENGTH: 735
<212> TYPE: DNA
<213> ORGANISM: Pseudomonas sp. HR199

<400> SEQUENCE: 62
atgagcccaa ctctcaatcg agagatggtc gaggttctgg aggtgctgga gcaggacgca    60
gatgctcgcg tgcttgttct gactggtgca ggcgaatcct ggaccgcggg catgacctg   120
aaggagtatt ccgcgagacc gatgctggc cccgaaattc tgcaagagaa gattcgtcgc   180
gaagcgtcga cctggcagtg gaagctcctg cggatgtaca ccaagccgac catcgcgatg   240
gtcaatggct ggtgcttcgg cggcggcttc agcccgctgg tggcctgtga tctggccatc   300
tgtgccgacg aggccacctt tggcctgtcc gagatcaact ggggcatccc gccgggcaac   360
ctggtgagta aggctatggc cgacaccgtg gtcaccgcg agtcccttta ctacatcatg   420
actggcaaga catttggcgg tcagcaggcc gccaagatgg ggcttgtgaa ccagagtgtt   480
ccgctggccg agctgcgcag tgtcactgta gagctggctc agaacctgct ggacaagaac   540
cccgtagtgc tgcgtgccgc caaaataggc ttcaagcgtt gccgcgagct gacttgggag   600
cagaacgagg actacctgta cgccaagctc gaccaatccc gtttgctcga tccggaaggc   660
ggtcgcgagc agggcatgaa gcagttcctt gacgagaaaa gcatcaagcc gggcttgcag   720
acctacaagc gctga                                                   735

<210> SEQ ID NO 63
<211> LENGTH: 840
<212> TYPE: DNA
<213> ORGANISM: Delftia acidovorans

<400> SEQUENCE: 63
atgagcaccg aacgtaccga agaacagacc gtgtcctgca ccgtcacagg ccgcgtggcc    60
tgggtgaaat caaccgccc tgaaaagcgc aacgccatga gccccagct caaccgccag   120
atgatgcgtg tgctcgacga cctggagttc cgtgacgacg tgggcgtggt cgtgcttgca   180
ggcgaaggca cggcctggac ggccggcatg gacctgaagg aatacttccg cgagaccgag   240
gccaccggcc tggccggaac ccgcaaggcc cagcgcgaga gctatggctg gtggcgccgc   300
ctgcgctggt ccagaagcc gaccattgcc atggtcaacg gctggtgctt cggcggcggc   360
tacggcccgc tgttcgcctg cgacctggcc tttgcctcgg atgacgccaa gttcggcctg   420
tccgaaatca ctggggcat cctgcccggt ggcggcgcct ccaaggtggc ggtgaactg   480
ctgtccttcc gccgtgccat gtaccacgcc atgctgggcg agaacatcga cggccgcacg   540
gccgccgagt ggggcctggt caacgagtcg ctgccggccg atcgcctgca gaccgcgtc   600
accgaagtgg ccgaggccct gctgcagaag aaccccagcg ccctgaaggc caccaaggac   660
```

| | |
|---|---|
| gccatccgcc gcgtgcgcga catgagctac gacaacgccg aggactacct ggtgcgcgcc | 720 |
| caggaagccg ccaacagcta cgacaacgaa ggccgcaagg aaggcatgcg ccagttcctc | 780 |
| gacgacaaga cctacaagcc cggcctgggc acctacgacc tctcgaagca aaagtcctga | 840 |

<210> SEQ ID NO 64
<211> LENGTH: 864
<212> TYPE: DNA
<213> ORGANISM: Amycolatopsis HR167

<400> SEQUENCE: 64

| | |
|---|---|
| atgagcacag cggtcggcaa cgggcgggtc cggacggagc cgtggggcga cacggttctg | 60 |
| gtggagttcg acgaaggcat cgcctgggtc atgctcaacc ggccggacaa gcgcaacgcc | 120 |
| atgaaccca ccctgaacga cgagatggtg cgggtgctgg accacctgga gggcgacgac | 180 |
| cgctgccgag tgctggtgct gaccggcgcg ggcgagtcgt tctccgcggg catggacctc | 240 |
| aaggagtact ccgcgaggt cgacgccacc ggcagcaccg ccgtgcagat caaggtgcgg | 300 |
| cgggccagcg cggagtggca gtggaagcgg ctggcgaact ggagcaagcc gacgatcgcg | 360 |
| atggtcaacg gctggtgctt cggcggcgcg ttcaccccgc tggtggcctg cgacctggcc | 420 |
| ttcgccgacg aggacgcgcg gttcgggctg tccgaggtca actgggcat cccgccgggc | 480 |
| ggcgtggtca gccgggcgct ggcggcgacc gtgccgcagc gcgacgcgct gtactacatc | 540 |
| atgaccggtg agcccttcga cggcccgccg cgcgcggaga tgcgcctggt caacgaggcg | 600 |
| ctgcccgccg accggctgcg ggagcgcacc cgcgaggtgg cgctgaagct cgcgtcgatg | 660 |
| aaccaggtgg tcctgcacgc ggccaagacc gggtacaaga tcgcccagga gatgccctgg | 720 |
| gagcaggccg aggactacct ctacgccaag ctcgaccagt cccagttcgc cgacaaggcg | 780 |
| ggcgcccgcg ccaaggggct gacccagttc ctcgaccaga agtcctaccg gcccggcctg | 840 |
| agcgccttcg acccggagaa gtag | 864 |

<210> SEQ ID NO 65
<211> LENGTH: 1437
<212> TYPE: DNA
<213> ORGANISM: Vitis sp.

<400> SEQUENCE: 65

| | |
|---|---|
| atgggatctg aatcaaagct agttcatgtg ttttttggttt ccttccctgg acaagggcat | 60 |
| gtcaacccctt tgctcaggct ggggaagcgt ctggcttcaa agggcttgct tgttaccttc | 120 |
| tccactccag agagtatcgg gaagcagatg aggaaagcca gtaacattac tgaccagccg | 180 |
| acaccggtcg agaaggtct gatcaggttc gagtttttcg aagatgagtg ggacgagaac | 240 |
| gagcccaagc gccaagattt ggacctttac ttgccccagc tggagctcgt gggcaaaaag | 300 |
| gttcttcctc agatgatcaa aaaacacgca gagcaggatc gacctgtctc ctgcctcatc | 360 |
| aacaacccat ttattccatg ggtttctgat gtagcagctc atcttggaat ccccagtgcc | 420 |
| atgctttggg ttcaatcttg cgcttgcttt tctacgtatt accactacta ccatggctta | 480 |
| gtccctttc cctccgaagc tgagcctgaa atcgatgttc aattgccatg tatgcctctc | 540 |
| ttgaagtatg atgaagtcgc tagcttcttg tacccgacca ctccctaccc attcctgagg | 600 |
| agagctatct taggccagta caggaacctg acaagccct tctgtatatt gatggacacg | 660 |
| ttccaagaac tggaacccga agtcatcgaa tacatgtcca agatctgccc gatcaagcct | 720 |
| gtaggacctt tatacaagaa ccctaaagtg ccaaacgccg ctgtccgtgg cgacttcatg | 780 |
| aaggccgacg actgcatcga gtggctcgac tccaagcctc cctcctccat cgtctacgtc | 840 |

-continued

| | |
|---|---|
| tcttttggaa gcgtcgtgta cctgaaacaa gaccaagtag acgagatcgc ttatgggctc | 900 |
| ttaaactccg gcctgcaatt cttatgggtg atgaaaccgc cgcacaaaga cgccggcctg | 960 |
| gaactcctag ttcttccaga agggttcttg gaaaaggccg gtgacaaagg caaggtggtg | 1020 |
| caatggagcc cgcaagagca agtcttagct caccccctccg ttgcctgttt cgttacccac | 1080 |
| tgtggatgga actcatccat ggaggctctc agctccggca tgccggtggt ggcgttccca | 1140 |
| cagtggggag atcaagtcac cgacgccaag tacttggtgg acgaattcaa aattggagtg | 1200 |
| agaatgtgca gaggcgaggc cgaaaacaag ctcatcaccc gggacgaggt ggagaagtgt | 1260 |
| ttgatcgagg ccaccaccgg accaaaggca gcggagttga agcaaaacgc catgaagtgg | 1320 |
| aagaaggcgg cagagcaggc ggtggcgagg gcggttcct ccgaacggaa tctacagggt | 1380 |
| tttgtcgacg aggttcggag aaggagcatt gagatcattt acaaaacaaa aatttaa | 1437 |

<210> SEQ ID NO 66
<211> LENGTH: 1536
<212> TYPE: DNA
<213> ORGANISM: Eucalyptus grandis

<400> SEQUENCE: 66

| | |
|---|---|
| atggggtcgg aggcacttgt ccacgtcctc ttggtctcat tccctggcca gggccacgtc | 60 |
| aacccgctcc tgaggcttgg caagcgcctc gcctccaagg gcctgctcgt caccttcacg | 120 |
| accccagaga gcatcgggaa ggcaatgcgc aaggcgagca acatcggcga ggagctctcc | 180 |
| ccggtcggtg atggcttcat ccggtttgag ttcttcgagg acgggtggga cgaggacgag | 240 |
| atacgccgcc aggacctcga ccagtacctc ccccagctcg agaaggtcgg gaaggtcctc | 300 |
| atccctgaga tgatccggcg caacgccgag caaggccgcc ctatctcttg cctcatcaac | 360 |
| aatcctttca tccctgggt ctccgatgtt gccgatagcc tcggcctccc ctcggcgatg | 420 |
| ctctgggtgc aatcctgtgc atgcttcact tcgtactact actactacca tggcctggtc | 480 |
| cccttcccgt ctgagacagc gatggagatc gatgtgcaac tcccttgcat gccgctccta | 540 |
| aagcacgacg aggtcccgag cttcttgtac ccaacgaccc cgtaccctt cctccggcgg | 600 |
| gcgatcatgg ggcagtacaa gaacttggac aagccattct gcatcctgat ggacacgttc | 660 |
| caggagctcg agcatgagat cattgagtac atgtccaaga tcagccccat caagacagtc | 720 |
| gggccgctct tcaagaaccc taaggccccg aacgccactg tcaagggcga tttcatgaag | 780 |
| gctgacgact cgtcggctg gctcgactca aagcctgctt cctcgatcgt ttacgtgtcg | 840 |
| tttgggagcg tcgtgtactt gaagcaagac cagtgggatg agattgctta tgggctgttg | 900 |
| aactccgggg tcaacttctt gtgggtcatg aagcctccac acaaggactc tggctatgag | 960 |
| gttctcaaaa tgcctgaagg gttcttggag aaggctggtg ataggggcaa ggtggtgcag | 1020 |
| tggagcccgc aagagcaagt cctggctcac ccctcggtgg cctgcttcgt cacgcactgc | 1080 |
| ggttggaact cgaccatgga ggccttgacc tctggcatgc ctgtggtggc gttcccgcag | 1140 |
| tggggtgacc aggtcaccga cgccaagtac ctagtcgacg tgttcaaggt cggggtgagg | 1200 |
| atgtgccggg gcgaggcaga gaacaagctg atcacgcggg acgtggtcga gcagtgcctc | 1260 |
| cgcgaggcaa cctcgggcc caaggccgag gagatgaagc agaacgcgat gaagtggagc | 1320 |
| gcggcagcgg aggcggctgt ggcagagggt ggctcctcag accggaacat ccaggccttc | 1380 |
| gtggacgagg tgaagaggag gagcctggag gtgctggctg cgagtggcaa gtcaacggcc | 1440 |
| aacggagggg cggacttggc caacaaagtg gcggccaatg gggttgcgga gctgggcgag | 1500 |

```
ccaaaggtca acggggagtt aaaggtggtg tcgtga                                    1536

<210> SEQ ID NO 67
<211> LENGTH: 1515
<212> TYPE: DNA
<213> ORGANISM: Citrus mitis

<400> SEQUENCE: 67
atgggaactg aatctcttgt tcacgtctta ctagtttcat tccccggcca tggccacgta          60
aacccgcttc tgaggctcgg cagactcctt gcttcaaagg gtttctttct caccttgacc        120
acacctgaaa gctttggcaa acaaatgaga aagcgggta acttcaccta cgagcctact         180
ccagttggcg acggcttcat tcgcttcgaa ttcttcgagg atggatggga cgaagacgat        240
ccaggacgcc gagatcttga ccaatacatg gctcaacttg agcttattgg caaacaagtg        300
attccaaaaa taatcaagaa aagcgctgaa gaatatcgcc ccgtttcttg cctgatcaat        360
aacccattta tcccttgggt ttccgatgtt gctgaatccc tagggcttcc gtctgctatg        420
ctttgggttc aatcttgtgc ttgttttgct gcttattacc attactttca cggtttggtt        480
ccatttccta gtgaaaaaga acccgaaatt gatgttcagt tgccgtgcat gccactactg        540
aagcatgatg aagtgcctag cttcttgcat ccgtcaactc cttatccttt cttgagaaga        600
gctatttggg ggcagtacga aaatcttggc aagccgtttt gcatattgtt ggacactttc        660
tatgagcttg agaaagagat tatcgattac atggcaaaaa tttgccctat taaacccgtc        720
ggccctctgt tcaaaaaccc taagctccca accttaaccg tccgcgatga ctgcatgaaa        780
cccgatgaat gcatagactg gctcgacaaa aagccaccat catccgttgt atacatctct        840
ttcggcacgg ttgtctactt gaagcaagaa caagttgaag aaattggcta tgcattgttg        900
aactcgggga tttcgttctt gtgggtgatg aagccgccgc tgaagactc tggcgttaaa        960 attgttgacc tgccagatgg gttcttggag aaagttggag ataagggcaa agttgtgcaa       1020
tggagtccac aagaaaaagt gttggctcac cctagtgttg cttgctttgt gactcactgc       1080
ggctggaact caaccatgga gtcgttggca tcggggtgc cggtgatcac cttcccgcaa       1140
tggggtgatc aagtaactga tgccatgtat ttgtgtgatg tgttcaagac cggtttaaga       1200
ttgtgccgtg gagaggcaga gaacaggata atttcaaggg atgaagtgga gaagtgcttg       1260
ctcgaggcca cggccggacc taaggcggcg gagctgaagg agagcgcgct gaagtggaag       1320
caggaggcgg aggaagctgt ggccgatggt ggctcgtcgg ataggaacat tcaggctttc       1380
gttgatgaag taagaaggag aagtgtgggg attataacca gcagcaagtc gaagtcaatc       1440
cacagagtta aggaattagt ggagaagacg gcaacggcaa ctgcaaatga caaggtagaa       1500
ttggtggagt catga                                                        1515

<210> SEQ ID NO 68
<211> LENGTH: 31
<212> TYPE: DNA
<213> ORGANISM: artificial sequence
<220> FEATURE:
<223> OTHER INFORMATION: Primer

<400> SEQUENCE: 68
ccaaggaccg catatgacag acgccaacga c                                        31

<210> SEQ ID NO 69
<211> LENGTH: 32
<212> TYPE: DNA
<213> ORGANISM: artificial sequence
```

```
<220> FEATURE:
<223> OTHER INFORMATION: Primer

<400> SEQUENCE: 69 cctcccctc gcaagctttc agctctgctt gg                              32

<210> SEQ ID NO 70
<211> LENGTH: 33
<212> TYPE: DNA
<213> ORGANISM: artificial sequence
<220> FEATURE:
<223> OTHER INFORMATION: Primer

<400> SEQUENCE: 70
gagagcatcc atatgagcac atacgaaggt cgc                            33

<210> SEQ ID NO 71
<211> LENGTH: 33
<212> TYPE: DNA
<213> ORGANISM: artificial sequence
<220> FEATURE:
<223> OTHER INFORMATION: Primer

<400> SEQUENCE: 71
cgcagcgtca agcttcagcg tttatacgct tgc                            33

<210> SEQ ID NO 72
<211> LENGTH: 22
<212> TYPE: DNA
<213> ORGANISM: artificial sequence
<220> FEATURE:
<223> OTHER INFORMATION: Primer

<400> SEQUENCE: 72
tgagagattc agatgcccag aa                                        22

<210> SEQ ID NO 73
<211> LENGTH: 20
<212> TYPE: DNA
<213> ORGANISM: artificial sequence
<220> FEATURE:
<223> OTHER INFORMATION: Primer

<400> SEQUENCE: 73
tggattccag cagcttccat                                           20

<210> SEQ ID NO 74
<211> LENGTH: 25
<212> TYPE: DNA
<213> ORGANISM: artificial sequence
<220> FEATURE:
<223> OTHER INFORMATION: Actin probe

<400> SEQUENCE: 74
tcttgttcca gccctcgttt gtggg                                     25

<210> SEQ ID NO 75
<211> LENGTH: 20
<212> TYPE: DNA
<213> ORGANISM: artificial sequence
<220> FEATURE:
<223> OTHER INFORMATION: Primer

<400> SEQUENCE: 75
gcctgggtga agttcaatcg                                           20
```

```
<210> SEQ ID NO 76
<211> LENGTH: 19
<212> TYPE: DNA
<213> ORGANISM: artificial sequence
<220> FEATURE:
<223> OTHER INFORMATION: Primer

<400> SEQUENCE: 76
ccatcatgcg acggttcag                                              19

<210> SEQ ID NO 77
<211> LENGTH: 23
<212> TYPE: DNA
<213> ORGANISM: artificial sequence
<220> FEATURE:
<223> OTHER INFORMATION: HCHL probe

<400> SEQUENCE: 77
cccgataagc gcaactgcat gag                                         23

<210> SEQ ID NO 78
<211> LENGTH: 15
<212> TYPE: DNA
<213> ORGANISM: artificial sequence
<220> FEATURE:
<223> OTHER INFORMATION: Primer

<400> SEQUENCE: 78
tgcgccgacg aagca                                                  15

<210> SEQ ID NO 79
<211> LENGTH: 16
<212> TYPE: DNA
<213> ORGANISM: artificial sequence
<220> FEATURE:
<223> OTHER INFORMATION: Primer

<400> SEQUENCE: 79
gttgcccggc gggata                                                 16

<210> SEQ ID NO 80
<211> LENGTH: 23
<212> TYPE: DNA
<213> ORGANISM: artificial sequence
<220> FEATURE:
<223> OTHER INFORMATION: Primer

<400> SEQUENCE: 80
ttcggtctct cggaaatcaa ctg                                         23

<210> SEQ ID NO 81
<211> LENGTH: 814
<212> TYPE: DNA
<213> ORGANISM: Zea mays

<400> SEQUENCE: 81
ctatcttaat atgccccgat tcaacagcac ccagtcgagt cattgcgttc tggagattct   60
tgcagcgcat ttccatgttt aagaccttat tatgaaatgt ctggcattcg tggatccact  120
gagcttcttt ctgcgaatgt gccatatcgt ggcattggcc gaagcaacca aacatttgtt  180 gccctttttgt gtcggtgttt tataaagtac ctcaatgacg atacagcctc agggcgcttc  240
ctgcttttgc acttattcgg agttcaggcg agttaacgaa gttcagacgg ttctgaagag  300
aggccgtgtt gtgttttgtc ggcgtggtat cgcgcaagca catgtgtctt tggtaagatg  360
```

```
gtctggatgg ctgtcctacc acctgccatt tatacacaca ctgacttcac cgtcacactg    420
gcacgacatg agctcgccat cctaccagaa acgctgagac gtcaccggca accacccctc    480
tcgctcgctc tggcctctgc tcctgatttg atttggacag aaaactgggc agggcagggc    540
gcgctcagca cgtttgcttc ggaaacactg cgagtgtgcg acacatttcc cggcttgatc    600
tcgaagcgag ccctgatgtg tttgtcatgc acctgcctgc cttggcttgt gctctaatca    660
acgccggact ccccaactca cggttggtgc gggacgccac cccgccacct taccgcccgc    720
ctcggcgcct caccagtcac cacacctcgc gcctgccatc agctatatca ccgtggccac    780
ttccgtgtcc cttcacggat acctcacccc caca                                 814

<210> SEQ ID NO 82
<211> LENGTH: 598
<212> TYPE: DNA
<213> ORGANISM: Zea mays

<400> SEQUENCE: 82
tatattgatt ttacatatga tagtgatgtt actccttccg tatctatatt ttatattagt     60
ttttatctcc tggcaacacg gtcacaacag aagagaagtt tttcagaccg attccaggat    120
cgattttttt tttatatctg ggctaagaca tcaggtagag attgtttaac ctttgcggct    180
ttccgcactg acggacccac ccccaccgca tcaacggaac ctaccaacca cccccgtgct    240 ccgaccccc atctgcccgt cttccaggtt acgcccgcg cggccgcgcg cgcggaagct    300 gtatcaccc cccgtcgac gtcgtcttcg cttcgaaacc ccgcaaaacc ccgcggaaaa    360
aacccacctg ctgcacgcac gcacccctc cctctccctc ccatggcgc ctcccctcac    420 ccaactcttt gcttccattc tttccatcca cccgccaatg cgacgccgac gccgcaactc    480 caccaccgc ctgccagcgc cacctcaccg caccgcttcc atcacccgc gatcatgggc    540 taccgctata tcaccacgcc tccaacctcc ggcacgctta gcctctctct cccattct     598

<210> SEQ ID NO 83
<211> LENGTH: 724
<212> TYPE: DNA
<213> ORGANISM: Zea mays

<400> SEQUENCE: 83
aaatttgaca caatattgaa atttgaatgg ttttaacatt tgaaggctga aaaccaaaat     60
actttgtagc taagtgttgg aaacccgact cggccaataa gtcgacagac cgtaaaataa    120
ggtcaatcta aactttatga taaatattct tgtttgatag caatagcatt gcaggaccag    180
gacccaaggg aagagaagat gccaaatccc atcgaggcta aagcaaaaac gatccaattt    240
atgagcaaac ccacactgaa gtttcaaaat tgttttctga aaaaaagta accagcaagt    300 taaaaaatga gatggcggga aagccaagtc tcggttggtc gagggggttgg ttggggcgca    360 gcctgacaag tgacaacggc agcaggatag tagcatcagg cgcaagccag cgcaggcggc    420
agcgcgagga tttcgcttca cttagcggca acggagacgc tgcacccaac caacacgagc    480 tcccctcac ccgctgcgac gcgcgcgtcc cacgagcgga agcccccgc gccgacgcga    540 gcgcgggggc tcgaccgacc gacccaacgc ctccatctcc accgcgcgca ccaaatcgca    600
ctcccgtccg ccccgccgat cgaacagcca ccgctcacct ctcccacccg ccaaaaacct    660
ccggcctcct ctcatattca tagctgagct agcccctgcc acaaggtaga gcrtcgctca    720
cacc                                                                  724
```

METHOD TO PRODUCE PARA-HYDROXYBENZOIC ACID IN THE STEM TISSUE OF GREEN PLANTS BY USING A TISSUE-SPECIFIC PROMOTER

FIELD OF THE INVENTION

The invention relates to the fields of plant gene expression, molecular biology, and microbiology.

BACKGROUND OF THE INVENTION

Recent advances in genetic engineering have enabled the development of new biological platforms for the production of molecules, heretofore only synthesized by chemical routes. Although microbial fermentation is routinely exploited to produce of small molecules and proteins of industrial and/or pharmaceutical importance (antibiotics, enzymes, vaccines, etc.), the possibility of using green plants to manufacture a high volume of chemicals and materials has become an increasingly attractive alternative.

Using green plants to produce large amounts of compounds has two significant advantages over traditional chemical synthesis. First, green plants constitute a renewable energy source, as opposed to finite petrochemical resources. Because of photosynthesis, the only raw materials that are required to produce carbon-based compounds in green plants are carbon dioxide, water, and soil. Sunlight is the ultimate source of energy. Second, in comparison to existing fermentation facilities that are expensive and limited in size, green plants constitute a huge available biomass that could easily accommodate the large amounts of chemicals that are required for certain high-volume, low-cost applications.

Producing para-hydroxybenzoic acid in green plants transformed with 4-hydroxycinnamoyl-CoA hydratase/lyase (HCHL) has been previously described (Mayer et al., Plant Cell, 13:1669-1682 (2001) and U.S. Ser. No. 10/359,369). Mitra et al. (PLANTA, 215:79-89 (2002)) express an HCHL in hairy root cultures of Datura stramonium. Expression of HCHL enzymes in plant cells leads to production of para-hydroxybenzoic acid (pHBA) from 4-coumaroyl-CoA (pHCACoA). The pHBA produced in plants is rapidly glucosylated by one or more endogenous UDP-glucosyltransferases into pHBA glucosides (both phenolic and ester glucosides) (Mayer et al., supra; Mitra et al., supra, and U.S. Ser. No. 10/359,369) that are subsequently sequestered in the plants' vacuoles.

pHCACoA is normally used by plants to make molecules that are secondary metabolites with roles as plant growth regulators, UV protectants, or cell wall components such as lignin, cutin, or suberin. Examples of secondary metabolites made from pHCACoA include caffeoyl-CoA and feruloyl-CoA. Expression of HCHL genes in tobacco plants under the control of a constitutive promoter (CaMV35S) leads to plant growth defects such as interveinal leaf chlorosis, stunting, low pollen production, and male sterility (Mayer et al., supra). As a result of constitutive HCHL expression (in all plant tissues), pHCACoA levels were depleted to a point where molecules derived from pHCACoA that are essential for plant growth and reproduction were no longer produced in adequate amounts.

HCHL expression needs to be targeted to cells where suitable pools of pHCACoA exist and where conversion to pHBA does not detrimentally affect plant growth and reproduction. Plant stem tissue contains a significant pool of available pHCACoA and can accommodate large fluxes to the phenylpropanoid pathway. In order to exploit the available substrate pool without causing detrimental effects to the plant, HCHL expression needs to be limited to plant stem tissue. In addition, expression levels need to be high enough to produce suitable quantities of pHBA. Robust tissue-specific plant promoters, namely those which are known to drive genes involved in cell wall biosynthesis, represent an attractive group of candidate promoters for HCHL expression.

Genes involved in the production of phenylpropanoid derivatives used in plant cell wall biosynthesis (which are expected to show a tissue-specific expression pattern) represent a source of possible promoters to drive tissue-specific HCHL expression. Examples of these genes include cinnamate-4-hydroxylase (C4H; GenBank® U71080), 4-coumaroyl-Coenzyme A ligase (4CL1; GenBank® U18675), para-coumarate 3-hydroxylase (C3'H; AC011765), and the genes encoding proteins responsible for the catalytic activity of cellulose synthase (IRX1, IRX3, IRX5, and their respective orthologs from rice and maize)(Taylor et al., PNAS, 100(3):1450-1455 (2003)). Given the requirement that HCHL expression must be limited to stem tissue, it is unknown if any of these promoters are suitable for stem-specific expression. Use of these promoters for HCHL expression in plant stalk tissue has not been reported.

Cellulose is a polymer of $\beta(1,4)$-linked glucose. It is an essential component of both the primary and secondary cell walls in higher plants.

Cellulose can make up to 90% of the dry weight of the secondary walls. In the plant cell wall, individual cellulose chains crystallize to form microfibrils. Cells involved in synthesizing the cellulose for the secondary cell wall represent an attractive target for tissue-specific expression of HCHL.

Cellulose synthesis is believed to involve a multienzyme complex situated at the plasma membrane (Taylor et al., Plant Cell, 11 (5):769-779 (1999); Taylor et al., supra (2003)). Many of the cellulose synthase genes "CesA genes" are classified as such based on highly-conserved motifs (Richmond and Sommerville, Plant Physiol., 124:495-498 (2000) and Delmer, D P, Annu. Rev. Plant Physiol. Plant Mol. Biol., 50:245-276 (1999)). Many of the genes share homology with one another, yet appear to have different roles in cellulose biosynthesis. The CesA genes are a subset of a larger family of related genes which share some homology to one another. These genes form a family of cellulose synthase-like genes ("csl" genes; Taylor et al., supra (2003); Richmond, T., Genome Biol., 1 (4):reviews 3001.1-3001.6 (2000)) whose exact function is not known.

Use of promoters from CesA genes have previously been described. Turner et al. (WO 00/070058) describe the use of cellulose synthase genes or promoters (IRX3) for modulating enzymes involved in the synthesis of plant cell walls. Jones et al. (Plant Journal, 26(2):205-216 (2001)) described the utility of the IRX3 promoter to down-regulate genes involved with lignin synthesis in plant stalk tissue. Allen et al., (WO 00/04166) describe methods related to altering cellulose synthase genes (CesA). Stalker et al. (WO 98/18949) describe a CesA homolog from cotton (Gossypium hirsutem) and methods associated with altering cotton fiber and wood quality. Arioli et al. (WO 98/00549) describe methods for manipulating a cellulose synthase-like gene (rsw1) for altering cellulose biosynthetic properties. None of these references teach the use of a cellulose synthase-like gene promoter to drive HCHL expression.

The IRX3 gene was putatively identified as encoding the cellulose synthase catalytic subunit from Arabidopsis (Turner et al., *Plant Cell*, 9(5): 689-701 (1997). Expression of the IRX3 gene was shown to be normally limited to plant stem tissue as no detectable mRNA transcript was measured in leaf tissue (Taylor et al., supra (1999)). It was later reported that the catalytic activity of cellulose biosynthesis is attributed to a multi-subunit complex formed by the proteins encoded by the IRX1, IRX3, and IRX5 genes (Taylor et al., *Plant Cell*, 12:2529-2539 (2000) and Taylor et al., supra (2003)). These three genes identified from *Arabidopsis* show essentially the same expression patterns. Expression of these genes is normally limited to cells involved in secondary cell wall biosynthesis. Additionally, orthologs of these genes may exhibit similar tissue-specific expression patterns, namely expression in cells that produce cellulose for secondary cell wall synthesis. The prior art does not teach use of the promoters from IRX1, IRX3, or IRX5 (or orthologs thereof) for stem tissue expression of HCHL.

The problem to be solved is to identify regulatory sequences that allow targeted HCHL expression in plant tissues where significant pHBA accumulation can occur without adversely affecting the synthesis of compounds essential for plant growth and development. In other words, technology needs to be developed that allows for HCHL-mediated pHBA production in plants without negative effects on plant performance in the field.

SUMMARY OF THE INVENTION

Methods and materials are presented for the production of para-hydroxybenzoic acid in genetically modified green plants by selectively expressing hydroxycinnamoyl CoA hydratase/lyase genes using tissue-specific promoters. The promoters from the genes involved in the formation of the cellulose synthase catalytic complex are suitable for tissue-specific expression of HCHL in plants. The promoters from *Arabidopsis thaliana* genes AtCesA4 (IRX5), AtCesA7 (IRX3), and AtCesA8 (IRX1) are suitable for tissue-specific expression of HCHL. Additionally, the promoters of orthologous genes from maize and rice are also suitable for stem tissue targeted expression of HCHL.

The invention embodies a method to selectively produce para-hydroxybenzoic acid in plant stem tissue comprising:

a) growing a plant under suitable conditions, the plant comprising
   i) an endogenous source of para-coumaroyl-CoA;
   ii) a 4-hydroxycinnamoyl-CoA hydratase/lyase (HCHL) expression cassette comprising a tissue-specific promoter isolated from a cellulose synthase gene encoding a protein involved in the formation of a cellulose synthesis catalytic complex, wherein said cellulose synthesis catalytic complex catalyzes cellulose synthesis in secondary cell wall formation in plant vascular tissue, said tissue-specific promoter operably linked to a nucleic acid molecule encoding a 4-hydroxycinnamoyl-CoA hydratase/lyase enzyme; and
   iii) a gene encoding a para-hydroxybenzoic acid UDP-glucosyltransferase;
b) recovering unconjugated para-hydroxybenzoic acid and para-hydroxybenzoic acid glucoside from the plant;
c) hydrolyzing para-hydroxybenzoic acid glucoside; and
d) recovering unconjugated para-hydroxybenzoic acid.

The tissue-specific promoter is selected from the group consisting of SEQ ID Nos:26, 43, 44, 45, 46, 49, 81, 82, and 83. The HCHL expression cassette is represented by SEQ ID NO:30. The nucleic acid molecule encoding HCHL is isolated from a bacterium selected from the group consisting of *Pseudomonas, Caulobacter, Delftia, Sphingomonas*, and *Amycolatopsis*. The bacteria from which the nucleic acid is isolated is selected from the group consisting of *Pseudomonas putida* (DSM 12585), *Pseudomonas fluorescens* AN103, *Pseudomonas putida* WCS358, *Pseudomonas* sp. HR199, *Delftia acidovorans, Amycolatopsis* sp. HR167, *Sphingomonas paucimobilis*, and *Caulobacter crescentus*.

The nucleic acid molecule encoding HCHL is selected from the group consisting of SEQ ID NO:5, 58, 59, 60, 62, 63, and 64. The nucleic acid molecule encoding HCHL encodes the polypeptide of SEQ ID 61. The nucleic acid molecule encoding HCHL coding is isolated from *Psuedomonas putida* DSM 12585. The nucleic acid molecule encoding HCHL encodes the polypeptide of SEQ ID NO:6. The nucleic acid molecule encoding HCHL is SEQ ID NO:5. The gene encoding the para-hydroxybenzoic acid UDP-glucosyltransferase may be endogenous or exogenous to the plant. The gene encoding para-hydroxybenzoic acid UDP-glucosyltransferase is selected from the group consisting of SEQ ID NOs:65, 66, and 67 and is recombinantly expressed in the plant whereby para-hydroxybenzoic acid glucose ester is selectively produced. The tissue-specific promoter of said HCHL expression cassette preferentially expresses active HCHL in said plant stem tissue at levels at least ten, times higher than expression levels measured in leaf tissue of said plant. More preferred embodiments show preferential expression levels of active HCHL in said plant stem tissue of 20 times to 50 times greater than expression levels measured in the leaf tissue of the plant.

Another method to selectively produce para-hydroxybenzoic acid in plant stem tissue comprises a) Providing a plant comprising
   i. an endogenous source of para-coumaroyl-CoA;
   ii. a 4-hydroxycinnamoyl-CoA hydratase/lyase (HCHL) expression cassette comprising a tissue-specific promoter isolated from a cellulose synthase gene encoding a protein involved in the formation of the cellulose synthesis catalytic complex, the tissue-specific promoter operably linked to a nucleic acid molecule encoding a 4-hydroxycinnamoyl-CoA hydratase/lyase enzyme from *Caulobacter crescentus* having at least 50% higher catalytic efficiency in converting para-hydroxycinnamoyl-CoA to para-hydroxybenzoic acid in comparison to catalytic efficienty of an HCHL enzyme from *Psuedomonas putida* or *Pseudomonas fluorescens* expressed under similar conditions; wherein said cellulose synthesis catalytic complex catalyzes cellulose synthesis in secondary cell wall formation in plant vascular tissue; and
   iii. a gene encoding a para-hydroxybenzoic acid UDP-glucosyltransferase;
b. growing a plant under suitable conditions whereby unconjugated para-hydroxybenzoic acid and para-hydroxybenzoic acid glucosides are produced;
c. recovering unconjugated para-hydroxybenzoic acid and para-hydroxybenzoic acid glucoside from the plant;
d. hydrolyzing para-hydroxybenzoic acid glucoside; and
e. recovering unconjugated para-hydroxybenzoic acid.

The nucleic acid molecule used in this method encodes an amino acid sequence as provided by SEQ ID NO:61. The plant is selected from the group consisting of tobacco, *Arabidopsis*, sugar beet, sugar cane, soybean, rapeseed, sunflower, cotton, corn, alfalfa, wheat, barley, oats, sorghum, rice, canola, millet, beans, peas, rye, flax, and forage grasses. The tissue-specific promoter is isolated from a gene selected from the group consisting of: AtCesA4 (IRX5), AtCesA7 (IRX3), AtCesA8 (IRX1), ZmCesA10, ZmCesA11, ZmCesA12, the *Oryza savita* (japonica cultivar) ortholog of ZmCesA10, the *Oryza savita* (japonica cultivar) ortholog of ZmCesA11, and the *Oryza savita* (japonica cultivar) ortholog of ZmCesA12.

The tissue-specific promoter is selected from the group consisting of SEQ ID NOs:26, 43, 44, 45, 46, 49, 81, 82, and 83. The gene encoding para-hydroxybenzoic acid UDP-glucosyltransferase may be endogenous or exogenous to the plant and is recombinantly expressed in the plant whereby para-hydroxybenzoic acid glucose ester is selectively produced. The gene encoding para-hydroxybenzoic acid UDP-glucosyltransferase is selected from the group consisting of SEQ ID NOs:65, 66, and 67.

BRIEF DESCRIPTION OF THE FIGURES AND SEQUENCE DESCRIPTIONS

The invention can be more fully understood from the sequence listing, the Figures, and the detailed description that together form this application.

FIG. 1 shows the enzyme pathway to produce pHBA in transgenic plants. The HCHL enzyme converts 4-coumaroyl-CoA to pHBA in the cytosol. A pHBA UDP-glucosyltransferase glucosylates the pHBA to produce a pHBA glucoside. The pHBA glucoside is subsequently stored and accumulated in the plant's vacuoles.

FIG. 2 shows Michaelis-Menten and Wolf-Augustinsson-Hofstee plots illustrating kinetic properties of the recombinantly produced, purified HCHL enzyme of *Pseudomonas putida* (DSM 12585).

Figure 4:
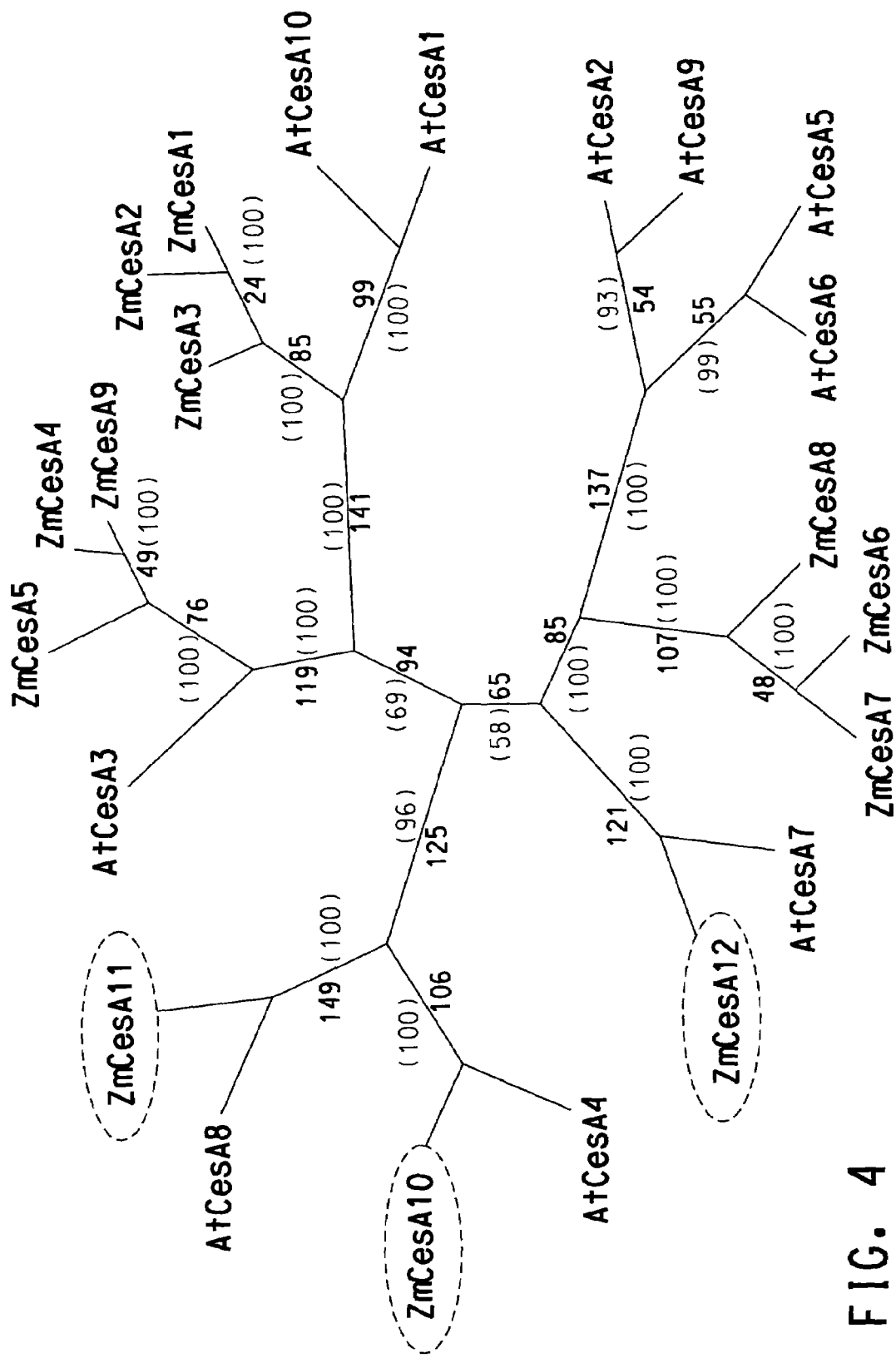

FIG. 4 shows an unrooted single most parsimonious tree of the CesA proteins from maize and *Arabidopsis* found by the Branch and Bound algorithm of the PAUP program. (Swofford, DL, PAUP*: Phylogenetic analysis using parsimony (and other methods), Volume Version 4 (Sinauer Associates, Sunderland, Mass.)). Branch lengths are proportionate to the inferred number of amino acid substitutions, which are shown in bold font. Bootstrap values (%) supporting the monophyletic groups are shown along the branches in parentheses. *Arabidopsis* CesA protein sequences were deduced from the publicly available GenBank® nucleotide sequence (Table 7). (See also Example 4.)

Figure 5A:
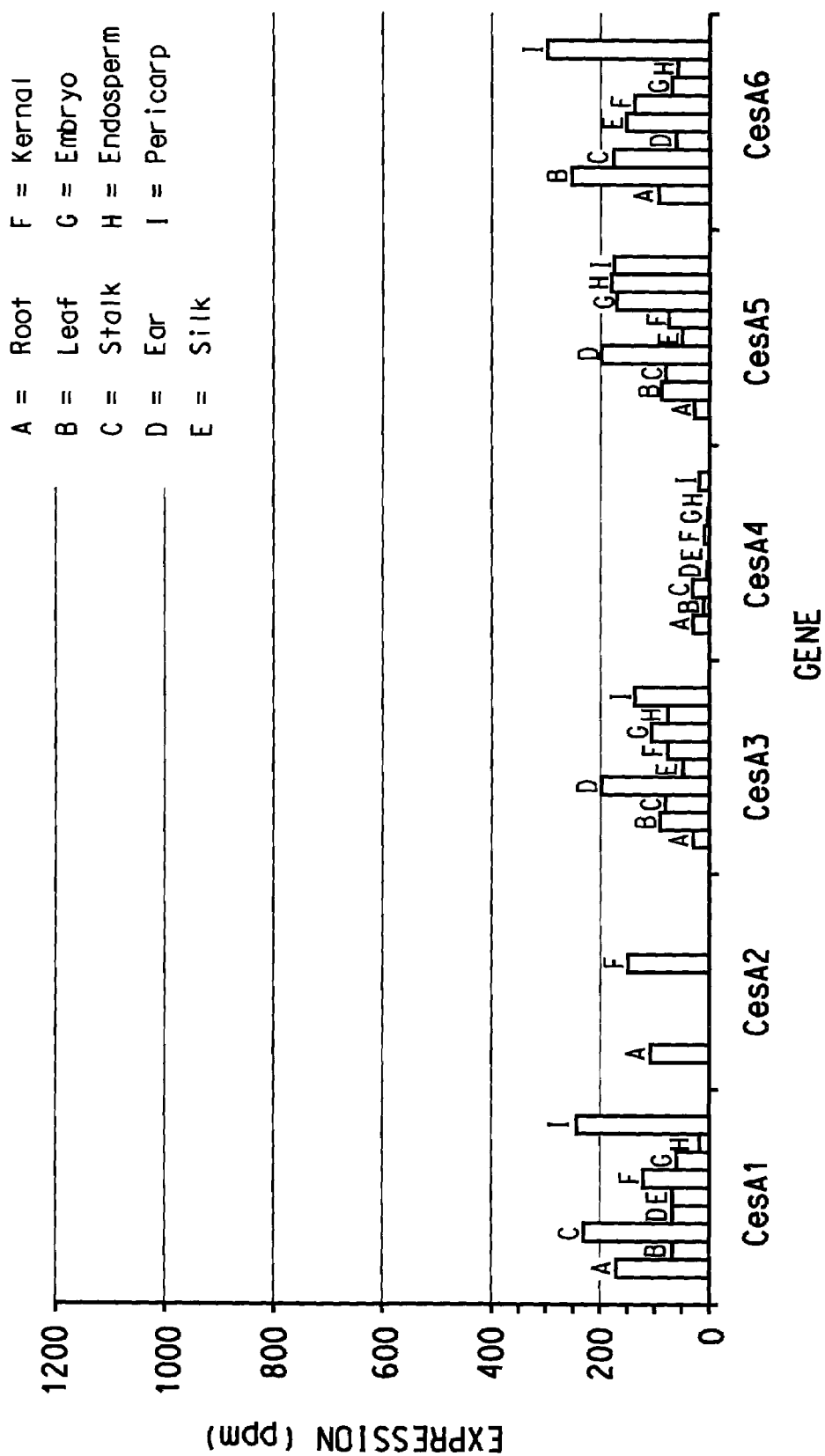
Figure 5B:
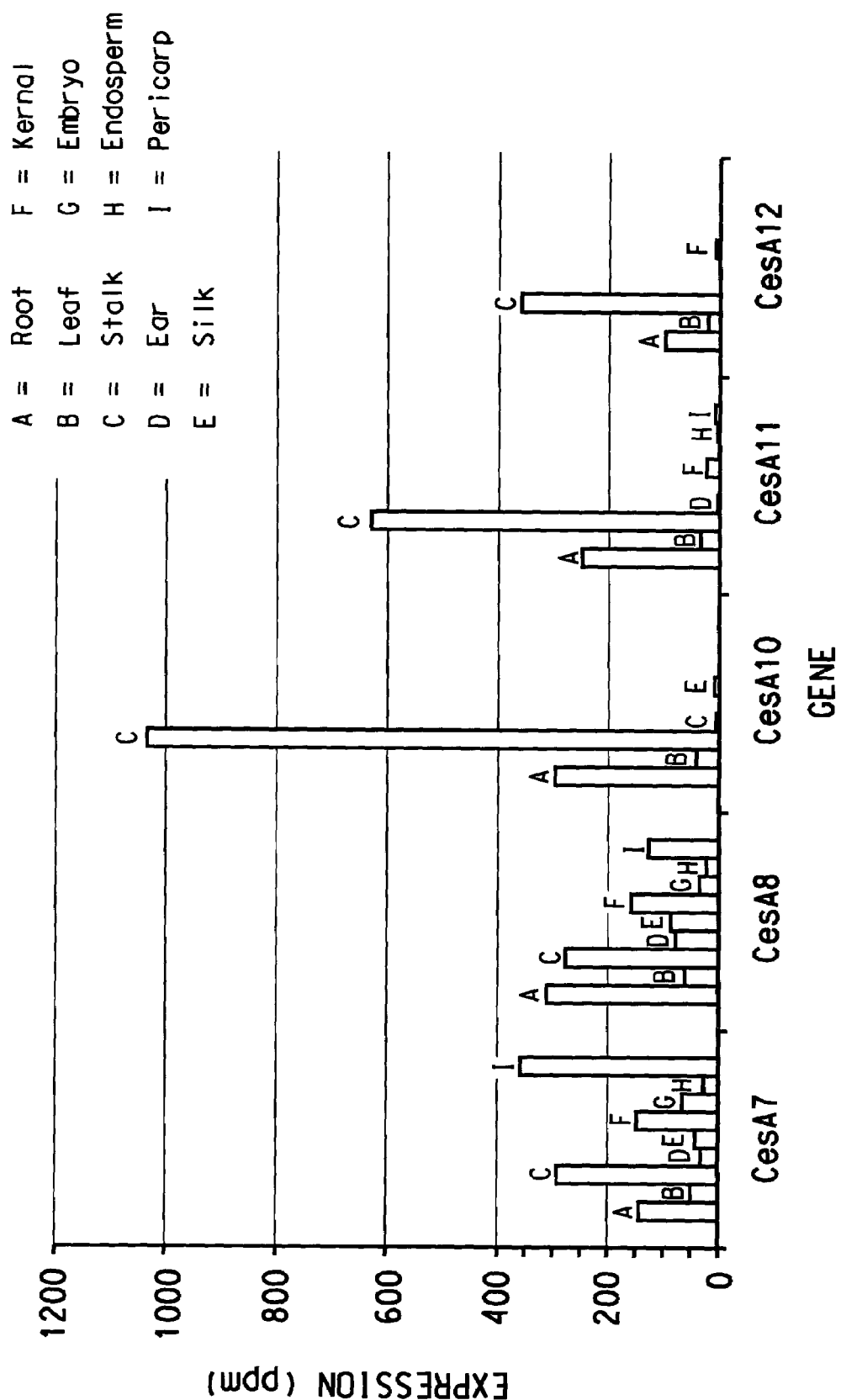

FIG. 5: Expression of the maize CesA genes in different tissues as compiled from the Massively Parallel Signature Sequencing (MPSS) database (Brenner et al., *Proc. Natl. Acad. Sci. USA*, 97(4):1665-1670 (2000); Brenner et al., *Nat. Biotech.*, 18:630-634 (2000); Hoth et al., *J. Cell. Sci.*, 115:4891-4900 (2002); Meyers et al., *Plant J.*, 32:77-92 (2002); U.S. Pat. No. 6,265,163; and U.S. Pat. No. 6,511, 802). A comparison of stem versus leaf tissue expression was tabulated from the expression data (See also Example 5, and Table 9).

Figure 6:
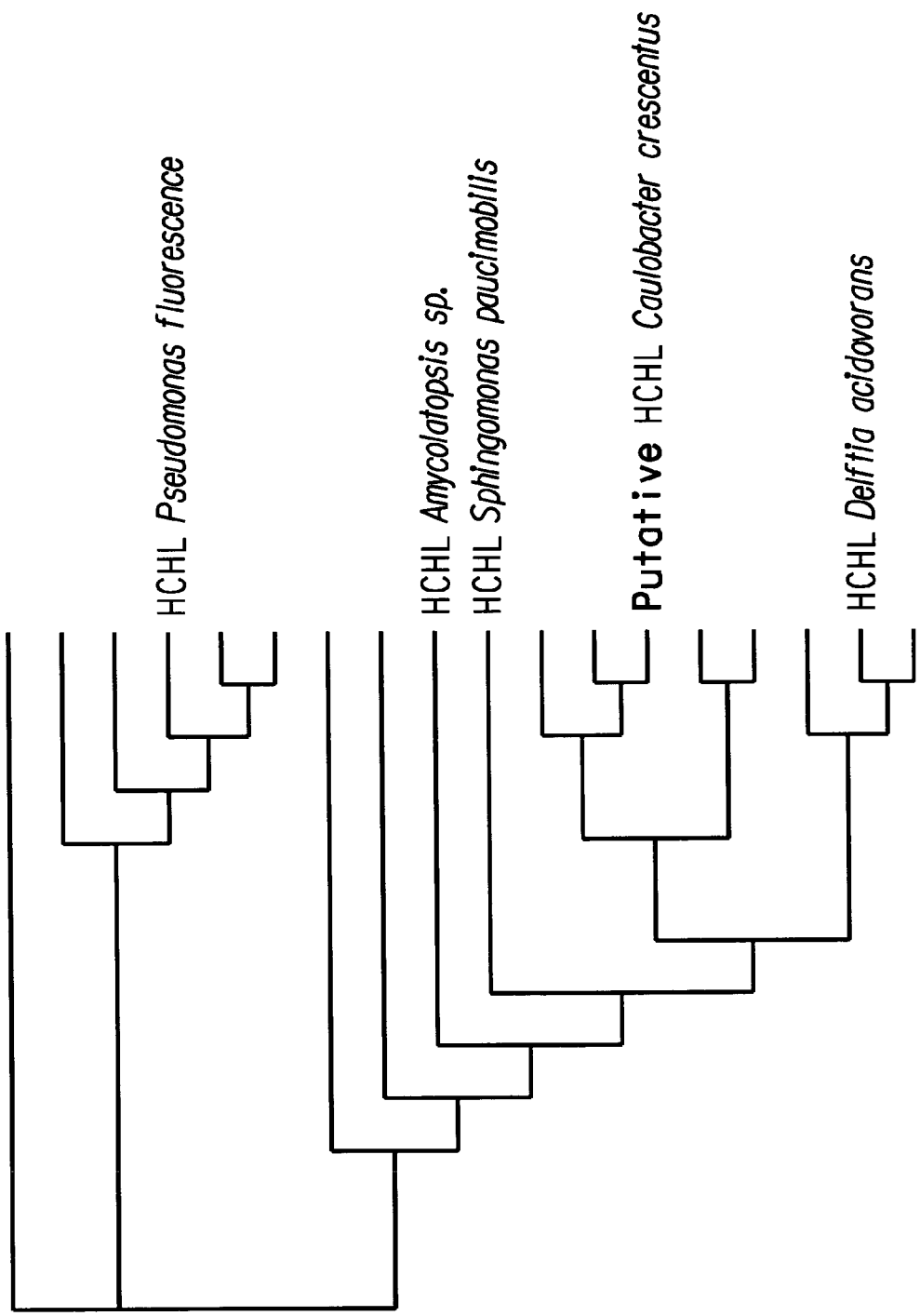

FIG. 6 shows a phylogenetic tree produced by CLUSTAL W of putative and bona fide HCHL enzymes identified from a BLAST search of public databases.

Figure 7:
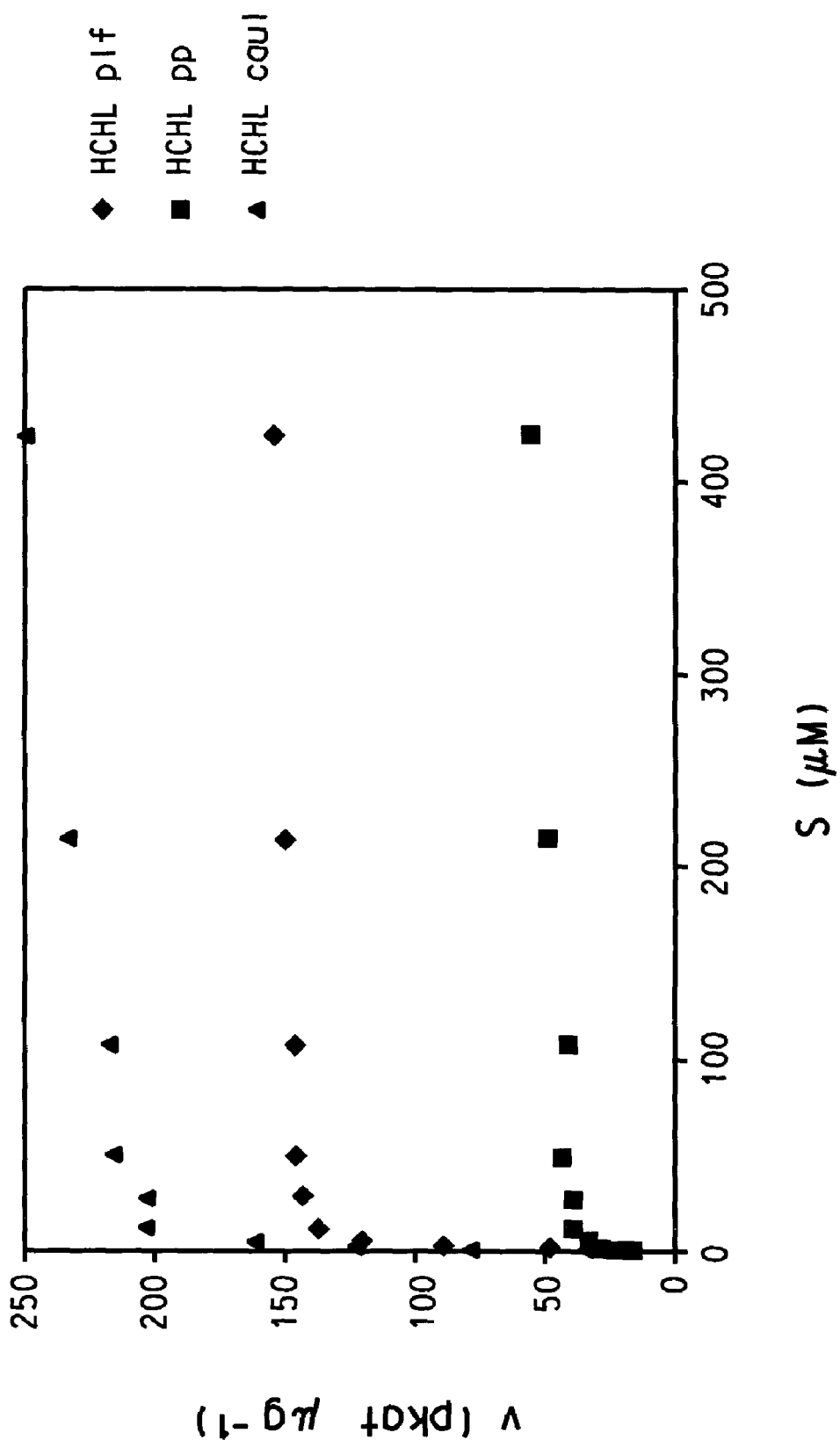

FIG. 7 shows the Michaelis-Menten plot illustrating the kinetic properties of recombinantly produced HCHL enzymes from *Caulobacter crescentus*, *Pseudomonas putida* (DSM12585), and *Pseudomonas fluorescens* AN103.

The following 83 sequence descriptions and sequences listings attached hereto comply with the rules governing nucleotide and/or amino acid sequence disclosures in patent applications as set forth in 37 C.F.R. §1.821-1.825. The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal* 219 (No. 2):345-373 (1984) which are herein incorporated by reference. The symbols and format used for nucleotide and amino acid sequence data comply with the rules set forth in 37 C.F.R. §1.822.

SEQ ID NO:1 is the nucleic acid sequence of the 5' primer (Primer 1) useful for amplifying the 4CL-1 open reading frame (ORF) from *Arabidopsis thaliana* and its cloning into the *E. coli* expression vector pET28a.

SEQ ID NO:2 is the nucleic acid sequence of the 3' primer (Primer 2) useful for amplifying the 4CL-1 ORF of *Arabidopsis thaliana* and its cloning into the *E. coli* expression vector pET28a.

SEQ ID NO:3 is the nucleic acid sequence of the 5' primer (Primer 3) useful for amplifying the HCHL gene of *Pseudomonas putida* (DSM 12585) from genomic DNA of this organism.

SEQ ID NO:4 is the nucleic acid sequence of the 3' primer (Primer 4) useful for amplifying the HCHL gene of *Pseudomonas putida* (DSM 12585) from genomic DNA of this organism.

SEQ ID NO:5 is the nucleic acid sequence of the HCHL coding sequence from *Pseudomonas putida* (DSM 12585).

SEQ ID NO:6 is the deduced amino acid sequence of the HCHL protein of *Pseudomonas putida* (DSM 12585).

SEQ ID NO:7 is the nucleic acid sequence of the 5' primer (Primer 5) useful for amplifying the HCHL coding sequence from *Pseudomonas putida* (DSM 12585) and its cloning into the *E. coli* expression vector pET29a.

SEQ ID NO:8 is the nucleic acid sequence of the 3' primer (Primer 6) useful for amplifying the HCHL coding sequence from *Pseudomonas putida* (DSM 12585) and its cloning into the *E. coli* expression vector pET29a.

SEQ ID NO:9 is the nucleic acid sequence of another 3' primer (Primer 7) useful for amplifying the HCHL ORF from *Pseudomonas putida* (DSM 12585) flanked by NdeI and HindIII restriction sites and its cloning into the *E. coli* expression vector pET29a.

SEQ ID NO:10 is the amino acid sequence of a variant of the HCHL protein expressed from pET29a carrying a hexa-histidine tag.

SEQ ID NO:11 is the nucleic acid sequence of the 5' primer (Primer 8) useful for amplifying the promoter from the ACTIN2 gene of *Arabidopsis thaliana* from genomic DNA of this organism.

SEQ ID NO:12 is the nucleic acid sequence of the 3' primer (Primer 9) useful for amplifying the promoter from the ACTIN2 gene of *Arabidopsis thaliana* from genomic DNA of this organism.

SEQ ID NO:13 is the nucleic acid sequence of the ACTIN2 promoter used by applicants for expression of the HCHL coding sequence in plants.

SEQ ID NO:14 is the nucleic acid sequence of another 5' primer (Primer 10) useful for amplifying the HCHL coding sequence of *Pseudomonas putida* (DSM 12585) that introduces a PagI restriction site at the start codon of the gene.

SEQ ID NO:15 is the nucleic acid sequence of the 5' primer (Primer 11) useful for amplifying the C4H promoter of *Arabidopsis thaliana* from genomic DNA of this organism.

SEQ ID NO:16 is the nucleic acid sequence of the 3' primer (Primer 12) useful for amplifying the C4H promoter of *Arabidopsis thaliana* from genomic DNA of this organism.

SEQ ID NO:17 is the nucleic acid sequence of the C4H promoter of *Arabidopsis thaliana*.

SEQ ID NO:18 is the nucleic acid sequence of the 5' primer (Primer 13) useful for amplifying the 4CL-1 promoter of *Arabidopsis thaliana* from genomic DNA of this organism.

SEQ ID NO:19 is the nucleic acid sequence of the 3' primer (Primer 14) useful for amplifying the 4CL-1 promoter of *Arabidopsis thaliana* from genomic DNA of this organism.

SEQ ID NO:20 is the nucleic acid sequence of the 4CL-1 promoter of *Arabidopsis thaliana*.

SEQ ID NO:21 is the nucleic acid sequence of the 5' primer (Primer 15) useful for amplifying the C3'H promoter of *Arabidopsis thaliana* from genomic DNA of this organism.

SEQ ID NO:22 is the nucleic acid sequence of the 3' primer (Primer 16) useful for amplifying the C3'H promoter of *Arabidopsis thaliana* from genomic DNA of this organism.

SEQ ID NO:23 is the nucleic acid sequence of the C3'H promoter of *Arabidopsis thaliana*.

SEQ ID NO:24 is the nucleic acid sequence of the 5' primer (Primer 17) useful for amplifying the AtCesA7 (IRX3) promoter of *Arabidopsis thaliana* from genomic DNA of this organism.

SEQ ID NO:25 is the nucleic acid sequence of the 3' primer (Primer 18) useful for amplifying the AtCesA7 (IRX3) promoter of *Arabidopsis thaliana* from genomic DNA of this organism.

SEQ ID NO:26 is the nucleic acid sequence of the AtCesA7 (IRX3) stem-specific promoter of *Arabidopsis thaliana*.

SEQ ID NO:27 is the nucleic acid sequence of the C4H promoter fused to the HCHL coding sequence of *Pseudomonas putida* (DSM 12585).

SEQ ID NO:28 is the nucleic acid sequence of the 4CL-1 promoter fused to the HCHL coding sequence of *Pseudomonas putida* (DSM 12585).

SEQ ID NO:29 is the nucleic acid sequence of the C3'H promoter fused to the HCHL coding sequence of *Pseudomonas putida* (DSM 12585).

SEQ ID NO:30 is the nucleic acid sequence of the AtCesA7 (IRX3) promoter fused to the HCHL coding sequence of *Pseudomonas putida* (DSM 12585).

SEQ ID NO:31 is the nucleic acid sequence of the ZmCesA10 gene coding sequence (GenBank® Accession No. AY372244).

SEQ ID NO:32 is the deduced amino acid sequence of the ZmCesA10 enzyme.

SEQ ID NO:33 is the nucleic acid sequence of the ZmCesA11 gene coding sequence (GenBank® Accession No. AF372245).

SEQ ID NO:34 is the deduced amino acid sequence of the ZmCesA11 enzyme.

SEQ ID NO:35 is the nucleic acid sequence of the ZmCesA12 gene coding sequence (GenBank® Accession No. AF372246).

SEQ ID NO:36 is the deduced amino acid sequence of the ZmCesA12 enzyme.

SEQ ID NO:37 is the nucleic acid sequence of the rice gene identified as the ortholog to the ZmCesA10 gene.

SEQ ID NO:38 is the deduced amino acid sequence of the rice gene identified as the ortholog to the ZmCesA10 gene.

SEQ ID NO:39 is the nucleic acid sequence of the rice gene identified as the ortholog to the ZmCesA11 gene.

SEQ ID NO:40 is the deduced amino acid sequence of the rice gene identified as the ortholog to the ZmCesA11 gene.

SEQ ID NO:41 is the nucleic acid sequence of the rice gene identified as the ortholog to the ZmCesA12 gene.

SEQ ID NO:42 is the deduced amino acid sequence of the rice gene identified as the ortholog to the ZmCesA12 gene.

SEQ ID NO:43 is the nucleic acid sequence of the 2500 nucleotide bp 5' to the start codon of the rice gene orthologous to ZmCesA10 considered to be a rice promoter useful for driving stem tissue-specific HCHL expression.

SEQ ID NO:44 is the nucleic acid sequence of the 2500 nucleotide bp 5' to the start codon of the rice gene orthologous to ZmCesA11 considered to be a rice promoter useful for driving stem tissue-specific HCHL expression.

SEQ ID NO:45 is the nucleic acid sequence of the 2500 nucleotide bp 5' to the start codon of the rice gene orthologous to ZmCesA12 considered to be a rice promoter useful for driving stem tissue-specific HCHL expression.

SEQ ID NO:46 is the nucleic acid sequence of the *Arabidopsis* AtCesA4 (IRX5) stem-specific promoter.

SEQ ID NO:47 is the nucleic acid sequence of the 5' primer (Primer 19) useful for amplifying the AtCesA4 (IRX5) promoter of *Arabidopsis thaliana* from genomic DNA of this organism.

SEQ ID NO:48 is the nucleic acid sequence of the 3' primer (Primer 20) useful for amplifying the AtCesA4 (IRX5) promoter of *Arabidopsis thaliana* from genomic DNA of this organism.

SEQ ID NO:49 is the nucleic acid sequence of the *Arabidopsis* AtCesA8 (IRX1) stem-specific promoter.

SEQ ID NO:50 is the nucleic acid sequence of the 5' primer (Primer 21) useful for amplifying the AtCesA8 (IRX1) promoter of *Arabidopsis thaliana* from genomic DNA of this organism.

SEQ ID NO:51 is the nucleic acid sequence of the 3' primer (Primer 22) useful for amplifying the AtCesA8 (IRX1) promoter of *Arabidopsis thaliana* from genomic DNA of this organism SEQ ID NO:52 is the nucleic acid sequence of the first member of a primer pair (Primer 23) used to amplify the promoter of the rice gene identified as the ortholog of the ZmCesA10 gene.

SEQ ID NO:53 is the nucleic acid sequence of the second member of a primer pair (Primer 24) used to amplify the promoter of the rice gene identified as the ortholog of the ZmCesA10 gene.

SEQ ID NO:54 is the nucleic acid sequence of the first member of a primer pair (Primer 25) used to amplify the promoter of the rice gene identified as the ortholog of the ZmCesA11 gene.

SEQ ID NO:55 is the nucleic acid sequence of the second member of a primer pair (Primer 26) used to amplify the promoter of the rice gene identified as the ortholog of the ZmCesA11 gene.

SEQ ID NO:56 is the nucleic acid sequence of the first member of a primer pair (Primer 27) used to amplify the promoter of the rice gene identified as the ortholog of the ZmCesA12 gene.

SEQ ID NO:57 is the nucleic acid sequence of the second member of a primer pair (Primer 28) used to amplify the promoter of the rice gene identified as the ortholog of the ZmCesA12 gene.

SEQ ID NO:58 is the nucleic acid sequence of an HCHL gene from Psuedomonas fluorescens AN103 (GenBank® Accession No. Y13067).

SEQ ID NO:59 is the nucleic acid sequence of an HCHL gene from Pseudomonas putida WCS358 (GenBank® Accession No. Y14772).

SEQ ID NO:60 is the nucleic acid sequence of the coding sequence of an HCHL gene from Caulobacter crescentus.

SEQ ID NO:61 is the deduced amino acid sequence of the HCHL polypeptide from Caulobacter crescentus.

SEQ ID NO:62 is the nucleic acid sequence of an HCHL gene from Pseudomonas sp. HR199 (GenBank® Accession No. Y11520.1).

SEQ ID NO:63 is the nucleic acid sequence of an HCHL gene from Delftia acidovorans (GenBank® Accession No. AJ300832).

SEQ ID NO:64 is the nucleic acid sequence of an HCHL gene from Amycolatopsis sp. HR167 (GenBank® Accession No. AJ290449).

SEQ ID NO:65 is the nucleic acid sequence of a pHBA UDP-glucosyltransferase isolated from grape (Vitis sp.; U.S. Ser. No. 10/359,369).

SEQ ID NO:66 is the nucleic acid sequence of a pHBA UDP-glucosyltransferase isolated from Eucalyptus grandis (U.S. Ser. No. 10/359,369).

SEQ ID NO:67 is the nucleic acid sequence of a pHBA UDP-glucosyltransferase isolated from Citrus mitis (U.S. Ser. No. 10/359,369).

SEQ ID NO:68 is the nucleic acid sequence of a primer (Primer 29) used to amplify an HCHL ORF from Caulobacter crescentus.

SEQ ID NO:69 is the nucleic acid sequence of a primer (Primer 30) used to amplify the HCHL ORF from Caulobacter crescentus.

SEQ ID NO:70 is the nucleic acid sequence of a primer (Primer 31) used to amplify the HCHL ORF from Pseudomonas fluorescens AN103.

SEQ ID NO:71 is the nucleic acid sequence of a primer (Primer 32) used to amplify the HCHL ORF from Pseudomonas fluorescens AN103.

SEQ ID NO:72 is the nucleic acid sequence of a primer (Primer 33) used to amplify the ACTIN2 gene from Arabidopsis thaliana for real time PCR analysis.

SEQ ID NO:73 is the nucleic acid sequence of a primer (Primer 34) used to amplify the ACTIN2 gene from Arabidopsis thaliana for real time PCR analysis.

SEQ ID NO:74 is the nucleic acid sequence of a primer (Primer 35) used as a probe for the ACTIN2 gene from Arabidopsis thaliana for real time PCR analysis.

SEQ ID NO:75 is the nucleic acid sequence of a primer (Primer 36) used to amplify the Caulobacter HCHL gene during real time PCR analysis.

SEQ ID NO:76 is the nucleic acid sequence of a primer (Primer 37) used to amplify the Caulobacter HCHL gene during real time PCR analysis.

SEQ ID NO:77 is the nucleic acid sequence of a primer (Primer 38) used as a probe for the Caulobacter HCHL gene during real time PCR analysis.

SEQ ID NO:78 is the nucleic acid sequence of a primer (Primer 39) used to amplify the Pseudomonas HCHL gene during real time PCR analysis.

SEQ ID NO:79 is the nucleic acid sequence of a primer (Primer 40) used to amplify the Pseudomonas HCHL gene during real time PCR analysis.

SEQ ID NO:80 is the nucleic acid sequence of a primer (Primer 41) used as a probe for the Pseudomonas HCHL gene during real time PCR analysis.

SEQ ID NO:81 is the nucleic acid sequence of the ZmCesA10 promoter.

SEQ ID NO:82 is the nucleic acid sequence of the ZmCesA11 promoter.

SEQ ID NO:83 is the nucleic acid sequence of the ZmCesA12 promoter.

DETAILED DESCRIPTION OF THE INVENTION

The present invention provides methods and materials to produce para-hydroxybenzoic acid in the stalk tissue of genetically modified plants at commercially useful levels. Stem tissue-specific promoters have been identified from genes involved cellulose synthesis during plant secondary cell wall formation. Unexpectedly only promoters of certain cellulose synthase genes, when operably linked to an HCHL coding sequence, significantly limit HCHL expression to plant stem tissue. Promoter of genes controlling lignin biosynthesis in the plant stalk on the other hand failed to significantly increase stalk-specificity of HCHL expression. The use of cellulose synthase promoters for targeting HCHL expression to plant stem tissue resulted in significant pHBA production in the plants without the negative phenotypic changes associated with constitutive expression. A family of genes has been identified which represent a suitable source of stem tissue-specific promoters. Additionally, an HCHL enzyme from Caulobacter crescentus has been identified with superior catalytic efficiency for converting pHCACoA into pHBA.

The pHBA produced in the transgenic plants was converted to a mixture of pHBA glucoside (phenolic) and pHBA glucose ester by naturally occurring UDP-glucosyltransferases. Optionally, a foreign UDP-glucosyltransferase may be introduced into the transgenic plant for selective production of the pHBA glucose ester.

Transgenic plants (Arabidopsis) were modified to functionally express several chimeric genes encoding a 4-hydroxycinnamoyl-CoA hydratase/lyase (HCHL). The chimeric genes were created by fusing various promoters to the coding sequence of the HCHL gene from Pseudomonas putida (DSM 12585). Several stem tissue-specific promoters were compared to constitutive promoters (non-tissue-specific) for their ability to 1) functionally express HCHL at levels comparable to the constitutive promoters for the production of pHBA, and 2) significantly limit expression of HCHL to plant stem tissue. The Arabidopsis AtCesA7 (IRX3) promoter was shown to limit expression of HCHL to plant stem tissue. This parallels the expression pattern observed for the endogenous AtCesA7 gene. Consequently, additional genes were identified as suitable sources of promoters for stem tissue-specific expression based on their observed expression patterns. Promoter sequences are provided that are suitable for driving tissue-specific HCHL expression. These include the Arabidopsis promoters derived from the AtCesA4 (IRX5) and AtCesA8 (IRX1) genes, as well as promoters from orthologous genes from maize and rice.

Methods are provided for the producing of pHBA from pHCACoA in plant stem tissue using an HCHL enzyme. Plant stem tissue is a natural reservoir where suitable levels of pHCACoA exist and where significant fluxes to the phenylpropanoid pathway can occur. Constitutive expression of HCHL (in all plant tissues) results in negative effects on the plant's agronomic performance. Methods are provided for tissue-specific expression of HCHL, resulting in production of pHBA in industrially-suitable amounts without negative phenotypic changes to the plant. Expression of HCHL needs to be limited to plant stem tissue. Tissues, such as leaf, do not contain suitable amounts of pHCACoA necessary for pHBA production. A unique set of tissue-specific promoters has been identified which are suitable for HCHL expression in plants.

The pHBA produced in the transgenic plants was converted to a mixture of pHBA glucoside (phenolic) and pHBA glucose ester by naturally occurring UDP-glucosyltransferases. Optionally, a foreign UDP-glucosyltransferase may be introduced into the transgenic plant for selective production of the pHBA glucose ester.

Definitions:

In this disclosure, a number of terms and abbreviations are used. The following definitions are provided.

"Polymerase chain reaction" is abbreviated "PCR".

"Para-hydroxybenzoic acid" or "p-hydroxybenzoic acid" is abbreviated "pHBA".

"Para-coumaroyl-CoA" is abbreviated "pHCACoA".

"Chorismate pyruvate lyase" is abbreviated "CPL" and refers to an enzyme which catalyzes the conversion of chorismate to pyruvate and pHBA.

"4-hydroxycinnamoyl-CoA hydratase/lyase" is abbreviated "HCHL" and refers to an enzyme (EC 4.2.1.101/EC 4.1.2.41) that catalyzes the hydration of the double bond of a hydroxycinnamoyl CoA thioester followed by a retro aldol cleavage reaction that produces a benzoyl aldehyde and acetyl CoA. The HCHL enzyme converts 1 mol of pHCA-CoA to 1 mol of acetylCoA and 1 mol of p-hydroxybenzaldehyde (pBALD). In plants, pBALD is subsequently converted to pHBA through the action of endogenous enzymes that are present in the cytoplasm.

"Homolog", "homologue", and "homologous gene" are terms used to describe a gene having similar structure, nucleic acid sequence, and evolutionary origin in comparison to another gene.

"Ortholog", "orthologue", and "orthologous gene" are terms used to describe a gene having similar structure, nucleic acid sequence, and evolutionary origin in comparison to another gene in a different species. Orthologs are homologs that usually share the same function and organization within a biosynthetic pathway. In the present invention, the orthologous genes encoding the subunits of the cellulose synthesis catalytic complex (associated with cells involved in the secondary cell wall synthesis) exhibit evolutionarily conserved structure, function, expression pattern, and organization. The conserved structure, function, expression pattern, and organization are believed to pre-date the evolutionary divergence of monocots and dicots. Promoters isolated from the *Arabidopsis thaliana* genes AtCesA8 (IRX1), AtCesA7 (IRX3), and AtCesA4 (IRX5), as well as promoters of the orthologous genes from maize and rice, are suitable for stem tissue-specific expression of HCHL.

"Paralog", "paralogue", and "paralogous gene" are terms used to describe a homolog where sequence divergence follows a gene duplication event within the same lineage. Paralogs are homologs that usually have different function.

"Cellulose synthase gene", "CESA", and "CesA" are terms used to describe a family of genes encoding proteins (EC 2.4.1.12) involved in cellulose synthesis. They generally exhibit significant homology to one another and share a conserved sequence motif (Taylor et al., supra (2003)). The various members of this family (at least 12 identified in *Arabidopsis*) differ in their expression patterns and functions. Three CesA family members that encode for proteins involved in formation of the cellulose synthesis catalytic complex responsible cellulose production during secondary cell wall formation, have been identified in *Arabidopsis* (AtCesA8, AtCesA7, AtCesA4) as well as their orthologs from maize and rice. AtCesA8, AtCesA7, and AtCesA4 encode proteins that have been identified as absolutely necessary for cellulose synthesis in secondary cell wall formation. Expression of these three genes (as well as orthologs thereof) is significantly limited to cells involved in secondary cell wall biosynthesis (a significant portion of the cells in plant stem tissue). The promoters from these genes regulate an expression pattern suitable for recombinant HCHL expression in plant stem tissue.

"AtCesA8" and "AtCesA8 (IRX1)" are terms used to describe one of the three genes identified in *Arabidopsis thaliana* encoding a cellulose synthase family protein that is a component of the cellulose synthesis catalytic complex. This gene, identified by Taylor et al. (supra (2003)) by an irregular xylem mutation "IRX1", is expressed in cells involved in secondary cell wall synthesis. The promoter from this gene exhibits a suitable tissue-specific expression pattern for driving recombinant HCHL expression in plant stem tissue.

"AtCesA7" and "AtCesA7 (IRX3)" are terms used to describe one of the three genes identified in *Arabidopsis thaliana* encoding a cellulose synthase family protein that is a component of the cellulose synthesis catalytic complex. This gene, identified by Taylor et al. (supra (2003)) by an irregular xylem mutation "IRX3", is expressed in cells involved in secondary cell wall synthesis. The promoter from this gene exhibits a suitable tissue-specific expression pattern for driving recombinant HCHL expression in plant stem tissue.

"AtCesA4" and "AtCesA4 (IRX5)" are terms used to describe one of the three genes identified in *Arabidopsis thaliana* encoding a cellulose synthase family protein that is a component of the cellulose synthesis catalytic complex. This gene, identified by Taylor et al. (supra (2003)) by an irregular xylem mutation "IRX5", is expressed in cells involved in secondary cell wall synthesis. The promoter from this gene exhibits a suitable tissue-specific expression pattern for driving recombinant HCHL expression in plant stem tissue.

"ZmCesA10" is a gene identified in *Zea mays* that is an ortholog of AtCesA4 (IRX5) based on comparative sequence analysis (FIG. 4). The gene encodes a cellulose synthase family protein that is a component of the cellulose synthesis catalytic complex. ZmCesA10 expression is limited to cells involved in synthesizing cellulose for secondary cell wall formation. The promoter from this gene exhibits a suitable tissue-specific expression pattern for driving recombinant HCHL expression in plant stem tissue.

"ZmCesA11" is a gene identified in *Zea mays* that is an ortholog of AtCesA8 (IRX1) based on comparative sequence analysis (FIG. 4). The gene encodes a cellulose synthase family protein that is a component of the cellulose synthesis catalytic complex. ZmCesA11 expression is limited to cells involved in synthesizing cellulose for secondary cell wall formation. The promoter from this gene exhibits a suitable tissue-specific expression pattern for driving recombinant HCHL expression in plant stem tissue."

"ZmCesA12" is a gene identified in *Zea mays* that is an ortholog of AtCesA7 (IRX3) based on comparative sequence analysis (FIG. 4). The gene encodes a cellulose synthase family protein that is a component of the cellulose synthesis catalytic complex. ZmCesA12 expression is limited to cells involved in synthesizing cellulose for secondary cell wall formation. The promoter from this gene exhibits a suitable tissue-specific expression pattern for driving recombinant HCHL expression in plant stem tissue.

"Rice orthologs" and "rice orthologous genes" are terms used to describe genes identified in *Oryza savita* (japonica cultivar group) which are orthologs to various maize cellulose synthase catalytic subunit genes (i.e. ZmCesA10, Zm,CesA11, and ZmCesA12) based on BLAST analysis of the publicly-available rice BAC database (National Center for Biotechnology Information (NCBI), U.S. National Library of Medicine, Bethesda, Md.). Based on the conserved nature of the expression patterns of the genes encoding proteins involved in the formation of the cellulose synthesis catalytic complex between monocots (i.e. *Zea mays*) and dicots (i.e. *Arabidopsis thaliana*) and the somewhat closer phylogenic relationship between maize and rice, the expression pattern of these genes are expected to parallel that of their orthologous counterparts in maize and *Arabidopsis*. The genes are believed to encode a cellulose synthase family protein that is a component of the cellulose synthesis catalytic complex. Suitable promoters derived from rice orthologs are those that significantly limit HCHL expression to plant stem tissue.

"Suitable tissue-specific promoter" is a term used in the present invention to describe a promoter that exhibits a stem tissue-specific expression pattern. Expression of chimeric genes created by the fusion of such a promoter to the HCHL coding sequence must be significantly limited to stem tissue cells where either suitable levels of pHCACoA exist or where large fluxes to the phenylpropanoid pathway can occur. Insignificant expression levels measured in non-stem tissues (especially leaf tissue) are acceptable as long as no detrimental effects on agronomic performance are observed. Preferred suitable tissue-specific promoters include those that exhibit the ability to preferentially expression active HCHL protein at least 10-fold higher in stem tissue in comparison to leaf tissue (stem:leaf≧10:1). More preferred promoters are those that exhibit at least a 20-fold preference for HCHL expression in stem tissue in comparison to leaf tissue (stem:leaf≧20:1). Most preferred are those promoters that are capable of at least 50-fold stem to leaf tissue HCHL expression ratio (stem:leaf≧50:1).

"4CL1" is the promoter from the gene encoding the 4CL enzyme. 4-Coumarate-coenzymeA ligase (4CL) enzymes are operationally soluble, monomeric enzymes of 60 kDa molecular weight belonging to the class of adenylate forming CoA ligases.

"C4H" is the promoter from the gene encoding the C4H enzyme. Cinnamate-4-hydroxylase (C4H) catalyzes the 4-hydroxylation of the aromatic ring of cinnamic acid.

"C3'H" is the promoter from the gene encoding the p-coumarate-3-hydrolyase enzyme. The p-coumarate-3-hydroxylase (C3H) enzyme (CYP98A3, GenBank® Accession No. AC011765) generates the 3,4-hydroxylated caffeoyl intermediate in lignin biosynthesis.

"ACT2" is a term used to describe the promoter from the ACTIN2 gene. The promoter confers a constitutive pattern of reporter gene expression in plants (An et al., *Plant Journal*, 10(1):107-121 (1996)).

"35SCaMV" is a term used to describe the promoter isolated from the Cauliflower Mosaic Virus that is commonly used in genetic engineering for constitutive expression of proteins.

"Cellulose synthesis catalytic complex" is a complex of at least 3 distinct cellulose synthase catalytic subunits that are required for secondary cell wall cellulose synthesis in plants. The genes encoding the members of this complex in *Arabidopsis* include AtCesA4 (IRX5), AtCesA7 (IRX3), AtCesA8 (IRX1) (Taylor et al., supra (2003)). All three subunits are required for correct assembly of the protein complex. The genes encoding the catalytic subunits exhibit a tissue-specific expression pattern suitable for HCHL expression. Corresponding orthologs in maize are shown by example to exhibit a similar expression pattern.

The terms "p-hydroxybenzoic acid glucoside" and "pHBA glucoside" refer to a conjugate comprising pHBA and a glucose molecule. pHBA glucose conjugates include the pHBA phenolic glucoside and pHBA glucose ester.

The terms "UDP-glucosyltransferase" and "glucosyltransferase" are abbreviated as "GT" and refer to enzymes (EC 2.4.1.194) involved in the formation of glucose-conjugated molecules. Such proteins catalyze a reaction between UDP-glucose and an acceptor molecule to form UDP and the glucosylated acceptor molecule. In most cases the hydroxyl group on C1 β-D-glucose is attached to the acceptor molecule via a 1-O-β-D linkage.

The term "aglycone" refers to substrates of the present invention that lack a glucose moiety (i.e., unconjugated pHBA).

The term "pHBA derivative" refers to any conjugate of pHBA that may be formed in a plant as the result of the catalytic activity of the HCHL enzyme.

As used herein, an "isolated nucleic acid fragment" is a polymer of RNA or DNA that is single- or double-stranded, optionally containing synthetic, non-natural, or altered nucleotide bases. An isolated nucleic acid fragment in the form of a polymer of DNA may be comprised of one or more segments of cDNA, genomic DNA or synthetic DNA.

"Gene" refers to a nucleic acid fragment that expresses a specific protein, including regulatory sequences preceding (5' non-coding sequences) and following (3' non-coding sequences) the coding sequence. "Native" or "wild type" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "exogenous" gene refers to a gene not normally found in the host organism, but that is introduced into the host organism by gene transfer. "Foreign" may also be used to describe a nucleic acid sequence not found in the wild-type host into which it is introduced. Foreign genes can comprise native genes inserted into a non-native organism, or chimeric genes. A "transgene" is a gene that has been introduced into the genome by a transformation procedure.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing sites, effector binding sites, and stem-loop structures.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters that cause a nucleic acid fragment to be expressed in most cell types at most times are commonly referred to as "constitutive promoters". Tissue-specific promoters are those which direct expression of genes in limited tissue types. However, many "tissue-specific" promoters exhibit expression that is not significantly limited to the tissue of interest. Suitable tissue-specific promoters of the present invention are those that limit chimeric gene expression to stem tissue without significant expression in other tissues resulting in adverse phenotypic changes to the plant. The *Arabidopsis* AtCesA8 (IRX1), AtCesA7 (IRX3), and AtCesA4 (IRX5) promoters, as well as promoters isolated from the respective orthologous genes from rice and maize (ZmCesA11, ZmCesA12, and ZmCesA10), are examples of suitable tissue-specific promoters useful in the present invention. The expression pattern associated with these promoters is highly correlated and significantly limited to plant stem tissue (FIG. 5, Table 8). New promoters of various types useful in plant cells are constantly being discovered; numerous examples may be found in the compilation by Okamuro and Goldberg (In *The Biochemistry of Plants*, Vol. 15 published by Academic Press, Burlington, Mass., pages 1-82, (1989)). It is further recognized that in most cases the exact boundaries of regulatory sequences have not been completely defined, nucleic acid fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic", "recombinant", or "transformed" organisms.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humana: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.).

pHBA Production in Transgenic Plants Using HCHL pHBA is naturally occurring in nearly all plants, animals, and microorganisms, albeit in miniscule quantities. In plants, pHBA has been found in carrot tissue (Schnitzler et al., *Planta*, 188:594, (1992)), in a variety of grasses and crop plants (Lydon et al., *J. Agric. Food. Chem.*, 36:813, (1988)), in the lignin of poplar trees (Terashima et al., *Phytochemistry*, 14:1991, (1972)), and in a number of other plant tissues (Billek et al., *Oesterr. Chem.*, 67:401, (1966)). The fact that plants possess all of the necessary enzymatic machinery to synthesize pHBA suggests that they may be a useful platform for producing this monomer. For example, as a renewable resource a plant platform would require far less energy and raw materials than either petrochemical or microbial methods for producing the monomer. Similarly, a plant platform represents a far greater available biomass for monomer production than a microbial system. Finally, the natural presence of pHBA in plants suggests that host toxicity (a result of overproduction of the compound) might not be a problem.

Transgenic plants that accumulate significantly higher levels of pHBA than wild-type plants have been described. 4-Hydroxycinnamoyl-CoA hydratase/lyase (HCHL) isolated from *Pseudomonas fluorescens* AN103 is a bacterial enzyme that when expressed in transgenic tobacco (*Nicotiana tabacum* cv. Xanthi XHFD8) resulted in significant accumulation of pHBA glucosides (Mayer et al., supra). Expression of HCHL in the transgenic plant's cytosol redirected the carbon flux from the phenylpropanoid pathway into the production of pHBA glucosides. However, constitutive expression of HCHL in plant tissues (such as leaf) where inadequate amounts of pHCACoA exist or where a high-flux to the phenylpropanoid pathway cannot occur, significantly depletes of secondary metabolites having roles as plant growth regulators, UV protectants, or cell wall components such as lignin, cutin, or suberin. Depletion of secondary metabolites in these tissues resulted in adverse plant growth defects such as interveinal leaf chlorosis, stunting, low pollen production, and male sterility.

Sterility is very likely caused by severe reduction in flavonoid levels. For example, pHCACoA-derived flavonols are required for pollen germination in solanaceous plants like tobacco (Napoli et al., *Plant Physiology*, 120(2):615-622 (1999)). Premature senescence and dwarfism may be caused by the depletion of ferulic acid-derived dehydrodiconiferyl alcohol glucosides (Teutonico et al., *Plant Physiology*, 97(1):288-97 (1991)). There is evidence that these molecules are components of a cytokinin-mediated regulatory circuit controlling cell division in plants (Teutonico et al., supra). (Cytokinin is obviously an important signaling component that counteracts senescence (Gan and Amasino, *BioEssays*, 18(7):557-565 (1996))). The cytokinin-like activity of these molecules could lead one to speculate that their depletion is also responsible for the early-senescence phenotype of some HCHL-expressing plants.

The source of the HCHL gene used for engineering transgenic plants for pHBA production is not limited to *Pseudomonas fluorescens* AN103 (Gasson et al., *J Bio Chem*, 273(7):4163-4170 (1998)); WO 97/35999; and U.S. Pat. No. 6,323,011). Additional microorganisms reported to have genes encoding HCHL activity include, but are not limited to, *Pseudomonas putida* DSM 12585 (Muheim and Lerch, *Appl Microbiol Biotechnol*, 51:456-461 (1999)), *Pseudomonas putida* WCS358 (Venturi et al., *Microbiol*, 144(4):965-973 (1998)); *Pseudomonas* sp. HR199 (Priefert et al., *J Bacteriol*, 179(8):2595-2607 (1997)), *Delftia acidovorans* (Plagenborg et al., *FEMS Microbiol Lett*, 205(1): 9-16 (2001)), and Amycolatopsis HR167 (Achterholt et al., *Appl Microbiol Biotechnol*, 54(6): 799-807 (2000); WO 01/044480).

The use of the HCHL gene from *Pseudomonas putida* DSM 12585 is illustrated in the present invention. However, the source of suitable HCHL genes useful for plant transformation and production of pHBA is not limited to the examples provided herein. Examples include, but are not limited to, those HCHL genes listed in Table#1. The coding sequence from any HCHL gene is suitable in the present invention based on the reported ability to functionally express various bacterial HCHL genes in the cytosol of plant cells (Mitra et al., supra; Mayer et al., supra; and WO 97/35999). Additionally, an HCHL isolated from *Caulobacter crescentus* (SEQ ID NOs:60 and 61) is provided that exhibits increased kinetic properties for pHBA synthesis as compared to the HCHL enzymes from *P. putida* DSM 12685 and *P. fluorescens* AN103.

TABLE 1

Source of HCHL Genes

| GenBank ® Accession Number and (Source Organism) | Sequence Identification Number (SEQ ID NO) |
|---|---|
| (*Pseudomonas putida* DSM 12585) | 5 |
| Y13067 | 58 |
| (*Pseudomonas fluorescens* AN103) | |
| Y14772 | 59 |
| (*Pseudomonas putida* WCS358) | |
| AE005909.1 | 60 |
| (*Caulobacter crescentus*) | |
| Y11520.1 | 62 |
| (*Pseudomonas* sp. HR199) | |
| AJ300832 | 63 |
| (*Delftia acidovorans*) | |
| AJ290449 | 64 |
| (*Amycolatopsis* sp. HR167) | |

HCHL Expression Cassette

An expression cassette useful for the producing of pHBA in plant stem tissue includes a suitable stem tissue-specific promoter operably linked to the HCHL coding sequence. Typically, the expression cassette will comprise (1) the cloned HCHL coding sequence under the transcriptional control of 5' (suitable stem cell specific promoter) and 3' regulatory sequences and (2) a dominant selectable marker. The present expression cassette may also contain a transcription initiation start site, a ribosome-binding site, an RNA processing signal, a transcription termination site, and/or a polyadenylation signal. Optionally, the cassette may also comprise one or more introns in order to facilitate HCHL expression.

The most well characterized HCHL gene has been isolated from *Pseudomonas fluorescens* AN103 (GenBank® Accession No. Y13067.1). DNA sequence of an HCHL gene from *Pseudomonas putida* DSM 12585 (Muheim and Lerch, *App. Micro. Biotech.*, 51(4):456-461 (1999)) and the deduced amino acid sequence of the HCHL protein of this organism is set forth herein as SEQ ID NO:5 and SEQ ID NO:6, respectively. This gene has been isolated by the Applicants and is useful for producing of pHBA in transgenic plants.

Tissue-Specific Promoters for Expression of HCHL

The use of tissue-specific promoters is known in the art. However, many of these reported promoters exhibit only preferential expression in certain plant and/or animal tissues, allowing significant expression in other tissues, albeit at levels at or below the target tissue. HCHL expression in this invention is selectively limited to where a suitable substrate pool is available or where large fluxes to the phenylpropanoid pathway may occur since expression in other tissues, such as leaf, has been shown to be detrimental to the agronomic performance of the plant (Mayer et al., *Plant Cell*, 13:1669-1682 (2001)).

Genes involved in lignin biosynthesis were tested as a source of suitable tissue-specific promoters. These promoters were operably linked to the coding sequence of an HCHL gene. The chimeric constructs were tested for tissue-specific expression in plants (*Arabidopsis*). HCHL expression was not significantly limited to plant stem tissue (Table 6). Because of this, these promoters were not considered suitable for HCHL expression.

Plant stem tissue contains significant amount of cellulose. Genes encoding enzyme involved in cellulose synthesis were identified as possible source for tissue-specific promoters suitable for chimeric HCHL expression. Three genes from *Arabidopsis thaliana* were identified as critical to cellulose synthesis in cells involved in secondary cell wall formation. These genes, AtCesA4 (IRX5), AtCesA7 (IRX3), and AtCesA8 (IRX1), have been shown to have a desirable expression pattern suitable for chimeric HCHL expression. The proteins encoded by these genes interact and form the cellulose synthesis catalytic complex (Taylor et al., supra (2003)). Their expression is closely correlated with one another, essentially limited to cells involved in producing cellulose for secondary cell wall formation. The promoter from one of the genes (AtCesA7 (IRX3)), was isolated and operably linked to the coding sequence of an HCHL gene. HCHL expression was measured between the stem tissue versus leaf tissue in *Arabidopsis* plants transformed with the chimeric constructs. HCHL expression was not significantly limited to plant stem tissue (Table 6).

It has been reported that the genetic organization of the genes encoding proteins involved in forming the cellulose synthesis catalytic complex have been conserved across monocots and dicots (Holland et al., *Plant Physiol*., 123: 1313-1323 (2000)). Expression analysis of orthologous genes from *Zea mays* (ZmCesA10, ZmCesA11, and ZmCesA12) also shows a similar pattern, namely gene expression that is essentially limited to cells involved in cellulose synthesis during secondary cell wall formation. Consequently, promoters from these genes as well as promoters from orthologous genes from rice (*Oryza savita* (japonica cultivar group)) are suitable for stem-specific expression of HCHL.

In the present invention, suitable promoters for HCHL expression control an HCHL expression pattern—where HCHL activity is at least 20-fold higher in stem tissue in comparison to leaf tissue. More preferred promoters are those that control an HCHL expression pattern where HCHL activity is at least 30-fold higher in stem tissue when compared to leaf tissue. Most preferred promoters suitable in the present invention are those that control an HCHL expression pattern where HCHL activity is at least 50-fold higher in stem tissue when compared to leaf tissue. Suitable promoters can be identified by comparison of HCHL activity converting pHCACoA to p-Hydroxybenzaldehyde (expressed as pkcat/mg protein) in stem and leaf tissue of transgenic plants expressing HCHL genes under the control of tissue-specific promoters. Alternatively, suitable promoters can be identified by comparing pHBA production observed in stem and leaf tissues of transgenic plants expressing HCHL genes under the control of tissue-specific promoters. Suitable promoters when fused to HCHL genes will generate a pattern of pHBA accumulation where pHBA accumulation in stalk tissue is >10 higher than pHBA accumulation in leaf tissue. Alternatively, suitable promoters can be identified by performing MPSS analysis of gene expression in various plant tissues. Promoters suitable for HCHL gene expression in plants are those that show high levels of gene expression in stalk tissue (>350 ppm) and show a pattern of gene expression were gene expression is at least 10-fold higher in stalk tissue when stalk and leaf tissues are compared. More preferred promoters show a pattern of gene expression were gene expression is at least 20-fold higher in stalk tissue when stalk and leaf tissues are compared. More preferred promoters show a pattern of gene expression were gene expression is at least 50-fold higher in stalk tissue when stalk and leaf tissues are compared.

UDP-Glucosyltransferases

Most of the products of secondary metabolism in plants are glycosylated (Harborne, J., *Introduction to Ecological Biochemistry*, 4$^{th}$ ed.; Academic Press: London, 1993), as are many herbicides after modification by phase I enzymes. An impressive array of conjugated species, including coumaryl glucosides, flavonoids, anthocyanins, cardenolides, soponins, cyanogenic glucosides, glucosinolates, and betalains, are known to be stored in the vacuole (Wink, M., In *The Plant Vacuole: Advances in Botanical Research*; Leigh, R. A., Sanders, D. and Callow, J. A., Eds.; Academic Press: London, N.Y., 1997; Vol. 25, pp 141-169). Based on these observations and the fact that most UDP-glucosyltransferases are located in the cytosol, glucosylation has been invoked as a prerequisite for uptake and accumulation in the vacuole. In addition, in vitro experiments clearly demonstrate that isolated vacuoles and/or vacuolar membrane vesicles are able to take up certain glucose conjugates, while the parent molecules are not transported (Wink, M., supra).

It has been shown that the vast majority of pHBA produced in transgenic plant cells is rapidly converted by endogenous UDP-glucosyltransferases to two glucose conjugates, a phenolic glucoside with the glucose moiety attached to the aromatic hydroxyl group, and a glucose ester where the sugar is attached to the aromatic carboxyl group (Siebert et al., *Plant Physiol*. 112:811-819 (1996); Mayer et al., supra; Mitra et al., supra; and U.S. Ser. No. 10/359,369). The vast majority of plants contain endogenous UDP-glucosyltransferases that form both glucose conjugates of pHBA. Although both glucose conjugates accumulate in the vacuole, they have very different chemical properties and physiological roles.

For example, the pHBA glucose ester (like other acetal esters) is characterized by high free energy of hydrolysis, which makes it very simple to recover the parent compound with low concentrations of either acid or base. This could greatly reduce the cost of producing pHBA in plants. Furthermore, it is well established that certain glucose esters are able to serve as activated acyl donors in enzyme-mediated transesterification reactions (Li et al., *Proc. Natl. Acad. U.S.A*., 97(12):6902-6907 (2000); Lehfeldt et al., *Plant Cell*, 12(8):1295-1306 (2000)). In light of these observations, it would be extremely desirable to control the partitioning of pHBA glucose conjugates in vivo. For example, by overexpressing an appropriate glucosyltransferase in transgenic plants that generate large amounts of pHBA, it might be possible to accumulate all of the desired compound as the glucose ester, which can be easily hydrolyzed to free pHBA. While the above scenario is extremely attractive, it requires an enzyme with the appropriate properties and molecular information that would allow access to the gene (e.g., its nucleotide or primary amino acid sequence).

Commonly owned U.S. Ser. No. 10/359,369, hereby incorporated by reference, provides examples of UDP-glucosyltransferases that preferentially use pHBA as a substrate and which selectively convert pHBA to pHBA glucose ester. Examples of nucleic acid molecules encoding these pHBA UDP-glucosyltransferases are represented by SEQ ID NOs: 65, 66, and 67, respectively. In a preferred embodiment of the invention, genes encoding pHBA UDP-glucosyltransferases that preferentially convert pHBA to pHBA glucose ester are used to transform plants functionally expressing HCHL in plant stem tissue.

Plant Gene Expression

Promoters useful for expressing the genes are numerous and well known in the art. Plant tissue-specific promoters have been reported (Yamamoto et al., *Plant Cell Phys.* 35(5):773-778 (1994); Kawamata et al., *Plant Cell Phys.*, 38(7):792-803 (1997); Rinehart et al., *Plant Phys.*, 112: 1331-1341 (1996); Van Camp et al., *Plant Phys.*, 112:525-535 (1996); Canevascini et al., *Plant Phys.*, 112:513-524 (1996); Guevara-Garcia et al., *Plant Journal*, 4(3):495-505 (1993); and Yamamoto et al., *Plant Journal*, 12(2):255-265 (1997)). However, the ability of these promoters to limit HCHL expression to plant stem tissue has not been reported. It has been shown that HCHL expression must be limited to plant tissues where a significant pool of substrate (pHCA-CoA) is available and where high flux to the phenylpropanoid pathway is possible.

A preferred embodiment of the current invention is the use of an exogenous UDP-glucosyltransferase for selection production of pHBA glucose ester (U.S. Ser. No. 10/359, 369). Any combination of any promoter and any terminator capable of inducing expression of the exogenous UDP-glucosyltransferase may be used in the present invention. Expression of an exogenous pHBA UDP-glucosyltransferase does not need to be targeted to a specific plant tissue. Some suitable examples of promoters and terminators include those from nopaline synthase (nos), octopine synthase (ocs), and cauliflower mosaic virus (CaMV) genes. Such promoters, in operable linkage with the pHBA UDP-glucosyltransferases of the present invention, are capable of promoting expression of these genes for selective production of pHBA glucose ester. High-level plant promoters that may be also be used in this invention include the promoter of the small subunit (ss) of the ribulose-1,5-bisphosphate carboxylase from soybean (Berry-Lowe et al., *J. Mol. App. Gen.*, 1:483-498 (1982)), and the promoter of the chlorophyll a/b binding protein. These two promoters are known to be light-induced in plant cells (See, for example, *Genetic Engineering of Plants, an Agricultural Perspective*, A. Cashmore, Plenum, N.Y. (1983), pages 29-38; Coruzzi, G. et al., *J. Bio. Chem.*, 258:1399 (1983); and Dunsmuir et al., *J. Mol. App. Gen.*, 2:285 (1983)).

Where polypeptide expression is desired, it is generally desirable to include a polyadenylation region at the 3'-end of each gene's coding region in the present invention. The polyadenylation region can be derived from a variety of plant genes or from T-DNA. For example, the 3' end sequence to be added can be derived from the nopaline synthase or octopine synthase genes, or alternatively from another plant gene, or, less preferably, from any other eukaryotic gene.

An intron sequence can be added to the 5' untranslated region or the coding sequence of the partial coding sequence to increase the amount of the mature message that accumulates in the cytosol. Inducing a spliceable intron in the transcription unit of both plant and animal expression constructs has been shown to increase gene expression at both the mRNA and protein levels up to 1000-fold (Buchman and Berg, *Mol. Cell Biol.*, 8:4395-4405 (1988); Callis et al., *Genes Dev.*, 1:1183-1200 (1987)). Such intron enhancement of gene expression is typically greatest when placed near the 5' end of the transcription unit. Use of maize introns Adh1-S intron 1, 2, and 6, the Bronze-1 intron are known in the art. (See generally, *The Maize Handbook*, Chapter 116, Freeling and Walbot, Eds., Springer, N.Y. (1994).)

Virtually any plant host that is capable of supporting the expression of the genes in the present invention will be suitable; however, crop plants are preferred for their ease of harvesting and large biomass. Suitable plant hosts include, but are not limited to, both monocots and dicots such as soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa*, L), sorghum (*Sorghum bicolor*), rice (*Oryza sativa*), Arabidopsis, sugar beet, sugar cane, canola, millet, beans, peas, rye, flax, and forage grasses. Preferred plant hosts are tobacco, *Arabidopsis thaliana*, sugarcane, and sugar beet.

Plant Transformation

A variety of techniques are available and known to those skilled in the art to introduce constructs into a plant cell host. These techniques include transformation with DNA employing *A. tumefaciens* or *A. rhizogenes* as the transforming agent, electroporation, and particle acceleration (EP 295959 and EP 138341). One suitable method involves the use of binary type vectors of Ti and Ri plasmids of *Agrobacterium* sp. Ti-derived vectors transform a wide variety of higher plants including monocotyledonous and dicotyledonous plants such as soybean, cotton, rape, tobacco, and rice (Pacciotti et al., *Bio/Technology*, 3:241 (1985); Byrne et al., *Plant Cell, Tissue and Organ Culture*, 8:3 (1987); Sukhapinda et al., *Plant Mol. Biol.*, 8:209-216 (1987); Lorz et al., *Mol. Gen. Genet.*, 199:178 (1985); Potrykus et al., *Mol. Gen. Genet.*, 199:183 (1985); Park et al., *J. Plant Biol.*, 38(4): 365-71 (1995); and Hiei et al., *Plant J.*, 6:271-282 (1994)). The use of T-DNA to transform plant cells has received extensive study and is amply described (EP 120516; Hoekema, In: *The Binary Plant Vector System*, Offset-drukkerij Kanters B. V.; Alblasserdam (1985), Chapter V; Knauf et al., *Genetic Analysis of Host Range Expression by Agrobacterium* In: *Molecular Genetics of the Bacteria-Plant Interaction*, Puhler, A. ed., Springer-Verlag, New York, 1983, p. 245; and An et al., *EMBO J.*, 4:277-284 (1985)). For introduction into plants, the chimeric genes can be inserted into binary vectors as described in the examples.

Other transformation methods are known to those skilled in the art. Examples include direct uptake of foreign DNA constructs (EP 295959), techniques of electroporation (Fromm et al., *Nature* (London), 319:791 (1986)), and high-velocity ballistic bombardment with metal particles coated with the nucleic acid constructs (Kline et al., *Nature* (London), 327:70 (1987); and U.S. Pat. No. 4,945,050).

Once transformed, the cells can be regenerated by those skilled in the art. Of particular relevance are the recently described methods to transform foreign genes into commercially important crops, such as rapeseed (De Block et al., *Plant Physiol.*, 91:694-701 (1989)), sunflower (Everett et al., *Bio/Technology*, 5:1201 (1987)), soybean (McCabe et al., *Bio/Technology*, 6:923 (1988); Hinchee et al., *Bio/Technology* 6:915 (1988); Chee et al., *Plant Physiol.*, 91:1212-1218 (1989); Christou et al., *Proc. Natl. Acad. Sci. USA*, 86:7500-7504 (1989); EP 301749), rice (Hiei et al., supra), and corn (Gordon-Kamm et al., *Plant Cell*, 2:603-618 (1990); and Fromm et al., *Biotechnology*, 8:833-839 (1990)).

Transgenic plant cells are placed in an appropriate medium to select for the transgenic cells that are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic such as kanamycin, G418, bleomycin, hygromycin, chloramphenicol, herbicide, or the like). The particular marker used will select for transformed cells as compared to cells lacking the DNA that has been introduced. Components of DNA constructs including transcription cassettes may be prepared from sequences which are native (endogenous) or foreign (exogenous) to the host. Heterologous constructs will contain at least one region that is not native to the gene from which the transcription-initiation-region is derived. To confirm the presence of the transgenes in transgenic cells and plants, a Southern blot analysis can be performed using methods known to those skilled in the art.

Promoters from Orthologs of *Arabidopsis* AtCesA8 (IRX1), AtCesA7 (IRX3), and AtCesA4 (IRX5) Genes The proteins (catalytic subunits) involved in forming the cellulose synthesis catalytic complex are encoded by three genes (Taylor et al., supra (2003)). In *Arabidopsis thaliana* these genes have been designated AtCesA8 (IRX1), AtCesA7 (IRX3), and AtCesA4 (IRX5) using the current naming convention ("At"=*Arabidopsis thaliana*; "CesA"=cellulose synthase gene followed by an assigned number designation; Delmer, DP., *Annu Rev Plant Physiol Plant Mol Biol.*, 50:245-276 (1999)). The roles these genes play in cellulose biosynthesis in secondary cell wall formation were identified by the mutations effecting xylem formation (irregular xylem; IRX1, IRX3, and IRX5, corresponding to AtCesA8, AtCesA7, and AtCesA4; respectively) (Taylor et al., supra (2003); Taylor et al., supra (2000); and Richmond and Somerville, supra). The expression pattern comparisons of these genes, and corresponding orthologs in other plants, indicates that 1) there is a high correlation between the expression of these genes and the tissue in which they are expressed and 2) their expression is essentially limited to stem tissue in both monocots and dicots. In *Arabidopsis* (dicot), Taylor et al. (supra (2003)) illustrate how AtCesA8 (IRX1), AtCesA7 (IRX3), and AtCesA4 (IRX5) expression is essentially limited to stem tissue. Orthologs from maize (monocot), namely ZmCesA10, ZmCesA11, and ZmCesA12 exhibit the same expression pattern, indicating that the functional relationship and tissue-specificity has been evolutionarily conserved (Example 5; FIG. 4). Groupings of CesA orthologs show greater similarity than paralogs (Holland et al., supra). As shown in FIG. 4, both monocots and dicots group within the same classes when comparing plant cellulose synthase proteins, indicating that the divergence into at least some of these subclasses may have arisen relatively early in the evolution of these genes (Holland et al., supra).

Rice (*Oryza sativa* (japonica cultivar group)) has orthologs of the maize ZmCesA10, ZmCesA11, and ZmCesA12 genes. Based on the conserved expression patterns observed between *Arabidopsis* and maize and the somewhat closer phylogenic relatedness between maize and rice (both monocots), promoters from orthologous rice genes were identified by sequence analysis using the maize ZmCesA10, ZmCesA11, and ZmCesA12 genes. A comparison of the respective gene from *Arabidopsis*, maize, and rice is provided in Table 2. The promoter sequences for the ZmCesA10, ZmCesA11, and ZmCesA12 genes were identified by sequencing genomic DNA upstream of the start codon for each respective gene. The promoter sequences for the ZmCesA10, ZmCesA11, and ZmCesA12 promoters are provided as SEQ ID NOs:81, 82, and 83, respectively. The respective rice promoter sequences (defined in the present invention as the 2500 bp 5' to the start codon of each respective ortholog) are provided as SEQ ID NOs:43, 44, and 45.

TABLE 2

Orthologous Genes from *Arabidopsis*, Maize (*Zea mays*), and Rice (*Oryza savita*) Associated with the Formation of the Cellulose Synthesis Catalytic Complex

| *Arabidopsis thaliana* Gene | Corresponding Orthologs Identified from: | |
|---|---|---|
| | *Zea mays* | *Oryza savita* |
| AtCesA8 (IRX1) | ZmCesA11 (SEQ ID NO: 33) | Rice ortholog of ZmCesA11 (SEQ ID NO: 39) |
| AtCesA7 (IRX3) | ZmCesA12 (SEQ ID NO: 35) | Rice ortholog of ZmCesA12 (SEQ ID NO: 41) |
| AtCesA4 (IRX5) | ZmCesA10 (SEQ ID NO: 31) | Rice ortholog of ZmCesA10 (SEQ ID NO: 37) |

Gene Expression Analysis

Gene expression analysis of various cellulose synthase genes has been reported. Taylor et al. (*PNAS*, 100(3):1450-1455 (2003) and *Plant Cell*, 12:2529-2539 (2000)) reported that proteins encoded by the *Arabidopsis* cellulose synthase genes encoding proteins forming the cellulose synthesis catalytic complex (AtCesA8, AtCesA7, and AtCesA4) are co-expressed in exactly the same cells. The data indicates that the promoters from these genes are suitable for stem tissue expression.

Orthologs from maize exhibit a nearly identical tissue-specific expression pattern in comparison to *Arabidopsis* (FIGS. 4 and 5; Table 9) as illustrated by MPSS (Lynx Therapeutics, Hayward, Calif.) analysis (Brenner et al., *PNAS*, 97(4):1665-1670 (2000); U.S. Pat. No. 6,265,163; and U.S. Pat. No. 6,511,802; hereby incorporated by reference). MPSS is a technique in which cDNA is attached to the surface of a unique microbead. Highly expressed mRNA is represented on a proportionally larger number of microbeads. Signature sequences of approximately 16-20 nucleotides are then obtained from these microbeads by iterative cycles of restriction with a type IIs endonuclease, adaptor ligation, and hybridization with encoded probes. cDNA was collected from various maize tissues and analyzed by MPSS. The level of expression of a gene is determined by the abundance of its signature in the total pool (FIG. 5, Example 5, Table 9).

The expression levels of active HCHL from the genetic construct comprising the AtCesA7 (IRX3) promoter operably linked to an HCHL coding sequence were indirectly measured by comparing the enzymatic activity of the expressed HCHL protein isolated from stem and leaf tissue from a transformed model plant (Table 6).

Promoters derived from the AtCesA8, AtCesA7, and AtCesA4 genes and the promoters derived from the corresponding orthologous genes from maize and rice exhibit suitable tissue-specific expression patterns useful for stem tissue-specific HCHL expression.

Enzyme Kinetics

Important parameters of enzyme-catalyzed reactions include 1) turnover number (Kcat), a unit for catalytic power of a monomeric enzymatic catalyst expressed as μmol of product formed per second per μmol of enzyme, and 2) Km, a unit for affinity of the enzyme to a particular substrate, expressed as the substrate concentration at which 50% of maximum velocity is achieved. Catalytic efficiency is usually expressed as Kcat/Km. The greater the value of Kcat/Km, the more rapidly and efficiently the substrate is converted into product.

Expression of Divergent HCHL Sequences

Cosuppression suppression, also known as sense suppression, is a phenomenon that can occur at the transcriptional or post-transcriptional level. One major factor that determines whether or not post-transcriptional silencing occurs is the level of homology between coding sequences of homologous genes. Decreasing the level of sequence homology between coexpressed genes correlates with a decrease in post-transcriptional gene silencing. Thierry and Vaucheret (*Plant Mol. Biol.*, 32:1075-1083) describe how post-transcriptional gene silencing was observed when two genes sharing 84% identity were coexpressed while a transgene sharing only 76% identity to an endogenous plant gene escaped cosuppression. Niebel et al. (*Plant Cell*, 7:347-358 (1995)) described how selective cosuppression may occur as a consequence of the higher degree of DNA sequence identity. Genes having coding sequences sharing 81% identity were cosuppressed while those sharing 63% identity were not.

Applicants disclose (in Example 2) that HCHL expression level and not abundance of the HCHL substrate pHCACoA limits pHBA accumulation in the plant stalk. Thus, further improvements in pHBA accumulation in the plant stalk could be achieved by introducing of DNA elements that consist of multiple HCHL expression cassettes each comprised of suitable promoter, an HCHL coding sequence, and a terminator sequence. Promoters and HCHL coding sequences in the expression cassettes need to be divergent in sequence in order to avoid transcriptional and post-transcriptional gene silencing effects that are triggered when identical or highly similar genes are expressed in the same eukaryotic cell. Applicants provide both divergent promoters (of cellulose synthase genes) and an HCHL gene of *Caulobacter crescentus* that shares only 57% sequence identity to HCHL genes from *Pseudomonas*. Applicants predict that DNA elements containing two different HCHL genes from *Pseudomonas* and *Caulobacter* under the control of different cellulose synthase promoters would provide a route to pHBA accumulation in the plant stalk that would exceed that observed with DNA elements containing only one HCHL gene or two closely related HCHL genes.

DESCRIPTION OF PREFERRED EMBODIMENTS

Examples 1 and 2 illustrate the isolation and effects of constitutive expression of an HCHL gene from *Pseudomonas putida* (DSM 12585) on plant development. Enzymatic activity and pHBA accumulation are compared to show that HCHL is substrate-limited in plant leaf tissue, confirming the observation that constitutive HCHL expression produces negative phenotypic changes to the plant.

Example 3 provides a comparison of several tissue-specific promoters. Of the various HCHL expression cassettes assayed, only the chimeric gene comprising a promoter isolated from the *Arabidopsis thaliana* AtCesA7 (IRX3) gene exhibited suitable tissue-specific expression. The AtCesA7 (IRX3) gene has been reported to exhibit a suitable tissue-specific expression pattern, identical to the desired expression pattern for stem-specific expression of HCHL. Two additional genes isolated from *Arabidopsis thaliana*, namely AtCesA4 (IRX5) and AtCesA8 (IRX1), have been reported to have nearly identical expression to that of AtCesA7 (IRX3) (Taylor et al., supra (2003)). These three genes encode cellulose synthesis catalytic subunits. Expression of these genes is normally limited to cells involved in plant secondary cell wall formation in the vascular tissue (stem tissue). Promoters from these genes were identified as suitable for tissue-specific HCHL expression.

Orthologous genes exhibiting a conserved expression pattern, sequence similarity, and function were identified in *Zea mays* (Examples 4 and 5; FIG. 4). Phylogenic analysis revealed that the structure, function, and overall organization in the cellulose synthesis pathway were evolutionarily conserved suggesting that this conserved relationship predates that divergence of monocots and dicots. The promoters from *Zea mays* genes ZmCesA10, ZmCesA11, and ZmCesA12 are suitable for creating chimeric HCHL expression cassettes.

Examples 6 and 7 illustrate the identification of orthologous rice genes that are expected to have similar structure, function, and overall organization in the cellulose synthesis pathway in comparison to genes from *Zea mays*. Closely related genes were identified which are orthologs of the ZmCesA10, ZmCesA11, and ZmCesA12 genes. The promoters were identified as those sequences approximately 2500 bp 5' to the gene's coding sequence.

Prophetic Example 8 provides a method to create various chimeric HCHL constructs using the suitable tissue-specific promoters identified previously. This method is an example of how to create suitable HCHL expression cassettes. One skilled in the art can easily recognize that the source of HCHL gene is not limited to that which is provided in the examples (i.e., *Pseudomonas putida* DSM 12585).

pHBA by HCHL in stalk tissue is limited by enzymatic activity, even when stalk-specific promoters are used. Example 9 provides comparative enzyme kinetic data for HCHL enzymes from *Pseudomonas putida* (DSM 12585), *Pseudomonas fluorescens* AN103, and *Caulobacter crescentus* (previously uncharacterized). Kinetic analysis revealed that the HCHL from *C. crescentus* has superior catalytic efficiency (Kcat/Km) when compared to the other enzyme sources (50% improvement).

The present methods illustrate the creation of an HCHL expression cassette: the expression cassette comprising a tissue-specific promoter operably linked to an HCHL coding sequence. Numerous sources of suitable HCHL genes are known in the art. Several examples are provided in Table 1. Preferred are HCHL genes isolated from a bacterium selected from the group consisting of *Pseudomonas, Caulobacter, Delftia, Amycolatopsis,* and *Sphingomonas*. More preferred sources of HCHL genes are *Pseudomonas putida* (DMS 12585), *Pseudomonas fluorescens* AN103,

*Pseudomonas putida* WCS358, *Caulobacter crescentus*, *Pseudomonas* sp. HR199, *Delftia acidovorans*, *Amycolatopsis* sp. HR167, and *Sphingomonas paucimobilis*. Most preferred sources of HCHL genes are *Pseudomonas putida* (DSM 12585) and *Caulobacter crescentus*.

The tissue-specific promoters of the present invention useful for expressing an HCHL enzyme in plant stem tissue are those isolated from genes encoding a subunit of the cellulose synthesis catalytic complex involved in the synthesis of cellulose during plant secondary cell wall formation in the plant vascular tissue (stem tissue). Preferred tissue-specific promoters are isolated from *Arabidopsis thaliana* genes AtCesA4, AtCesA7, and AtCesA8; *Zea mays* genes ZmCesA10, ZmCesA11, and ZmCesA12; and the *Oryza savita* orthologs of ZmCesA10, ZmCesA11, and ZmCesA12. More preferred tissue-specific promoters are isolated from AtCesA4, AtCesA7, AtCesA8, the *Oryza savita* ortholog of ZmCesA10, the *Oryza savita* ortholog of ZmCesA11, and the *Oryza savita* ortholog of ZmCesA12. Even more preferred are the promoters isolated from the AtCesA4, AtCesA7, and AtCesA8. Most preferred is the promoter isolated from AtCesA7.

Plant suitable for production of pHBA using the present methods include tobacco, *Arabidopsis*, sugar beet, sugar cane, soybean, rapeseed, sunflower, cotton, corn, alfalfa, wheat, barley, oats, sorghum, rice, canola, millet, beans, peas, rye, flax, and forage grasses. Preferred plant hosts are tobacco, *Arabidopsis thaliana*, sugar cane, and sugar beet.

The pHBA produced within the plant is rapidly glucosylated by a pHBA UDP-glucosyltransferase into the pHBA glucoside or pHBA glucose ester for storage in the plant's vacuoles. The UDP-glucosyltransferase can be either endogenous or foreign to the plant. Preferred are recombinant UDP-glucosyltransferases that preferentially catalyze the formation of pHBA glucose ester. More preferred are those recombinant UDP-glucosyltransferase gene isolated from *Vitis* sp., *Eucalyptus grandis*, and *Citrus mitis*. More preferred are those UDP-glucosyltransferases represented by SEQ ID NOs:65, 66, and 67. The pHBA glucose ester can be easily hydrolized to form unconjugated pHBA. Expression of a recombinant pHBA UDP-glucosyltransferase is not limited to the use of stem specific promoters.

Lastly, the low level (<57%) sequence identity of the HCHL coding sequences of *Pseudomonas putida* (DSM 12585) and *Pseudomonas fluorescens* AN103 relative to the HCHL coding sequence of *Caulobacter crescentus* is expected to allow co-expression of both HCHL genes (i.e. without sense suppression) in the same plant providing an additional means to increase pHBA production in plant stem tissue. Preferably, the HCHL genes targeted for coexpression should have less than 70% sequence identity between coding sequences. More preferably, the sequence identity should be less than 65%. Most preferably, the sequence identity is less than 60%.

General Methods

Standard recombinant DNA and molecular cloning techniques used in the Examples are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L., and Enquist, L. W., *Experiments with Gene Fusions*, Cold Spring Harbor Laboratory Cold Press Spring Harbor, N.Y. (1984) (hereinafter "Silhavy"); and by Ausubel, F. M. et al., *Current Protocols in Molecular Biology*, published by Greene Publishing Assoc. and Wiley-Interscience (1987) (hereinafter "Ausubel").

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg, and G. Briggs Phillips, eds), American Society for Microbiology, Washington, D.C. (1994)) or Brock (supra). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

Manipulations of genetic sequences were accomplished using the suite of programs available from the Genetics Computer Group Inc. (Wisconsin Package Version 9.0, Genetics Computer Group (GCG), Madison, Wis.). The GCG program "Pileup" used the gap creation default value of 12, and the gap extension default value of 4. The CGC "Gap" or "Bestfit" programs used the default gap creation penalty of 50 and the default gap extension penalty of 3. In any case where GCG program parameters were not prompted for, in these or any other GCG program, default values were used.

Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS.*, 5:151-153 (1989); Thompson et al., *Nucleic Acids Res.*, 22:4673-4680 (1994)) with default parameters (GAP PENALTY=10, GAP LENGTH PENALTY=10). Default parameters for pairwise alignments using the Clustal method are: KTUPLE=1, GAP PENALTY=3, WINDOW=5 and DIAGONALS SAVED=5.

The meaning of abbreviations is as follows: "h" means hour(s), "min" means minute(s), "sec" means second(s), "d" means day(s), "mL" means milliliters, "L" means liters, "μL" means microliters, "g" means grams, "mg" means milligrams, "μg" means micrograms, "ng" means nanograms, "nm" means nanometer, "M" means molar, "mM" means millimolar, and "μM" mean micromolar.

1. Enzymatic Synthesis and Purification of pHCACoA, the Substrate for HCHL Enzyme Assays.

Expression Cloning of pHCA-CoA Ligase and Recombinant Production of pHCA-CoA Ligase Measuring hydroxycinnamoyl hydratase/lyase (HCHL) activity in plant extracts and of recombinantly produced enzyme requires pHCACoA, a chemical that is not commercially available. pHCACoA was synthesized enzymatically using a recombinantly produced pHCACoA-ligase enzyme from *Arabidopsis thaliana* (At4CL1, GenBank® U18675) and purified by preparative chromatography on C18 reverse-phase cartridges. Briefly, a cDNA clone (acs1c.pk003.m10) was identified in DuPont's expressed sequence tag (EST) database that corresponds to a full-length clone of the At4CL1 transcript. Two primers Primer 1 ACTATTTCATATGGCGCCACAAGAACAAG (SEQ ID NO:1) and Primer 2: GGTTGAAATCAAGCTTCA-CAATCCCATTTG (SEQ ID NO:2) were used to amplify an open reading frame that is flanked by NdeI and HindIII restriction sites for cloning into the *E. coli* expression vector pET28A. The resulting construct expresses a variant of the 4CL1 protein that has an N-terminal hexa-histidine tag. The plasmid construct was introduced into BL21 DE3 cells (Invitrogen, Carlsbad, Calif.) and recombinant protein production was induced under standard conditions at 27° C. by adding IPTG (0.2 mM final concentration). pHCACoA ligase activity was extracted and measured spectrophotometrically as described by Gross et al. (*Biochemie und Physiologie der Pflanzen*, 168(1-4):41-51 (1975)). Specific pHCACoA ligase activity of cell free extract of *E. coli* cells (36 mg/mL protein) was 28.6 nkat/mg protein. The extract was supplemented with glycerol (7.5% final concentration), stored at −80° C., and used for preparative pHCACoA synthesis without further purification.

Preparative Synthesis and Purification of pHCACoA

Preparative synthesis of pHCACoA was carried out at 30° C. in aliquots of 10 mL in the presence of 0.3 mM free CoA (Sigma, USA), 5 mM ATP, 0.5 mM pHCA, 0.2 M Mops (pH 7.5), and 10 mM $MgCl_2$. Enzymatic synthesis was started by addition of 600 μL cell-free *E. coli* extract (22 mg protein and 630 nkat of At4CL1 enzyme). Formation of pHCACoA was monitored by HPLC analysis pHCA was detected at λ=290 nm and pHCACoA at λ=335 nm. After 15 min, quantitative conversion of pHCA to pHCACoA was achieved. pHCACoA was purified using C18 reverse-phase cartridges (900 mg resin, Burdick and Jackson, USA) hooked up to a Pharmacia FPLC system (Amersham, USA). Fifty milliliters, equaling five combined enzyme reaction mixtures, were loaded onto the cartridge. The cartridge was washed with 30 mL of 0.2 M Mops (pH 7.5) and pHCACoA was eluted with 20% MeOH. Fractions containing pHCACoA were identified visually. pHCACoA is bright yellow. Fractions were pooled, lyophilized, and resuspended in 5 mL of 10 mM ammonium acetate (pH 4.7). pHCACoA was quantitated spectrophotometrically using the published the molar absorption coefficient of 21 $mM^{-1}$. The pHCACoA concentration in the resuspended, lyophilized sample was 3.2 mM, thus this method yielded about 15 mg of pHCACoA. pHCACoA was divided into 100 μL aliquots and stored at −80° C.

2. HCHL Enzyme Assays

The standard HCHL assay was comprised of 100 mM Tris/HCL (pH 8.5), 0.25-0.5 mM pHCACoA, and enzyme sample (2.5-25 μg of total plant protein, 2.5-20 ng of purified HCHL enzyme) in a final volume of 25 μL. Assays were conducted at 30° C. and stopped by adding of an equal volume of 12% acetic acid in methanol. Formation of p-hydroxybenzaldehyde (pHBALD) from pHCACoA in the enzyme assay was measured by HPLC analysis. The reaction mixture was cleared by centrifugation. Reaction products (10 μL) were injected onto a Nova Pak C18 column (3.9×150 mm, 60 Å, 4 μm) (Waters, Mass., USA). The column was developed at a flow-rate of 1 mL/min under the following conditions: Solvent A ($H_2O$/1.5% $HPO_4$), Solvent B (50% MeOH/$H_2O$/1.5% $HPO_4$); 0-5 min 0% B, 5-20 min 0-100% B (linear gradient), 20-21 min 100-0% B, and 21-25 min 0% B. pHBALD was detected at 283 nm and quantitated using standard curves established by HPLC separation of known concentration of commercially-available pHBALD (Sigma, USA).

3. Plant Growth and Transformation

Plant Growth

If not stated otherwise, plants were grown under standard conditions (14 h light, 12 h darkness) in a greenhouse. Plants expressing HCHL genes where grown at 100 μE $m^{-2}$ $sec^{-1}$, 14 h light (23° C.), 12 h (18° C.) darkness and 70% relative humidity in growth chambers (Conviron, USA). Sterile plant cultures were maintained under identical conditions in a plant growth chamber (Percival, USA).

Plant Transformation

*Arabidopsis thaliana* plants were transformed using *Agrobacterium* strains (C58, C1 GV3101 MP90) (Koncz, C. and Schell, J., *Mol. Gen. Genet.*, 204:383-396 (1986)) and published protocols of the in-planta transformation method (Desfeux et al., *Plant Physiology*, 123(3):895-904 (2000)). Selection for transformants carrying the NPTII gene was conducted on sterile growth media in the presence of 50 mg/L kanamycin. Selection for transformants carrying the BAR gene was conducted on sterile growth media in the presence of 7.5 mg/L glufosinate or by germinating seed in soil followed by spray-application of an aqueous solution (6 mg/L) of glufosinate herbicide (Sigma, USA) 7 days after germination. Plants destined for plant transformation experiments were grown under permanent light at 23° C. to accelerate flower development.

4. pHBA Analysis pHBA was quantitated in plant tissue by HPLC analysis. For determination of pHBA conjugates, fresh oven-dried or lyophilized tissue was extracted with 50% MeOH. To quantitate free pHBA plant samples (fresh, dried, lyophilized plant tissue or dried-down methanol extracts of plant tissue) were subjected to acid hydrolysis. Dried or lyophilized tissue was ground to a fine powder using a Cyclotec 1093 tissue mill (Foss Tecator, Sweden) prior to hydrolysis. Tissue (5-25 mg of dried or lyophilized material, 10-100 mg of fresh tissue) was supplemented with 500-750 μL of 1M HCl and incubated at 100° C. for 1-3 h. The hydrolysate was adjusted to alkaline pH by addition of one volume of 1.1 M NaOH. The hydrolysate was cleared by centrifugation and/or filtration and analyzed by HPLC as described above. pHBA or pHBA conjugates were detected at 254 nm and quantitated using standard curves established by HPLC separation of known concentration of commercially-available pHBA or chemically synthesized pHBA conjugates.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Cloning and Characterization of an HCHL Gene from *Pseudomonas putida* (DSM 12585)

Evaluation of HCHL-mediated pHBA production in *Arabidopsis* focused on the HCHL gene from *Pseudomonas putida* (DSM 12585). Muheim and Lerch (*Appl Microbiol Biotechnol*, 51:456-461(1999)) reported that this strain was able to convert ferulic acid to vanillin and several studies have reported the cloning of an HCHL gene from closely related *Pseudomonas* strains encoding the HCHL enzyme that is responsible for this activity. The *Pseudomonas* strain described by Muheim and Lerch (supra) was ordered from the DSM (Deutsche Sammlung von Microorganismen und Zelkulturen, Braunschweig, Germany). The strain was able to grow on minimal media (Miller, J; *Experiments in Molecular Genetics*, 1972, Cold Spring Harbour Laboratory Press) containing 1-10 mM pHCA as sole carbon source providing strong support for the presence of an HCHL enzyme in this organism. Genomic DNA was isolated from this strain using standard methods (Maniatis, supra) and used as template in a PCR reaction. Two oligonucleotide primers Primer 3: CCATGAGCACATACGAAG-GTCGCTGG, (SEQ ID NO:3) and Primer 4: TCAGCGCT-TGATGGCTTGCAGGCC (SEQ ID NO:4) were used to generate a PCR fragment of approximately 900 bp that was cloned into EcoRV linearized pSKII+ (Stratagene, Calif., USA)) that had been modified for cloning of PCR products. Eight independent plasmid clones were recovered and sequenced. BLAST analysis revealed that consensus nucleotide sequence (SEQ ID NO:5) and deduced amino acid sequence (SEQ ID NO:6) of the HCHL gene of *Pseudomonas putida* (DSM 12585) shared 88% and 93% identity to HCHL gene and protein of *Pseudomonas fluorescens* AN103 (GenBank® Y13067), respectively.

Expression Cloning, Purification and Determination of Kinetic Properties

Two primers, Primer 5: CATATGAGCACATACGAAG-GTCGC (SEQ ID NO:7), and Primer 6 AAGCT-TCAGCGCTTGATGGCTTGCAGG (SEQ ID NO:8) and DNA from the plasmid containing the HCHL gene of *Pseudomonas putida* (DSM 12585) were used to amplify an open reading frame that is flanked by NdeI and HindIII restriction sites for cloning into the *E. coli* expression vector pET29A (Novagen, USA). PCR products were cloned into pSKII+. The HCHL gene expression cassette was excised and ligated to NdeI and HindIII-digested pET29a DNA. Amino acid sequence of the HCHL protein expressed from the pET29a HCHL construct is identical to that set forth as SEQ ID NO:6. A second expression construct was generated that expresses a variant of the HCHL protein that carries a C-terminal hexa-histidine tag. Two primers, Primer 5 (SEQ ID NO:7) and Primer 7: AAGCTTGCGCTTGATGGCTTG-CAG (SEQ ID NO:9), and DNA from a plasmid containing the HCHL gene of *Pseudomonas putida* (DSM 12585) were used to amplify an open reading frame that is flanked by NdeI and HindIII restriction sites for cloning into the *E. coli* expression vector pET29A. PCR products were cloned into pSKII+. The HCHL gene expression cassette was excised and ligated to NdeI, HindIII-digested pET29a DNA. Amino acid sequence of the HCHL protein expressed from the pET29a HCHL 6×His Tag construct is set forth as SEQ ID NO:10.

Purification and Kinetic Properties of the His-Tagged HCHL Enzyme from *Pseudomonas putida* (DSM 12585)

LB medium (200 mL containing 50 mg/L kanamycin) was inoculated with a single colony of *E. coli* BL21 DE3 cells harboring the pET29a HCHL 6×His Tag expression construct. Cells were grown to an $OD_{\lambda=600\ nm}$ of 0.6 and protein production was induced by addition of 0.2 mM IPTG. Cells were grown at room temperature for 24 h. Cells were harvested by centrifugation (5000×g for 10 min) and resuspended in 2.5 mL of 100 mM Tris/HCl (pH 8.5), 20 mM DTT, and 300 mM NaCl. The cell suspension was passed twice through a French press and cleared by centrifugation (30000×g, 20 min, at 4° C.). The cell-free extract was buffer-exchanged using PD10 columns into 20 mM $NaPO_4$ (pH 7.5), 500 mM NaCl, and 10 mM imidazole and loaded on a 5 mL HiTrap chelating chromatography cartridge (Amersham Pharmacia, USA). The column was washed with 20 mL of loading buffer and 20 mL of loading buffer containing 70 mM imidazole. The his-tagged HCHL protein was eluted from the column with a linear gradient from 70-1000 mM imidazole in loading buffer.

HCHL activity in the fractions was determined using a visual assay. Briefly, 0.5 µL of chromatography fractions were added to 25 µL of an HCHL reaction mix (see general methods) that contained feruloylCoA. In the presence of HCHL enzyme activity, the yellow feruloylCoA was rapidly converted to vanillin, which is accompanied by a disappearance of color. Two 1-mL fractions with HCHL activity were pooled and desalted into HCHL extraction buffer. Visual inspection of Coomassie-stained PAGE gels indicated that the HCHL enzyme was greater than 95% pure. HCHL enzyme concentration was determined spectrophotometrically using an extinction coefficient of 54,600 $M^{-1}$ at 280 nm as determined by the GCG Peptidesort program using the amino acid composition of the his-tagged enzyme variant. The final concentration of the purified recombinant HCHL protein was 2.077 mg/mL, which corresponds to a monomer concentration of 64.139 µM and a concentration of active sites of 32.069 µM. Remaining fractions with HCHL activity were pooled and quantitated in a similar fashion. HCHL protein (17 mg) was purified from 250 mg of total *E. coli* protein indicating that the recombinant protein represented at least 7% of the total protein. Kinetic properties of the HCHL enzyme were determined. Standard HCHL assays were conducted using pHCACoA and feruloylCoA concentrations ranging from 343 to 2.7 µM and 293 to 2.3 µM, respectively. Assays were incubated for 5.5 min and pHBALD and vanillin were quantitated by HPLC.

The Michaelis-Menten and Wolf-Augustinsson-Hofstee plots (FIG. 2) of the data indicate that the Km and Vmax values of the his-tagged HCHL enzyme from *Pseudomonas putida* for pHCACoA and feruloylCoA were 2.53 µM, 53.8 nkat/mg, and 2.39 µM, 37.3 nkat/mg, respectively. The Vmax of the enzyme with pHCACoA translates into a catalytic center activity of 3.4/sec (per enzyme dimer), which was calculated using a molecular weight of 32,348.8 Da per monomer. This is in very close agreement with the published Vmax and Km values of the HCHL enzyme from *Pseudomonas fluorescens* AN103 (Mitra et al., *Arch. Biochem. Biophys.*, 365(1):6-10 (1999)). The values were reported to be 5.3 µM, 73 nkat/mg for pHCACoA and 2.4 µM, 36.5 nkat/mg for feruloylCoA.

Purification and Kinetic Properties of the Native HCHL Enzyme from *Pseudomonas putida* (DSM 12585)

LB medium (500 mL containing 50 mg/L) kanamycin was inoculated with a single colony of *E. coli* BL21 DE3 cells harboring the pET HCHL expression construct. Cells were grown to an $OD_{\lambda=600\ nm}$ of 0.6 and protein production was induced by the adding of 0.2 mM IPTG. Cells were grown at room temperature for 24 h. Cells were harvested by centrifugation (5000×g for 10 min) and resuspended in 15 mL of 100 mM Tris/HCl (pH 8.5), 20 mM DTT, and 300 mM NaCl. The cell suspension was passed twice through a French press and cleared by centrifugation (30000×g, 20 min, at 4° C.) resulting in 15 mL of cell-free extract (38.3 mg/mL protein). Two 2.5-mL aliquots of the cell-free extract were buffer-exchanged using PD10 columns into 50 mM Tris/HCl (pH 7.6), 10 mM $Na_2SO_3$, and 1 mM EDTA. Buffer-exchanged extract (7 mL) was loaded onto a Q-sepharose column (15 mL gel bed volume). The column was developed at a flow rate of 4 mL/min at 4° C. as follows: Solvent A (50 mM Tris/HCl (pH 7.6), 10 mM $Na_2SO_4$, and 1 mM EDTA), Solvent B (1 M NaCl, 50 mM Tris/HCl (pH 7.6), 10 mM $Na_2SO_3$, and 1 mM EDTA); 0-20 min 0% B, 20-80 min (linear gradient) 0-100% B, 80-100 min 100% B, and 101-120 min 0% B. Fractions (4 mL) were collected and HCHL activity was monitored visually as described previously. A fraction with HCHL activity was purified further by chromatography on hydroxyapatide (Biorad Econo-Pac cartridge CHT-II, 1 mL gel bed volume (Biorad, Calif., USA)). Approximately 2.5 mL was buffer-exchanged into (10 mM NaPO$_4$, (pH 6.8) and 10 µM CaCl$_2$). The column was developed at a flow rate of 2 mL/min at 4° C. as follows: Solvent A (10 mM NaPO$_4$, (pH 6.8) and 10 µM CaCl$_2$), Solvent B (350 mM NaPO$_4$, (pH 6.8) and 10 µM CaCl$_2$); 0-10 min 0% B, 10-30 min (linear gradient) 0-100% B, 30-50 min 100% B, and 51-70 min 0% B. Fractions (1 mL) were collected, assayed for HCHL activity as described above, and analyzed by PAGE. Visual inspection of Coomassie-stained gels indicated that in some chromatography fractions the HCHL enzyme was greater than 90% pure. HCHL enzyme concentration was determined spectrophotometrically using an extinction coefficient of 54,600 M$^{-1}$ at 280 nm as determined by the GCG Peptidesort program using the amino acid composition of the native enzyme. The final concentration of the purified recombinant HCHL protein in this fraction was 0.311 mg/mL, which corresponds to a monomer concentration of 10.073 µM and a concentration of active sites of 5.04 µM.

The Michaelis-Menten and Wolf-Augustinsson-Hofstee plots of the data indicate Km and Vmax values of the native HCHL enzyme from *Pseudomonas putida* for pHCACoA were 2.4 µM and 43 nkat/mg' respectively. The Vmax of the enzyme with pHCACoA translates into a catalytic center activity of 2.65/sec (per enzyme dimer) that was calculated using a molecular weight of 30,865.1 Da per monomer. This is in close agreement with the published Vmax and Km values of the HCHL enzyme of *Pseudomonas fluorescens* AN103 (Mitra et al., supra). The kinetic properties of the *Pseudomonas putida* HCHL enzyme for conversion of pHCACoA to pHBALD did not deviate significantly from values published for the HCHL enzyme of *Pseudomonas fluorescens* AN103.

Example 2

Plant Expression of the HCHL Gene of *Pseudomonas putida* (DSM 12585) Under the Control of Constitutive Promoters.

Construction of Binary Vectors

For constitutive expression of the *Pseudomonas putida* (DSM 12585) HCHL enzyme in plants, two binary vectors were generated. In one construct, the HCHL gene was under the control of the promoter of the ACTIN2 gene from *Arabidopsis*. It had been shown previously that this promoter confers a constitutive pattern of reporter gene expression in plants (An et al., *Plant Journal*, 10(1): 107-121 (1996)). In the other construct, the HCHL coding sequence was fused to the CaMV35S promoter.

Genomic DNA from *Arabidopsis thaliana* plants and two PCR primers used to amplify a 1220 bp fragment of the ACTIN2 gene that comprised promoter region and 5'UTR of the gene: Primer 8 CAACTATTTTTATGTATGCAAGAGTCAGC (SEQ ID NO:11) and Primer 9 CCATGGTTTATGAGCTGCAAACACAC (SEQ ID NO:12). The sequence of the ACTIN2 promoter ("ACT2") fragment is set forth in SEQ ID NO:13. Primer 9 introduced an NcoI site (CCATGG) at the start codon and permitted generation of translational fusions (at the start codon) of the ACT2 promoter to any gene of interest that has been modified to carry an NcoI or PagI site at the start codon. The ACT2 promoter fragment was cloned into an EcoRV linearized pSKII+ vector modified for cloning of PCR products. Four plasmid clones were recovered in which the 3' end of the promoter was proximal to the T7 promoter in the pSKII+ vector. The ACT2 promoter was released from the vector using the restriction enzymes HindIII and NcoI.

The *P. putida* (DSM 12585) HCHL coding sequence was amplified from the plasmid template (see above) using two primers: Primer 10: TCATGAGCACATACGAAGGTCGC (SEQ ID NO:14) and Primer 4 (SEQ ID NO:4). Primer 10 introduced a PagI (TCATGA) at the start codon and facilitated the fusion of the HCHL coding sequence to the ACT2 promoter. The PCR products were cloned into pSKII+ and two clones were recovered in which the start codon of the HCHL coding sequence is proximal to the to the T7 promoter in the pSKII+ vector. Plasmid DNA of these clones was linearized by partial digestion with Pag1 and the HCHL coding sequence was released from the vector by complete digestion with SstI. The HCHL coding sequence and ACT2 promoter were assembled in a three-way ligation to HindIII and SstI digested pSKII+ vector DNA. The ACT2-HCHL expression cassette was excised and ligated to HindIII/SstI digested DNA of the binary vector pGPTVBar (Becker et al., *Plant Molecular Biology*, 20(6):1195-7 (1992)). Recombinant Plasmid DNA was isolated from *E. coli* and introduced into *Agrobacterium tumefaciens* for transformation of wild type *Arabidopsis* plants.

A CaMV35S promoter with a duplicated enhancer element was excised from the plasmid pJIT60 (Transformation of *Brassica oleracea* with paraquat detoxification gene(s) mediated by *Agrobacterium tumefaciens*. Latifah, A.; Salleh, M. A.; Basiran, M. N.; Karim, A. G. Abdul. Faculty Life Sciences, University Kabangsaan Malaysia, Malay. Editor(s): Shamann, Nor Aripin. Applications of Plant In Vitro Technology, Proceedings of the International Symposium, Serdang, Malay., Nov. 16-18, 1993 (1993), 145-50) using restriction digestion with KpnI and HindIII and cloned into pSKII+. The modified pSKII+ vector was digested with EcoRV and T-tailed for cloning of PCR products using Taq polymerase. The HCHL coding sequence of *P. putida* was amplified from a PSKII+ plasmid template using Primer 10 (SEQ ID NO:14) and Primer 4 (SEQ ID NO:4) and inserted downstream of the CaMV35S ("35S") promoter in the modified pSKII+ vector. Four plasmid clones were recovered in which the start codon of the HCHL coding sequence is proximal to the 3' end of the CaMV35S promoter. Insert DNA was excised from these plasmids by digestion with KpnI/SstI and ligated to pGEM7zf+ (Promega, USA) digested with the same enzymes. This cloning step introduced an XbaI site at the 5' end of the 35S HCHL expression cassette. The pGEM7zf+ construct was linearized with XbaI by partial digestion. The HCHL expression cassette was released from the vector by complete digestion with SstI. The 35S—HCHL expression cassette was ligated to XbaI/SstI digested DNA of the binary vector pGPTVBar (Becker et al., supra). Recombinant Plasmid DNA was used for transformation of wild type *Arabidopsis* plants as described in general methods.

Analysis of pHBA Levels in Leaves of Primary Transformants

Act2 HCHL: 105 primary transformants were identified based on their ability to survive application of the glufosinate herbicide. These transformants were grown in soil for 28 days. pHBA content of leaf tissue was determined by HPLC analysis as described in the general methods. pHBA content in leaf tissue of the primary transformants ranged from 0.59 to 5.47 mg/g DW. One line (119) was self-crossed and T2 seed were harvested. Segregation analysis of the selectable marker was conducted at the T2 level and seed batches homozygous for the T-DNA insertion were identified in the T3 generation. Homozygous seed material of this line was used for subsequent experimentation.

CaMV35S HCHL: 16 primary transformants were identified based on their ability to survive application of the glufosinate herbicide. These transformants were grown in soil for 28 days. pHBA content of leaf tissue was determined by HPLC analysis as described in the general methods. pHBA content in leaf tissue of the primary transformants ranged from 0.95 to 7.69 mg/g DW. One line (11) was self-crossed and T2 seed were harvested. Segregation analysis of the selectable marker was conducted at the T2 level and seed batches homozygous for the T-DNA insertion were identified in the T3 generation. Homozygous seed material of this line was used for subsequent experimentation.

Substrate Limitation in Leaf Tissue

To gain insights into the limitations of HCHL-mediated pHBA production in leaf tissue, wild type *Arabidopsis* plants and homozygous plants of lines 11 and 119 were grown in soil. Leaf material was harvested six weeks after germination. Concentrations pHBA and sinapic acid were determined by HPLC analysis.

In leaf tissues of *Arabidopsis* the substrate of HCHL, pHCACoA, is used as an intermediate for synthesis of aromatic secondary metabolites such as flavonoids and UV-fluorescent sinapic acid esters. The accumulation of the latter in the cells of the upper leaf epidermis endows the *Arabidopsis* leaves with a characteristic green-blue fluorescence under long wave UV light. Leaves of wild type and transgenic lines expressing the HCHL gene were illuminated with long wave UV light ($\lambda$=366 nm). Applicants observed a red fluorescence under long wave UV light of leaves of transgenic lines 11 and 119. This indicates the depletion of sinapate esters as result of HCHL expression. This conclusion was further confirmed by HPLC analysis (Table 3) demonstrating that formation of pHBA from pHCACoA by HCHL is accompanied by a significant depletion of sinapic acid. This result indicates that, in leaf tissue, formation of pHCACoA limits the rate of pHBA synthesis by HCHL. In other words, HCHL is operating in substrate-limited mode in leaf tissue. It is interesting to note that in the best HCHL expressing line (11) the observed level of pHBA accumulation is achieved through a five-fold increase of flux through the phenylpropanoid pathway when compared to wild type plants. This corroborates findings by Mayer et al. (supra), indicating that an increase of steady-state transcript levels of genes such as PAL, C4H, and 4CL accompany expression of an HCHL gene in transgenic tobacco.

TABLE 3

| Construct | Sinapic acid (μmol/g FW) | pHBA (μmol/g FW) |
| --- | --- | --- |
| WT | 1.65 | 0 |
| Act2 HCHL (119) | 0.71 | 4.32 |
| 35S HCHL (11) | 0.09 | 8.71 |

Leaves Versus Stems

Figure 1:
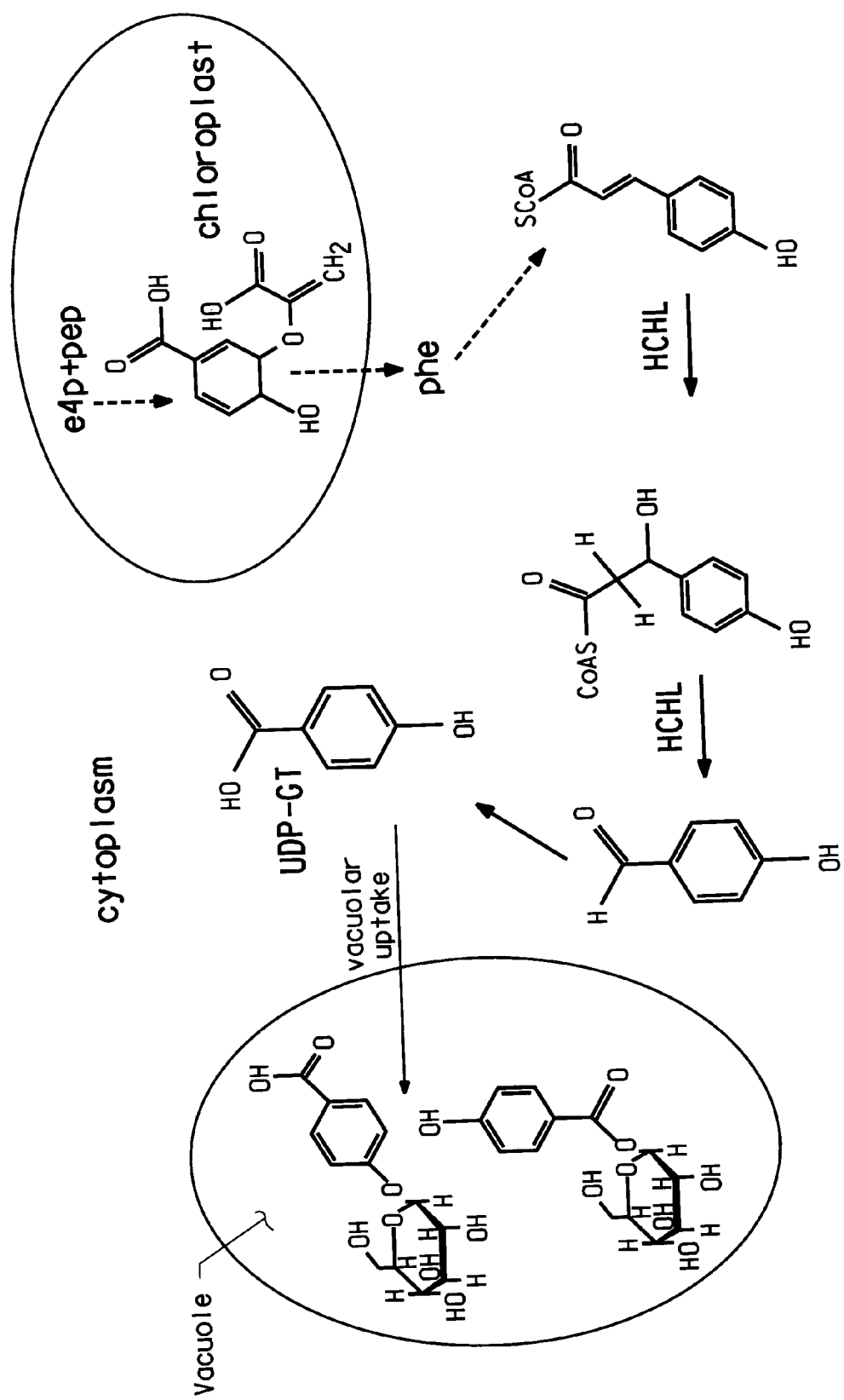

The next objective was to investigate the efficaciousness of the HCHL route of pHBA production in stalk tissue. In this tissue the HCHL substrate, pHCACoA, is a central intermediate of a high flux pathway that provides precursors for lignin biosynthesis shown in FIG. 1. The high flux nature of this pathway is illustrated by the fact that even in herbaceous plants, such as *Arabidopsis*, lignin constitutes approximately 20% of the dry matter of the stalk tissue.

Homozygous transgenic lines 119 and 11 were grown in soil for 8 weeks. Leaf and stalk tissue was harvested, lyophilized, and ground to a powder that was subjected to analysis of pHBA content by acid hydrolysis and HPLC. In transgenic lines constitutively expressing HCHL, pHBA accumulation in the stalk tissue was dramatically higher in stalk tissue in comparison to leaf tissue. pHBA levels of 18.3 mg/g DW and 6.9 mg/g DW were detected in whole stalk tissue from lines 11 and 119, respectively. This is significantly higher than 13 mg/g DW and 3.8 mg/g DW detected in leaf tissue of the same lines.

In order to confirm that the high impact of HCHL on pHBA production in stalk tissue reflected substrate availability and not enzyme activity in this tissue, leaf and stalk tissue of line 11 (35S HCHL) was assayed for HCHL enzyme activity and pHBA content was determined (Table 4). For this experiment the basal stem segment was used. Table 4 shows that although HCHL enzyme activity differs only by 60% when leaf and stalk tissue are compared, pHBA content is 6-fold higher in stalk tissue.

TABLE 4

| Line | Tissue | HCHL activity (pkat/mg) | pHBA (mg/g DW) |
| --- | --- | --- | --- |
| 35S HCHL (11) | leaves | 100 | 4.6 |
|  | stems | 160 | 30.5 |

Correlation of HCHL Enzyme Activity and pHBA Accumulation in Stalk Tissue

Figure 3:
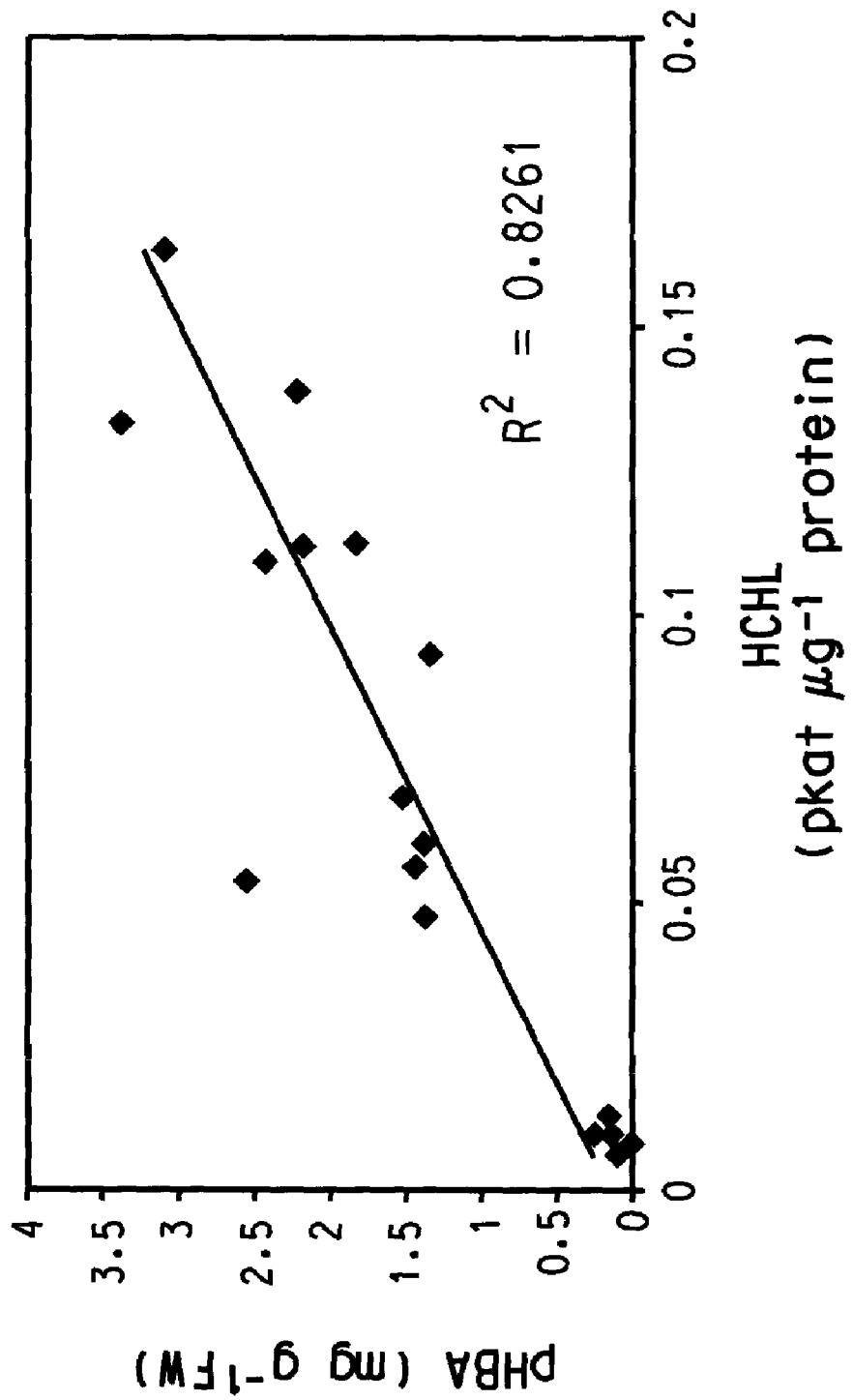
FIG. 3 shows the linear relationship between HCHL activity and pHBA production in stalk tissue of transgenic lines expressing the HCHL gene of *Pseudomonas putida* (DSM 12585).

As a prelude to work on further improvements of HCHL-mediated pHBA production in stalk tissue, Applicants investigated whether there is any indication of substrate limitation of HCHL in stalk tissue of the transgenic lines generated so far. T2 seed material of different transgenic *Arabidopsis* lines expressing the 35S HCHL transgene was germinated on phosphinotrine-containing growth media and herbicide-resistant plants were grown in soil for eight weeks. Stalk tissue was harvested and subjected to pHBA analysis and HCHL assays. HCHL transformants were selected for this experiment that covered a wide range of pHBA accumulation in leaf tissue of primary transformants. FIG. 3 shows a linear correlation ($R^2$=0.8261) between specific HCHL activity and pHBA content over a wide range of specific HCHL activity, indicating that in the lines with the highest specific HCHL activity in stalk tissue there is no indication of substrate limitation.

Example 3

Stalk-Specific Expression of HCHL in Plants

In this Example, the utility of different stalk-specific promoters was determined. A pattern of HCHL expression that targeted the specialized cell types having a high rate of pHCACoA synthesis would produce a high level of pHBA in the stalk. Lignin biosynthesis is a cell autonomous process. RNA blot experiments, expression of reporter gene constructs, and immunolocalization studies of enzymes of the phenylpropanoid pathway suggest that the bulk of monolignols is produced in the cells that undergo lignification. There is only a limited transfer of monolignols from neighboring xylem or ray parenchyma cells to tracheids or vessel elements (presumably at later stages of cell differentiation) to sustain lignification after the water-conducting cells have undergone autolysis. The promoters of genes closely related to the synthesis of (or consumption of) pHCACoA in lignin biosynthesis were selected in order to target HCHL expression to plant stalk tissue. The goal was to identify those promoters that would lead to pHBA accumulation, in excess of the the levels observed with a constitutive promoter, such as CaMV35S, by targeting the cells with the highest concentration of the pHCACoA substrate. Successful targeting of HCHL to these cell types was expected to avoid the detrimental effects associated with depleting of pHCACoA in tissues other than stalk tissue.

Construction of Plasmids for Expression of HCHL in Plants Under Control of C4H, 4CL1, C3'H, and IRX3 Promoters.

Cinnamate-4-hydroxylase (C4H) catalyzes the 4-hydroxylation of the aromatic ring of cinnamic acid. C4H (CYP73A5; GenBank® Accession No. U71080) is a cytochrome P450-dependent monooxygenase encoded by a single gene in most plants. Genomic DNA was isolated from *Arabidopsis* plants and the primers Primer 11: GAGAG-CATCCATATGAGCACATACGAAGGTCGC (SEQ ID NO:15) and Primer 12: CGCAGCGTCAAGCT-TCAGCGTTTATACGCTTGC (SEQ ID NO:16) were used to amplify 2721 nucleotides of the C4H promoter (SEQ ID NO:17). PCR products were cloned into the pCR2.1 vector (Invitrogen, USA). Primer 12 introduces a NcoI site (CCATGG) at the initiator methionine codon of the C4HL gene and facilitates the generation of translational fusions of genes that contain PagI (TCATGA) or NcoI sites at the start codon. A pSKII+ plasmid containing a PCR-generated variant of the HCHL gene containing a PagI site at the start codon was partially digested with PagI and a PagI/SstI fragment was released from the vector by complete digestion with SstI. The C4H promoter was released from the pCR2.1 vector by digestion with XbaI/PagI. The C4H promoter and HCHL gene were assembled in the XbaI-SstI cut pGPTVBar vector (Becker et al., supra) in a three-way ligation. Plasmid DNA was used for *agrobacterium*-mediated transformation of *Arabidopsis* plants.

4-Coumarate-coenzymeA ligase (4CL) enzymes are operationally soluble, monomeric enzymes of 60 kDa molecular weight belonging to the class of adenylate forming CoA ligases. There is clearly redundancy at the level of 4CL enzyme activity both in gymnosperms and angiosperms. Angiosperm 4CL proteins belong to two groups of evolutionarily divergent sequences. For example, in *Arabidopsis* there are three distinct 4CL proteins that share only 60% sequence identity. The 4CL1 (GenBank® Accession No. U18675) gene is constitutively and abundantly expressed in plant stem tissue, indicating that it carries out an important role in lignin biosynthesis. In contrast, the expression pattern of the 4CL2 and 4CL3 genes are expressed in response to environmental cues and is also observed in tissues other than the stalk (Ehlting et al., *PLANT JOURNAL*, 19(1):9-20 (1999)).

Genomic DNA was isolated from *Arabidopsis* plants and the primers Primer 13: CCTAGAAGTGTTGCAGCTGMG-GTACTMC (SEQ ID NO:18) and Primer 14: GTTCT-TGTGGCGCCATGGTAAATAGTAAAT (SEQ ID NO:19) were used to amplify 2739 nucleotides of the 4CL1 promoter (SEQ ID NO:20). PCR products were cloned into the pCR2.1 vector. Primer 14 introduced an NcoI site (CCATGG) at the initiator methionine codon of the 4CL1 gene and facilitated the generation of translational fusions of genes that contain PagI (TCATGA) or NcoI sites at the start codon. A pSKII+ plasmid containing a PCR-generated variant of the HCHL gene containing a PagI site at the start codon was partially digested with PagI and a PagI/SstI fragment was released from the vector by complete digestion with SstI. The 4CL1 promoter was released from the pCR2.1 vector by digestion with XbaI/PagI. The 4CL1 promoter and HCHL gene were assembled in the XbaI-SstI cut pGPTVBar vector in a three-way ligation. Plasmid DNA was used for *agrobacterium*-mediated transformation of *Arabidopsis* plants.

The p-coumarate-3-hydroxylase gene (C3'H) encodes a 3-hydroxylase enzyme (CYP98A3, GenBank® Accession No. AC011765) that generates the 3,4-hydroxylated caffeoyl intermediate in lignin biosynthesis. Characterization of the kinetic properties and substrate specificity of this enzyme revealed that shikimate and quinate esters of the 4-hydroxylated coumaryl moiety constitute the preferred substrate of the 3-hydroxylase (Schoch et al., *J. Biol. Chem.*, 276(37): 36566-36574 (2001)).

Genomic DNA was isolated from *Arabidopsis* plants and the primers Primer 15: CGATTTTGATCGTTGACTAGC-TATACAATCCC (SEQ ID NO:21) and Primer 16: GCTATTAGAAACCACGCCATGGAGTTTTGCTTC (SEQ ID NO:22) were used to amplify 2705 nucleotides of the C3'H promoter (SEQ ID NO:23). PCR products were cloned into the pCR2.1 vector. Primer 16 introduces a NcoI site (CCATGG) at the initiator methionine codon of the C3'H gene and thus facilitates the generation of translational fusions of genes that contain PagI (TCATGA) or NcoI sites at the start codon. A pSKII+ plasmid containing a PCR-generated variant of the HCHL gene containing a PagI site at the start codon was partially digested with PagI and a PagI/SstI fragment was released from the vector by complete digestion with SstI. The C3'H promoter was released from the pCR2.1 vector by partial digestion with XbaI and complete digestion with PagI. The C3'H promoter and HCHL coding sequence were assembled in the XbaI-SstI cut pGPTVBar vector in a three-way ligation. Plasmid DNA was used for *agrobacterium*-mediated transformation of *Arabidopsis* plants.

The IRX3 (irregular xylem 3) gene of *Arabidopsis* encodes one of the catalytic subunits comprising the cellulose synthesis catalytic complex (AtCESA7, GenBank® Accession No. AF091713) that is essential for cellulose synthesis in stalk tissue (Turner et al., *Plant Cell*, 9(5):689-701 (1997); Taylor et al., supra (1999); and Taylor et al., supra (2003)). The corresponding wild type version of this gene is denoted at AtCesA7. The role of this gene in forming of the plant stalk was revealed by genetic analysis. A mutation in this gene almost completely abolishes cellulose deposition in secondary cell walls in the stalk, but does not affect cellulose deposition in primary cell walls and other tissues of the plant. The promoter of this gene has been employed for down-regulation of enzymes involved in lignin biosynthesis (Jones et al., *Plant Journal*, 26(2):205-216 (2001)). Although the AtCesA7 (IRX3) gene product does not have a role in lignin biosynthesis, it controls a process that is closely associated with lignin deposition in the secondary cell walls of the stalk. The AtCesA7 (IRX3) promoter was evaluated for its utility in targeting HCHL expression to the plant stalk.

Genomic DNA was isolated from *Arabidopsis* plants and the primers Primer 17: CAGTTTATCTGGGTAAGTTCT-TGATTTTAAGC (SEQ ID NO:24) and Primer 18: GAC-CGGCGCTAGCTTTCATGAGGACGGCCGGAG (SEQ ID NO:25) were used to amplify 2780 nucleotides of the AtCesA7 (IRX3) promoter. PCR products were cloned into a pCR2.1 vector. Primer 18 introduced a PagI site (TCATGA) at the initiator methionine codon of the AtCesA7 (IRX3) gene and facilitated the generation of translational fusions of genes that contain PagI (TCATGA) or NcoI sites at the start codon. A pSKII+ plasmid containing a PCR-generated variant of the HCHL gene containing a PagI site at the start codon was partially digested with PagI and a PagI/SstI fragment was released from the vector by complete digestion with SstI. A 2134 bp fragment (SEQ ID NO:26) of the AtCesA7 (IRX3) promoter was released from the pCR2.1 vector by digestion with XbaI and PagI. The AtCesA7 (IRX3) promoter and HCHL gene were assembled in the XbaI-SstI cut pGPTVBar vector in a three-way ligation. Plasmid DNA was used for *agrobacterium*-mediated transformation of *Arabidopsis* plants.

Sequences of fusion products between the HCHL gene from *Pseudomonas putida* (DSM 12585) and the promoters from the C4H, 4CL1, C3'H, and AtCesA7 (IRX3) genes of *Arabidopsis thaliana* are set forth as SEQ ID NOs:27, 28, 29, and 30, respectively.

Analysis of pHBA in Stalk Tissue of Primary Transformants

Primary transformants were grown in soil for eight weeks. A stem segment of 2 cm was harvested at the base of the stem from each transformant and subjected to analysis of pHBA content by acid hydrolysis and HPLC. Seed material was harvested from the ten best transformants and the remaining stalk material was harvested, dried, ground, and subjected to analysis of pHBA content. Table 5 shows that the C4H, AtCesA7 (IRX3), and 4CL1 promoters were able to target HCHL-mediated pHBA production to levels that was comparable to the CaMV35 promoter. AtCesA7 (IRX3) and 4CL1 lines contained 60% of the pHBA levels found in the best 35S HCHL line. pHBA content of whole stalk tissue in the best C4H HCHL line was 106% in comparison to the levels generated by the 35S line.

TABLE 5

| Construct | n | Basal stalk pHBA average (mg/g FW) | Basal stalk pHBA highest (mg/g FW) | Whole stalk pHBA highest (mg/g DW) |
|---|---|---|---|---|
| 35S HCHL | 43 | 0.82 | 5.86 | 22.08 (line 276) |
| C4H HCHL | 78 | 0.89 | 5.54 | 23.42 (line 35) |
| 4CL1 HCHL | 71 | 0.55 | 3.87 | 12.93 (line 183) |
| C3'H HCHL | 64 | 0.41 | 1.65 | 9.52 (line 227) |
| AtCesA7 (IRX3) HCHL | 46 | 1.21 | 3.91 | 12.96 (line 366) |

Analysis of Whole Stalk pHBA and HCHL Enzyme Activity in Pooled Leaf and Stalk Tissue of T2 Lines The primary transformants were self crossed and T2 seed material was germinated on selective media containing glufosinate, transferred to soil, and grown for eight weeks. Leaf and stalk tissue was harvested and subjected to pHBA analysis and assayed for HCHL activity (Table 6). All promoters provided improved of stalk specificity at the level of HCHL enzyme activity. However, since HCHL runs substrate-limited in leaf tissue, the HCHL activity measured in leaf tissue of the C4H, 4CL1, and C3H lines was still sufficient to convert all available pHCACoA to pHBA. The improved stalk specificity of HCHL expression did not translate into improved stalk specificity of pHBA deposition in these lines. In other words, the three promoters from genes involved in lignin biosynthesis (C4H, C3'H, and 4CL1) permitted significant HCHL expression in leaf tissue.

Leaf tissue from transgenic lines expressing the HCHL gene under the control of the AtCesA7 (IRX3) promoter, on the other hand, exhibited no detectable HCHL activity. pHBA accumulation was reduced more than ten-fold when compared to the 35S HCHL line. The data indicated that only certain cellulose synthase promoters provide the ideal molecular tools to target HCHL to the plant stalk at levels that can sustain pHBA production comparable to levels achieved with constitutive promoters. The AtCesA7 (IRX3) HCHL lines were phenotypically indistinguishable from wild type plants, indicating that restricting of HCHL expression to the plant stalk was compatible with normal plant growth and development.

TABLE 6

| Tissue | Construct | Line | HCHL activity (pkat/mg protein) | PHBA (mg/g DW) | Ratio stem/leaf pHBA | HCHL efficacy (pHBA/pkat/mg) |
|---|---|---|---|---|---|---|
| stem | 35S HCHL | 276 | 160.2 | 19.8 | 3.6 | 0.12 |
| leaf | | | 65.8 | 5.5 | | |
| stem | AtCesA7 (IRX3) HCHL | 366 | 24.6 | 23.2 | 43 | 0.94 |
| leaf | | | 0.0 | 0.5 | | |
| stem | AtCesA7 (IRX3) HCHL | 365 | 25.4 | 13.3 | 29 | 0.52 |
| leaf | | | 0.0 | 0.5 | | |
| stem | C4H HCHL | 35 | 48.4 | 15.5 | 3.8 | 0.32 |
| leaf | | | 5.3 | 4.1 | | |
| stem | C4H HCHL | 72 | 25.8 | 9.2 | 2.6 | 0.36 |
| leaf | | | 1.5 | 3.5 | | |
| stem | C3'H HCHL | 227 | 14.7 | 9.1 | 4.2 | 0.61 |
| leaf | | | 1.0 | 2.1 | | |
| stem | 4CL1 HCHL | 140 | 29.0 | 19.6 | 5.5 | 0.67 |
| leaf | | | 3.1 | 3.5 | | |

Example 4

Isolation of Maize (Zea mays) CesA cDNA Clones and Amino Acid Sequence Comparisons to Arabidopsis CesA Proteins Applicants have demonstrated how promoters of certain cellulose synthase genes controlling cellulose deposition in the secondary cell walls of the plant vascular system allow precise targeting of HCHL expression and pHBA production to the plant stalk. Certain grasses (monocotyledonous plants), such as sugar cane, would provide an ideal platform for producing of pHBA in stalk tissue. Not only does the stalk of sugar cane plants provide plentiful biomass, but it also possesses established infrastructure for harvesting and isolating of small water-soluble molecules. We hypothesized genes from monocotyledonous plants that are orthologs (i.e., those that carry out the function of the AtCesA8 (IRX1), AtCesA7 (IRX3), and AtCesA4 (IRX5) genes of *Arabidopsis*) would provide promoter sequences suitable for precise targeting of HCHL expression to the stalk based on the expression pattern reported for these genes in *Arabidopsis* (Taylor et al., supra (2003)).

Holland et al. isolated and characterized nine members (ZmCesA1-ZmCesA9) of the cellulose synthase gene family of corn (*Zea mays*) (*Plant Physiol.*, 123:1313-1324 (2000) Table 7.). Using methodology described by Holland et al. (supra), Applicants have isolated three new members of the maize CesA gene family (ZmCesA10, ZmCesA11, and ZmCesA12) from the elongation and transition zones of an elongating maize internode. Coding sequences for *Zea mays* ZmCesA10, ZmCesA11, and ZmCesA12 genes and the corresponding deduced amino acid sequences are provided as SEQ ID NOs:31-36 (Table 7). The DNA upstream of the respective start codon for ZmCesA10, ZmCesA11, and ZmCesA12 was sequenced. The respective promoter sequences were identified and are provided as SEQ ID Nos:81, 82, and 83.

Maize and *Arabidopsis* CesA genes were aligned using the CLUSTAL W program (Thompson et al., *Nucleic Acids Res.*, 22:4673-4680(1994)). Protein sequences for the *Arabidopsis* CesA proteins were deduced from the publically available nucleotide sequences in GenBank® (Table 7). Maize sequences for the genes ZmCesA1 through ZmCesA12 are available in GenBank® (Table 7; Holland et al., supra).

Parsimony and neighbor-joining analyses were performed using the PAUP program (Swofford, DL, PAUP*: Phylogenetic analysis using parsimony (and other methods), Volume Version 4 (Sinauer Associates, Sunderland, Mass.)). To assess the degree of support for each branch on the tree, bootstrap analysis with 500 replicates was performed (Felsenstein, J., *Evolution*, 39:783-791 (1985)). A maximum-likelihood tree was also reconstructed using proML algorithm implemented in the PHYLIP package by J. Felsenstein (Phylogeny Inference Package, version 3.6a2.1; available from the University of Washington, Seattle, Wash.). Both neighbor-joining and maximum-likelihood trees showed very similar tree topologies (maximally parsimonious tree with minor terminal branch differences).

The result of this analysis is an unrooted cladogram (FIG. 4) comprising the maize and *Arabidopsis* CesA proteins. The deduced amino acid sequences of the maize ZmCesA10, ZmCesA11, and ZmCesA12 genes cluster with the corresponding deduced proteins from *Arabidopsis* (AtCESA4 (IRX5), AtCESA8 (IRX1), and AtCESA7 (IRX3), respectively) known to be involved in secondary wall formation. This suggests that the different subclasses of the CesA genes diverged early in evolution, at least before monocots and dicots separated (Holland et al., supra). Each of the IRX genes is expressed in the same cell type in the vascular tissue in *Arabidopsis* (Taylor et al., supra (2003)). Phylogenetic clustering of the maize CesA proteins with the IRX proteins from *Arabidopsis* and the observation that the highest expression was measured in the transition zone of the internode suggest that these genes are involved in secondary wall formation.

TABLE 7

Genes and Corresponding GenBank® Accession Numbers

| Gene Name[1] | GenBank® Accession Number |
|---|---|
| AtCesA1 | AF027172 |
| AtCesA2 | AF027173 |
| AtCesA3 | AF027174 |
| AtCesA4 | AB006703 |
| AtCesA5 | AB016893 |
| AtCesA6 | AF062485 |
| AtCesA7 | AF088917 |
| AtCesA8 | AL035526 |
| AtCesA9 | AC007019 |
| AtCesA13 | AC006300 |
| ZmCesA1 | AF200525 |
| ZmCesA2 | AF200526 |
| ZmCesA3 | AF200527 |
| ZmCesA4 | AF200528 |
| ZmCesA5 | AF200529 |
| ZmCesA6 | AF200530 |
| ZmCesA7 | AF200531 |
| ZmCesA8 | AF200532 |
| ZmCesA9 | AF200533 |
| ZmCesA10 (SEQ ID NOs: 31 and 32) | AY372244 |
| ZmCesA11 (SEQ ID NOs: 33 and 34) | AY372245 |
| ZmCesA12 (SEQ ID NOs: 35 and 36) | AY372246 |

[1]Source organism represented by first 2 letters of gene name. At = *Arabidopsis thaliana*, Zm = *Zea mays*.

Example 5

Expression Analysis of Zea mays ZmCesA10, ZmCesA11, and ZmCesA12 Genes Using MPSS Expression profiling of the CesA gene family: The expression pattern of the maize CesA genes in different tissues was studied using the MPSS technology Brenner et al., *Proc. Natl. Acad. Sci. USA*, 97(4):1665-1670 (2000); (Brenner et al., *Nat. Biotech.*, 18:630-634 (2000); Hoth et al., *J. Cell. Sci.*, 115:4891-4900 (2002); Meyers et al., *Plant J.*, 32:77-92 (2002); U.S. Pat. No. 6,265,163; and U.S. Pat. No. 6,511,802). This technology involves attaching each expressed cDNA to the surface of a unique bead. As a result, a highly expressed mRNA is represented on a proportionately large number of beads. Signature sequences of 16-20 nucleotides are then obtained by iteratively restricting the cDNA on a bead with the type IIs endonuclease, adaptor ligation, and hybridizing with an encoded probe. Sequencing of more than a million signatures from each tissue library allows 'electronic Northern' analysis to be carried out. The abundance of a particular mRNA is judged by the ratio of its specific signatures to the total mRNA molecules sequenced and is represented in parts per million (ppm).

Data averaged across multiple libraries for similar tissues (e.g., leaf, stalk, root) are presented in FIG. 5. The data are averaged over 76 different libraries. The number of libraries for each tissue was: root, 12; leaf, 13; stalk, 6; ear, 10; silk, 7; kernel, 2; embryo, 10; endosperm, 13; and pericarp, 3. The average for the total number of tags across the 76 libraries was 1,370,525 with a range of 1,223 (721 for a stalk library to 2,154,139 for a root library). The average for the adjusted number of unique tags was 45,293 with a range of 15,226 in an endosperm library to 87,030 for a root library. Similar data from a smaller set of libraries were presented in a previous report (Dhugga, K., Curr. Opin. Plant Biol., 4:488-493 (2001)).

Two general conclusions can be drawn from the data: 1) CesA genes 1-8 (with the exception of CesA2) are expressed at different levels in a majority of the tissues and 2) CesA10-12 are selectively expressed in those tissues that are rich in secondary wall. For CesA1-8, the data are in overall agreement with the previously reported data with the exception of CesA2, which, after reanalysis is found to be expressed only in the root and the kernel tissues and at a very low level in the silk tissue (Dhugga, K., supra). CesA5 and CesA6 are the highest expressed CesA genes in the endosperm and leaf tissues, respectively. CesA10, CesA11, and CesA12 are most highly expressed in the stalk tissue. The expression of none of the CesA genes is detected in the mature pollen grain.

Theoretically, the whole expressed genome is analyzed by the MPSS technology each time a library is screened for unique tags. Quantitative measures of the expression levels of different gene tags in the MPSS, as opposed to the ratios across paired tissues or treatments in the microarray-based platforms, combined with the depth of signature sequencing (>1 million) for each of the libraries make it possible to compare gene expression patterns across multiple, independent experiments. A correlation coefficient matrix showing the relationship for the expression pattern among the maize CesA genes is shown in Table 8.

TABLE 8

Correlation coefficient matrix for the expression pattern of maize CesA genes as compiled by the MPSS data. The same data set as used in FIG. 5 were used to calculate the correlation coefficients.

| Gene Name | CesA1 | CesA2 | CesA3 | CesA4 | CesA5 | CesA6 | CesA7 | CesA8 | CesA10 | CesA11 | CesA12 |
|---|---|---|---|---|---|---|---|---|---|---|---|
| CesA1 | 1.00 | | | | | | | | | | |
| CesA2 | 0.29 | 1.00 | | | | | | | | | |
| CesA3 | 0.05 | −0.08 | 1.00 | | | | | | | | |
| CesA4 | 0.37 | 0.17 | −0.12 | 1.00 | | | | | | | |
| CesA5 | −0.20 | −0.15 | 0.54 | −0.21 | 1.00 | | | | | | |
| CesA6 | 0.33 | 0.01 | 0.02 | 0.09 | −0.15 | 1.00 | | | | | |
| CesA7 | 0.70 | 0.21 | −0.02 | 0.39 | −0.13 | 0.29 | 1.00 | | | | |
| CesA8 | 0.63 | 0.34 | −0.06 | 0.62 | −0.38 | 0.22 | 0.60 | 1.00 | | | |
| CesA10 | 0.30 | 0.03 | −0.15 | 0.18 | −0.25 | 0.13 | 0.41 | 0.24 | 1.00 | | |
| CesA11 | 0.32 | 0.09 | −0.16 | 0.19 | −0.27 | 0.16 | 0.45 | 0.31 | 0.93 | 1.00 | |
| CesA12 | 0.33 | 0.02 | −0.10 | 0.19 | −0.23 | 0.19 | 0.51 | 0.27 | 0.89 | 0.85 | 1.00 |

All three of the secondary wall forming CesA proteins reported in *Arabidopsis* (IRX1, IRX3, and IRX5) have been reported to be involved in the formation of a functional cellulose synthase catalytic complex (Taylor et al., supra (2003)). For the ZmCesA10, ZmCesA11, and ZmCesA12 genes, the correlation coefficients are around 0.9 among different pairs, indicating that these genes are mostly coexpressed.

A comparison between the expression levels of the *Zea mays* CesA genes in stem and leaf tissue was conducted using the MPSS expression data from FIG. 5 and tabulated in Table 9. Suitable promoters for driving HCHL expression must show a significant tissue-specific expression pattern. Based on the data provided in Table 9, it is clear that the promoters of the genes for ZmCesA10, ZmCesA11, and ZmCesA12 exhibit a suitable tissue-specific expression pattern. The respective promoter sequences were identified and are provided as SEQ ID NOs:81, 82, and 83.

TABLE 9

Comparison Between Expression Levels of Various *Zea mays* CesA Genes in Stem and Leaf Tissue Using MPSS

| Gene Name | Leaf (ppm) | Stalk (ppm) | Stalk/leaf |
|---|---|---|---|
| CesA1 | 63 | 230 | 3.6 |
| CesA2 | 0 | 0 | 0.0 |
| CesA3 | 46 | 73 | 1.6 |
| CesA4 | 8 | 30 | 3.7 |
| CesA5 | 86 | 83 | 1.0 |
| CesA6 | 262 | 179 | 0.7 |
| CesA7 | 51 | 296 | 5.8 |
| CesA8 | 63 | 284 | 4.5 |
| CesA10 | 41 | 1033 | 25.0 |
| CesA11 | 37 | 639 | 17.2 |
| CesA12 | 16 | 370 | 22.8 |

Example 6

Identification of *Oryza savita* Orthologs Using Maize Genes Encoding the Cellulose Synthesis Catalytic Complex The nucleic acid sequences for ZmCesA10 (SEQ ID NO:31), ZmCesA11 (SEQ ID NO:33), and ZmCesA12 (SEQ ID NO:35) were used for a BLAST analysis against the rice BAC DNA (National Center for Biotechnology Information, Bethesda, Md.) database. The results of the analysis, including the closest matching entry in the rice BAC database are listed in Table 10. Thus, the rice genome appears to contain three genes that are very closely related to ZmCesA10, ZmCesA11, and ZmCesA12, respectively. The nucleic acid sequences of the corresponding rice orthologs are set forth as SEQ ID NOs:37, 39, and 41, respectively. The corresponding deduced amino acid sequences are set for as SEQ ID NOs:38, 40, and 42, respectively.

TABLE 10

Sequence Analysis Results

| Gene Name | Similarity Identified in Rice BAC Database (NCBI) | Identities[a] | Score (bits) | E-value[b] |
|---|---|---|---|---|
| ZmCesA10 | gi\|22711595\|gb\|AC022457.8 | 543/597 (90%) | 381 | 0.0 |
| ZmCesA11 | gi\|15146360\|dbj\|AP003237.2 | 487/524 (92%) | 745 | 0.0 |
| ZmCesA12 | gi\|21396530\|dbj\|AP005420.1 | 564/613 (92%) | 827 | 0.0 |

[a]Identity is defined as percentage of nucleic acids that are identical between the two nucleic acid sequences.
[b]Expect value. The Expect value estimates the statistical significance of the match, specifying the number of matches, with a given score, that are expected in a search of a database of this size absolutely by chance.

Example 7

Identification of Promoters from *Oryza savita* (Japonica Cultivar Group) Genes Orthologous to *Zea mays* ZmCesA10, ZmCesA11, and ZmCesA12 Genes Based on sequence homology to the *Arabidopsis* genes AtCesA8 (IRX1), AtCesA7 (IRX3), and AtCesA4 (IRX5) and the tissue-specific expression pattern of the maize genes ZmCesA10, ZmCesA11, and ZmCesA12, it appears that these genes encode proteins involved in the formation of the cellulose synthesis catalytic complex catalytic responsible for cellulose deposition in the secondary cell walls of the vascular system of the corn stalk. In Example 6, the sequences of the maize genes were used to identify the sequences of the orthologous genes of rice. Also disclosed is the unexpected finding that gene function and the expression pattern of secondary cell wall-forming cellulose synthases is conserved between dicotyledonous plants (*Arabidopsis thaliana*) and monocotyledonous plants (*Zea mays*). This finding strongly suggests that the rice orthologues of ZmCesA10, ZmCesA11, and ZmCesA12 will have an expression pattern that is indistinguishable from those of their corn counterparts. Sequences set forth as SEQ ID NOs:43, 44, and 45 represent 2500 bp of rice genomic DNA sequence found immediately upstream (5') of the inferred start codon of the three genes (SEQ ID NOs:37, 39, and 41, respectively) that are orthologs of the ZmCesA10, ZmCesA11, and ZmCesA12 genes, respectively. The sequences include putative regulatory elements such as cis-acting elements, transcription start sites and 5' UTRs of the rice genes. These sequences or part of these sequences can be used as promoters to target expression of HCHL genes to the plant stalk as outlined in Examples 3 and 8. These promoters will be of particular use to target expression of HCHL genes in transgenic monocotyledonous plants such as sugar cane.

Example 8

Expression of HCHL in Plants Using Tissue-Specific Promoters

The isolation of the gene encoding the *Pseudomonas putida* DSM 12585 HCHL enzyme is described in Example 1. The methods for constructing plasmids for tissue-specific expression are described in Examples 2 and 3. Briefly, primer pairs can be chosen to amplify the suitable promoters from *Arabidopsis thaliana* and *Oryza savita* (japonica cultivar group), respectively. Genomic DNA from each respective source organism can be isolated using methods known in the art (Maniatis, supra). Primer pairs are chosen to amplify the respective genes from the genomic DNA (Table 11). The second member of the primer pair is designed to introduce a NcoI site (CCATGG) at the initiator methionine codon of the respective gene and facilitates generation of translational fusions of genes that contain PagI (TCATGA) or NcoI sites at the start codon (Table 11). A pSKII+ plasmid containing a PCR-generated variant of the HCHL gene containing a PagI site at the start codon is partially digested with PagI and a PagI/SstI fragment is released from the vector by complete digestion with SstI. In this example, the variant is created using the *Pseudomonas putida* DSM 12585 HCHL coding sequence (SEQ ID NO:5). However, methods to PCR-generate variants of genes so that a PagI site is introduced at the initiator methionine codon for translational fusions is known in the art (Maniatis, supra). The respective promoter is released from the pCR2.1 vector by digestion with XbaI/PagI. The respective promoter and the HCHL gene are assembled in a suitable plant transformation vector that has been digested with suitable restriction enzymes such as XbaI and SstI in a three-way ligation. Plasmid DNA is used for *agrobacterium*-mediated transformation of *Arabidopsis* plants as previously described.

TABLE 11

Examples of Primer Pairs Suitable to Create Various Chimeric HCHL genes (based on *Pseudomonas putida* DSM 12585 HCHL)

| Genomic DNA Source | Promoter | Primer Pair Member #1 | Primer Pair Member #2 |
|---|---|---|---|
| A. thaliana | AtCesA4 (IRX5) (SEQ ID NO: 46) | Primer 19 (SEQ ID NO: 47) | Primer 20 (SEQ ID NO: 48) |
| A. thaliana | AtCesA8 (IRX1) (SEQ ID NO: 49) | Primer 21 (SEQ ID NO: 50) | Primer 22 (SEQ ID NO: 51) |
| O. savita (japonica cultivar) | Ortholog of Z. mays ZmCesA10 (SEQ ID NO: 43) | Primer 23 (SEQ ID NO: 52) | Primer 24 (SEQ ID NO: 53) |
| O. savita (japonica cultivar) | Ortholog of Z. mays ZmCesA11 (SEQ ID NO: 44) | Primer 25 (SEQ ID NO: 54) | Primer 26 (SEQ ID NO: 55) |
| O. savita (japonica cultivar) | Ortholog of Z. mays ZmCesA12 (SEQ ID NO: 45) | Primer 27 (SEQ ID NO: 56) | Primer 28 (SEQ ID NO: 57) |

Analysis of chimeric gene expression and kinetic analysis can be accomplished as described in Example 4.

Example 9

Evaluation of Alternative HCHL Enzymes

Producing pHBA by HCHL in stalk tissue is limited by enzyme activity even if stalk-specific promoters are employed. Thus, further pHBA productivity improvements require the application of HCHL enzymes with better catalytic efficiency or the co-expression of several divergent HCHL enzymes that can be co-expressed without triggering transcriptional or posttranscriptional gene silencing. A BLAST search of the public domain databases for putative HCHL enzymes was conducted. FIG. 6 shows a phylogenetic tree of a CLUSTAL W alignment of putative and bona fide HCHL enzymes in public databases. With the exception of a putative HCHL enzyme of *Caulobacter crescentus*, the name of the other potential HCHL enzymes are not provided since their catalytic activities have not been investigated. FIG. 6 illustrates that a large source of divergent "HCHL-like" enzymes that could be exploited for further improvements of pHBA accumulation in plants. The putative HCHL enzyme of *Caulobacter crescentus* shares only 54% amino acid identity to the HCHL enzymes from *Pseudomonas putida* and *Pseudomonas fluorescens* AN103 based on BLAST analysis.

Expression Cloning of HCHL Gene of *Caulobacter Crescentus*

Genomic DNA of the *Caulobacter crescentus* strain used for the genome sequencing project (Nierman et al., *PNAS*, 98(7):41364141 (2001)) was obtained from ATCC and used for PCR amplification of the HCHL ORF using the Primer 29: CCAAGGACCGCATATGACAGACGCCAACGAC (SEQ ID NO:68) and Primer 30: CCTCCCCCTCG-CAAGCTTTCAGCTCTGCTTGG (SEQ ID NO:69). The primers introduce NdeI and HindIII sites flanking the ORF. The PCR product was digested with Hind III and NdeI and ligated to the pET29a vector DNA that had been cut with the same restriction enzymes. Recombinant plasmid DNA was sequenced and introduced into BL21DE3 cells.

Expression Cloning of HCHL Gene of *Pseudomonas fluorescens* (AN103)

To evaluate the utility of the *Caulobacter* HCHL enzyme for producing pHBA in plants, it was important to compare its kinetic properties to those of the two *Pseudomonas* enzymes that have been previously utilized to produce pHBA in plants. The Applicants cloned, expressed, and purified the HCHL enzyme of *Pseudomonas fluorescens* (AN103). Plasmid DNA of pSP72 (Promega) containing the *Pseudomonas fluorescens* (AN103) HCHL ORF is described in Mayer et al. (supra). It was used for PCR amplification of the HCHL ORF using the Primer 31: GAGAGCATC-CATATGAGCACATACGAAGGTCGC (SEQ ID NO:70) and Primer 32: CGCAGCGTCAAGCTTCAGCGTT-TATACGCTTGC (SEQ ID NO:71). The primers introduce NdeI and HindIII sites flanking the ORF. The PCR product was digested with Hind III and NdeI and ligated to the pET29a vector DNA that had been cut with the same restriction enzymes. Recombinant plasmid DNA was sequenced and introduced into BL21 DE3 cells.

Recombinant Production, Purification, and Analysis of Kinetic Properties.

HCHL enzymes were purified from cell-free extracts of BL21 DE3 cells expressing the pET29a expression constructs by chromatography on Q-sepharose and hydroxyapatide as described in Example 1 for the native HCHL enzyme from *Pseudomonas putida* (DSM 12585). The following calculated properties of the HCHL proteins were used to determine kinetic properties of the HCHL enzymes.

HCHL *Caulobacter crescentus*: Molecular weight: 31104.09, Molar extinction coefficient: 59690.

HCHL *Pseudomonas fluorescens* AN103: Molecular weight: 31007.39, Molar extinction coefficient: 50190.

The enzyme preparations used to determine the kinetic properties were analyzed by Coomassie staining of PAGE gels, indicating that the both enzymes were at least 90% pure.

FIG. 7 and Table 12 summarize kinetic properties of the HCHL enzymes with the pHCACoA substrate. They were determined in standard HCHL enzyme reactions by using 1.4, 2.6, and 0.8 ng of purified HCHL enzymes of *P. putida*, *P fluorescens*, and *C. crescentus*, respectively. pHCACoA concentrations were varied from 0.9 to 440 µM. The high turnover number of the HCHL enzyme of *Pseudomonas fluorescens* (AN103) was more than four times higher than the kcat reported by Mitra et al. for the same enzyme (*Arch.*

*Biochem. Biophys.*, 365(1):6-10 (1999)). The HCHL enzyme of *C. crescentus* unexpectedly showed a 50% improvement of catalytic efficiency (Kcat/Km) when compared to the *Pseudomonas fluorescens* AN103 enzyme. Thus, the *Caulobacter* HCHL protein provides an ideal candidate for a catalyst to achieve further improvements of pHBA productivity in plants.

TABLE 12

Kinetic activity comparison between various HCHL enzymes

| HCHL Enzyme Source | Km (µM) | Vmax (nkat mg$^{-1}$) | Kcat (s$^{-1}$) | Kcat/Km |
|---|---|---|---|---|
| *P. putida* | 2.4 | 43 | 3.4 | 1.41 |
| *P. fluorescens* | 3.8 | 157 | 9.7 | 2.55 |
| *C. crescentus* | 4 | 240 | 15.2 | 3.8 |

Constitutive Expression of *Pseudomonas fluorescens* AN103 and *Caulobacter crescentus* HCHL Genes in Plants Transgenic lines can be generated that express HCHL enzyme from *Pseudomonas fluorescens* and *Caulobacter crescentus* under the control of constitutive promoters. This should be considered as a first step to investigate whether improved kinetic properties of the HCHL enzymes of *Caulobacter* result in higher levels of accumulated pHBA in stalk tissue when compared to *Pseudomonas* HCHL enzymes.

Construction of a Vector for Expression of HCHL *Caulobacter crescentus* in Transgenic Plants To generate a construct for constitutive expression of the *Caulobacter crescentus* HCHL enzyme in transgenic plants, a 0.9 kb XbaI/HindIII DNA fragment (containing the full-length HCHL *Caulobacter* ORF and 42 bp of 5' untranslated DNA (derived from the pET29A vector) immediately upstream of the initiation codon) was excised from the pET29a construct used for recombinant enzyme production and cloned into the pGEM3zf+ vector (Promega). This cloning step introduces a BamHI site upstream of the *Caulobacter* HCHL start codon. Recombinant pGEM3zf+ DNA containing the HCHL gene was linearized by digestion with HindIII. Linearized plasmid DNA was purified and overhanging DNA ends were filled-in with T4 DNA polymerase (New England Biolabs, Mass., USA) according to manufacturer instructions. The HCHL gene was released from the plasmid by digestion with BamHI. The restriction fragment was ligated to BamHI and HpaI digested pBE856 DNA. This resulted in replacement of the FlpM recombinase ORF in pBE856 with the HCHL gene of Caulobacter, situated between the constitutive SCP1 promoter and 3' untranslated region of the potato proteinase inhibitor II (PIN II) gene. The resulting binary vector, HCHL *Caulobacter* expression construct was used for plant transformation as described in General Methods. Plasmid pBE856 (SCP-FlpM) was previously constructed by cloning a 2172 bp XbaI-EcoRI fragment containing a chimeric SCP1:FlpM:3' Pin gene into the multiple cloning site of the binary vector pBE673 (described below), after cleavage of the latter with XbaI and EcoRI.

The SCP1:FlpM:Pin gene is comprised of a synthetic 35S promoter (SCP1) (Bowen et al., U.S. (2000), 31 pp., Cont.-in-part of U.S. Ser. No. 661,601, abandoned. CODEN: USXXAM U.S. Pat. No. 6,072,050 A 20000606), which is fused at its 3' end to the ORF of the FlpM recombinase, which is fused at its 3' end to the 3' PIN region derived from the *Solanum tuberosum* proteinase inhibitor II gene (GenBank® Accession No. L37519). Plasmid pBE673 was derived from pBin 19 (GenBank® Accession No. U09365) by replacing an 1836 bp Bsu36a-Cla I fragment of pBin 19 (which contains the 3' end of the nopaline synthase (nos) promoter, the npt II (kanamycin resistance) ORF, and the 3' nos region) with a 949 bp Bsu361-Cla I fragment (which contains (5' to 3'): a 106 bp fragment comprising the 3' end of nos promoter (nucleotides 468-574 described in GenBank® Accession Nos. V00087 and J01541; see also Bevan et al., *Nucleic Acids Res.*, 11 (2), 369-385 (1983)), a 5 bp GATCC sequence, a 551 bp fragment corresponding to the *Streptomyces hygroscopicus* phosphothricin acetyl transferase (basta resistance) ORF (GenBank® Accession No. X17220) except that the termination codon was changed from TGA to TAG, an 8 bp TCCGTACC sequence, and a 279 bp 3' nos region (nucleotides 1824-2102 of GenBank® Accession Nos. V00087 and J01541 described above)).

Vector for Expression of HCHL *Pseudomonas fluorescens* (AN103) in Transgenic Plants The binary vector plasmid for expressing the HCHL gene of *Pseudomonas fluorescens* (AN103) in transgenic plants is described in detail by Mayer et al. (*Plant Cell*, 13:1669-1682 (2001)). Both binary vectors were introduced into *Arabidopsis* plants by *agrobacterium*-mediated transformation. Transgenic lines carrying the HCHL gene of *P. fluorescens* and *C. crescentus* were selected on kanamycin and phosphinotrine, respectively, and grown in soil for eight weeks. pHBA concentration was determined in basal stem segments. Table 13 shows that pHBA levels are significantly higher in the *Caulobacter* HCHL transgenics in comparison to the *Pseudomonas* HCHL transgenics. In the best *Caulobacter* HCHL transgenics, pHBA levels in the basal stem segments are nearly doubled.

Whole stalk material was harvested after ten weeks and subjected to pHBA analysis. This analysis confirmed our previous observation indicating that a new high threshold of pHBA accumulation in whole stalk tissue of nearly 50 mg/g DW (dry weight) could be established by expression of the *Caulobacter* HCHL gene under control of the constitutive SCP1 promoter.

T2 plants of the *Caulobacter* and *Pseudomonas fluorescens* HCHL transgenics were germinated on selective media and grown in soil for 6 weeks to obtain sufficient stalk tissue for analysis of HCHL enzyme activity. Table 14 shows that expression of the *Caulobacter* HCHL gene led to an increase of specific HCHL activity in stalk tissue when compared to the HCHL *Pseudomonas* transgenics that reflects the differences in kinetic properties between the two enzymes that were detected in vitro.

TABLE 13 pHBA levels measured in several HCHL transgenics

| Construct | n | Basal stalk pHBA average (mg/g FW) | Basal stalk pHBA highest (mg/g FW) |
|---|---|---|---|
| 35S HCHL P. fluorescens | 42 | 1.72 | 6.0 |
| SCP1 HCHL C. crescentus | 72 | 2.4 | 11.8 |

TABLE 14

HCHL specific activity measured between various constructs

| Construct | Line | Rate (pkat/mg protein) | pHBA (mg/g DW) |
|---|---|---|---|
| 35S HCHL P. putida | 276 | 160 | 19.8 |
| 35S HCHL P. fluorescens | 374 | 480 | 30.0 |
| SCP1 HCHL C. crescentus | 10 | 614 | 49.2 |
| SCP1 HCHL C. crescentus | 24 | 610 | 47.4 |
| SCP1 HCHL C. crescentus | 29 | 653 | 46.0 |

Data in Tables 13 and 14 show that the higher catalytic efficiency of the HCHL enzyme of *Caulobacter crescentus* compared to HCHL enzymes of *Pseudomonas* is responsible higher specific HCHL activity and higher levels of pHBA accumulation in transgenic plants. An alternative explanation for this observation, however, may lie in the nature of the constitutive promoters that are expressing the respective HCHL genes. The *Pseudomonas* genes are expressed under the control of the double enhanced 35S promoter. The HCHL gene of *Caulobacter*, on the other hand, is expressed under the control of the SCP1 promoter. Although both promoters are ultimately derived from the 35S promoter, the promoters may differ in the level of gene expression that they can confer. Thus, the higher levels of HCHL activity and pHBA accumulation of the *Caulobacter* HCHL transgenics may merely reflect higher transcript levels that are achieved with the SCP1 promoter. In order to investigate this further, seed material of lines 374 and 29 were germinated on MS media containing glufosinate. Herbicide-resistant plants were transferred to soil and grown for 8 weeks. Stalk tissue was harvested and subjected to RNA isolation using standard procedures (Maniatis, supra) and HCHL enzyme activity was measured. HCHL transcript levels in line 374 and 29 were detected by real time PCR as follows:

Real time RT-PCR data was generated on an ABI 7900 SDS instrument (Applied Biosystems, Calif., USA). Dual labeled Taqman probes and RT-PCR primers were designed for all mRNA targets using ABI Primer Express v 2.0 software package (Applied Biosystems, Calif., USA) using default settings. The probes were labeled at the 5' end with the reporter fluorochrome 6-carboxyfluorescein (6-FAM) and the quencher fluorochrome 6-carboxy-tetramethyl-rhodamine (TAMRA) at the 3' end. Real Time one step RT-PCR reactions were set up using 1 µM final concentration of both the forward and reverse RT-PCR primers, 250 nm final concentration of the Taqman probe, 5 U ABI Multiscribe Reverse transcriptase, 8 U ABI RNAse Inhibitor, and 10 µL ABI Taqman Universal PCR Master Mix. The reaction volume was adjusted to 19 µL with RNase free water and 1 µL RNA was added at concentrations of 50 to 0.78 ng/µL. Reverse transcription was carried out for 30 min at 48° C. followed by 10 min at 95° C. for AmpliTaq Gold activation. Real time data (Cycle threshold or "Ct's") was collected during 40 cycles of PCR; 95° C., 5 sec, 60° C., 1 min.

Actin Real Time Data

Real time RT-PCR data were generated using a set of primers and probes targeting the ACTIN2 gene of *Arabi-*

*dopsis* (GenBank® Accession No. U41998) which has been shown to be constitutively expressed (An et al., *Plant J.*, 10 (1):107-121 (1996)).

The following primers were used

```
                                          (SEQ ID NO:72)
Primer 33 (Actin2RT-FWD):
TGA GAG ATT CAG ATG CCC AGA A (SEQ ID NO:73)
Primer 34 (Actin2RT-REV):
TGG ATT CCA GCA GCT TCC AT (SEQ ID NO:74)
Primer 35 (Actin2Probe):
TCT TGT TCCA GCC CTC GTT TGT
```

The objective was to identify and normalize RNA concentration differences between the samples isolated from the *Caulobacter* HCHL transgenic (29) and the *Pseudomonas* HCHL transgenic (374). The real time data for 25 ng, 12.5 ng, and 6.25 ng total RNA is shown in Table 15. It lists threshold cycle (Ct) determined for both RNA samples. The Ct value identifies the PCR cycle number at which the reporter dye emission intensity rises above background noise. The Ct value is determined at the most exponential phase of the PCR reaction and is therefore a more reliable measure of PCR target concentration than end-point measurements of accumulated PCR products in conventional reverse transcriptase-PCR experiments. The Ct value is inversely proportional to the copy number of the target template. The mean Ct values of three independent analyses are shown; corresponding SD values are also indicated. Both RNA preparations show very similar Ct values for each of the three concentrations. The % difference between the two vary from 0.0% to 0.3%. Since the ACTIN2 gene is constitutively expressed this data indicates that the RNA samples are of very similar concentration. The actin real time PCR data was used to normalize the real time expression data for the HCHL genes shown below.

TABLE 15

Real time PCR analysis comparing the threshold cycles of the ACTIN2 control used for normalization.

| ng RNA | Ct Values<br>374 *Pseudomonas* Actin | Ct Values<br>29 *Caulobacter* Actin | % Difference |
|---|---|---|---|
| 25 | 19.38 ± 0.05 | 19.38 ± 0.12 | 0.0% |
| 12.5 | 20.34 ± 0.10 | 20.37 ± 0.12 | 0.1% |
| 6.25 | 21.97 ± 0.31 | 22.03 ± 0.20 | 0.3% |

HCHL Real Time Data

Real time RT-PCR data was generated using primers and probes designed specifically for the *Pseudomonas* or the *Caulobacter* HCHL gene. The following primers were used:

```
                                          (SEQ ID NO:75)
Primer 36 (HCHL CAUL RT-FWD):
GCC TGG GTG AAG TTC AAT CG (SEQ ID NO:76)
Primer 37 (HCHL CAUL RT-REV):
CCA TCA TGC GAC GGT TCA G
```

```
                                          (SEQ ID NO:77)
Primer 38 (HCHL CAUL Probe):
CCC GAT AAG CGC AAC
TGC ATG AG (SEQ ID NO:78)
Primer 39 (HCHL PFL RT-FWD):
TGC GCC GAC GAA GCA (SEQ ID NO:79)
Primer 40 (HCHL PFL RT-REV):
GTT GCC CGG CGG GAT A (SEQ ID NO:80)
Primer 41 (HCHL PFL Probe):
TTC GGT CTC TCG GAA ATC AACTG
```

The PCR efficiency of these two different RNA-primer sets was compared based on how the Ct values changed across the entire range of *Arabidopsis* RNA dilutions from 50 to 0.78 ng/reaction (rxn). Linear regression analysis of the obtained Ct values versus the log of the RNA concentration was performed. The slopes of the two sets of data were used to calculate the RT-PCR efficiency for both sets of RT-PCR primers and probes. The calculation was performed as described (Pfaffl, M. W., *Nucleic Acids Res.*, 29(9):e45 (2001)). The data is shown in Table 16. RT-PCR efficiency for the *Caulobacter* and *Pseudomonas* HCHL primers and probe is 1.96 and 1.94, respectively; 2.0 is the theoretical maximum efficiency for exponential amplification in a PCR reaction. The efficiencies are very similar. Therefore, the real time data acquired with the HCHL specific primers and probes can be directly compared. The actin data (Table 15) were used to normalize for differences in the RNA concentration of both RNA samples.

TABLE 16

Comparison of Real Time RT-PCT Efficiency.

| ng RNA | Log ng RNA | 29 *Caulobacter* Ct Values[a] | 374 *Pseudomonas* Ct Values[a] |
|---|---|---|---|
| 50.00 | 1.70 | 17.14 ± 0.02 | 15.91 ± 0.02 |
| 25.00 | 1.40 | 18.27 ± 0.03 | 17.00 ± 0.05 |
| 12.50 | 1.10 | 19.33 ± 0.05 | 17.92 ± 0.06 |
| 6.25 | 0.80 | 20.27 ± 0.06 | 19.07 ± 0.06 |
| 3.13 | 0.49 | 21.35 ± 0.00 | 20.11 ± 0.04 |
| 1.57 | 0.19 | 22.35 ± 0.05 | 21.16 ± 0.04 |
| 0.78 | −0.11 | 23.38 ± 0.05 | 22.16 ± 0.04 |
| | Slope: | −3.43 | −3.47 |
| | Correlation Coefficient ($R^2$) | 1.00 | 1.00 |
| | RT-PCR Efficiency[b]: | 1.96 | 1.94 |

[a]Values represent the mean of n = 3 replicates, ± = SD
[b]Efficiency = $(10^{(-1/\text{slope})})$; 2.0 is maximum value for exponential amplification Relative Expression in *Arabidopsis* of the *Pseudomonas* and *Caulobacter* HCHL gene The real time data from the tables above was used to calculate the expression of the *Caulobacter* HCHL gene relative to the *Pseudomonas* HCHL gene (Pfaffl, M. W., supra). The relative expression data is shown in Table 17 for three different dilutions of the *Arabidopsis* RNA preps. The data indicate that for every mRNA transcript of the *Pseudomonas* HCHL gene that is produced only 0.40-0.46 *Caulobacter* transcripts are produced in the equivalent amount of *Arabidopsis* tissue.

TABLE 17

Relative Expression of Arabidopsis RNA

| ng RNA in RT-PCR | HCHL Efficiency | Actin Efficiency | CT HCHL* (Pseudo - Caulo) | CT Actin* (Pseudo - Caulo) | Relative Expression *Caulobacter* relative to *Pseudomonas* |
|---|---|---|---|---|---|
| 25 ng RNA | 1.95 | 1.7 | −1.27 ± 0.06 | 0 ± 0.13 | 0.43 ± 0.06 |
| 12.5 ng RNA | 1.95 | 1.7 | −1.41 ± 0.07 | −0.03 ± 0.15 | 0.40 ± 0.07 |
| 6.25 ng RNA | 1.95 | 1.7 | −1.2 ± 0.09 | −0.06 ± 0.37 | 0.46 ± 0.09 |

*Difference of means of n = 3 replicates; ± = 1SD

HCHL Enzyme Activity

The tissue used for RT-PCR experiments was also subjected to assays of HCHL activity. Table 18 shows that specific HCHL enzyme activity in stem tissue line 29 is 26% higher than in line 374. Real time PCR experiments revealed that HCHL transcript levels in lines 29 are lower than those detected in 374. Thus, strong evidence is provided for the conclusion that enhanced HCHL enzyme activity and pHBA accumulation observed in transgenic plants expressing the HCHL gene of *Caulobacter crescentus* is due to in improved kinetic properties of the HCHL enzyme.

TABLE 18

Comparison of HCHL enzyme activity in stem tissue of various constructs

| Construct | Line | HCHL rate (pkat/mg protein) |
|---|---|---|
| 35S HCHL *P. fluorescens* | 374 | 254 +/− 9 |
| SCP1 HCHL *C. crescentus* | 29 | 320 +/− 2 |

The HCHL gene from *Caulobacter crescentus* (with prior undisclosed activity) shows a 50% improvement of catalytic efficiency (Kcat/Km) when compared in vitro to a *Pseudomonas* HCHL enzyme described in the literature. Expression of this HCHL gene in transgenic plants resulted in increased pHBA accumulation in stalk tissue from 3% DW (observed with HCHL gene from *Pseudomonas*) to 4.9% DW. Transgenic plants expressing the HCHL gene of *Caulobacter* under control of constitutive promoters exhibited detrimental phenotypes similar to those observed when HCHL genes of *Pseudomonas* were expressed in transgenic plants. These phenotypes included delayed development, depletion of soluble phenylpropanoids (sinapoyl malate) in leaf tissue and early senescence in leaf tissue. However, as described in Example 3 of this application, these negative side effects can be avoided through expression of HCHL genes under the control of tissue-specific promoters; specifically promoters of cellulose synthase genes that represent AtCesA8 (IRX1), AtCesA7 (IRX3), and AtCesA4 (IRX5) or promoters of orthologous genes present in other plant species.

The low level (<57%) of sequence identity of HCHL genes of *Pseudomonas putida* (DSM 12585) and *Pseudomonas fluorescens* AN103 relative to the HCHL gene of *Caulobacter crescentus* enables co-expression of both HCHL genes in a single plant cell. This elegant route to even higher levels of HCHL gene expression in plant cells avoids co-suppression problems that would arise from co-expression of closely-related HCHL genes in plants.

---

What is claimed is:

1. A method to selectively produce para-hydroxybenzoic acid in plant stem tissue comprising:
   a. growing a plant under suitable conditions, the plant comprising
      i. an endogenous source of para-coumaroyl-CoA; and
      ii. at least one 4-hydroxycinnamoyl-CoA hydratase/lyase (HCHL) expression cassette comprising a nucleic acid molecule encoding a polypeptide having hydroxycinnamoyl CoA hydratase/lyase activity, wherein said nucleic acid molecule is selected from the group consisting of:
         (a) a nucleic acid molecule comprising a nucleic acid sequence selected from the group consisting of SEQ ID NOs: 5, 58, 59, 60, 62, 63, and 64; and
         (b) a nucleic acid molecule encoding a polypeptide comprising an amino acid sequence selected from the group consisting of SEQ ID NO: 6 and SEQ ID NO: 61;
         operably linked to a tissue-specific promoter selected from the group consisting of SEQ ID NOs: 26, 43, 44, 45, 46, 49, 81, 82, and 83;
   b. recovering unconjugated para-hydroxybenzoic acid and para-hydroxybenzoic acid glucoside from the plant;
   c. hydrolyzing para-hydroxybenzoic acid glucoside; and
   d. recovering unconjugated para-hydroxybenzoic acid.

2. The method according to claim 1 wherein the plant is selected from the group consisting of tobacco, *Arabidopsis*, sugar beet, sugar cane, soybean, rapeseed, sunflower, cotton, corn, alfalfa, wheat, barley, oats, sorghum, rice, canola, millet, beans, peas, rye, flax, and forage grasses.

3. A method according to claim 1 wherein the HCHL expression cassette is SEQ ID NO:30.

4. A method according to claim 1 wherein the nucleic acid molecule encoding HCHL encodes the polypeptide of SEQ ID 61.

5. A method according to claim 1 wherein the nucleic acid molecule encoding HCHL encodes the polypeptide of SEQ ID NO:6.

6. A method according to claim 1 wherein the plant further comprises at least one nucleic acid molecule encoding a polypeptide having UDP-glucosyltransferase activity, said at least one nucleic acid molecule comprising a nucleic acid sequence selected from the group consisting of SEQ ID NO: 65, 66, and 67; wherein said at least one nucleic acid molecule is operably linked to a suitable regulatory sequence.

7. The method according to claim 1 wherein the tissue-specific promoter of said HCHL expression cassette preferentially expresses active HCHL in said plant stem tissue at levels at least ten times higher than expression levels measured in leaf tissue of said plant.

8. A method to selectively produce para-hydroxybenzoic acid in plant stem tissue comprising:
   a. providing a plant comprising
      i. an endogenous source of para-coumaroyi-CoA;
      ii. a 4-hydroxycinnamoyl-CoA hydratase/lyase (HCHL) expression cassette comprising a tissue-specific promoter selected from the group consisting of SEQ ID NOs: 26, 43, 44, 45, 46, 49, 81, 82, and 83 operably linked to a nucleic acid molecule encoding a polypeptide having hydroxycinnamoyl CoA hydratase/lyase activity having an amino acid sequence SEQ ID NO: 61; and
   b. growing a plant under suitable conditions whereby unconjugated para-hydroxybenzoic acid and para-hydroxybenzoic acid glucosides are produced;
   c. recovering unconjugated para-hydroxybenzoic acid and para-hydroxybenzoic acid glucoside from the plant;
   d. hydrolyzing para-hydroxybenzoic acid glucoside; and
   e. recovering unconjugated para-hydroxybenzoic acid.

9. The method according to claim 8 wherein the plant is selected from the group consisting of tobacco, *Arabidopsia*, sugar beet, sugar cane, soybean, rapeseed, sunflower, cotton, corn, alfalfa, wheat, barley, oats, sorghum, rice, canola, millet, beans, peas, rye, flax, and forage grasses.

10. A method according to claim 8 wherein the plant further comprises at least one nucleic acid molecule encoding a polypeptide having UDP-glucosyltransferase activity, said nucleic acid molecule comprising a nucleic acid sequence selected from the group consisting of SEQ ID NO: 65, 66, and 67; wherein said at least one nucleic acid molecule is operably linked to a suitable regulatory sequence.

* * * * *